United States Patent
Griffioen et al.

(10) Patent No.: US 7,960,556 B2
(45) Date of Patent: Jun. 14, 2011

(54) THIADIAZOLE DERIVATIVES FOR THE TREATMENT OF NEURO-DEGENERATIVE DISEASES

(75) Inventors: Gerard Griffioen, Linden (BE); Stefaan Wera, Bierbeek (BE); Hein Roger Duhamel, Kessel-Lo (BE); Ellen Gommé, Opvelp (BE); Nele Van Damme, Kessel-Lo (BE)

(73) Assignee: NV reMYND, Leuven (BE)

( * ) Notice: Subject to any disclaimer, the term of this patent is extended or adjusted under 35 U.S.C. 154(b) by 0 days.

(21) Appl. No.: 12/515,824

(22) PCT Filed: Nov. 22, 2007

(86) PCT No.: PCT/EP2007/010192
§ 371 (c)(1),
(2), (4) Date: Oct. 12, 2009

(87) PCT Pub. No.: WO2008/061781
PCT Pub. Date: May 29, 2008

(65) Prior Publication Data
US 2010/0144709 A1 Jun. 10, 2010

(30) Foreign Application Priority Data
Nov. 22, 2006 (GB) .................. 0623258.1

(51) Int. Cl.
*C07D 285/08* (2006.01)
*A61K 31/41* (2006.01)
(52) U.S. Cl. ...................... 548/128; 514/361
(58) Field of Classification Search .......... None
See application file for complete search history.

(56) References Cited

FOREIGN PATENT DOCUMENTS
WO 2005/020991 A1 3/2005
WO 2005/095368 A1 10/2005
WO 2006/002981 A1 1/2006

OTHER PUBLICATIONS

Vippagunta, et al "Crystallune Solids" Advanced Drug Delivery Reviews, 48 (2001) pp. 3-26.*
International Search Report in PCT/EP2007/010192.
Written Opinion in PCT/EP2007/010192.
International Preliminary Report on Patentability in PCT/EP2007/010192.

* cited by examiner

*Primary Examiner* — Kamal A Saeed
*Assistant Examiner* — Nyeemah Grazier
(74) *Attorney, Agent, or Firm* — Kristina Castellano; Castellano PLLC

(57) ABSTRACT

The invention provides novel 1,2,4-thiadiazole derivatives useful for preventing or treating an α-synucleopathy such as Parkinson's disease, as well as pharmaceutical compositions including them as biologically active ingredients, and methods for manufacturing them.

18 Claims, 4 Drawing Sheets

THIADIAZOLE DERIVATIVES FOR THE TREATMENT OF NEURO-DEGENERATIVE DISEASES

CLAIM FOR PRIORITY

Figure 1:
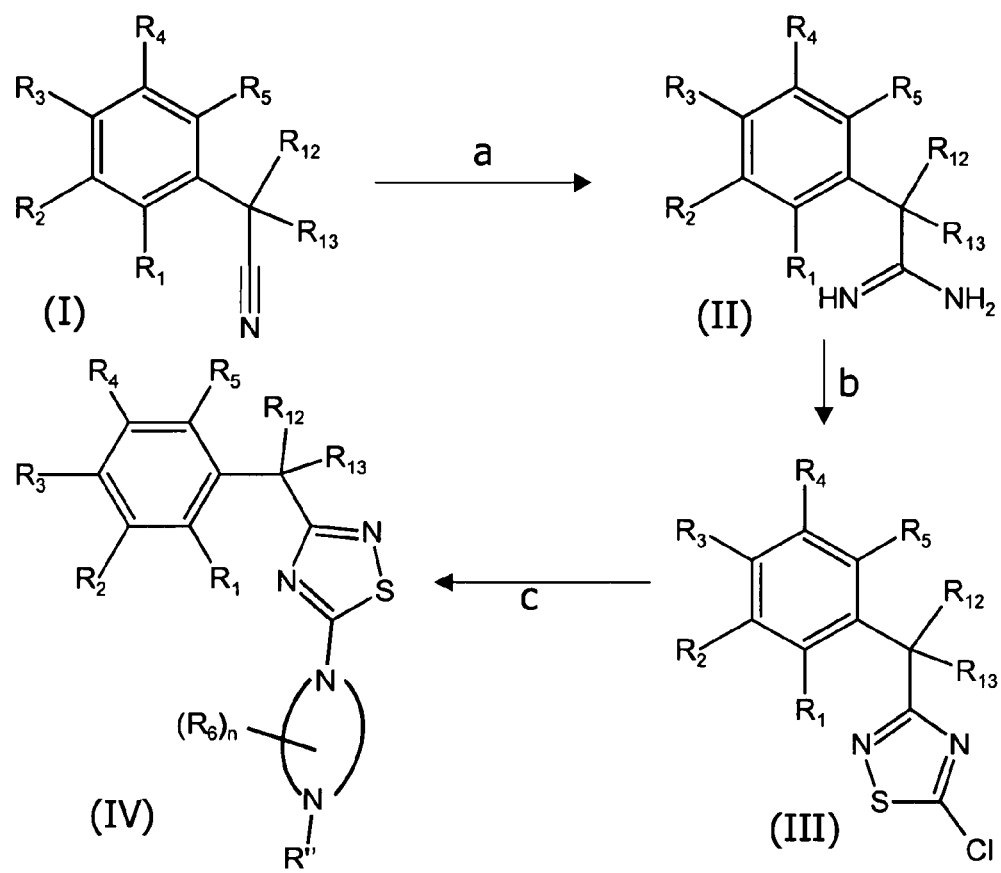

This application is a U.S. National Stage Application of PCT/EP2007/010192 filed on Nov. 22, 2007, claiming priority to Great Britain application 0623258.1 filed Nov. 22, 2006, the contents of both of which are incorporated herein by reference.

FIELD OF THE INVENTION

The present invention relates to novel thiadiazole derivatives useful for treating certain neurological disorders characterised by cytotoxic α-synuclein amyloidogenesis. The invention further relates to methods of treatment or prevention of such neurological disorders by the administration of a pharmaceutical composition, comprising one or more thiadiazole derivatives in an amount which alleviates or prevents the cytotoxic properties of α-synuclein. The invention further relates to methods of preparing novel thiadiazole derivatives, as well as certain classes of intermediates useful in such preparation.

BACKGROUND OF THE INVENTION

α-Synuclein is a neuronal protein which originally has been associated with neuronal plasticity during Zebra finch song learning. Although its role at the molecular level is at present largely elusive it appears to have lipid bi-layer (or membrane) binding properties important for preserving proper transport of neurotransmitter vesicles to the axonal ends of neurons presumably to ensure proper signalling at the synapse.

Apart from its physiological role in brain cells, human α-synuclein also possesses pathological features that underlies a plethora of neurodegenerative diseases including Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy and Alzheimer's disease. These neurological disorders are characterised by the presence of insoluble α-synuclein polymers or aggregates usually residing within neuronal cells, although in the case of Alzheimer's disease α-synuclein (or proteolytic fragments thereof) constitutes the non-amyloid component of extracellular "amyloid-β plaques". It is widely believed that the amyloidogenic properties α-synuclein disrupt cellular integrity leading to dysfunctioning or death of affected neurons resulting in cognitive and/or motoric decline as it is found in patients suffering from such diseases. The aggregation of α-synuclein is at present very poorly defined, but constitutes most likely a multi-step process wherein self-polymerization of α-synuclein into insoluble aggregates is preceded by the formation of soluble protofibrils of α-synuclein monomers. Self-association may be triggered by the formation of alternative conformations of α-synuclein monomers with high propensity to polymerize. Several studies using neuronal cell lines or whole animals have shown that formation of reactive oxygen species (hereinafter abbreviated as ROS) appear to stimulate noxious α-synuclein amyloidogenesis. For instance paraquat (an agent stimulating ROS formation within the cell) has been recognized as a stimulator of α-synuclein aggregation. Like in animals, exposure to paraquat is believed to induce the formation of synuclein inclusions, and consequently neurodegeneration, especially of dopaminergic neurons in humans. Dopaminergic neurons appear to be particularly sensitive because the concurrent dopamine metabolism may on the one hand contribute significantly to the oxidative stress load but may on the other hand result in kinetic stabilisation of highly toxic protofibrillar α-synuclein species by dopamine (or its metabolic derivatives). Parkinson's disease is characterised by a selective loss of dopaminergic substantia nigra cells and therefore treatment of animals (or neuronal cells) with paraquat is a common well-accepted experimental set-up for studying synucleopathies, in particular Parkinson's disease.

Apart from ROS, mutations in the coding region of the α-synuclein gene have also been identified as stimulators of self-polymerization resulting in early disease onset as it is observed in families afflicted by such mutations. Finally, increased expression of α-synuclein also promotes early disease onset as evidenced by a duplication or triplication of the α-synuclein gene in the genome of some individuals. The molecular mechanism by which α-synuclein self-association triggers cellular degeneration is at present largely unknown. Although it has been speculated that insoluble aggregates affect cellular integrity, it has recently been suggested that soluble protofibrillar intermediates of the aggregation process are particularly toxic for the cell as opposed to mature insoluble fibrils which may be inert end-products or may even serve as cytoprotective reservoirs of otherwise harmful soluble species. Therapeutic attempts to inhibit formation of insoluble aggregates may therefore be conceptually wrong, possibly even promoting disease progress.

While the identification of pathological α-synuclein mutations unequivocally revealed a causative factor of a plethora of neurodegenerative disorders, treatments ensuring suppression of toxic α-synuclein amyloidogenesis are presently not available. Only symptomatic treatments of Parkinson's disease exist, which aim e.g. at increasing dopamine levels in order to replenish its lowered level due to degeneration of dopaminergic neurons, for instance by administrating L-DOPA or inhibitors of dopamine breakdown. Although such treatments suppress disease symptoms to some extent, they are only temporarily effective and certainly do not slow down ongoing neuronal degeneration.

Thus there is a need in the art for designing new drugs for therapeutic treatments that target the underlying molecular mechanism of α-synuclein related pathologies in order to reduce neuronal cell death and/or degeneration.

WO 99/51584 discloses 5-piperazinyl-1,2,4-thiadiazoles as inhibitors of proton pump $H^+/K^+$-ATPase and therefor useful in the treatment of peptic ulcer. However these compounds are not suggested for use in the prevention or treatment of neuro-degenerative disorders.

WO 2006/002981 teaches thiazole and thiadiazole derivatives including a propynoyl linker for use in the field of pain relief, through acting on the mGluR5-receptor regulation.

SUMMARY OF THE INVENTION

The present invention relates to different classes of 1,2,4-thiadiazole derivatives that have been shown to effectively counteract or inhibit the toxic properties of α-synuclein. Administration of these compounds to patients suffering from a neurodegenerative disease characterised by noxious α-synuclein amyloidogenesis therefore constitutes an effective therapeutic and/or prophylactic method of treatment.

According to a first aspect, the present invention provides a first class of novel 1,2,4-thiadiazole derivatives having the structural formula (A):

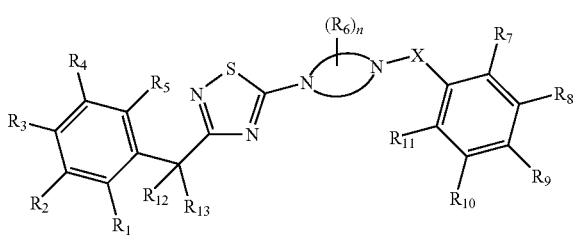

or, more specifically, the structural formula (B):

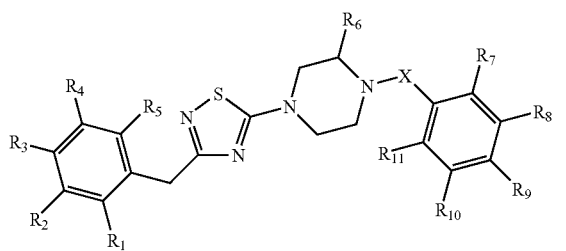

wherein the divalent group schematically represented by the structural formula (A')

(A')

includes an optionally mono-substituted or poly-substituted, saturated or partly unsaturated heterocyclic ring with at least two nitrogen atoms in the said heterocyclic ring and with a total of 5 to 7 atoms in the said heterocyclic ring, and further wherein:

each $R_6$ is a substituent on a carbon atom of said heterocyclic ring and is independently selected from the group consisting of oxo, aryl and $C_{1-4}$ alkyl, or two substituents $R_6$ on the same carbon atom of said heterocyclic ring together form a heterocyclic or homocyclic ring system;

n is selected from the group consisting of 0, 1, 2 and 3;

$R_1$, $R_2$, $R_3$, $R_4$ and $R_5$ are each independently selected from the group consisting of hydrogen, $C_{1-4}$ alkyl, $C_{1-4}$ alkoxy, aryl, aryloxy, aryl-$C_{1-4}$ alkyloxy, heteroaryloxy, benzenesulfonate, amino, hydroxy, nitro, trifluoromethyl, trifluoromethoxy and halogen, or any two adjacent substituents selected from the group consisting of $R_1$, $R_2$, $R_3$, $R_4$ and $R_5$ form, together with the phenyl ring carbon atoms to which they are attached, a saturated or unsaturated ring fused to said phenyl ring and having from 5 to 7 ring members, said saturated or unsaturated ring optionally comprising one or two oxygen atoms and being optionally substituted with one or more halogen atoms;

$R_7$, $R_8$, $R_9$, $R_{10}$ and $R_{11}$ are each independently selected from the group consisting of hydrogen, $C_{1-10}$ alkyl, $C_{1-6}$ alkoxy, aryl, hydroxy, acyl (in particular acetyl), nitro, trifluoromethyl, trifluoromethoxy, mono-$C_{1-6}$alkylamino, di-$C_{1-6}$alkyl-amino, $C_{1-6}$ alkylcarbonyloxy, $C_{1-6}$ alkylthio, cyano, heterocyclic, benzyloxy, dialkylaminosulfonyl and halogen; or any two adjacent substituents selected from the group consisting of $R_7$, $R_8$, $R_9$, $R_{10}$ and $R_{11}$ form, together with the phenyl ring carbon atoms to which they are attached, a saturated or unsaturated ring fused to said phenyl ring and having from 5 to 7 ring members, said saturated or unsaturated ring optionally comprising one or two heteroatoms independently selected from the group consisting of oxygen, sulfur and nitrogen; and each of said $C_{1-6}$ alkyl, $C_{1-6}$ alkoxy, aryl or fused ring is optionally substituted with one or more halogen atoms;

$R_{12}$ and $R_{13}$ are each independently selected from the group consisting of hydrogen, $C_{1-6}$ alkyl, aryl-$C_{1-4}$ alkyl, aryl and N-containing heterocyclic rings, or $R_{12}$ and $R_{13}$ together form a $C_{3-6}$ cycloalkyl or heterocyclic group; and X is a linking moiety selected from the group consisting of a single bond; —C(=O)—; —S(=O)$_2$—; divalent saturated, ethylenically unsaturated or acetylenically unsaturated non-cyclic hydrocarbon groups comprising from 1 to 8 atoms (preferably from 1 to 6 atoms) in the main chain, each of said atoms in the main chain being independently selected from the group consisting of carbon, nitrogen and sulfur, and each of said carbon atoms in the main chain being optionally substituted with one or more substituents independently selected from the group consisting of oxo, thioxo, $C_{1-4}$ alkyl and halogen, provided that the number of heteroatoms in the main chain of said divalent saturated or unsaturated non-cyclic hydrocarbon group is 0, 1 or 2; and divalent saturated or unsaturated heterocyclic groups comprising from 2 to 6 carbon atoms and from 1 to 3 heteroatoms independently selected from the group consisting of oxygen, sulfur and nitrogen in the said heterocyclic group; or X together with one of $R_7$ and $R_{11}$ forms a saturated or unsaturated ring having from 5 to 7 ring members and being fused to the phenyl ring bearing said one of $R_7$ and $R_{11}$, said saturated or unsaturated ring optionally comprising one or two heteroatoms independently selected from the group consisting of oxygen, sulfur and nitrogen, and said saturated or unsaturated ring optionally comprising one or more substituents independently selected from the group consisting of $C_{1-4}$ alkyl and trifluoromethyl;

or a stereoisomer or solvate thereof, or a pharmaceutically acceptable salt thereof.

The present invention further provides a second class of novel 1,2,4-thiadiazole derivatives having the structural formula (C):

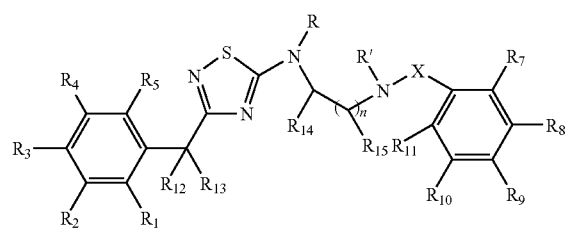

wherein X, $R_1$, $R_2$, $R_3$, $R_4$, $R_5$, $R_7$, $R_8$, $R_9$, $R_{10}$, $R_{11}$, $R_{12}$ and $R_{13}$ are as defined with respect to formulae (A) and (B), and further wherein:

n is an integer from 0 to 11, $R_{14}$, $R_{15}$, R and R' are each independently selected from hydrogen and $C_{1-4}$ alkyl, or a stereoisomer or a solvate thereof, or a pharmaceutically acceptable salt thereof.

The present invention further provides a third class of novel 1,2,4-thiadiazole derivatives having the structural formula (D):

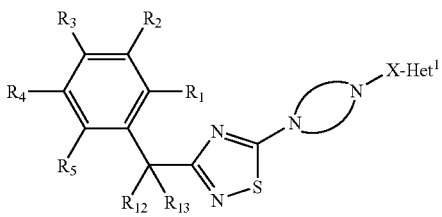

or more specifically the structural formula (E):

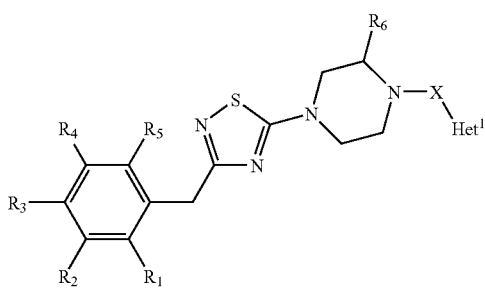

wherein X, $R_1$, $R_2$, $R_3$, $R_4$, $R_5$, $R_6$, $R_{12}$ and $R_{13}$ and n are as defined with respect to formulae (A) and (B), and further wherein $Het^1$ is a heteroaryl group optionally substituted with one or more substituents independently selected from the group consisting of halogen, trifluoromethyl, nitro, cyano and $C_{1-10}$ alkyl.

The present invention further provides a fourth class of novel 1,2,4-thia-diazole derivatives having the structural formula (F):

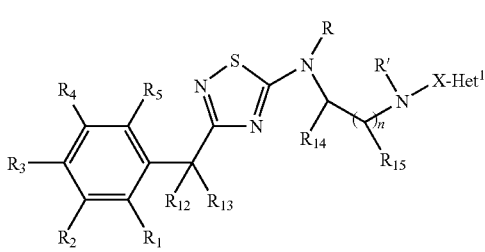

wherein X, $R_1$, $R_2$, $R_3$, $R_4$, $R_5$, $R_6$, $R_{12}$, $R_{13}$, R, R', $R_{14}$, $R_{15}$ and n are as defined with respect to formula (C), and further wherein $Het^1$ is a heteroaryl group.

Particular embodiments of the present invention relate to 1,2,4-thiadiazole derivatives belonging to the third class and fourth class defined above, wherein $Het^1$ is selected from the group consisting of furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, benzothiophenyl, indazolyl, benzimidazolyl, benzthiazolyl, benzisothiazolyl, benzisoxazolyl, purinyl, quinazolinyl, quinolizinyl, quinolinyl, isoquinolinyl, quinoxalinyl, naphthyridinyl, pteridinyl carbazolyl, azepinyl, diazepinyl, acridinyl, pyrrolinyl, pyrazolinyl, indolinyl, pyrrolidinyl, piperidinyl, piperazinyl, azepinyl, diazepinyl, morpholinyl, thiomorpholinyl, oxazolidinyl, oxazolinyl, oxazepinyl, aziridinyl and tetrahydrofuranyl. Due to the limited number of heteroaryl compounds commercially or readily available for the production of 1,2,4-thiadiazole derivatives having the structural formulae (D), (E) and (F), $Het^1$ may be preferably selected from the group consisting of thienyl, furyl, pyrrolyl and pyridyl.

Compounds belonging to all classes (i.e. structural formulae A, B, C, D, E and F) of the 1,2,4-thiadiazole derivatives of the present invention are capable of inhibiting or significantly reducing α-synuclein-instigated loss of neuronal cell integrity.

According to a second aspect, therefore the present invention provides each class of these compounds for use as active ingredients in the manufacture of medicaments, more particularly for use in the treatment of α-synucleopathies in particular in humans. According to this second aspect, the invention also provides pharmaceutical compositions comprising an effective amount of one or more of such 1,2,4-thiadiazole derivatives, said pharmaceutical compositions being useful for the prevention and/or treatment of an α-synucleopathy such as, but not limited to, Parkinson's disease, diffuse Lewy body disease, multiple system atrophy and Alzheimer's disease, preferably in humans. Accordingly, the present invention also relates to the treatment and/or prevention of α-synucleopathies, such as, but not limited to Parkinson's disease, diffuse Lewy body disease, multiple system atrophy and Alzheimer's disease by the administration, to a patient in need thereof, of a therapeutically effective amount of one or more of such 1,2,4-thiadiazole derivatives. In a third aspect, the present invention provides methods for preparing such 1,2,4-thiadiazole derivatives in good yield via synthetic routes including a limited number of steps and starting from commercially available materials or easily obtainable analogues thereof.

DEFINITIONS

As used herein with respect to a substituting group, and unless otherwise stated, the term "$C_{1-4}$ alkyl" means straight and branched chain saturated acyclic hydrocarbon monovalent groups having from 1 to 4 carbon atoms such as, for example, methyl, ethyl, propyl, n-butyl, 1-methylethyl (isopropyl), 2-methylpropyl (isobutyl) and 1,1-dimethylethyl (ter-butyl). By analogy, the term "$C_{1-6}$alkyl" refers to such radicals having from 1 to 6 carbon atoms, including 2-methylbutyl, n-pentyl, dimethylpropyl, n-hexyl, 2-methylpentyl, 3-methylpentyl, and the like. By analogy, the term "$C_{1-10}$ alkyl" refers to such radicals having from 1 to 10 carbon atoms, including n-heptyl, n-octyl, n-nonyl, n-decyl and the like.

As used herein with respect to a linking group, and unless otherwise stated, the term "$C_{1-6}$ alkylene" means a divalent hydrocarbon radical corresponding to the above defined $C_{1-6}$alkyl, such as methylene, bis(methylene), tris(methylene), tetramethylene, hexamethylene and the like.

As used herein with respect to a substituting group, and unless otherwise stated, the term "$C_{3-6}$ cycloalkyl" means a mono- or polycyclic saturated hydrocarbon monovalent group having from 3 to 6 carbon atoms, such as for instance cyclopropyl, cyclobutyl, cyclopentyl, cyclohexyl, and the like.

As used herein with respect to a substituting group, and unless otherwise stated, the term "aryl" designate any monoor polycyclic aromatic monovalent hydrocarbon group having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_{4-8}$ cycloalkyl groups such as, for instance, indanyl, tetrahydronaphthyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein with respect to a substituting group, and unless otherwise stated, the terms "$C_{1-4}$ alkoxy", "$C_{1-6}$ alkoxy" and "aryloxy", refer to substituents wherein a carbon atom of a $C_{1-4}$ alkyl, respectively a $C_{1-6}$ alkyl or an aryl group (each of them such as defined herein), is attached to an oxygen atom through a single bond such as, but not limited to, methoxy, ethoxy, propoxy, butoxy, pentoxy, isopropoxy, sec-butoxy, tert-butoxy, isopentoxy, phenoxy, and the like.

As used herein with respect to a substituting group, and unless otherwise stated, the terms "$C_{1-6}$ alkylthio", refer to substituents wherein a carbon atom of a $C_{1-6}$ alkyl group (such as defined herein), is attached to a sulfur atom through a single bond such as, but not limited to, methylthio or ethylthio.

As used herein with respect to a substituent, and unless otherwise stated, the term "acyl" broadly refers to a carbonyl (oxo) group being adjacent to a $C_{1-6}$ alkyl, aryl or heterocyclic group, all of them being such as herein defined; representative examples of acyl include, but are not limited to, acetyl, pivaloyl, benzoyl, naphthoyl and the like.

As used herein with respect to a substituent, and unless otherwise stated, the term "mono-$C_{1-6}$ alkylamino" means that one $C_{1-6}$ alkyl group (such as defined herein) is attached to a nitrogen atom through a single bond such as, but not limited to, methylamino, ethylamino, isopropylamino, n-butylamino and tert-butylamino. As used herein with respect to a substituent, and unless otherwise stated, the term "di-$C_{1-6}$ alkylamino" means that two $C_{1-6}$ alkyl groups (such as defined herein) are attached to a nitrogen atom through a single bond such as, but not limited to, dimethylamino, diethylamino, diisopropylamino, di-n-butylamino and di-tert-butylamino.

As used herein, e.g. with respect to a substituent or a combination of substituents, and unless otherwise stated, the term "homocyclic" means a mono- or polycyclic, saturated or mono-unsaturated or polyunsaturated hydrocarbon radical having from 4 up to 15 carbon atoms but including no heteroatom in the said ring.

As used herein with respect to a substituent, and unless otherwise stated, the term "heterocyclic" means a mono- or polycyclic, saturated or mono-unsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl (oxo) or thiocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphto-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxathiinyl, benzodioxinyl, benzodithiinyl, benzoxazepinyl, benzothiazepinyl, benzodiazepinyl, benzodioxepinyl, benzodithiepinyl, benzoxazocinyl, benzothiazocinyl, benzo-diazocinyl, benzoxathiocinyl, benzodioxocinyl, benzotrioxepinyl, benzoxathiazepinyl, benzoxadiazepinyl, benzothiadiazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypoxanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzocarbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphtindazolyl, naphtindolyl, naphtothiazolyl, naphtothioxolyl, naphtoxindolyl, naphto-triazolyl, naphtopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydro-pyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimi-dazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, pheno-metoxazinyl, phenoparoxazinyl, phentriazinyl, thiodiazinyl, thiodiazolyl, indoxyl, thioindoxyl, benzodiazinyl (e.g. phtalazinyl), phtalidyl, phtalimidinyl, phtalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of said heterocyclic ring may furthermore be independently substituted with a substituent selected from the group consisting of halogen, nitro, $C_{1-7}$ alkyl (optionally containing one or more functions or radicals selected from the group consisting of carbonyl (oxo), alcohol (hydroxyl), ether (alkoxy), acetal, amino, imino, oximino, alkyloximino, amino-acid, cyano, carboxylic acid ester or amide, nitro, thio $C_{1-6}$ alkyl, thio $C_{3-6}$ cycloalkyl, $C_{1-6}$ alkylamino, cycloalkylamino, alkenylamino, cycloalkenylamino, alkynylamino, arylamino, arylalkylamino, hydroxylalkylamino, mercaptoalkylamino, heterocyclic-substituted alkylamino, heterocyclic amino, heterocyclic-substituted arylamino, hydrazino, alkylhydrazino, phenylhydrazino, sulfonyl, sulfonamido and halogen), $C_{2-6}$ alkenyl, $C_{2-6}$ alkynyl, halo $C_{1-6}$ alkyl, $C_{3-6}$ cycloalkyl, aryl, arylalkyl, alkylaryl, alkylacyl, arylacyl, hydroxyl, amino, $C_{1-6}$ alkylamino, cycloalkylamino, alkenylamino, cycloalkenylamino, alkynylamino, arylamino, arylalkylamino, hydroxyalkylamino, mercaptoalkylamino, heterocyclic-substituted alkylamino, heterocyclic amino, heterocyclic-substituted arylamino, hydrazino, alkylhydrazino, phenylhydrazino, sulfhydryl, $C_{1-6}$ alkoxy, $C_{3-6}$ cycloalkoxy, aryloxy, arylalkyloxy, oxyheterocyclic, heterocyclic-substituted alkyloxy, thio $C_{1-6}$ alkyl, thio $C_{3-6}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof; depending upon the number of unsaturations in the 3 to 10 atoms ring, heterocyclic substituents may be sub-divided into heteroaromatic (or "heteroaryl") and non-aromatic heterocyclic substituents; when a heteroatom of said non-aromatic heterocyclic radical is nitrogen, the latter may further be substituted with a substituent selected from the group consisting of $C_{1-6}$ alkyl, C cycloalkyl, aryl, arylalkyl and alkylaryl.

As used herein with respect to a substituting atom, and unless otherwise stated, the term halogen means any atom selected from the group consisting of fluorine, chlorine, bromine and iodine.

As used herein with respect to a substituent, and unless otherwise stated, the term "halo $C_{1-6}$ alkyl" means a $C_{1-6}$ alkyl radical (such as above defined) in which one or more hydrogen atoms are independently replaced by one or more halogen atoms (preferably fluorine, chlorine or bromine) such as, but not limited to, difluoromethyl, trifluoromethyl, trifluoroethyl, octafluoropentyl, dichloromethyl and the like.

As used herein, and unless otherwise stated, the term "heterocyclylsulfonyl" embraces heterocyclyl radicals as described above, attached to a divalent sulfonyl radical.

As used herein and unless otherwise stated, the term "stereoisomer" refers to all possible different isomeric as well as conformational forms which the compounds of structural formula (A) may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a derivative of this invention with a suitable inorganic solvent (e.g. hydrates) or organic solvent, such as but not limited to alcohols, ketones, esters, ethers, nitriles and the like.

The term "α-synucleopathy" as used herein, unless otherwise stated, refers to a disease characterised by the presence of pathological deposition of insoluble α-synuclein polymers or aggregates intracellularly and/or extracellularly. Such diseases include, but are not limited to, Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy and Alzheimer's disease.

As used herein, the term "Parkinson's disease" refers to a chronic progressive nervous disease characterised by neurodegeneration, especially degeneration of dopaminergic neurons. Symptoms include stooped posture, resting tremor, weakness of resting muscles, a shuffling gait, speech impediments, movement difficulties and an eventual slowing of mental processes and dementia.

The term "neuroprotective" agent, as used herein, refers to drugs or chemical agents intended to prevent neurodegeneration, including drugs that slow down or stop the progression of neuronal degeneration.

DETAILED DESCRIPTION OF THE INVENTION

The present invention relates, in a first aspect, to a group of novel 1,2,4-thiadiazole derivatives which have desirable biological properties such as an inhibitory effect on α-synuclein mediated toxicity. Based on this inhibitory activity, and the fact that these compounds are not toxic to neural cells, these compounds are useful in the prevention and/or treatment of α-synucleopathies, e.g. in humans. In the broadest expression of the invention, the six classes of novel 1,2,4-thiadiazole derivatives of this invention may be represented by the structural formulae (A), (B), (C), (D), (E) and (F), including stereoisomers, solvates and salts thereof. These broad classes may be sub-divided into several sub-classes, not only depending upon the specific structural formula (A) to (F) involved, but also wherein:
  each substituent $R_1$ to $R_5$ and $R_7$ to $R_{13}$, and the linking moiety X in each of the structural formulae (A), (B), (C), (D), (E) and (F), and
  when referring to the structural formulae (A) and (D), n and the optionally substituted divalent group (A'), and
  when referring to the structural formulae (A), (B), (D) and (E), each substituent $R_6$, and
  when referring to the structural formulae (C) and (F), n and each substituent $R_{14}$, $R_{15}$, R and R'
may be defined in a more restricted manner, at will and independently from each other. In a particular embodiment of the first, second, third and fourth classes of derivatives represented by the structural formulae (A), (B), (C), (D), (E) and (F), the linking moiety X is a divalent saturated non-cyclic group comprising two nitrogen atoms and 1 to 6 carbon atoms (preferably 1 to 4 carbon atoms) in the main chain, wherein one carbon atom in the main chain is optionally substituted with oxo or thioxo, e.g. said linking moiety X is or comprises a urea or thiourea group. In one embodiment of the second and fourth classes of derivatives represented by the structural formulae (C) and (F), each $R_{14}$ and each $R_{15}$ is hydrogen. In a particular embodiment of the third and fourth classes of derivatives represented by the structural formulae (D), (E)

and (F), the Het[1] group is selected from the group consisting of pyridinyl, ethylpyridinyl, quinolinyl (all isomers thereof), ethylquinolinyl, indolyl (all isomers thereof), pyrazolyl (all isomers thereof), imidazolyl, cyanoimidazolyl, dicyanoimidazolyl, and pyrimidinyl (all isomers thereof). Exemplary but non-limiting embodiments of such sub-classes are illustrated in the following examples and defined in the set of claims. As will be readily understood by the skilled person, the possibility to independently combine one or more sub-sets of definitions for each of the substituents optionally present, and the linking moiety X, results from the independent consecutive steps involved in the synthetic route described herein for making these compounds. For reasons linked to the availability of non-cyclic branched diamines, it is for instance preferred that n is 1 or 2 when one of $R_{14}$ and $R_{15}$ is not hydrogen in the definitions of structural formulae (C) and (F).

The ability of the compounds of the invention to inhibit α-synuclein mediated toxicity is based on their activity in the α-synuclein cytotoxicity test described in the examples section herein. Treatment of mice with mitochondrial complex I inhibitors such as paraquat or MPTP (1-methyl-4-phenyl-1,2,3,6-tetrahydropyridine) is a well-accepted and commonly used experimental set-up to study neuronal degeneration. Paraquat triggers synuclein-aggregation, which allegedly triggers a specific loss of dopaminergic neurons and ultimately a decline in the locomotion function. Briefly, one or more compounds are administered to paraquat-receiving mice and the onset of motoric dysfunction is assessed using a rotary rod device. A delay or absence in the occurrence of motoric problems in compound treated mice (compared to control mice treated with only vehicle) indicates that the compound(s) inhibit(s) synuclein-dependent degeneration of dopaminergic cells.

In the assays used herein, compounds were considered to be active when inhibiting α-synuclein cytotoxicity by more than 25% relative to controls at a concentration of 20 μg/mL or lower. Dose responses were carried out on all compounds found to be active (10 point curves in duplicate). Although the pharmacological properties of the compounds disclosed in this invention vary with structural change as expected, active compounds particularly possess EC50's in a cell-based assay of synuclein cytotoxicity in the range 0.0001 to 10 μM.

Based on these findings, methods for treating and preventing disorders or diseases provoked by cytotoxic intracellular α-synuclein in mammals, e.g. in humans are provided herein. These methods comprise administering to a subject, e.g. a human being, suffering from or susceptible to such a disease or disorder, an effective amount of one or more inhibitors of α-synuclein cytotoxicity as defined by one of the broad structural formulae (A), (B), (C), (D), (E) and (F), or any sub-classes thereof.

As used herein, the term "effective amount" designates an amount sufficient to effect beneficial or desired clinical or biochemical results. An effective amount can be administered one or more times. For purposes of this invention, an effective amount of an inhibitor of α-synuclein cytotoxicity is an amount that is sufficient to palliate, ameliorate, stabilize, reverse, slow down or delay the progression of a disease state or condition. In a particular embodiment of the invention, the "effective amount" is defined as an amount of compound capable of preventing deposition of insoluble α-synuclein polymers or aggregates and/or capable of preventing the cytotoxic effects triggered by aggregation or polymerization of α-synuclein, and is an amount that substantially reduces the symptoms of an α-synucleopathy, such as Parkinson's disease. Other forms of effective amount may be for the treatment or prevention of the learning or memory impairment related to Alzheimer's disease.

As used herein, the terms "mammal", "subject" or "patient" for the purposes of a therapeutic or prophylactic treatment refers to any animal classified as a mammal, including humans, domestic and farm animals, such as but not limited to dogs, cats, pigs, horses, sheep, and the like. Most particularly, the mammal is a human being.

The various 1,2,4-thiadiazole compounds of the present invention can be synthesised in an effective manner according to the methods schematically described in the attached figures and more specifically illustrated in the following specific examples. These methods of producing the 1,2,4-thiadiazole compounds of the invention comprise a limited number of steps and start from commercially available, or readily accessible, materials. Generally, 1,2,4-thiadiazole compounds represented by the structural formulae (A), (B), (D) and (E) can be synthesised by a procedure including a sequence of steps according as shown in FIG. 1 and, more specifically with regard to compounds represented by formulae (A) and (B), as shown in FIG. 2.

Figure 2:
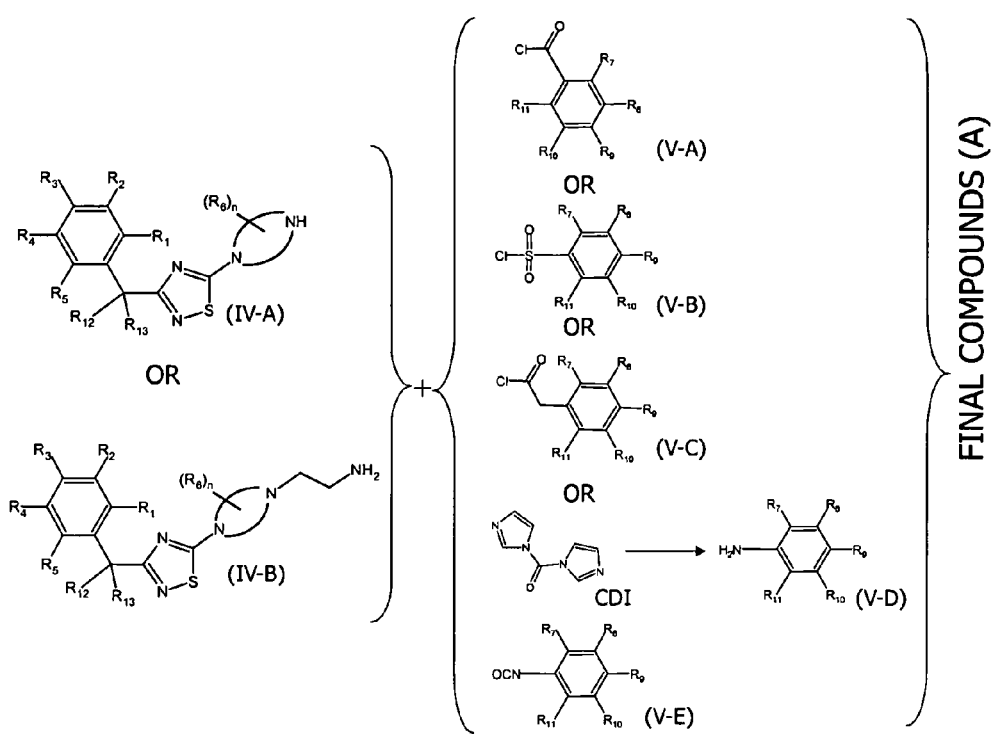

In step (a) of FIG. 1, the benzonitrile derivative represented by the structural formula (I), optionally substituted on the aromatic ring and/or in alpha position to the cyano group, is reacted with ammonia, either as a gas or in aqueous solution, thus yielding the corresponding amidine represented by the structural formula (II).

The direct synthesis of amidines from nitriles and ammonia may be greatly facilitated by the presence of electron-withdrawing groups on the benzonitrile derivative represented by the structural formula (I). Optionally, this reaction may be carried out in the presence of an effective amount of one or more Lewis acids such as but not limited to $AlCl_3$ or $ZnCl_2$ at temperatures ranging from 20° C. up to a maximum of 150-200° C. Alternative methods for producing an amidine represented by the structural formula (II) from a benzonitrile derivative represented by the structural formula (I) have been described for instance in *Albany Molecular Research Technical Reports* (2000) volume 4, number 3.

Nitriles or cyanides that may be used in step (a) include, but are not limited to, 4-aminobenzylcyanide, 4-bromo-2,2-diphenylbutyronitrile, 3-chlorobenzylcyanide, 4-chlorobenzylcyanide, cyclohexylphenylacetonitrile, 4-hydroxybenzylcyanide, α-methyl-benzylcyanide, 2-methylbenzylcyanide, 3-methylbenzylcyanide, 4-methylbenzyl-cyanide, 4-cyano-4-phenylcyclohexanone, 1-(2,4-dichlorophenyl)-1-cyclopropyl-cyanide, 4-fluorophenylacetonitrile, diphenylacetonitrile, 3,4,5-trimethoxy-phenyl-acetonitrile, 2,2-diphenylpropionitrile, 4-bromophenylacetonitrile, 1-phenylcyclobutane-carbonitrile, 2,6-dichlorophenylacetonitrile, (3,4-dimethoxy-phenyl)acetonitrile, 4-nitrophenylacetonitrile, 1-phenyl-1-cyclopropanecarbonitrile, 1-(4-chlorophenyl)-1-cyclopropanecarbonitrile, 1-(4-methylphenyl)-1-cyclopropane-carbonitrile, 1-phenyl-1-cyclohexanecarbonitrile, 1-(4-chlorophenyl)-1-cyclohexane-carbonitrile, 1-(4-methylphenyl)-1-cyclohexanecarbonitrile, 1-(4-methoxyphenyl)-1-cyclohexanecarbonitrile, 2-nitrophenylacetonitrile, (4-methoxyphenyl)acetonitrile, 2,4-dichlorophenyl-acetonitrile, (2-methoxyphenyl)acetonitrile, benzyl cyanide, 2-chlorobenzyl cyanide, 3-phenoxy-benzaldehyde-cyanohydrin, 3-(trifluoromethyl)-phenylacetonitrile, (3-methoxyphenyl)-acetonitrile, 2-chloro-6-fluorophenylacetonitrile, 3,4-dichlorophenylacetonitrile, 4-amino-2-chlorodiphenylacetonitrile, 2-fluorophenyl-acetonitrile, 3-fluorophenylacetonitrile, 2,3,4,5,6-pentafluorophenylacetonitrile, 3,4-difluorophenylacetonitrile, 3-bromophenyl-acetonitrile, 2-chloro4fluorobenzyl cyanide, 1-(2-fluorophenyl)-cyclopentanecarbonitrile, 1-(2-fluorophenyl)-cyclohexane-carbonitrile, 1-(3-fluorophenyl)-cyclopentanecarbonitrile, 1-(3-fluorophenyl)-cyclo-hexanecarbonitrile, 1-(4-fluorophenyl)-cyclopentanecarbonitrile, 1-(4-fluorophenyl)-cyclohexanecarbonitrile, 1-(2-chloro-4-fluorophenyl)-cyclopentane-carbonitrile, 1-(2-chloro-4-fluorophenyl)-cyclohexanecarbonitrile, 1-(2-chloro-6-fluorophenyl)-cyclopentanecarbonitrile, 1-(2-chloro-6-fluorophenyl)-cyclohexanecarbonitrile, 2,4-difluorophenylacetonitrile, 2,5-difluorophenylacetonitrile, 2,6-difluorophenyl-acetonitrile, 4-(trifluoromethyl)phenylacetonitrile, 2-(trifluoromethyl)-phenylacetonitrile, 3,5-bis-(trifluoromethyl)phenylacetonitrile, 2,5-dimethylphenylacetonitrile, 2-bromo-phenylacetonitrile, 2,4,6-trimethylbenzylcyanide, 2,3-dichlorophenylacetonitrile, 3,4-(methylenedioxy)phenylacetonitrile, 1-(4-methoxyphenyl)-1-cyclopentanecarbonitrile, 1-(4-chlorophenyl)-1-cyclobutanecarbonitrile, 2-(4-chloro-2-fluorophenyl)-acetonitrile, 2-(3,5-difluorophenyl)-acetonitrile, 2-(4-isobutylphenyl)-propanenitrile, 2-[-4[(4-methylbenzyl)-oxy]phenyl]acetonitrile, 1-(3-chlorophenyl)-1-cyclohexanecarbonitrile, 3-chloro-5-fluorophenylcetonitrile, 4-(trifluoromethoxy)-phenylacetonitrile, 2-phenyl-2-piperidinoacetonitrile, 4-bromo-2-fluorobenzyl-cyanide, 2-(4-chlorophenyl)-2-morpholinoacetonitrile, 1-(4-methoxyphenyl)-1-cyclopropanecarbonitrile, 2-(4-aminophenyl)-3-[4-(dimethylamino)phenyl]propanenitrile, and 2-(4-hydroxyphenyl)-2-morpholinoacetonitrile.

According to a particular embodiment of the invention, the starting materials are selected from the group comprising 4-fluorobenzyl cyanide, 4-chlorobenzyl cyanide, 4-methylbenzyl cyanide, 3-methoxybenzyl cyanide and benzyl cyanide.

Alternatively an amidine represented by the structural formula (II) may be commercially available, either in the form of a base or preferably for stability reasons in the form of a salt, for example 2-(2,6-dichlorophenyl)ethanimidamide in its hydrochloride salt form, and may then be used as the starting point of FIG. 1.

Subsequently, the thiadiazole core of the compounds of this invention is synthesised in step (b) of FIG. 1 in a manner similar to that described in WO 99/51584. For instance, the amidine compound represented by the structural formula (II) may be reacted with $CCl_3SCl$ to form the corresponding 3-substituted-5-chloro-thiadiazole compound represented by the structural formula (III) (step (b) of FIG. 1). The latter may then be reacted (step (c) of FIG. 1) under suitable conditions with a saturated or partly unsaturated heterocyclic derivative having the formula R"-A'H wherein A' is an optionally $R_6$-substituted heterocyclic ring with at least two nitrogen atoms (e.g. piperazine or similar) as defined hereinabove and wherein R" is attached to one nitrogen atom of said heterocyclic ring through a linking moiety to obtain either final compounds of the invention or intermediates therefor having the structural formula (IV), depending upon the exact nature of R". More specifically, attachment of R" may be according to the formula:

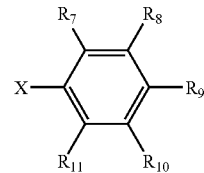

or the formula X-Het[1] (wherein each of X, Het[1], $R_7$, $R_8$, $R_9$, $R_{10}$, and $R_{11}$ is independently as hereinabove defined), or attachment of R" may be suitable for producing intermediates having the structural formula (IV-A) (i.e. wherein R" is H) and intermediates having e.g. the structural formula (IV-B) (i.e. wherein R" is aminoethyl) shown in FIG. 2. The present invention thus also includes (although not specifically shown in FIGS. 1 and 2), for producing derivatives represented by the structural formulae (D) and (E), a reaction with a heterocyclic derivative wherein the linking moiety X (which may be a single bond) is located between a first (preferably saturated) optionally substituted heterocyclic ring A' with at least two nitrogen atoms (e.g. piperazine or similar, as detailed below) and a second (preferably unsaturated nitrogen-containing) heterocyclic ring Het[1] (instead of the optionally substituted phenyl ring shown above), wherein said second (preferably unsaturated nitrogen-containing) heterocyclic ring Het[1] may further be substituted with one or more substituents independently selected from the group consisting of halogen, trifluoromethyl, nitro, cyano and $C_{1-10}$ alkyl. A few illustrative heterocyclic derivatives corresponding to the latter embodiment of the invention are also listed below.

Piperazine derivatives useful for the displacement reaction in step (c) of FIG. 1 and thus directly yielding final compounds of the present invention—as defined by the structural formulae (A), (B), (D) and (E)—include, but are not limited to, 1-(4-nitrophenyl)piperazine, 1-(2-methoxyphenyl)piperazine, 1-(3-methoxyphenyl) piperazine dihydrochloride, 1-phenylpiperazine, 1-(3-chlorophenyl)piperazine, 1-(4-chlorophenyl)piperazine, 1-(3,4-dichlorophenyl)piperazine, 1-(2,3-dimethylphenyl) piperazine, 1-(2,4-dimethylphenyl) piperazine, 1-(2,5-dimethylphenyl)piperazine, 1-(3,4-dimethylphenyl)piperazine, 1-(5-chloro,2-methylphenyl)piperazine, 2-methyl-1-(3-methylphenyl)piperazine, 4-piperazinoacetophenone, 1-(4-fluorophenyl)piperazine, 1-(2-methoxyphenyl)piperazine hydrochloride, 1-(4-methoxyphenyl)piperazine, 1-(2-fluorophenyl)piperazine, 1-(3-methylphenyl)piperazine, 1-(4-methoxyphenyl)-2-methylpiperazine, 1-(2,4-di-fluorophenyl)piperazine, N-(α,α,α-trifluoro-p-tolyl)piperazine, 1-(4-hydroxyphenyl)piperazine, 1-(4-methylphenyl)piperazine, 1-[2-nitro-4-(trifluoromethyl)phenyl]piperazine, 1-(2-hydroxyphenyl)piperazine, benzyl 3-oxo-piperazine-1-carboxylate, 1-(2-chlorophenyl) piperazine, 1-(2-methylphenyl)pipera-zine, 1-cinnamylpiperazine, trans-1-cinnamylpiperazine, 1-(4-fluorobenzyl) piperazine and 2-methyl-4-piperazinoquinoline.

Alternatively, using the same synthetic pathway, another (i.e. non piperazinyl) preferably saturated or partly unsaturated heterocyclic ring having the structural formula (A') with at least two nitrogen atoms in the said heterocyclic ring and with a total of 5 to 7 atoms in the said heterocyclic ring may be introduced onto the thiadiazole core during step (c) of FIG. 1. Suitable alternative heterocyclic rings having the structural formula (A') include, but are not limited to, homopiperazinyl, pyrazolinyl, thiadiazinyl, oxadiazinyl, imidazolinyl, imidazolidinyl and pyrazolidinyl.

Commercially available reagents for such synthesis step (c) of FIG. 1, yielding final compounds of the present invention defined by the structural formulae (A) and (D) with a homopiperazinyl ring A' connected to the thiadiazole core include, but are not limited to, 1-(4-bromo-2-fluorobenzyl)-1,4-diazepane, 1-(4-bromo-2-fluoro-benzyl)-1,4-diazepane, 1-(mesitylmethyl)-1,4-diazepane, 1-(4-bromo-benzyl)-1,4-diazepane, 6-chloro-2-(1,4-diazepan-1-yl)-1,3-benzothiazole, 1-(2-chloro-6-fluorobenzyl)-1,4-diazepane, 1-(4-fluorobenzyl)-1,4-diazepane, 5-(1,4-diazepan-1-yl)-3-phenyl-1,2,4-thiadiazole, 1-[3-chloro-5-(trifluoromethyl)-2-pyridyl]-1,4-diazepane, 1-[4-(trifluoro-methyl)pyrimidin-2-yl]-1,4-diazepane, 1-(5-nitro-2-pyridyl)-1,4-diazepane, 2-(1,4-diazepan-1-yl)-nicotinonitrile, 6-chloro-2-(1,4-diazepan-1-yl)-1,3-benzothiazole, 6-(1,4-diazepan-1-yl)-nicotinonitrile, and 1-(6-methylpyrazin-2-yl)-1,4-diazepane.

Commercially available reagents for such synthesis step (c) of FIG. 1, yielding final compounds of the present invention defined by the structural formulae (A) and (D) with an imidazolidinyl ring A' connected to the thiadiazole core include, but are not limited to, 1-phenyl-1,3,8-triazaspiro[4.5]decan-4-one. In the latter specific embodiment, the resulting imidazolidinyl ring A' is illustrative of a saturated heterocyclic ring wherein two substituents (denoted as $R_6$ in the structural formulae A and D) on the same carbon atom of said heterocyclic ring together form a heterocyclic ring system (in casu a 6-membered nitrogen-containing heterocyclic ring).

Commercially available reagents for such synthesis step (c) of FIG. 1, yielding final compounds of the present invention defined by the structural formulae (A) and (D) with a pyrazolidinyl ring A' connected to the thiadiazole core include, but are not limited to, 1-phenyl-3-pyrazolidinone, 1-phenyl-4-methyl-3-pyrazolidinone, 4,4-dimethyl-1-phenyl-3-pyrazolidinone and 4-hydroxymethyl-4-methyl-1-phenyl-3-pyrazolidinone.

When not commercially available for synthesis step (c) of FIG. 1, reagents yielding final compounds of the present invention defined by the structural formulae (A) and (D) with a pyrazolidinyl, imidazolidinyl, oxadiazinyl, thiadiazinyl, piperazinyl or homopiperazinyl ring A' connected to the thiadiazole core can be tailor-made according to specific prerequisites while using synthetic routes well known to the skilled person.

FIG. 2 schematically illustrates alternative methods to prepare compounds according to structural formula (A) wherein step (c) of FIG. 1 comprises two subsequent reaction sub-steps. Although not specifically shown in FIG. 2, such alternative methods are also applicable to the preparation of compounds according to structural formula (D), provided that in the second sub-step a suitable heteroaryl carbonyl chloride, heteroaryl sulfonyl chloride, heteroarylamine, heteroaryl isocyanate or heteroaryl isothiocyanate, wherein the heteroaryl group may be anyone of the $Het^1$ species described above, is used in place of the corresponding arylcarbonyl chloride, aryl sulfonyl chloride, arylamine, aryl isocyanate or aryl isothiocyanate (wherein, as shown in FIG. 2, the aryl group is optionally substituted with one up to five substituents $R_7$, $R_8$, $R_9$, $R_{10}$ and $R_{11}$).

In a first sub-step, a thiadiazole intermediate compound represented by the structural formula (III) in FIG. 1 is first reacted under suitable conditions with a saturated or partly unsaturated heterocyclic derivative including an optionally $R_6$-substituted heterocyclic ring A' with at least two nitrogen atoms and with a total of 5 to 7 atoms in said heterocyclic ring, said heterocyclic derivative having at least one amino group available for reaction with the chloro atom of the 3-substituted-5-chloro-thiadiazole compound represented by the structural formula (III) and another amino group available for reaction with an aryl derivative represented by a structural formula (V-A), (V-B), (V-C), (V-D) or (V-E) shown in FIG. 2, or a corresponding heteroaryl derivative including a heteroaryl group $Het^1$ as defined above. Examples of such heterocyclic compounds for use in the first sub-step of step (c) for the synthesis of appropriate intermediates having the structural formulae (IV-A) and (IV-B) shown in scheme 2 comprise, but are not limited to, the following:

piperazinyl derivatives including piperazine, 2-methylpiperazine (either (R)-(−)-2-methylpiperazine or (S)-(+)-2-methylpiperazine), trans-2,5-dimethylpiperazine, and amino alkyl-substituted piperazines such as 1-(2-aminoethyl)piperazine, 1-(aminomethyl)piperazine, 1-(3-aminopropyl)piperazine, 1-(4-aminobutyl)-piperazine, 1-(6-aminohexyl)piperazine, and the like;

homopiperazinyl derivatives including homopiperazine;

imidazolidinyl derivatives including 2-imidazolidone, 2-imidazolidinethione, 4-methylimidazolidine-2-thione, aminomethylimidazolidine, aminoethylimidazolidine, aminopropylimidazolidine, aminobutylimidazolidine, and 1-3-diazaspiro[4.5]decane-2,4-dione (in this specific embodiment, the resulting imidazolidinyl ring A' is illustrative of a saturated heterocyclic ring wherein two substituents, denoted as $R_6$ in the structural formula A, on the same carbon atom of said heterocyclic ring together form a homocyclic ring system, in casu a cyclohexyl group), hydantoin and hydantoin derivatives such as, but not limited to, 5,5-dimethylhydantoin, 2-thiohydantoin, 5-(4-methylphenyl)-5-phenylhydantoin, 5,5-diphenylhydantoin and 5-methyl-5-phenylhydantoin;

pyrazolidine and aminoalkyl-substituted pyrazolidines such as aminomethylpyrazolidine, aminoethylpyrazolidine, aminopropylpyrazolidine and aminobutylpyrazolidine.

Due to the balance between nucleophilicity and steric hindrance of each of the two amino groups present in the saturated or partly unsaturated heterocyclic derivative used in the first sub-step, it may be desirable (in order to avoid the possibility of producing a mixture of intermediates that may later have to be separated before performing the next reaction steps) to perform the above-mentioned reaction by:

first reacting a saturated or partly unsaturated heterocyclic derivative wherein the amino group available for reaction (e.g. subsequent reaction) with an aryl derivative (formulae (V-A) to (V-E) shown in FIG. 2), or a $Het^1$-containing heteroaryl derivative has been protected with an amino-protecting group, and secondly, after the reaction of said first sub-step has been substantially completed, deprotecting the resulting intermediate compound to achieve an amino-containing intermediate, e.g. as represented by structural formulae (IV-A) and (IV-B) in FIG. 2, that is readily available for the next reaction step.

N-protecting groups and amino-deprotecting techniques suitable for this particular purpose are well known to the person skilled in the art. Commonly used N-protecting groups are disclosed e.g. in Greene, "Protective Groups in Organic Synthesis" (John Wiley & Sons, New York, 1981). Suitable exemplary N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, .alpha.-chlorobutyryl, benzoyl, 4-chloro-benzoyl, 4-bromobenzoyl, 4-nitrobenzoyl, and the like; sulfonyl groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitro-benzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro-4,5-dimethoxy-benzyloxycarbonyl, 3,4,5-trimethoxybenzylox-carbonyl, 1-(p-biphenylyl)-1-methyl-ethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethcmcarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; arylalkyl groups such as benzyl, triphenylmethyl, benzyloxymethyl and the like; and silyl groups such as trimethylsilyl and the like. The most appropriate N-protecting groups include formyl, acetyl, benzoyl, pivaloyl, t-butylacetyl, phenylsulfonyl, benzyl, t-butoxycarbonyl (BOC) and benzyloxycarbonyl.

Subsequently, the N-protecting group may be removed by deprotection methods conventional in the art, such as, but not limited to:

when the amino-protecting group is a phenylmethoxycarbonyl group, cleavage of the benzylic ether function by hydrogenolysis, e.g. using $H_2$, Pd—C at about 25° C., or under strongly acidic conditions (e.g. making use of bromhydric acid), or when the amino-protecting group is a tert-butoxycarbonyl group, by treatment with an acid, e.g. using aqueous hydrochloric acid or trifluoroacetic acid (hereinafter referred as TFA), under conditions mild enough to avoid further cleavage of the molecule, or when the amino-protecting group is a 9-fluorenylmethoxycarbonyl group, by treatment with a base such as piperidine.

In a second reaction sub-step as shown in FIG. 2, intermediate compounds represented by the structural formulae (IV-A) or (IV-B) are reacted under suitable conditions with a reagent susceptible to nucleophilic attack by a non-tertiary amino group, e.g. the secondary NH group present in intermediate compounds according to structural formula (IVA), or the terminal primary amino group present in intermediate compounds according to structural formula (IVB). Suitable such reagents include, but are not limited to, acid chlorides such as carbonyl chlorides or sulfonyl chlorides, or activated acids such as carboxylic acid anhydrides. Particular carbonyl chlorides for use in this reaction sub-step include benzoyl chlorides (as shown in structural formula V-A in FIG. 2, resulting in final compounds with a linking moiety X=C (=O) when starting from intermediate compounds according to structural formula (IV-A), or a linking moiety $X=(CH_2)_2$ NHC(=O) when starting from intermediate compounds according to structural formula (IV-B)) and phenyl acetyl chlorides (as shown in formula V-C in FIG. 2, resulting in final compounds with a linking moiety $X=C(=O)CH_2$ when starting from intermediate compounds according to structural formula (IV-A), or a linking moiety $X=(CH_2)_2NHC(=O)$ $CH_2$ when starting from intermediate compounds according to structural formula (IV-B)). Particular sulfonyl chlorides for use in this reaction sub-step include phenylsulfonyl chlorides (as shown in formula V-B in FIG. 2, resulting in final compounds with a linking moiety $X=S(=O)_2$ when starting from intermediate compounds according to structural formula IV-A), or a linking moiety $X=(CH_2)_2NHS(=O)_2$ when starting from intermediate compounds according to structural formula IV-B).

Benzoyl chlorides (as shown in formula V-A) suitable for use in the synthesis of the compounds of the present invention include, but are not limited to, benzoyl chloride, p-anisoylchloride, 2-bromobenzoyl chloride, 4-bromobenzoyl chloride, 3-chlorobenzoyl chloride, pentafluorobenzoyl chloride, 2-chlorobenzoyl chloride, p-toluoyl chloride, 4-chlorobenzoyl chloride, 2,4-dichlorobenzoyl chloride, 3,4-dichlorobenzoyl chloride, 4-nitrobenzoyl chloride, 4-fluorobenzoyl chloride, 2-fluoro-benzoyl chloride, o-toluoyl chloride, m-toluoyl chloride, 4-cyanobenzoyl chloride, 3-nitrobenzoyl chloride, 4-tert-butyl-benzoyl chloride, 4-biphenylcarbonyl chloride, 3,5-dimethoxybenzoyl chloride, 3-fluorobenzoyl chloride, 2,6-dichlorobenzoyl chloride, 4-butylbenzoyl chloride, 4-heptyloxybenzoyl chloride, 4-hexylbenzoyl chloride, 4-hexyloxybenzoyl chloride, 4-pentylbenzoyl chloride, m-anisoyl chloride, 2,6-difluoro-benzoyl chloride, 2-nitrobenzoyl chloride, 4-chloro-3-nitrobenzoylchloride, 3,4-difluoro-benzoyl chloride, 2-iodobenzoyl chloride, 1-naphthoyl chloride, o-anisoyl chloride, 2,4-difluorobenzoyl chloride, 4-(trifluoromethyl)benzoyl chloride, m-anisoyl chloride, 2,6-difluorobenzoyl chloride, 2-nitrobenzoyl chloride, 4-chloro-3-nitro-benzoylchloride, 3,4-difluorobenzoyl chloride, 2-iodobenzoyl chloride, 1-naphthoyl chloride, o-anisoyl chloride, 2,4-difluorobenzoyl chloride, 4-(trifluoromethyl)benzoyl chloride, 3-(chloro-methyl)-benzoyl chloride, 4-(chloromethyl)-benzoyl chloride, 3-(dichloromethyl)-benzoyl chloride, 2,3,4,5-tetrafluorobenzoyl chloride, 2,4,6-trichlorobenzoyl chloride, 2,3,4-trifluorobenzoyl chloride, 2,4,6-trifluorobenzoyl chloride, 4-bromo-2-fluoro-benzoyl chloride, 2,3,5,6-tetrafluorobenzoyl chloride, 3,5-dinitrobenzoyl chloride, 4-heptylbenzoyl chloride, 4-iodobenzoyl chloride, 4-octylbenzoyl chloride, 4-pentyloxybenzoyl chloride, 4-phenylazobenzoyl chloride, 4-propylbenzoyl chloride, methyl 4-chloro-carbonylbenzoate, 3,5-dichlorobenzoyl chloride, 3-fluoro-4-trifluoromethylbenzoyl chloride, 2,6-dimethoxybenzoyl chloride, piperonyloyl chloride, 2,4-dimethoxybenzoyl chloride, 3,4-dihydro-2H-1,5-benzodioxepine-6-carbonyl chloride, 2,3-dihydro-1,4-benzodioxine-6-carbonyl chloride, 2,3-dihydro-1,4-benzodioxine-5-carbonyl chloride, 1-benzofuran-5-carbonyl chloride, 2,1,3-benzothiadiazole-4-carbonyl chloride, 2,1,3-benzothiadiazole-5-carbonyl chloride, 1,2,3-benzothia-diazole-5-carbonyl chloride, 2,1,3-benzoxadiazole-5-carbonyl chloride, 6-quinoxaline-carbonyl chloride, 4-(2-thienyl)-benzoyl chloride, 4-methyl-3,4-dihydro-2H-1, 4-benzoxazine-7-carbonyl chloride, 4-(1,2,3-thiadiazol-4-yl)benzoyl chloride, 4-(1H-pyrazol-1-yl)benzoyl chloride, 1-methyl-1H-1,2,3-benzotriazole-5-carbonyl chloride, 1-benzothiophene-5-carbonyl chloride, 2,2-dimethyl-2,3-dihydro-1-benzofuran-7-carbonyl chloride, 4-[(dipropylamino)sulfonyl]benzene-1-carbonyl chloride, 4-[3-(trifluoromethyl)-1H-pyrazol-1-yl]-benzoyl chloride, 2-bromo-5-methoxybenzene-1-carbonyl chloride, 5-bromo-2,3,4-trimethylbenzoyl chloride, 2-chloro-6-fluorobenzene-1-carbonyl chloride, 2,3-dimethylbenzene-1-carbonyl chloride, 3,4-dimethylbenzene-1-carbonyl chloride, 2-chloro-4-fluorobenzoyl chloride, 5,5,8,8-tetramethyl-5,6, 7,8-tetrahydro-2-naphthalene-carbonyl chloride, 2-(4-methoxyphenoxy)-5-nitrobenzene-1-carbonyl chloride, 2,3-difluorobenzoyl chloride, 2-fluoro-5-(trifluoromethyl)benzoyl chloride, 2,3,6-trifluoro-benzoyl chloride, 1-isopropyl-1H-1, 2,3-benzotriazole-5-carbonyl chloride, 1-isopropyl-1H-1,2, 3-benzotriazole-5-carbonyl chloride, 3-fluoro-4-methylbenzoyl chloride, 3-(cyclopentyloxy)-4-methoxybenzoyl chloride, 4-fluoro-3-(trifluoromethyl)benzoyl chloride, 2,3-dihydro-1-benzofuran-7-carbonyl chloride, 3-(2-methylthiazol-4-yl)-benzoyl chloride, 1-isopropyl-2-(trifluoromethyl)-1H-benzimida-zole-5-carbonyl chloride, 5-bromo-2, 3-di-hydrobenzo[b]furan-7-carbonyl chloride, 2,4,6-trimethylbenzoyl chloride, 2-(2-thienyl)-benzoyl chloride, 3-cyanobenzoyl chloride, acetylsalicyloyl chloride, 3-(5-methyl-1,2,4-oxadiazol-3-yl)-benzoyl chloride, and 4-(5-methyl-1,2,4-oxadiazol-3-yl)-benzoyl chloride.

According to a particular embodiment the benzoyl chloride reagent may be selected from the group consisting of 2-fluorobenzoyl chloride, 4-ethylbenzoyl chloride, 4-butylbenzoyl chloride, 4-methoxybenzoyl chloride, piperonyloyl chloride, 4-hexyl-benzoyl chloride, 3-chlorobenzoyl chloride, 4-fluorobenzoyl chloride, p-toluoyl chloride, 3-fluorobenzoyl chloride, 4-chlorobenzoyl chloride, benzoyl chloride, 4-tert-butylbenzoyl chloride, 4-biphenylcarbonyl chloride, o-anisoyl chloride, 1-naphthoyl chloride, 2-naphthoyl chloride, 4-pentylbenzoyl chloride, 4-bromobenzoyl chloride, 2,4-dimethoxybenzoyl chloride, 3,5-dichlorobenzoyl chloride, 3-bromobenzoyl chloride, 2-bromobenzoyl chloride 3-trifluoromethylbenzoyl chloride, 4-trifluoro-methylbenzoyl chloride and 2-ethylbenzoyl chloride.

Numerous other carbonyl chlorides are known to the person skilled in the art and commercially available for use as acylating reagent for use in the reaction step illustrated in FIG. 2. Particular carbonyl chlorides for use in the method of the invention include, but are not limited to, cinnamoyl chloride, hydrocinnamoyl chloride, 2-phenylbutyryl chloride, phenylacetyl chloride and 4-fluorophenylacetyl chloride.

Phenylsulfonyl chlorides (represented by the structural formula V-B) suitable for use in the synthesis of the compounds of the present invention include, but are not limited to, 4-fluorobenzenesulfonyl chloride, 2-mesitylenesulfonyl chloride, 4-methoxybenzene-sulfonyl chloride, p-toluenesulfonyl chloride, pentafluorobenzene-sulfonyl chloride, benzenesulfonyl chloride, 4-bromobenzenesulfonyl chloride, N-acetylsulfanilyl chloride, 2,4,6-triisopropyl-benzenesulfonyl chloride 2-naphthalenesulfonylchloride, 4-chlorobenzenesulfonyl chloride 3,5-dichloro-2-hydroxy-benzenesulfonylchloride, 2,5-dichloro-benzenesulfonyl chloride, pipsyl chloride, 1-naphthalenesulfonylchloride, methyl 2-(chlorosulfonyl)-benzoate, 4-tert-butylbenzene-sulfonyl chloride, 3-(trifluoromethyl) benzenesulfonyl chloride, 2-bromobenzenesulfonyl chloride, 4-acetylbenzene-sulfonylchloride, 2-(trifluoromethyl)-benzenesulfonyl chloride, 3,4-dichlorobenzene-sulfonyl chloride, 3,4-dimethoxybenzenesulfonyl chloride, 3-chlorobenzenesulfonyl chloride, 2-chloro-4-fluorobenzenesulfonyl chloride, 3,5-dichlorobenzenesulfonyl chloride, 3-chloro-4-fluorobenzenesulfonyl chloride, 2,4-dichlorobenzenesulfonyl chloride, 2,5-dimethoxybenzenesulfonyl chloride, 3-bromo-benzenesulfonyl chloride, 2,3-dichlorobenzenesulfonyl chloride, 5-fluoro-2-methylbenzenesulfonyl chloride, 3-fluorobenzenesulfonyl chloride, 2,3,5,6-tetramethyl-benzenesulfonyl chloride, 3-chloro-2-methylbenzenesulfonyl chloride, 2,5-dibromo-3,6-difluoro-benzenesulfonyl chloride, 2,6-difluorobenzenesulfonyl chloride, 2-chloro-benzenesulfonyl chloride, 5-bromo-2-methoxybenzenesulfonyl chloride, 5-chloro-2-methoxybenzenesulfonyl chloride, 2,4-difluorobenzenesulfonyl chloride, 2-cyano-benzenesulfonyl chloride, 2-chloro-5-(trifluoromethyl)-benzenesulfonyl chloride, 4-bromomethylbenzenesulfonyl chloride, 2,4-dimethoxybenzenesulfonyl chloride, 4-chloro-3-nitrobenzenesulfonyl chloride, 4-(chlorosulfonyl)-benzoic acid, 3-nitro-benzenesulfonyl chloride, 4-nitrobenzenesulfonyl chloride, 2-(methylsulfonyl)-benzenesulfonyl chloride, 4-(methylsulfonyl)-benzene-sulfonyl chloride, 3-(chlorosulfonyl)-benzoic acid, 2,4-dichloro-5-methylbenzene-sulfonyl chloride, 4-(trifluoro-methoxy)-benzenesulfonyl chloride, 2-methoxy-4-nitrobenzenesulfonyl chloride, 4-bromo-2-chlorobenzenesulfonyl chloride, 2,3-dihydro-1-benzofuran-5-sulfonyl chloride, 2,3-dihydro-1,4-benzodioxine-6-sulfonyl chloride, 1,3-benzothiazole-6-sulfonyl chloride, 2,1,3-benzothiadiazole4sulfonyl chloride, 2,1,3-benzothiadiazole-5-sulfonyl chloride, 2,1,3-benzoxadiazole-4-sulfonyl chloride, 3,4-dihydro-2H-1,5-benzodioxepine-7-sulfonyl chloride, 4-methyl-3,4-dihydro-2H-1,4-benzoxazine-7-sulfonyl chloride, 4-(1,3-oxazol-5-yl) benzenesulfonyl chloride, 4-(1,2,3-thiadiazol-4-yl) benzenesulfonyl chloride, 4-(1H-pyrazol-1-yl) benzenesulfonyl chloride, 4-(3-chloro-2-cyanophenoxy) benzene-1-sulfonyl chloride, 5-chlorosulfonyl-2-hydroxy-benzoic acid, 4-bromo-2,5-difluoro-benzene-1-sulfonyl chloride, 4-(acetylamino)-3-chloro-benzene-1-sulfonyl chloride, 3,5-di-(trifluoromethyl)-benzene-1-sulfonyl chloride, 2-fluorobenzenesulfonyl chloride, 4-methyl-3-nitrobenzene-1-sulfonyl chloride, 5-chloro-2,1,3-benzoxadiazole-4-sulfonyl chloride, 3-(5-methyl-1,3,4-oxadiazol-2-yl) benzenesulfonyl chloride, methyl 3-(chlorosulfonyl)-4-methoxybenzoate, 4-bromo-2-(trifluoromethyl)-benzenesulfonyl chloride, 2,2-dimethyl-6-chromanesulfonyl chloride, 4-(morpholine-4-sulfonyl) benzenesulfonyl chloride, 4-(pyrrolidine-1-sulfonyl)-benzene-sulfonyl chloride, 3-(2-methyl-4-pyrimidinyl)benzenesulfonyl chloride, 2-cyano-5-methylbenzenesulfonyl chloride, 2,5-dimethylbenzenesulfonyl chloride, 4-chloro-3-(trifluoromethyl)-benzenesulfonyl chloride, 4-bromo-2-methylbenzene-1-sulfonyl chloride, 2-chloro-4-(trifluoromethyl)-benzene-1-sulfonyl chloride, 2-chloro-4-cyano-benzene-1-sulfonyl chloride, 2,6-dichloro-4-(trifluoromethyl)-benzene-1-sulfonyl chloride, 3,4-difluorobenzene-1-sulfonyl chloride, 2-iodobenzene-1-sulfonyl chloride, 4-methyl-1-naphthalenesulfonyl chloride, 4-(trifluoromethyl)benzene-1-sulfonyl chloride, 2,6-dichlorobenzene-1-sulfonyl chloride, 2-(trifluoromethoxy)benzene-1-sulfonyl chloride, 4-cyanobenzene-1-sulfonyl chloride, 4-butoxybenzene-1-sulfonyl chloride, 2,3,4-trifluorobenzene-1-sulfonyl chloride, 4-bromo-2-(trifluoromethoxy) benzene-1-sulfonyl chloride, 3-cyanobenzene-1-sulfonyl chloride, 3-chloro-4-methylbenzene-1-sulfonyl chloride, 4-bromo-2-ethyl-benzene-1-sulfonyl chloride, 5,5,8,8-tetramethyl-5,6,7,8-tetrahydro-2-naphthalene-sulfonyl chloride, 4-(2-chloro-6-nitrophenoxy) benzene-1-sulfonyl chloride, 3,5-dichloro-4-(2-chloro-4-nitrophenoxy) benzene-1-sulfonyl chloride, 4-pentylbenzene-1-sulfonyl chloride, 4-ethylbenzene-1-sulfonyl chloride, 4-propylbenzene-1-sulfonyl chloride, 4-butylbenzene-1-sulfonyl chloride, 3-toluenesulfonyl chloride, 4-isopropyl-benzenesulfonyl chloride, 4-(2-oxo-1-pyrrolidinyl)benzene sulfonyl chloride, 4-(2-methoxyphenoxy)benzenesulfonyl chloride, 4-(2-chloro-phenoxy)benzenesulfonyl chloride, 4-(2-methylphenoxy) benzenesulfonyl chloride, 4'-chloro(1,1'-biphenyl)-4-sulfonyl chloride, 4'-fluoro(1,1'-biphenyl)-4-sulfonyl chloride, 4'-methoxy-(1,1'-biphenyl)-4-sulfonyl chloride, 3',4'-dichloro-(1,1'-biphenyl)-4-sulfonyl chloride, 4-phenoxybenzenesulfonyl chloride, 4'-methyl-(1, 1'-biphenyl)-4-sulfonyl chloride, 5-bromo-2,3-dihydrobenzo[b]furan-7-sulphonyl chloride, 3,4,5-trifluoro-benzenesulfonyl chloride, 3-(5-methyl-1,2,4-oxadiazol-3-yl) benzenesulfonyl chloride, 4-(2-methyl-1,3-thiazol-4-yl) benzenesulfonyl chloride, 1-acetyl-5-indolinesulfonyl chloride, 3-(2-methyl-1,3-thiazol-4-yl)benzene-sulfonyl chloride and 1,3-benzodioxole-5-sulfonyl chloride.

Phenylacetyl chlorides (structural formula V-C) suitable for use in the synthesis of the compounds of the present invention include, but are not limited to, phenylacetyl chloride, 4-methoxyphenylacetyl chloride, 2-(2-naphthyl)acetyl chloride, 2-(3,5-difluorophenyl)ethanoyl chloride, 2-(1-naphthyl)ethanoyl chloride, 4-chlorophenylacetyl chloride, 3-methoxyphenylacetyl chloride, and 4-fluorophenylacetyl chloride.

The intermediate compounds represented by the structural formulae (IV-A) and (IV-B) may also be reacted with an aryl isocyanate (structural formula V-E shown in FIG. 2) or a heteroaryl isocyanate in order to yield final compounds with structural formulae (A), (B), (D) or (E) wherein X is a urea linking moiety (when starting from intermediate compounds according to structural formula IV-A) or comprises a urea linkage (e.g. $X=(CH_2)_2NHC(=O)NH$ when starting from intermediate compounds according to structural formula IV-B), i.e. X corresponds to the definition of a divalent saturated non-cyclic hydrocarbon group comprising one or more carbon atoms and two nitrogen atoms in the main chain, one of said carbon atoms being substituted with oxo.

Aryl isocyanates (represented by the structural formula V-E) suitable for use in the synthesis of compounds of the present invention with structural formula (A) include, but are not limited to, 4-fluorophenyl isocyanate, phenyl isocyanate, m-tolyl isocyanate, p-tolyl isocyanate, 4-chlorophenyl isocyanate, ethyl 4-isocyanatobenzoate, 2-fluoro-phenyl isocyanate, 3-fluorophenyl isocyanate, α,α,α-trifluoro-o-tolyl isocyanate, tolylene-2,4-diisocyanate, tolylene 2,6-diisocyanate, 4-methoxyphenyl isocyanate, 4-bromophenyl isocyanate, 2-methoxy-phenyl isocyanate, 3-Methoxyphenyl isocyanate, 2,4-dichlorophenyl isocyanate, o-tolyl isocyanate, 3,4-dichlorophenyl isocyanate, 2-nitrophenyl isocyanate, 4-nitrophenyl isocyanate, 2,4-difluorophenyl isocyanate, 2-bromophenyl isocyanate, 2,6-difluoro-phenyl isocyanate, 2-(trifluoromethoxy)phenyl isocyanate, 2-chloro-5-(trifluoro-methyl)phenyl isocyanate, 4-chloro-2-(trifluoro-methyl)phenyl isocyanate, 4-chloro-3-(trifluoromethyl)phenyl isocyanate, 2,5-difluoro-phenyl isocyanate, 4-(trifluoromethoxy)phenyl isocyanate, 2-ethoxyphenyl isocyanate, 4-ethoxyphenyl isocyanate, 4-isopropylphenyl isocyanate, 3-acetylphenyl isocyanate, 2,6-diisopropylphenyl isocyanate, 3-bromophenyl isocyanate, 3,5-dichlorophenyl isocyanate, 4-fluoro-3-nitrophenyl isocyanate, 3,5-dimethylphenyl isocyanate, 3,5-bis(trifluoromethyl)phenyl isocyanate, 3-cyanophenyl isocyanate, 4-(methylthio)phenyl isocyanate, 2-ethylphenyl isocyanate, 2,6-dimethyl-phenyl isocyanate, α,α,α-trifluoro-p-tolyl isocyanate, 2,3-dichlorophenyl isocyanate, 4-methyl-3-nitrophenyl isocyanate, 2,4-dimethoxyphenyl isocyanate, 4-(chloro-methyl)phenyl isocyanate, 4-bromo-2-chlorophenyl isocyanate, 2-bromo-4,6-difluorophenyl isocyanate, 4-bromo-2-fluoro-phenyl isocyanate, 4-(dimethylamino)phenyl isocyanate, 2-fluoro-5-methylphenyl isocyanate, 4-fluoro-2-nitrophenyl isocyanate, 2-fluoro-3-(trifluoromethyl)phenyl isocyanate, 2-fluoro-5-(trifluoromethyl)phenyl isocyanate, 2-fluoro-6-(trifluoromethyl)phenyl isocyanate, 4-fluoro-2-(trifluoromethyl) phenyl isocyanate, 4-fluoro-3-(trifluoromethyl)phenyl isocyanate, 4-(heptyloxy)phenyl isocyanate, 2-iodophenyl isocyanate, 2-naphthyl isocyanate, 2-n-propylphenyl isocyanate, 4-(trifluoromethyl-thio)phenyl isocyanate, 2,3,4-trifluorophenyl isocyanate, 2,6-dichlorophenyl isocyanate, 3-nitrophenyl isocyanate, 3-chlorophenyl isocyanate, 2-chlorophenyl isocyanate, 1-naphthyl isocyanate, 2,3-dimethylphenyl isocyanate, 3-chloro-4-fluorophenyl isocyanate, 2,5-dimethylphenyl isocyanate, 3,4-difluorophenyl isocyanate, 2,3-dihydro-1-benzofuran-5-yl isocyanate, 2,3-dihydro-1,4-benzodioxin-6-yl isocyanate, 6-fluoro-4H-1,3-benzodioxin-8-yl isocyanate, 2,1,3-benzothiadiazol-4-yl isocyanate, 3,4-dihydro-2H-1,5-benzodioxepin-7-yl isocyanate, 3-(cyclopentyloxy)-4-methoxyphenyl isocyanate, 2-(methylthio)phenyl isocyanate, 2-(tert-butyl)phenyl isocyanate, 4-(tert-butyl)phenyl isocyanate, 3-chloro-2-methylphenyl isocyanate, 4-butyl-2-methylphenyl isocyanate, 2-ethyl-6-methylphenyl isocyanate, 4-chloro-3-nitrophenyl isocyanate, 4-bromo-2-methylphenyl isocyanate, 3-(methylthio)phenyl isocyanate, 5,5,8,8-tetramethyl-5,6,7,8-tetrahydro-2-naphthalenyl isocyanate, 5-fluoro-2-methylphenyl isocyanate, 4-phenoxyphenyl isocyanate, 4-methoxy-2-methyl-phenyl isocyanate, α,α,α-trifluoro-m-tolyl isocyanate, 2,6-dibromo-4-isopropylphenyl isocyanate, 2,6-dimethoxyphenyl isocyanate, 2-(4-isocyanatophenyl)thiophene, 4-(3-isocyanatophenyl)-2-methyl-1,3-thiazole, 3-(3-isocyanatophenyl)-5-methyl-1,2,4-oxa-diazole, 1-benzothiophen-5-yl isocyanate, 1-(3-isocyanatophenyl)-1H-pyrrole, 1-(4-isocyanatophenyl)-1H-pyrrole, 3,5-dimethoxyphenyl isocyanate and 2,4,6-trichlorophenyl isocyanate.

The intermediate compounds represented by the structural formulae (IV-A) and (IV-B) may also be reacted with an aryl or heteroaryl isothiocyanate in order to yield final compounds with structural formulae (A), (B), (D) or (E) wherein X is a thiourea linking moiety (when starting from intermediate compounds according to structural formula IV-A) or comprises a thiourea linkage (e.g. $X=(CH_2)_2NHC(=S)NH$ when starting from intermediate compounds according to structural formula IV-B), i.e. X corresponds to the definition of a divalent saturated non-cyclic hydrocarbon group comprising one or more carbon atoms and two nitrogen atoms in the main chain, one of said carbon atoms being substituted with thioxo. Aryl isothiocyanates suitable for use in the synthesis of the compounds of the present invention include, but are not limited to, phenyl isothiocyanate, 4-fluorophenyl isothiocyanate, methyl 2-isocyanatobenzoate, 2-chlorophenyl isothiocyanate, 3-chlorophenyl isothiocyanate, o-tolyl isothiocyanate, m-tolyl isothiocyanate, p-tolyl isothiocyanate, 2-methoxyphenyl isothiocyanate, 2-bromophenyl isothiocyanate, 3-bromophenyl isothiocyanate, 2,4-dichlorophenyl isothiocyanate, 2-fluoro phenyl isothiocyanate, 4-methoxyphenyl isothiocyanate, α,α,α-trifluoro-m-tolyl isothiocyanate, 3-fluorophenyl isothiocyanate, 3,5-bis(trifluoromethyl)phenyl isothiocyanate, 1-naphthyl isothiocyanate, 4-dimethylamino-1-naphthyl isothiocyanate, 4-(methylthio)phenyl isothiocyanate, 2-methoxy-5-methylphenyl isothiocyanate, 4-cyanophenyl isothiocyanate, 3-chloro-4-fluorophenyl isothiocyanate, 4-nitrophenyl isothiocyanate, 4-bromophenyl isothiocyanate, 2,3-dihydro-1,4-benzodioxin-6-yl isothiocyanate, 1,3-benzodioxol-5-yl isothiocyanate, 4-(1H-pyrazol-1-yl)phenyl isothiocyanate, 2-(trifluoromethyl) phenyl isothiocyanate, 2,3-dimethylphenyl isothiocyanate, 2-isopropyl phenyl isothiocyanate, 4-iso-propylphenyl isothiocyanate, 5-chloro-2-methoxyphenyl isothiocyanate, 2,4-dimethoxyphenyl isothiocyanate, 2,4-dichloro-6-methylphenyl isothiocyanate, 2-bromo-4-isopropylphenyl isothiocyanate, 5-chloro-2-fluorophenyl isothiocyanate, 4-(trifluoromethoxy)phenyl isothiocyanate, 3,5-dimethylphenyl isothiocyanate, 3,5-dimethoxyphenyl isothiocyanate, 4-chlorophenyl isothiocyanate, 3,4-dimethoxyphenyl isothiocyanate, 2,6-dimethylphenyl isothiocyanate, 3-methoxyphenyl isothiocyanate, mesityl isothiocyanate, 4-(benzyloxy)phenyl isothiocyanate, 2,4-dimethylphenyl isothiocyanate, 2-bromo-5-fluorophenyl isothiocyanate, 5-fluoro-2-methylphenyl isothiocyanate, 4-chloro-2,5-dimethoxyphenyl isothiocyanate, 2,5-dichlorophenyl isothiocyanate, 2-(tert-butyl)-4,5,6-trimethyl-3-nitrophenyl isothiocyanate, 2-isopropyl-6-methylphenyl isothiocyanate, 4-ethoxyphenyl isothiocyanate, 5-chloro-2- methylphenyl isothiocyanate, 2-ethyl-6-methylphenyl isothiocyanate and 4-(trifluoromethyl) phenyl isothiocyanate.

Alternatively, intermediates represented by the structural formula (IV-A) or (IV-B) may be derivatised with a carbonylation (acylation) agent (e.g. carbonyl diimidazole abbreviated as CDI in FIG. 2) and then reacted with an aromatic amine (e.g. represented by the structural formula (V-D) in FIG. 2) or a Het[1]-containing heteroaromatic amine. Suitable acylating agents include diphosgene and triphosgene, or may be represented by the structural formula Y—C(=O)—R''' wherein:

R''' denotes an aliphatic group having 1 to 4 carbon atoms which may be substituted by alkoxy having 1 to 3 carbon atoms; a cycloaliphatic group having 5 to 7 carbon atoms; a bicycloaliphatic group having 7 to 14 carbon atoms; a tricycloaliphatic group having 7 to 16 carbon atoms; an alkoxy group having 1 to 6 C atoms; an aryloxy group having 6 to 10 carbon atoms; an alkoxycarbonyl group having a total of 2 to 7 carbon atoms; an aryl group having 6 to 10 carbon atoms and optionally mono-, di- or trisubstituted by 1 to 3 halogen atoms and/or 1 to 3 alkyl groups having 1 to 3 carbon atoms and/or 1 to 3 alkoxy groups having 1 to 3 carbon atoms and/or 1 or 2 nitro groups; and Y is an atom or group of atoms which can be removed by a nucleophile. In this formula Y denotes, for example, in particular halogen, preferably chloro or bromo; hydroxyl; an alkoxy group in particular having 1 to 5 carbon atoms; an aryloxy group, in particular wherein aryl is a phenyl which may be monosubstituted or polysubstituted by alkyl and/or nitro (e.g. tolyl, dinitrophenyl or nitrophenyl); O(C=O)R'''; —O(C=O)O-alkyl, in particular having 1 to 5 carbon atoms in the alkyl radical; or the radical of an azole or benzazole bonded via a nitrogen atom and having at least two nitrogen atoms in the quasi-aromatic five-membered ring. Suitable acylating agents thus represent, for example, haloformic acid esters, of which chloroformic acid esters are preferred (Y=halogen); carboxylic acids (Y=OH); alkyl and aryl esters, of which the tolyl, 2,4-dinitro or 4-nitrophenyl esters are preferred; anhydrides; mixed carboxylic acid carbonic acid anhydrides; or heterocyclic amides or azolides, in particular of N,N'-carbonyldiazoles such as, for example, N,N'-carbonyldiimidazole, 2,2'-carbonyl-1,2,3-ditriazole, 1,1'-carbonyl-1,2,4-ditriazole, N,N'-carbonyl-dipyrazole, and 2,2'-carbonyl-ditriazole.

The resulting acylated derivative (e.g. an imidazo-carbonyl derivative when starting from CDI) may then be further reacted with an amino-containing compound, particularly an aniline derivative represented by the structural formula (V-D) as shown in FIG. 2, wherein $R_7$, $R_8$, $R_9$, $R_{10}$ and $R_{11}$ are as defined above, or a Het$_1$-containing heteroaryl amine, thereby providing further compounds of the invention with structural formulae (A), (B), (D) or (E). The carbonylation and further urea formation by reaction with an amino-containing compound may be most particularly carried out in a one-pot procedure. Amino-containing compounds suitable for the latter reaction include arylamines as shown in FIG. 2, but also arylalkylamines, arylalkenylamines, arylalkynylamines wherein one or more of the carbon atoms in the said alkyl, alkenyl or alkynyl moiety is optionally replaced by a heteroatom selected from the group consisting of O, N and S, and wherein the aryl group is optionally mono- or polysubstituted.

Suitable aniline derivatives represented by the structural formula (V-D) for use in the above reaction step include, but are not limited to, 2,6-dimethylaniline, 2-methylaniline, 3-fluoroaniline, 4-ethylaniline, 2,4-dimethoxyaniline, 2,6-dichloroaniline, 3-cyanoaniline, and 2,4-fluoroaniline. Also suitable are $C_{1-4}$ alkoxy-anilines and $C_{1-4}$ alkylthio-anilines (or salts thereof) being optionally further substituted at another position of the phenyl ring Representative examples of such optionally substituted $C_{1-4}$ alkoxy-anilines or $C_{1-4}$ alkylthio-anilines include, but are not limited to, 2-methoxyaniline, 3-methoxyaniline, 4-methoxyaniline, 2-ethoxyaniline, 3-ethoxyaniline, 4-ethoxyaniline, 4-bromo-3-ethoxyaniline hydrochloride, 2-propoxyaniline, 3-propoxyaniline, 4-propoxyaniline, 3-isopropoxyaniline, 4-isopropoxyaniline, 2,5-diethoxyaniline, 3,4-diethoxyaniline, 4-n-butoxyaniline, 3-n-butoxyaniline, 2-n-butoxyaniline, 4-iso-butoxyaniline, 3-isobutoxyaniline, 2-isobutoxyaniline, 2-methyl-4-methoxyaniline, 2-(methylthio)aniline, 3-(methylthio)aniline, 4-(methylthio)aniline, 2-trifluoromethoxy-aniline, 3-trifluoro-methoxyaniline, 4-trifluoromethoxyaniline, 5-chloro-2-(methylthio)-aniline, 2-bromo-4-methoxyaniline, 2-bromo-5-methoxyaniline, 3-bromo-4-methoxyaniline, 4-bromo-3-methoxyaniline, 5-bromo-2-methoxyaniline, 2-iodo-5-methoxyaniline, 3-iodo-4-methoxyaniline, 5-iodo-2-methoxyaniline, 2-chloro-5-methoxyaniline, 3-chloro-2-methoxyaniline, 3-chloro-4-methoxyaniline, 4-chloro-3-methoxyaniline, 5-chloro-2-methoxyaniline, 2-fluoro-4-methoxyaniline, 2-fluoro-6-methoxyaniline, 3-fluoro-2-methoxyaniline, 3-fluoro-4-methoxyaniline, 3-fluoro-5-methoxyaniline, 4-fluoro-3-methoxyaniline, 5-fluoro-2-methoxyaniline, 2-(difluoromethoxy)aniline, 3-(difluoromethoxy)aniline, 4-(difluoromethoxy)aniline and 2,4-dichloro-5-methoxyaniline.

Suitable arylalkylamines for use in the above reaction step include, but are not limited to, 2-chlorobenzylamine, 4-chlorobenzylamine, 2,4-dichlorobenzylamine, 3,4-dichlorobenzylamine, 4-methoxybenzylamine, 4-methylbenzylamine, piperonyl-amine, 3,4-dimethoxybenzylamine, 3-methylbenzylamine, 3-fluorobenzylamine, 2-methylbenzylamine, 2-methoxybenzylamine, 3-methoxybenzylamine, 2-fluorobenzylamine, 4-fluorobenzylamine, 3,4-dihydroxybenzylamine, 3-chlorobenzylamine, 4-(trifluoromethoxy)benzylamine, 2,6-difluorobenzylamine, 3,5-bis(trifluoromethyl)-benzylamine, 2,4-difluorobenzylamine, 2,5-difluorobenzylamine, 3,4-difluorobenzyl-amine, 2-(trifluoromethyl)benzylamine, 3-(trifluoromethyl)benzylamine, 2-bromobenzylamine, 4-bromobenzylamine, 2-chloro-6-fluorobenzylamine, 2,5-dimethylbenzylamine, 3,4,5-Trimethoxybenzylamine, 2,4,6-trimethylbenzylamine, 2,4-dimethylbenzylamine, 2,3-dichlorobenzylamine, 1-naphthalenemethylamine, 3-iodobenzylamine, 2-hydroxybenzylamine, 3-bromobenzylamine, 2,6-dichlorobenzylamine, 3,4-dihydro-2H-1,5-benzodioxepin-6-ylmethylamine, 2,3-dihydro-1,4-benzodioxin-6-ylmethylamine, 2,3-dihydro-1,4-benzodioxin-5-ylmethylamine, 1-benzofuran-5-ylmethylamine, 4-(thien-2-yl)benzylamine, 3,4-dihydro-2H-1,5-benzodioxepin-7-ylmethylamine, 4-morpholinobenzylamine, 4-(1H-pyrazol-1-yl)benzylamine, 4-(4-methylpiperazino)benzylamine, 2-piperidinobenzylamine, 3-(1H-pyrrol-1-yl)benzylamine, 2-morpholinobenzylamine, 4-(1H-pyrrol-1-yl)benzylamine, 2-chloro-6-phenoxybenzylamine, 2-(methylthio)benzylamine, 2-(trifluoromethoxy) benzylamine, 2,3-dimethylbenzylamine, 4-(trifluoromethyl)-benzylamine, 3,5-dichlorobenzylamine, 2-(aminomethyl)-3-fluoroaniline, 3-chloro-4-fluorobenzylamine, 2,5-dimethoxybenzylamine, 2,5-dichlorobenzylamine, 2,6-dimethoxybenzylamine, 2,4-dichloro-6-methylbenzylamine, 3-chloro-4-methylbenzylamine, 4-fluoro-3-(trifluoromethyl)benzylamine, 4-fluoro-2-(trifluoromethyl)benzylamine, 3-(piperidin-1-ylmethyl)benzylamine, 1-benzothiophen-5-ylmethylamine, 4-(morpholinomethyl)benzylamine, (3-((4-methylpiperidino)methyl)phenyl)methanamine, (4-piperidinophenyl)methylamine, (3-piperidinophenyl)methylamine, 1-[2-(4-methyl-piperazin-1-yl)phenyl]methanamine, (1,4-dimethyl-1,2,3,4-tetrahydroquinoxalin-6-yl)-methylamine, 3-(trifluoromethoxy)benzylamine, 4-bromo-2-fluorobenzylamine, 2-(1H-pyrazol-1-yl)benzylamine, tert-butyl-4-(2-(aminomethyl)phenyl)piperazine-1-carboxylate, (3-morpholinophenyl)methylamine, tert-butyl-N-[4-(aminomethyl)phenyl]carbamate, [2-(1H-pyrrol-1-yl)phenyl]methylamine, 1-[3-(4-methylpiperazin-1-yl)phenylimethanamine, [4-(1-pyrrolidinyl)phenyl]methylamine, (3-pyrrolidin-1-ylphenyl)methylamine, [4-(2-morpholinoethoxy)phenyl]methylamine, [2-(2-morpholinoethoxy)phenyl]methylamine, [3-(2-morpholinoethoxy)phenyl]methylamine, [3-(morpholinomethyl)phenyl]methylamine, [4-(piperidinomethyl)phenyl]methylamine, {4-[(4-methylpiperazin-1-yl)methyl]phenyl}methylamine, [4-(2-furyl)phenyl]methylamine, tert-butyl-4-[4-(aminomethyl)phenyl]tetrahydro-1(2H)-pyrazinecarboxylate, (2,2-dimethyl-2,3-dihydro-1-benzofuran-7-yl)methylamine, [3-(1H-1,2,4-triazol-1-yl)phenyl]-methylamine, (4-thien-3-ylphenyl)methylamine, 1-[2-(morpholin-4-ylmethyl)phenyl]methanamine, {2-[(4-methylpiperazin-1-yl)methyl]phenyl}methylamine, [3-(2-furyl)phenyl]methylamine, (3-(thien-2-yl)phenyl)methylamine, [2-(2-furyl)phenyl]nethylamine, 4-(pyrrolidin-1-ylmethyl)benzylamine, 4-[(4-methylperhydro-1,4-diazepin-1-yl)methyl]benzylamine, 4-[2-(dimethylamino) ethoxy]benzylamine, (2-pyrrolidin-1-ylphenyl)methylamine, [3-(1-pyrrolidinylmethyl)phenyl]methanamine, (3-thien-3-ylphenyl)methylamine, 2-[2-(dimethylamino)ethoxy]benzylamine, 2-(phenoxymethyl)benzylamine, (1-methyl-1H-indol-4-yl)methylamine, 4-(4-methylperhydro-1,4-diazepin-1-yl)benzylamine, (1-methyl-1H-indol-6-yl)methylamine, [3-(1,3-thiazol-2-yl)phenyl]methylamine, 3-(1H-pyrazol-1-ylmethyl)benzylamine, (1-Methyl-1H-indol-5-yl)methylamine, 3-(phenoxymethyl)benzylamine, 2-morpholino-5-(trifluoromethyl)benzylamine, [4-(1,3-thiazol-2-yl)phenyl]methylamine, 3-(1-methyl-1H-pyrazol-3-yl)benzylamine, 2-(4-methylperhydro-1,4-diazepin-1-yl)benzylamine, 4-[4-(dimethylamino)propoxy]benzylamine, 3-(2-methyl-1H-imidazol-1-yl)benzylamine, 4-(2-methyl-1H-imidazol-1-yl)benzylamine, 2-(2-methyl-1H-imidazol-1-yl)benzylamine, [4-(tetrahydropyran-4-yloxy)phenyl]methylamine, 3-[3-(dimethylamino)propoxy]benzylamine, 2-[3-(dimethylamino) propoxy]benzylamine, 3-pyrimidin-2-ylbenzylamine, 4-(1-methyl-1H-pyrazol-3-yl)benzylamine and 3-(1-methyl-1H-pyrazol-5-yl)benzylamine and 1-(1-benzothien-7-yl)methanamine.

Suitable $Het_1$-containing heteroaryl amines for use in the above reaction step include, but are not limited to, 6-ethylpyridin-2-amine, 2-(2-aminoethyl)pyridine, 3-(2-aminoethyl)pyridine, 4-(2-aminoethyl)pyridine, 2-amino-4-ethylpyridine, 2-amino-3-ethylquinoline, tryptamine, aminoindole (all isomers thereof), aminopyrazole (all isomers thereof), aminopyrimidine (all isomers thereof), aminoimidazole (all isomers thereof), amino-(cyanoimidazole), and amino-(dicyanoimidazole).

When step (c) comprises two sub-steps as described herein-above, the order of performing the different reactions is not critical for the present invention and therefore can be changed at will. For example, the amino-containing compound comprising an optionally substituted heterocyclic ring (A') with at least two nitrogen atoms in the said heterocyclic ring and with a total of 5 to 7 atoms may first be reacted with either one of the aryl-containing reagents represented by the structural formulae (V-A), (V-B), (V-E) or (V-C) or their $Het_1$-containing analogues, or CDI followed by reaction with an aryl-containing compound represented by the structural formula (V-D) or one of its $Het_1$-containing analogues. The resulting intermediate compound may then be used for reaction with the 3-substituted-5-chloro-thiadiazole represented by the structural formula (III) to yield a final compound according to the invention.

When one or more of $R_7$, $R_8$, $R_9$, $R_{10}$ and $R_{11}$ is a $C_{1-6}$ alkylcarbonyloxy group, and X is sulfonyl, it may be necessary to prepare the required phenyl-sulfonyl chloride having structural formula (V-B) by first reacting an optionally substituted phenol with a carboxylic acid chloride, such as described in U.S. Pat. No. 6,486,183 with respect to 3-fluoro-1-propionyloxybenzene, and then sulfonating the resulting product. An alternative method is also provided in the following examples.

Figure 3:
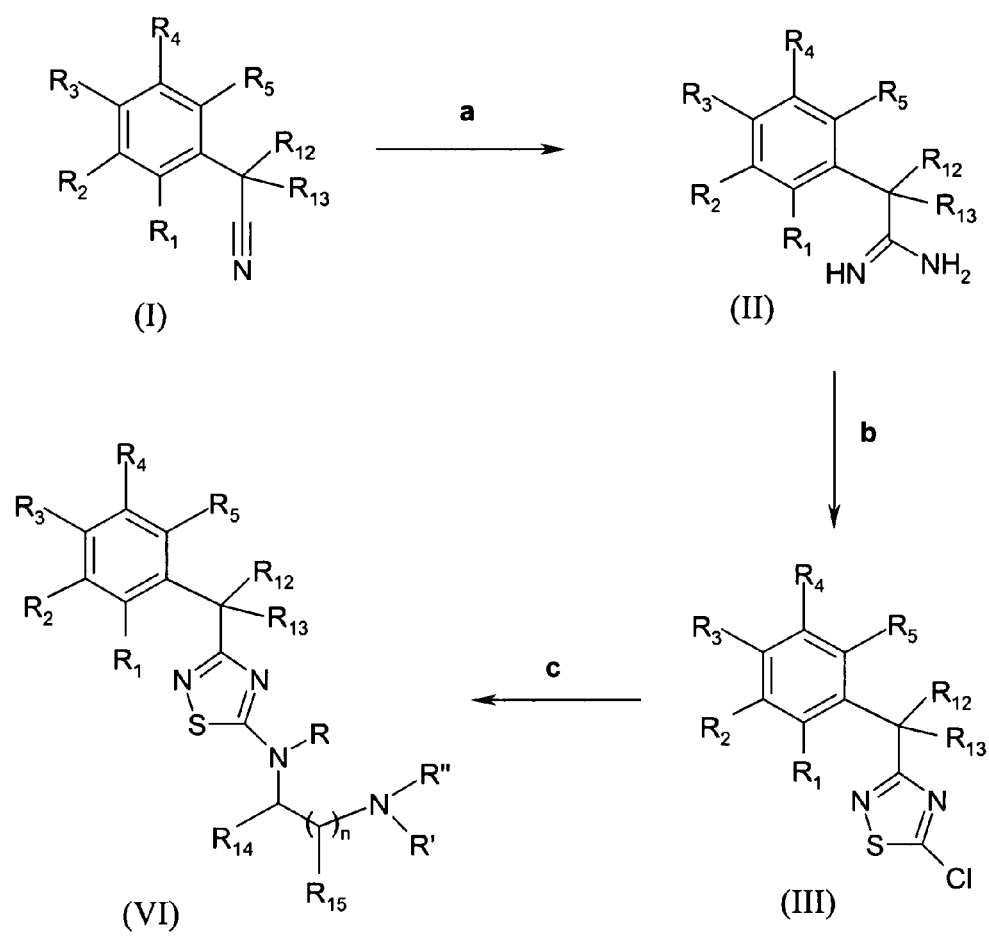
Figure 4:
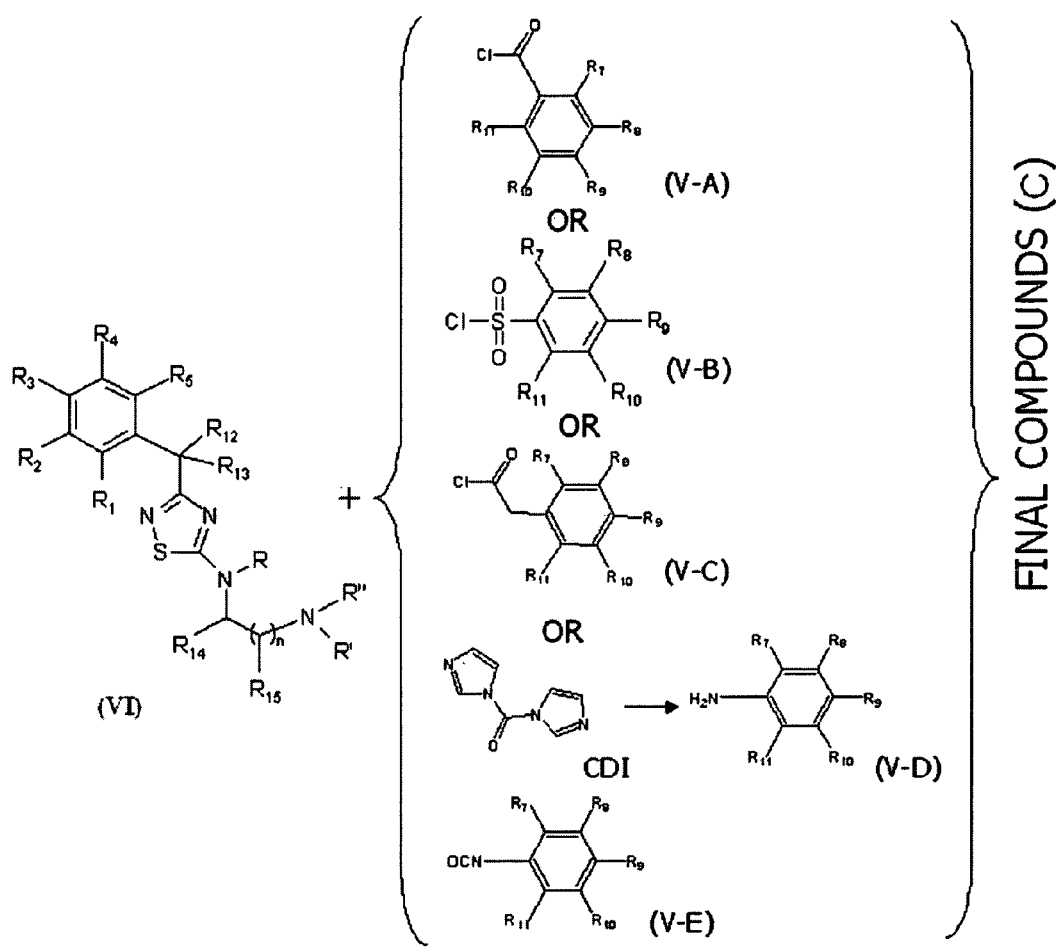

Generally, 1,2,4-thiadiazole compounds having the structural formula (C) can be synthesised according to the principles of FIGS. 3 and 4. Steps (a) and (b) of FIG. 3 proceed in the same way as described for FIG. 1 hereinbefore. In step (c) of FIG. 3, a non-cyclic diamine represented by the structural formula R'NH—$(CHR_{15})_n$—$CHR_{14}$—NHR, wherein n, R, R', $R_{14}$ and $R_{15}$ are as defined herein-above in the structural formula (C), is used as a reactant to convert the intermediate represented by the structural formula (III) into an intermediate represented by the structural formula (VI). The aliphatic chain comprised between the two nitrogen atoms of said non-cyclic diamine may be linear (i.e. $R_{14}$ and $R_{15}$ are both hydrogen) or may be branched (i.e. at least one of $R_{14}$ and $R_{15}$ is not hydrogen). Suitable examples of non-cyclic linear diamines include, but are not limited to, ethylenediamine, propylenediamine, N-methyl-ethylenediamine, N,N'-dimethylethylenediamine, N,N'-diisopropylethylene-diamine, N,N'-diethylethylenediamine, 1,4-diaminobutane, 1,5-diaminopentane, 1,6-diaminohexane, 1,7-diaminoheptane, 1,8-diaminooctane, 1,9-diamino-nonane, 1,10-diaminodecane and 1,12-diaminododecane, most of them being commercially available. Suitable examples of non-cyclic branched diamines include, but are not limited to, the commercially available 1,2-diaminopropane as well as the following:

2,3-diaminobutane, the preparation and characterisation of which are known from Scaros et al. in *Tetrahedron: Assymetry* (1997) 8(9):1501-1506 and from Sameski et al. in *Anal. Chem.* (1976) 48(9):1303-1308;

1,3-diaminobutane (CAS No. 590-88-5, ICSC No. 1078);

1,2-diaminobutane, the purification and characterisation of which are known from Douslin et al. in a report of the Bureau of Mines Bartlesville Okla. Petroleum Research Center (1967);

1,2-diaminopentane, the preparation of which is known from WO2006/034440; and 1,3-diaminopentane, the production of which is known from U.S. Pat. No. 5,898,085.

Suitable reaction conditions for the reaction of a non-cyclic linear or branched diamine having the structural formula R'—NH—$(CHR_{15})_n$—$CHR_{14}$—NHR with a 3-substituted-5-chloro-thiadiazole compound represented by the structural formula (III) are well known in the art. In certain situations where competing amino reactive sites may be present such as, but not limited to, when in the structural formula (C) R is hydrogen and R' is $C_{1-4}$ alkyl (illustrated below), or one of $R_{14}$ and $R_{15}$ is not hydrogen, it may be desirable (in order to reduce or avoid the possibility of producing a mixture of intermediates represented by the structural formula (VI) that may later have to be separated before performing the next reaction steps) to perform the above-mentioned reaction by first reacting a N-protected non-cyclic linear or branched diamine having the structural formula R'—N(PG)—$(CHR_{15})_n$—$CHR_{14}$—$NH_2$, wherein PG is an amino-protecting group, and after said reaction step (c) has been completed, secondly deprotecting the resulting intermediate compound to achieve an intermediate represented by the structural formula (VI). N-protecting groups and amino-deprotecting techniques suitable for this particular purpose are well known to the person skilled in the art. Commonly used N-protecting groups are disclosed e.g. in Greene, "Protective Groups in Organic Synthesis" (John Wiley & Sons, New York, 1981). Suitable exemplary N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, .alpha.-chlorobutyryl, benzoyl, 4-chloro-benzoyl, 4-bromobenzoyl, 4-nitrobenzoyl, and the like; sulfonyl groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitro-benzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methyl-ethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; arylalkyl groups such as benzyl, triphenylmethyl, benzyloxymethyl and the like; and silyl groups such as trimethylsilyl and the like. The most appropriate N-protecting groups include formyl, acetyl, benzoyl, pivaloyl, t-butylacetyl, phenylsulfonyl, benzyl, t-butoxycarbonyl (BOC) and benzyloxycarbonyl.

Finally, the N-protecting group may be removed by deprotection methods conventional in the art, such as, but not limited to:
  when the amino-protecting group is a phenylmethoxycarbonyl group, cleavage of the benzylic ether function by hydrogenolysis, e.g. using $H_2$, Pd—C at about 25° C., or under strongly acidic conditions (e.g. making use of bromhydric acid), or
  when the amino-protecting group is a tert-butoxycarbonyl group, by treatment with an acid, e.g. using aqueous hydrochloric acid or trifluoroacetic acid (hereinafter referred as TFA), under conditions mild enough to avoid further cleavage of the molecule, or
  when the amino-protecting group is a 9-fluorenylmethoxycarbonyl group, by treatment with a base such as piperidine.

When step (c) is sub-divided into two sub-steps, the second sub-step may proceed according to FIG. 4, i.e. by reacting an intermediate compound represented by the structural formula (VI) with an aryl derivative represented by a structural formula (V-A), (V-B), (V-C), (V-D) or (V-E) shown in FIG. 4, or a corresponding heteroaryl derivative including a heteroaryl group Het[1], said reaction proceeding in a manner similar to the corresponding reaction described for FIG. 2.

The above description provides general schemes for making all 1,2,4-thiadiazole compounds of the present invention. A list of exemplary, but non-limiting, compounds which have been effectively synthesised according to the described methods is provided in Table 1 herein.

The 1,2,4-thiadiazole derivatives having the above structural formulae (A), (B) and (C) may be in the form of a pharmaceutically acceptable salt. The latter include any therapeutically active non-toxic addition salt which 1,2,4-thiadiazole compounds having the general formulae (A), (B) and (C) are able to form with a salt-forming agent. Such addition salts may conveniently be obtained by treating the said derivative of the invention with an appropriate salt-forming acid or base. For instance, derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as but not limited to hydrohalides (e.g. hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzene-sulfonate, p-toluenesulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphtoate, hydroxyethanesulfonate, mandelate, methylsulfate, pantothenate, stearate, as well as salts derived from ethanedioic, propanedioic, butanedioic, (Z)-2-butenedioic, (E)2-butenedioic, 2-hydroxybutanedioic, 2,3-dihydroxybutane-dioic, 2-hydroxy-1,2,3-propanetricarboxylic and cyclohexanesulfamic acids and the like.

The 1,2,4-thiadiazole derivatives of the general formulae (A), (B) and (C) having acidic properties may be converted in a similar manner into the corresponding therapeutically active, non-toxic base addition salt form. Examples of appropriate salt-forming bases include, for instance, inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylenediamine, chloroprocaine, choline, diethanolamine, ethylene-diamine, N-methylglucamine, procaine and the like.

Reaction conditions for treating the 1,2,4-thiadiazole derivatives having the structural formulae (A), (B) and (C) of this invention with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water-solubility, lower toxicity, greater stability and/or slower dissolution rate to the derivative of this invention.

In order to suitably use a 1,2,4-thiadiazole compound disclosed in this invention or a pharmaceutically acceptable salt, pro-drug or solvate thereof, for the therapeutic treatment (including prophylactic treatment) of mammals including humans, it is usually formulated in accordance with standard pharmaceutical practice as a pharmaceutical composition including one or more appropriate pharmaceutically acceptable excipients.

In another embodiment, this invention provides combinations, preferably synergistic combinations, of one or more derivatives represented by the general formulae (A), (B) and (C) with one or more biologically-active drugs being preferably selected from the group consisting of neuro-protective agents and α-synuclein deposition inhibitors. As is conventional in the art, the evaluation of a synergistic effect in a drug combination may be made by analysing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively. As will be explained in more detail herein below, this principle may be applied to a number of desirable effects such as, but not limited to, an activity against neurodegenerative disorders.

The term "pharmaceutically acceptable carrier or excipient" as used herein in relation to pharmaceutical compositions and combined preparations means any material or substance with which the active principle, i.e. the 1,2,4-thiadiazole derivative of the general formulae (A), (B) and (C), and optionally the neuro-protective agent or α-synuclein deposition inhibitor, may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. may also be prepared by micronisation, for instance in view to obtain them in the form of microspheres usually having a diameter of about 1 to 10 μm, namely for the manufacture of microcapsules for controlled or sustained release of the biologically active ingredient(s).

Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalene-sulphonic acid/formaldehyde condensation product. Also suitable are the correspon-ding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanyl-phosphatidylcholine, dipalmitoylphoshatidylcholine and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-$C_{1-4}$ alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions and combined preparations of the invention. Control release compositions may thus be achieved by selecting appropriate polymer carriers such as for example polyesters, polyamino-acids, polyvinyl-pyrrolidone, ethylene-vinyl acetate copolymers, methylcellulose, carboxy-methylcellulose, protamine sulfate and the like. The rate of drug release and duration of action may also be controlled by incorporating the active ingredient into particles, e.g. microcapsules, of a polymeric substance such as hydrogels, polylactic acid, hydroxymethyl-cellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

In order to suitably use compounds disclosed in this invention—represented by structural formulae (A), (B) and (C)—for therapeutic or prophylactic purpose, such compounds are preferably administered so that a daily dose in the range of, for example, 0.1 mg to 75 mg per kg body weight is received, said daily dose being given if required in divided sub-doses. In general, lower doses will be administered when a parenteral route is employed. Thus, for example, for intravenous administration, a dose in the range of, for example, 0.5 mg to 30 mg per kg body weight will preferably be used. Similarly, for administration by inhalation, a dose in the range of, for example, 0.5 mg to 25 mg per kg body weight will preferably be used. According to a particular embodiment, the envisaged administration route for the compounds of the invention is oral administration, particularly in tablet form. Typically, unit dosage forms will contain about 1 mg to 500 mg of a compound of this invention.

Another embodiment of this invention includes the various precursor or "pro-drug" forms of the compounds of the present invention. It may be desirable to formulate the compounds of the present invention in the form of a chemical species which itself is not significantly biologically-active, but which when delivered to the body of a human being or higher mammal will undergo a chemical reaction catalysed by the normal function of the body, inter alia, enzymes present in the stomach or in blood serum, said chemical reaction having the effect of releasing a compound as defined herein. The term "pro-drug" thus relates to these species which are converted in vivo into the active pharmaceutical ingredient.

The pro-drugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used.

For the purposes of the present invention the term "therapeutically suitable pro-drug" is defined herein as "a compound modified in such a way as to be transformed in vivo to the therapeutically active form, whether by way of a single or by multiple biological transformations, when in contact with the tissues of humans or mammals to which the pro-drug has been administered, and without undue toxicity, irritation, or allergic response, and achieving the intended therapeutic outcome".

The following examples are provided for illustrative purpose only, and do not constitute an exhaustive list of compounds that can be made and used according to the above-mentioned general principles of the present invention.

Example 1

Amidine Formation

A few illustrative amidines corresponding to the structural formula (II) herein-above have been prepared according to step (a) of scheme 1, more schematically shown below:

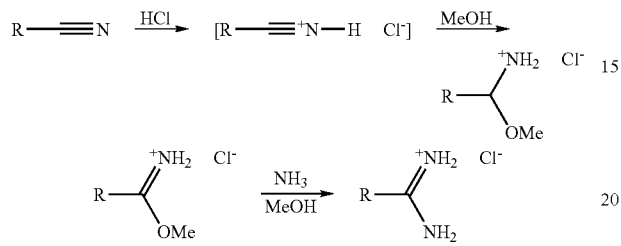

The above starting nitrile compound RCN, wherein R corresponds to $(R_1,R_2, R_3,R_4,R_5$-substituted phenyl)-$CR_{12}R_{13}$— in the structural formula (I) of scheme 1, is first treated with gaseous HCl in a mixture of anhydrous chloroform and methanol to yield the imino ether hydrochloride shown above. Subsequently, the mixture is treated with dry ammonia to yield the desired amidine compound.

Examples 2 to 13

Synthesis of 3-(substituted)benzyl-5-chloro-1,2,4-thiadiazole derivatives 3-(substituted)benzyl-5-chloro-1,2,4-thiadiazole intermediate derivatives represented by the structural formula (III) in step (b) of scheme 1 have been obtained according to the following detailed procedure:

In a three-necked 500 mL flask equipped with a mechanical stirrer, a dropping funnel and a thermometer, dichloromethane (DCM) (130 ml) was charged and the appropriate amidine hydrochloride from example 1 (0.1 mole) was suspended therein upon efficient stirring. Then perchloromethyl mercaptane (16.73 g, 0.09 mole) was added to the suspension. The stirred solution was cooled to −14° C. by using a ammonium chloride-ice cooling bath. Then an aqueous NaOH solution (20 g, 0.5 mole dissolved in 30 ml distilled water) was added dropwise to the solution upon efficient stirring while keeping the temperature below −8° C. When addition was completed, the reaction mixture was stirred for another hour while letting temperature rise up to room temperature. The precipitated NaCl was filtered off and washed with DCM. The organic phase of the filtrate was separated and saved. The aqueous phase was washed three times with 20 ml DCM. The collected organic phases including the previously saved solution were washed four times with water (20 ml). The organic phase was dried over anhydrous sodium sulphate and evaporated to dryness. The residue was distilled in high motor vacuum using a vacuum-jacketed Vigreux-column. In this way, the following species were obtained and characterized by their boiling point (b.p.) and molecular weight:

5-chloro-3-(4-methylbenzyl)-[1,2,1]thiadiazole (example 2): starting from 31.8 g (172 mmole) 4-methylbenzyl amidine hydrochloride, 16.7 g was obtained (yield 48%); molecular weight 224.7, b.p. 130-135° C./1 Hg mm.

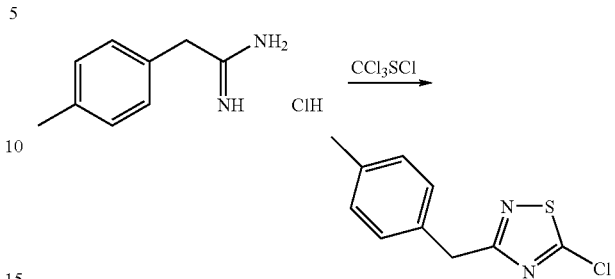

5-chloro-3-(4-fluorobenzyl)-[1,2,4]thiadiazole (example 3): starting from 18.4 g (97.5 mmole) 4-fluorobenzyl amidine hydrochloride, 13.45 g was obtained (yield: 67%); molecular weight 228.7, bp: 120-125° C./1 Hg mm.

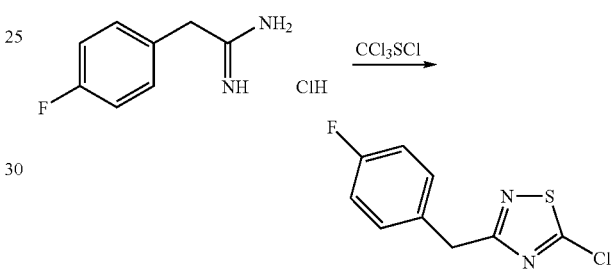

5-chloro-3-(3-methoxybenzyl)-[1,2,4]thiadiazole (example 4): starting from 84.8 g (423 mmole) 3-methoxybenzyl amidine hydrochloride, 68.7 g was obtained (yield: 75%); molecular weight 240.7, bp: 132-135° C./1 Hg mm.

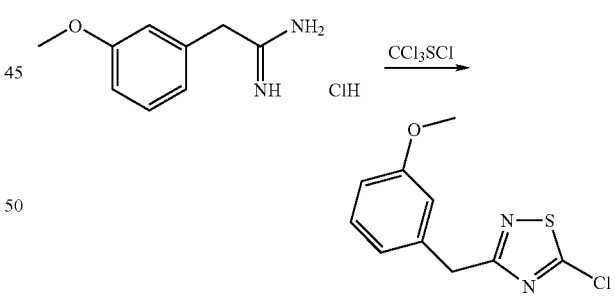

5-chloro-3-(3-fluoro-benzyl)-[1,2,4]thiadiazole (example 5): starting from 2-(3-fluoro-phenyl)-acetamidine hydrochloride (8.87 g, 47 mmole) 4.08 g (yield 38%) was obtained; b.p.: 98-100° C./0.1 Hg mm.

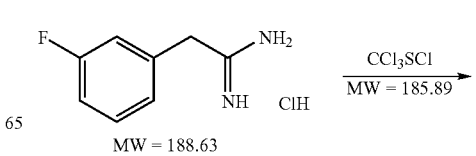

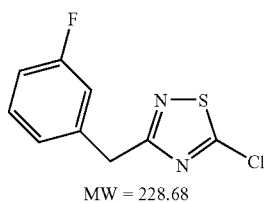

MW = 228.68

5-chloro-3-(2-fluoro-benzyl)-[1,2,4]thiadiazole (example 6): starting from 2-(2-fluoro-phenyl)-acetamidine hydrochloride (18.1 g, 96 mmole) 10.6 g (yield 48%) was obtained: b.p.: 105-107° C./0.1 Hg mm.

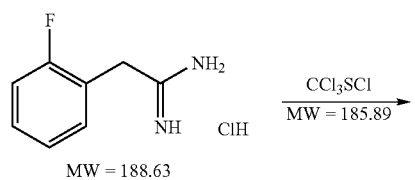

MW = 188.63

3-benzyl-5-chloro-[1,2,4]thiadiazole (example 7) starting from phenyl-acetamidine hydrochloride (10.5 g; 61.4 mmole) 3.3 g (yield 25%) was obtained; b.p.: 102-104° C./0.1 Hg mm.

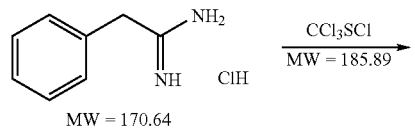

MW = 170.64

MW = 210.69

5-chloro-3-(3-methyl-benzyl)-[1,2,4]thiadiazole (example 8) starting from 2-m-tolyl-acetamidine hydrochloride (16.62 g; 90 mmole) 9.8 g (yield 48%) was obtained; b.p.: 114-118° C./0.2 Hg mm.

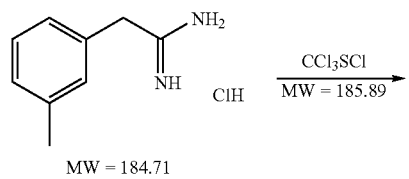

MW = 184.71

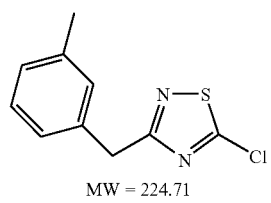

MW = 224.71

5-chloro-3-(2-methyl-benzyl)-[1,2,4]thiadiazole (example 9) starting from 2-o-tolyl-acetamidine hydrochloride (17.55 g; 95 mmole) 10.2 g (yield 48%) was obtained; b.p.: 112-114° C./0.2 Hg mm.

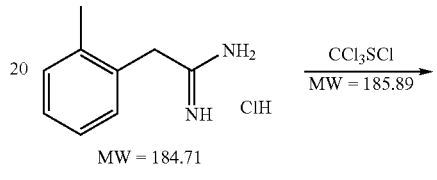

MW = 184.71

MW = 224.71

5-chloro-3-(2-methoxy-benzyl)-[1,2,4]thiadiazole (example 10) starting from 2-(2-methoxy-phenyl)-acetamidine hydrochloride (19.07 g; 95 mmole) 12.1 g (yield 53%) was obtained; b.p.: 132-134° C./1 Hg mm.

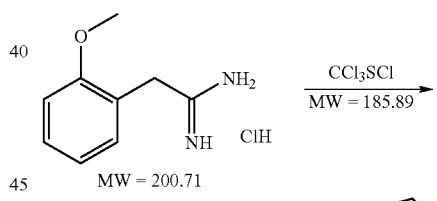

MW = 200.71

MW = 240.71

5-chloro-3-(4-methoxy-benzyl)-[1,2,4]thiadiazole (example 11) starting from 2-(4-methoxy-phenyl)-acetamidine hydrochloride (16.05 g; 80 mmole) 6.2 g (yield 32%) was obtained; b.p.: 138-140° C./1 Hg mm.

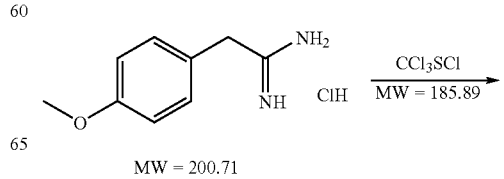

MW = 200.71

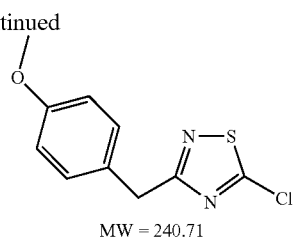

5-chloro-3-(3-methyl-4-fluoro-benzyl)-[1,2,4]thiadiazole (example 12) starting from 2-(3-methyl-4-fluoro-phenyl)-acetamidine hydrochloride (15.70 g; 77.46 mmole) 7.3 g (yield 39%) was obtained; b.p.: 113-115° C./0.5 Hg mm.

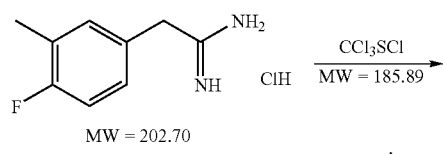

5-chloro-3-(4-chloro-benzyl)-[1,2,4]thiadiazole (example 13) starting from 2-(4-chloro-phenyl)-acetamidine hydrochloride (189 g; 918 mmole) 39.7 g (yield 20%) was obtained; b.p.: 132-135° C./1 Hg mm.

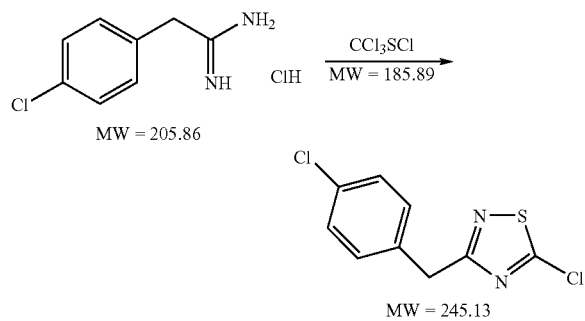

Examples 14 to

Nucleophilic Replacement with piperazines onto 5-chloro-3-(Substituted benzyl)-1,2,4-thiadiazole Derivatives 1,2,4-thiadiazole intermediate derivatives represented by the structural formula (IV) have been obtained according to step (c) of scheme 1, more schematically shown in scheme 3 below (i.e. wherein $Ar^1$ corresponds to ($R_1,R_2,R_3,R_4,R_5$-substituted phenyl), $R^2$ corresponds to $R_6$, and each of $R_{12}$ and $R_{13}$ in scheme 1 is hydrogen), using the following detailed procedure:

Scheme 3

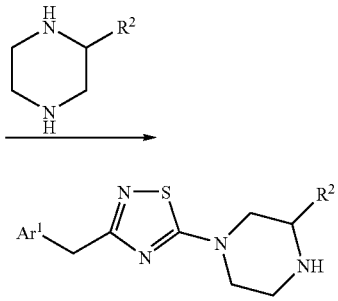

The piperazine derivative (used in a 5-fold molar excess) was dissolved in ethanol and a 3-(substituted benzyl)-5-chloro-1,2,4-thiadiazole derivative from examples 2-13 was added in portions. The reaction mixture was refluxed until the reaction was complete. The course of the reaction was monitored by thin layered chromatography (TLC) in an eluent mixture of DCM-EtOH 5:1. The reaction time ranged from 3 to 6 hours for the various intermediate compounds synthesised in this set of examples. When reaction was complete, the reaction mixture was evaporated to dryness. The residue was dissolved in water and the product was extracted with DCM. The organic phase was washed with water in order to remove remaining traces of the piperazine derivative, then it was dried over $MgSO_4$ and evaporated to dryness. Purity of the product obtained was checked by TLC using as an eluent mixture DCM:EtOH in a volume ratio 5:1 containing a few drops of a 25% aqueous ammonium hydroxide solution. When TLC showed apolar impurities, the product was dissolved in a 5% aqueous HCl solution and impurities were washed away with ethyl-acetate, the aqueous phase was made alkaline (pH: 10-11) with a 10% aqueous NaOH solution and the product was extracted with DCM. In this way, the following species were obtained and characterized by their molecular weight and nuclear magnetic resonance spectra:

3-methyl-1-[3-(4-methyl-benzyl)-[1,2,4]thiadiazol-5-yl]-piperazine (example 14): starting from 3.37 g of 5-chloro-3-(4-methylbenzyl)-[1,2,4]thiadiazole (example 2; 15 mmole) and 2-methyl-piperazine (7.51 g, 75 mmole), 4.05 g of the title compound (molecular weight 288.4) was obtained after a 3 hour reaction time (94% yield).

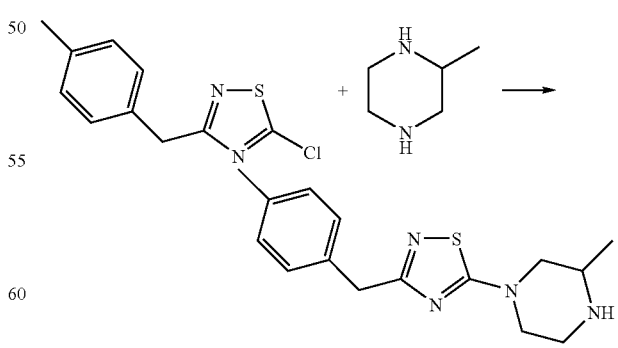

1-[3-(4-fluoro-benzyl)-[1,2,4]thiadiazol-5-yl]-piperazine (example 15): starting with 3.43 g of 5-chloro-3-(4-fluorobenzyl)-[1,2,4]thiadiazole (example 3; 15 mmole) and piperazine (6.46 g; 75 mmole), 3.73 g of the title compound (molecular weight 278.4) was obtained after 6 hours reaction (89% yield).

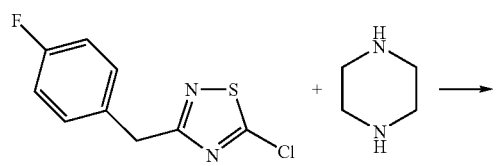

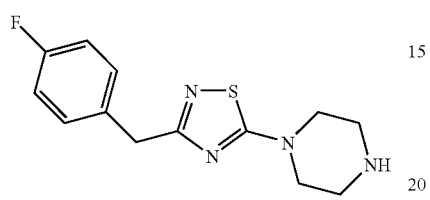

1-[3-(3-methoxy-benzyl)-[1,2,4]thiadiazol-5-yl]-piperazine (example 16): starting from 2.41 g of 5-chloro-3-(4-fluorobenzyl)-[1,2,4]thiadiazole (example 3; 10 mmole) and piperazine (4.31 g; 10 mmole), 2.65 g of the title compound (molecular weight 290.4) was obtained after 5 hours reaction time (91% yield).

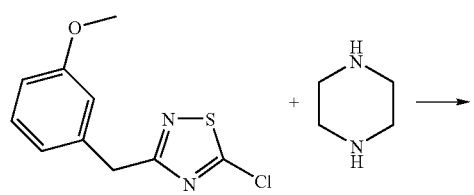

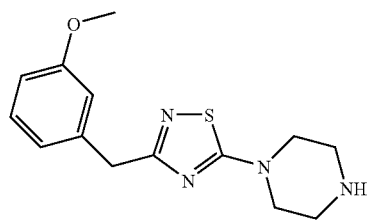

1.58 g (yield 89%) 1-[3-(3-fluoro-benzyl)-[1,2,4]thiadiazol-5-yl]-piperazine (example 17) was obtained starting from the 5-chloro-3-(3-fluoro-benzyl)-[1,2,4]thiadiazole of example 5 (1.6 g; 7.0 mmole) and piperazine (3.0 g; 35 mmole) after a reaction time of 5 hours.

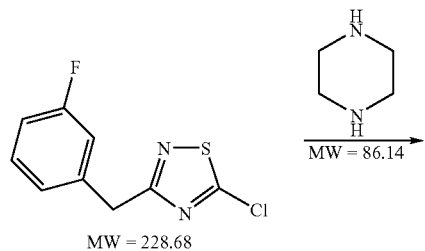

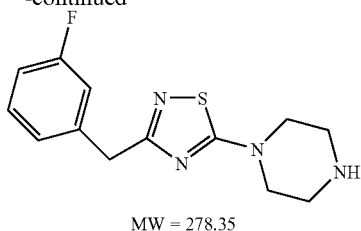

1.53 g (yield 78%) of 1-[3-(2-fluoro-benzyl)-[1,2,4]thiadiazol-5-yl]-piperazine (example 18) was obtained starting from the 5-chloro-3-(2-fluoro-benzyl)-[1,2,4]thiadiazole of example 6 (1.6 g; 7.0 mmole) and piperazine (3.0 g; 35 mmole) after a reaction time of 5 hours.

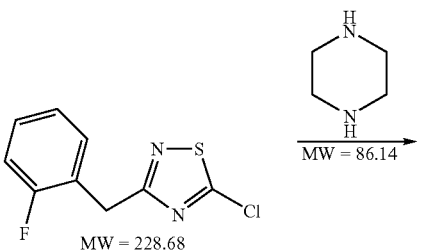

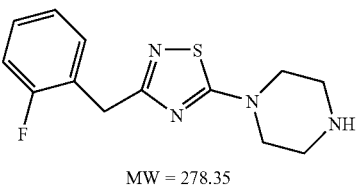

1.41 g (yield 77%) of 1-(3-benzyl-[1,2,4]thiadiazol-5-yl)-piperazine (example 19) was obtained starting from the 3-benzyl-5-chloro-[1,2,4]thiadiazole of example 7 (1.47 g; 7.0 mmole) and piperazine (3.0 g; 35 mmole) after a reaction time of 5 hours.

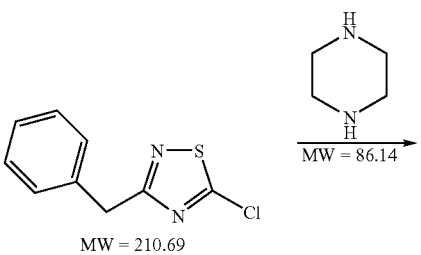

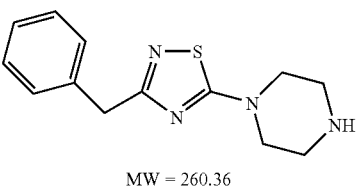

1.54 g (yield 80%) of 1-[3-(3-methyl-benzyl)-[1,2,4]thiadiazol-5-yl]-piperazine (example 20) was obtained starting from the 5-chloro-3-(3-methyl-benzyl)-[1,2,4]thiadiazole of example 8 (1.57 g; 7.0 mmole) and piperazine (3.0 g; 35 mmole) after a reaction time of 5 hours.

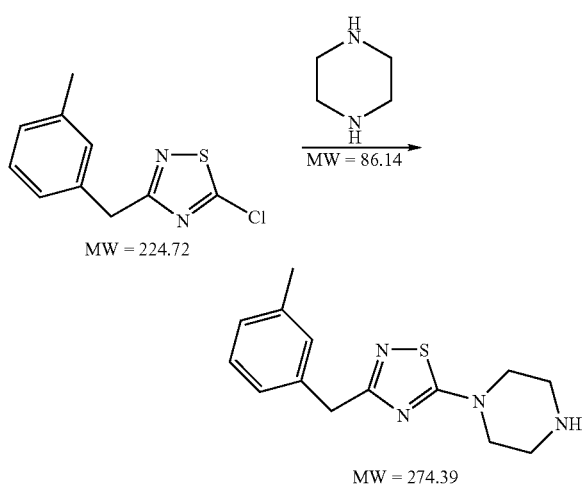

1.52 g (yield 79%) of 1-[3-(2-methyl-benzyl)-[1,2,4]thiadiazol-5-yl]-piperazine (example 21) was obtained starting from the 5-chloro-3-(2-methyl-benzyl)-[1,2,4]thiadiazole of example 9 (1.57 g; 7.0 mmole) and piperazine (3.0 g; 35 mmole) after a reaction time of 5 hours.

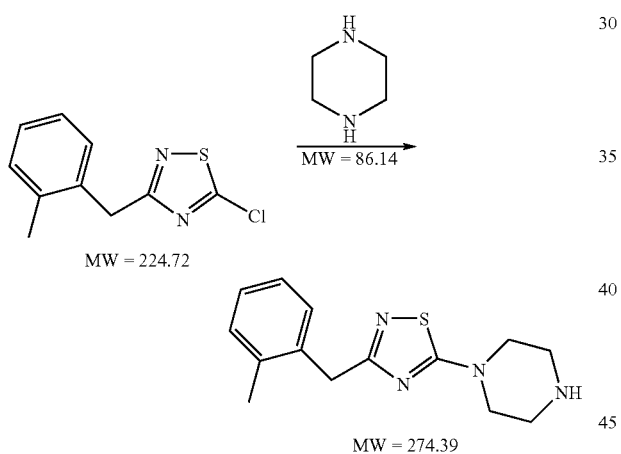

1.68 g (yield 83%) of 1-[3-(2-methoxy-benzyl)-[1,2,4]thiadiazol-5-yl]-piperazine (example 22) was obtained starting from the 5-chloro-3-(2-methoxy-benzyl)-[1,2,4]thiadiazole of example 10 (1.69 g; 7.0 mmole) and piperazine (3.0 g; 35 mmole) after a reaction time of 5 hours.

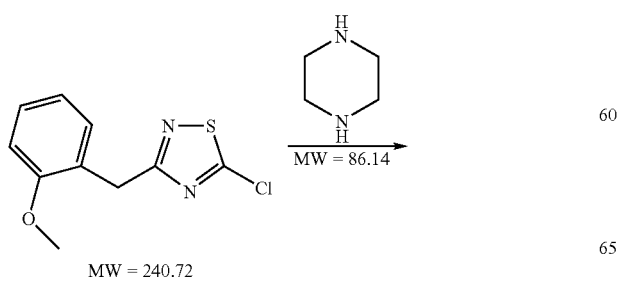

-continued

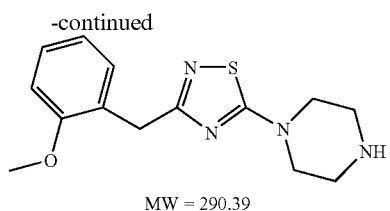

1.71 g (yield 84%) of 1-[3-(4-methoxy-benzyl)-[1,2,4]thiadiazol-5-yl]-piperazine (example 23) was obtained starting from the 5-chloro-3-(4-methoxy-benzyl)-[1,2,4]thiadiazole of example 11 (1.69 g; 7.0 mmole) and piperazine (3.0 g; 35 mmol) after a reaction time of 5 hours.

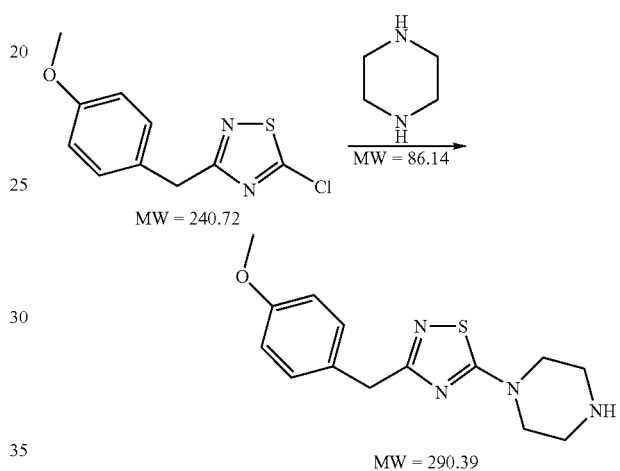

2.07 g (yield 86%) of 1-[3-(3-methyl-4-fluoro-benzyl)-[1,2,4]thiadiazol-5-yl]-piperazine (example 24) was obtained starting from the 5-chloro-3-(3-methyl-4-fluoro-benzyl)-[1,2,4]thiadiazole of example 12 (2.0 g; 8.24 mmole) and piperazine (3.55 g; 41.2 mmole) after a reaction time of 6 hours.

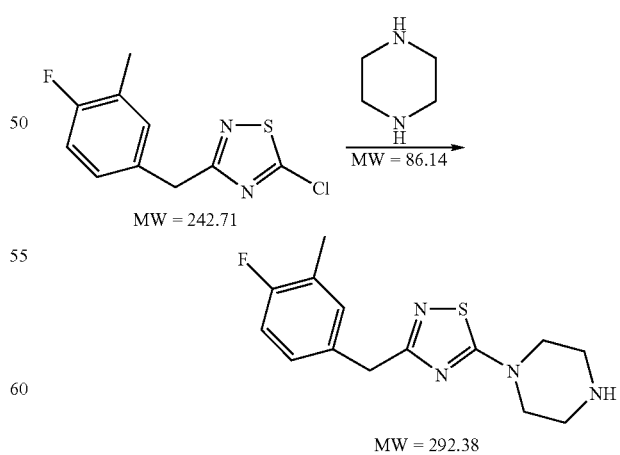

1.24 g (yield 88%) of 1-[3-(4-chloro-benzyl)-[1,2,4]thiadiazol-5-yl]-piperazine (example 25) was obtained starting from the 5-chloro-3-(4-chloro-benzyl)-[1,2,4]

thiadiazole of example 13 (1.18 g; 4.80 mmole) and piperazine (2.07 g; 24.0 mmole) after a reaction time of 6 hours.

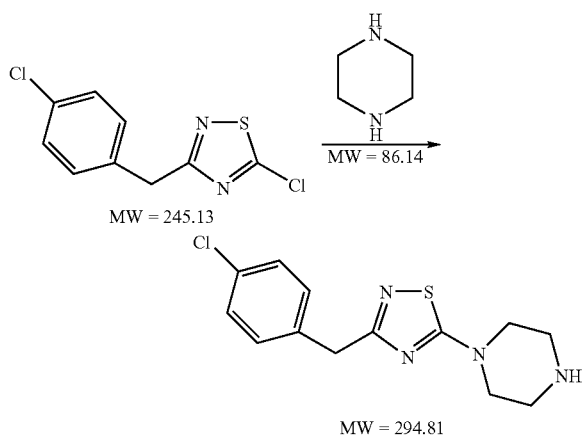

562 mg (yield 89%) of 1-[3-(3-methoxy-benzyl)-[1,2,4] thiadiazol-5-yl]-3-methylpiperazine (example 26) was obtained starting from the 5-chloro-3-(3-methoxy-benzyl)-[1,2,4]thiadiazole of example 4 (500 mg; 2.08 mmole) and 2-methylpiperazine (1.04 g; 10.4 mmole) after a reaction time of 6 hours.

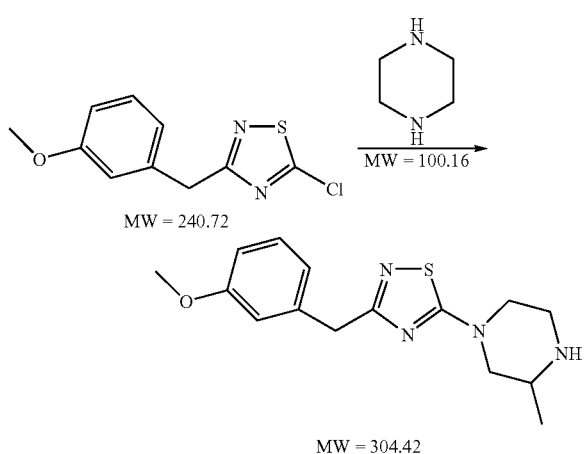

The following intermediate compounds are also synthesised, while using the above mentioned experimental conditions, from 2-methylpiperazine and the relevant 3-(substituted benzyl)-5-chloro-1,2,4-thiadiazole derivative from examples 2 to 13:
3-methyl-1-[3-(4-fluoro-benzyl)-[1,2,4]thiadiazol-5-yl]piperazine (example 27),
3-methyl-1-[3-(3-methoxy-benzyl)-[1,2,4]thiadiazol-5-yl]-piperazine (example 28),
3-methyl-1-[3-(3-fluoro-benzyl)-[1,2,4]thiadiazol-5-yl]-piperazine (example 29),
3-methyl-1-[3-(2-fluoro-benzyl)-[1,2,4]thiadiazol-5-yl]-piperazine (example 30),
3-methyl-1-(3-benzyl-[1,2,4]thiadiazol-5-yl)-piperazine (example 31),
3-methyl-1-[3-(3-methyl-benzyl)-[1,2,4]thiadiazol-5-yl]-piperazine (example 32),
3-methyl-1-[3-(2-methyl-benzyl)-[1,2,4]thiadiazol-5-yl]-piperazine (example 33),
3-methyl-1-[3-(2-methoxy-benzyl)-[1,2,4]thiadiazol-5-yl]-piperazine (example 34),
3-methyl-1-[3-(4-methoxy-benzyl)-[1,2,4]thiadiazol-5-yl]-piperazine (example 35),
3-methyl-1-[3-(3-methyl-4-fluoro-benzyl)-[1,2,4]thiadiazol-5-yl]-piperazine (example 36),
3-methyl-1-[3-(4-chloro-benzyl)-[1,2,4]thiadiazol-5-yl]-piperazine (example 37), and
3-methyl-1-[3-(3-methoxy-benzyl)-[1,2,4]thiadiazol-5-yl]-piperazine (example 38).

2.75 mg (yield 75%) of 1-[3-(3-methoxy-benzyl)-[1,2,4] thiadiazol-5-yl]-[1,4]diazepane (example 39) was obtained starting from the 5-chloro-3-(3-methoxy-benzyl)-[1,2,4]thiadiazole of example 4 (2.89 g; 12 mmoles) and homopiperazine (6.0 g; 60 mmoles) after a reaction time of 6 hours.

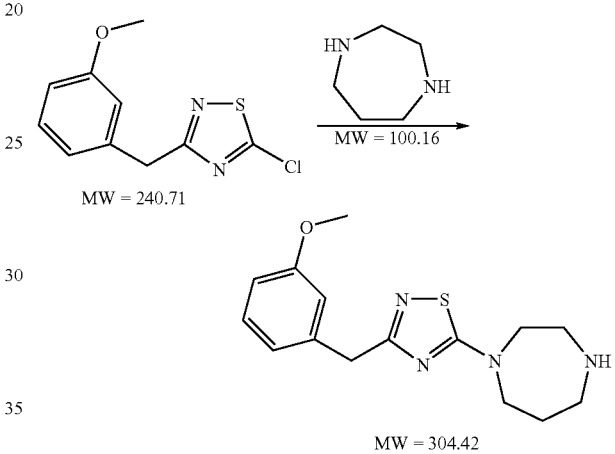

The following intermediate compounds are also synthesised from homopiperazine and the relevant 3-(substituted benzyl)-5-chloro-1,2,4-thiadiazole derivative from examples 2 to 13, while using the above mentioned experimental conditions:
1-[3-(4-methyl-benzyl)-[1,2,4]thiadiazol-5-yl]-1,4-diazepane (example 40),
1-[3-(4-fluoro-benzyl)-[1,2,4]thiadiazol-5-yl]-1,4-diazepane (example 41),
1-[3-(3-fluoro-benzyl)-[1,2,4]thiadiazol-5-yl]-1,4-diazepane (example 42),
1-[3-(2-fluoro-benzyl)-[1,2,4]thiadiazol-5-yl]-1,4-diazepane (example 43),
1-[3-(3-benzyl)-[1,2,4]thiadiazol-5-yl]-1,4-diazepane (example 44),
1-[3-(3-methyl-benzyl)-[1,2,4]thiadiazol-5-yl]-1,4-diazepane (example 45),
1-[3-(2-methyl-benzyl)-[1,2,4]thiadiazol-5-yl]-1,4-diazepane (example 46),
1-[3-(2-methoxy-benzyl)-[1,2,4]thiadiazol-5-yl]-1,4-diazepane (example 47),
1-[3-(4-methoxy-benzyl)-[1,2,4]thiadiazol-5-yl]-1,4-diazepane (example 48),
1-[3-(3-methyl-4-fluoro-benzyl)-[1,2,4]thiadiazol-5-yl]-1,4-diazepane (example 49), and
1-[3-(4-chloro-benzyl)-[1,2,4]thiadiazol-5-yl]-1,4-diazepane (example 50).

The following intermediate compounds are also synthesised from 2,5-dimethylpiperazine and the relevant 3-(substituted benzyl)-5-chloro-1,2,4-thiadiazole derivative from examples 2 to 13, while using the above mentioned experimental conditions:

2,5-dimethyl-1-[3-(4-fluoro-benzyl)-[1,2,4]thiadiazol-5-yl]-piperazine (example 51),
2,5-dimethyl-1-[3-(3-methoxy-benzyl)-[1,2,4]thiadiazol-5-yl]-piperazine (example 52),
2,5-dimethyl-1-[3-(3-fluoro-benzyl)-[1,2,4]thiadiazol-5-yl]-piperazine (example 53),
2,5-dimethyl-1-[3-(2-fluoro-benzyl)-[1,2,4]thiadiazol-5-yl]-piperazine (example 54),
2,5-dimethyl-1-(3-benzyl-[1,2,4]thiadiazol-5-yl)piperazine (example 55),
2,5-dimethyl-1-[3-(3-methyl-benzyl)-[1,2,4]thiadiazol-5-yl]-piperazine (example 56),
2,5-dimethyl-1-[3-(2-methyl-benzyl)-[1,2,4]thiadiazol-5-yl]-piperazine (example 57),
2,5-dimethyl-1-[3-(2-methoxy-benzyl)-[1,2,4]thiadiazol-5-yl]-piperazine (example 58),
2,5-dimethyl-1-[3-(4-methoxy-benzyl)-[1,2,4]thiadiazol-5-yl]-piperazine (example 59),
2,5-dimethyl-1-[3-(3-methyl-4-fluoro-benzyl)-[1,2,4]thiadiazol-5-yl]-piperazine (example 60),
2,5-dimethyl-1-[3-(4-chloro-benzyl)-[1,2,4]thiadiazol-5-yl]-piperazine (example 61), and
2,5-dimethyl-1-[3-(3-methoxy-benzyl)-[1,2,4]thiadiazol-5-yl]-piperazine (example 62).

The following intermediate compounds are also synthesised from 1-(2-aminoethyl)piperazine and the relevant 3-(substituted benzyl)-5-chloro-1,2,4-thiadiazole derivative from examples 2 to 13, while using the above mentioned experimental conditions:

2-{4-[3-(4-fluorobenzyl)-1,2,4-thiadiazol-5-yl]piperazin-1-yl}ethanamine (example 63),
2-{4-[3-benzyl-1,2,4-thiadiazol-5-yl]piperazin-1-yl}ethanamine (example 64),
2-{4-[3-(4-chlorobenzyl)-1,2,4-thiadiazol-5-yl]piperazin-1-yl}-ethanamine (example 65),
2-{4-[3-(4-methylbenzyl)-1,2,4-thiadiazol-5-yl]piperazin-1-yl}ethanamine (example 66),
2-{4-[3-(3-methoxybenzyl-1,2,4-thiadiazol-5-yl]piperazin-1-yl}ethanamine (example 67),
2-{4-[3-(3-fluorobenzyl)-1,2,4-thiadiazol-5-yl]piperazin-1-yl}ethanamine (example 68),
2-{4-[3-(2-fluorobenzyl)-1,2,4-thiadiazol-5-yl]piperazin-1-yl}ethanamine (example 69),
2-{4-[3-(3-methylbenzyl)-1,2,4-thiadiazol-5-yl]piperazin-1-yl}ethanamine (example 70),
2-{4-[3-(2-methylbenzyl)-1,2,4-thiadiazol-5-yl]piperazin-1-yl}ethanamine (example 71),
2-{4-[3-(2-methoxybenzyl)-1,2,4-thiadiazol-5-yl]piperazin-1-yl}ethanamine (example 72),
2-{4-[3-(4-methoxybenzyl)-1,2,4-thiadiazol-5-yl]piperazin-1-yl}ethanamine (example 73), and
2-{4-[3-(3-methyl-4-fluorobenzyl)-1,2,4-thiadiazol-5-yl]piperazin-1-yl}ethanamine (example 74).

In addition, the final compounds 113, 114 and 185 to 188 named and shown in table 1 below have been synthesised according to the above mentioned experimental conditions while starting from suitable N-substituted piperazine reagents (N-benzylpiperazine, N-(1,3-benzodioxol-5-ylmethyl)-piperazine, N-(2-methylphenyl)-piperazine, N-(2-ethoxyphenyl)-piperazine, N-(2-fluorophenyl)-piperazine and N-(3-trifluoromethylphenyl)-piperazine, respectively). However, for the isolation of the final desired product, the organic phase (DCM) was first washed with a 5% aqueous citric acid solution, water, a 5% aqueous Na2CO3 solution, and water, respectively. The organic phase was separated, dried over MgSO4, filtered and, evaporated to dryness. The residue was crystallised by diethyl ether to yield the desired compound.

Examples 75 to 182

Nucleophilic Replacement with Non-Cyclic Diamines onto 5-chloro-3-(substituted benzyl)-1,2,4-thiadiazole derivatives 1,2,4-thiadiazole intermediate derivatives represented by the structural formula (VI) have been obtained according to the following scheme 4, i.e. in a manner similar to step (c) of scheme 1, except that the diamine reagent is not a saturated or partly unsaturated heterocyclic diamine like a piperazine derivative, but a non-cyclic diamine.

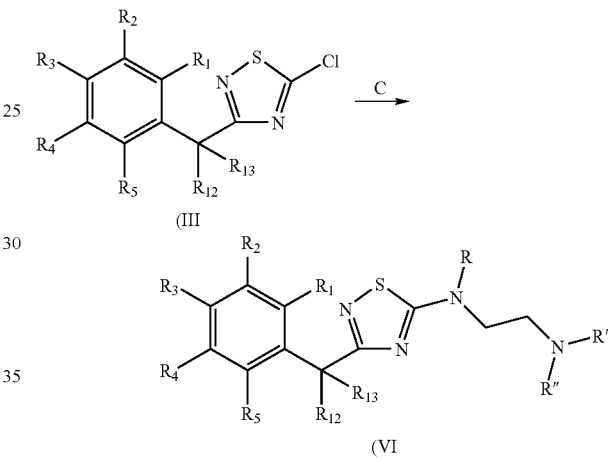

639 mg (yield 58%) of N-[3-(3-methoxy-benzyl)-[1,2,4]thiadiazol-5-yl]-ethane-1,2-diamine (example 75) was obtained starting from the 5-chloro-3-(3-methoxy-benzyl)-[1,2,4]thiadiazole (1.0 g; 4.15 mmole) of example 4 and ethylenediamine (1.25 g; 20.77 mmole) after a reaction time of 5 hours.

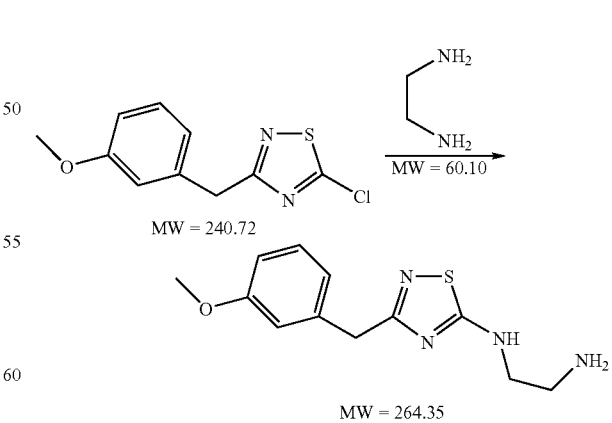

533 mg (yield 58%) of N-[3-(3-methoxy-benzyl)-[1,2,4]thiadiazol-5-yl]-propane-1,3-diamine (example 76) was obtained starting from the 5-chloro-3-(3-methoxy-benzyl)-[1,2,4]thiadiazole of example (800 mg; 3.23 mmole) and propylene diamine (1.23 g; 16.62 mmole) after a reaction time of 5 hours.

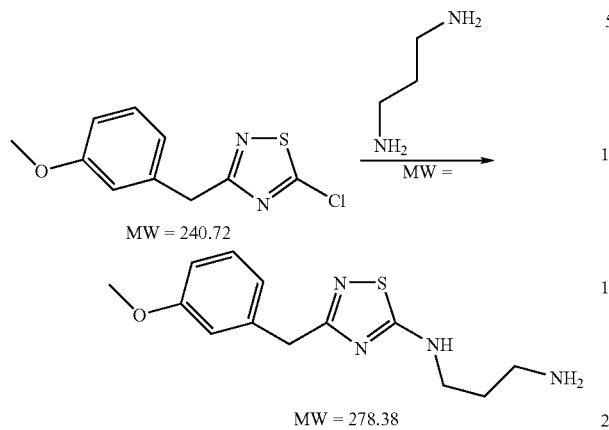

578 mg (yield 62%) of N-[3-(3-methoxy-benzyl)-[1,2,4]thiadiazol-5-yl]-N-methyl-ethane-1,2-diamine (example 77) was obtained starting from the 5-chloro-3-(3-methoxy-benzyl)-[1,2,4]thiadiazole of example 4 (800 mg; 3.23 mmole) and N-methyl-ethylenediamine (1.23 g; 16.6 mmol; 1.46 ml) after a reaction time of 100 minutes.

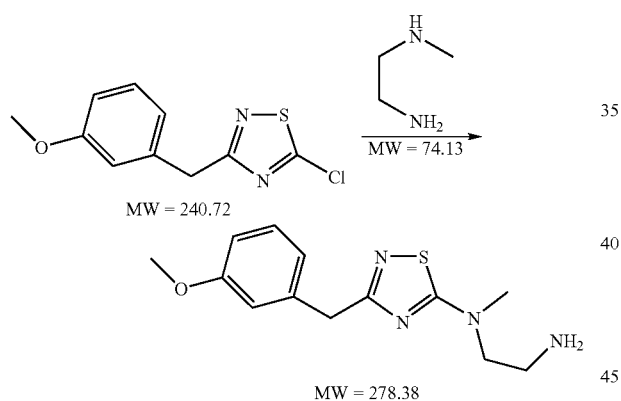

85 mg (yield 15%) of N-[3-(3-methoxy-benzyl)-[1,2,4]thiadiazol-5-yl]-N'-methyl-ethane-1,2-diamine (example 78) was prepared in two steps as follows. First, 786 mg (yield 100%) N-Boc-N-methyl-N'-[3-(3-methoxy-benzyl)-[1,2,4]thiadiazol-5-yl]-ethane-1,2-diamine was obtained according to the above procedure after a reaction time of 3 hours, starting from the 5-chloro-3-(3-methoxy-benzyl)-[1,2,4]thiadiazole (500 mg; 2.08 mmole) of example 4 and N-Boc-N-methyl-ethylenediamine. The obtained Boc-protected sample (786 mg; 2.08 mmole) was taken up into DCM (4 ml) and TFA (2 ml) was added dropwise to the mixture. The resulting solution was stirred for 3 hours at room temperature. The course of reaction was monitored by TLC using DCE-EtOH 10:1 as the eluent mixture. The pH of the reaction mixture was set to 11 by adding 10% aqueous sodium carbonate. The mixture was diluted with DCM (10 ml), the organic phase was separated, dried over MgSO$_4$, filtered and evaporated to dryness. The crude product was purified on a silica pad eluting with chloroform to yield the title product.

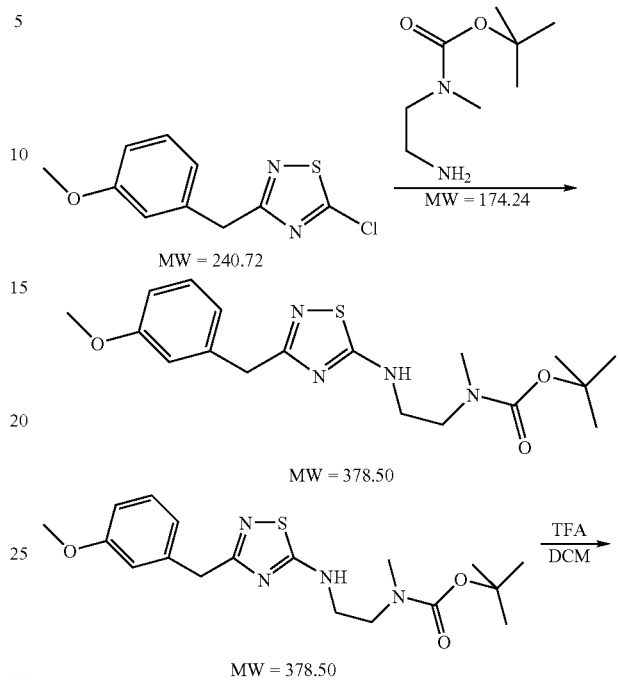

278 mg (yield 48%) of N-[3-(3-methoxy-benzyl)-[1,2,4]thiadiazol-5-yl]-propane-1,2-diamine (example 79) was obtained starting from the 5-chloro-3-(3-methoxy-benzyl)-[1,2,4]thiadiazole of example 4 (500 mg; 2.08 mmole) and 2-methyl-ethylenediamine (770 mg; 10.4 mmole) after a reaction time of 100 minutes.

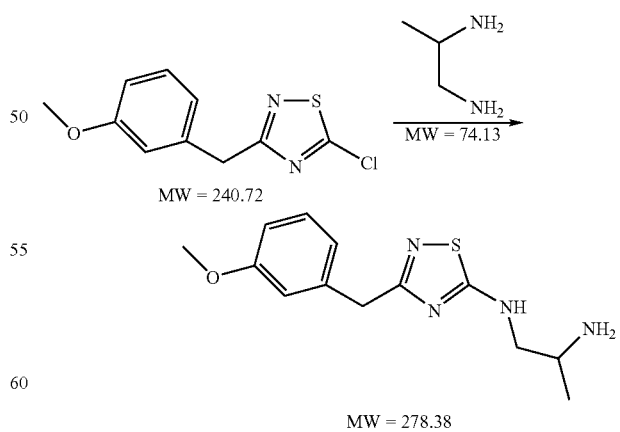

283 mg (yield 47%) of N-[3-(3-methoxy-benzyl)-[1,2,4]thiadiazol-5-yl]-N,N'-dimethyl-ethane-1,2-diamine (example 80) was obtained starting from 5-chloro-3-(3-methoxy-benzyl)-[1,2,4]thiadiazole (500 mg; 2.08 mmole) and N,N'-dimethyl-ethylenediamine (915 mg; 10.4 mmole) after a reaction time of 100 minutes.

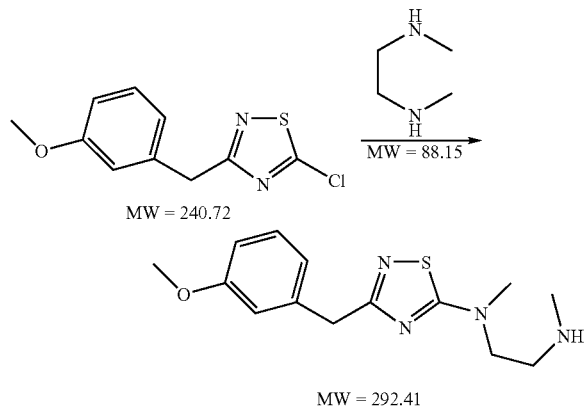

By analogy with example 75, the following intermediate compounds are also synthesised from ethylenediamine and the relevant 3-(substituted benzyl)-5-chloro-1,2,4-thiadiazole derivative from examples 2 to 13, while using the above mentioned experimental conditions:
N-[3-(4-methyl-benzyl)-[1,2,4]thiadiazol-5-yl]ethane-1,2-diamine (example 81),
N-[3-(4-fluoro-benzyl)-[1,2,4]thiadiazol-5-yl]-ethane-1,2-diamine (example 82),
N-[3-(3-fluoro-benzyl)-[1,2,4]thiadiazol-5-yl]-ethane-1,2-diamine (example 83),
N-[3-(2-fluoro-benzyl)-[1,2,4]thiadiazol-5-yl]-ethane-1,2-diamine (example 84),
N-[3-(3-benzyl)-[1,2,4]thiadiazol-5-yl]-ethane-1,2-diamine (example 85),
N-[3-(3-methyl-benzyl)-[1,2,4]thiadiazol-5-yl]-ethane-1,2-diamine (example 86),
N-[3-(2-methyl-benzyl)-[1,2,4]thiadiazol-5-yl]-ethane-1,2-diamine (example 87),
N-[3-(2-methoxy-benzyl)-[1,2,4]thiadiazol-5-yl]-ethane-1,2-diamine (example 88),
N-[3-(4-methoxy-benzyl)-[1,2,4]thiadiazol-5-yl]-ethane-1,2-diamine (example 89),
N-[3-(3-methyl-4-fluoro-benzyl)-[1,2,4]thiadiazol-5-yl]-ethane-1,2-diamine (example 90), and
N-[3-(4-chloro-benzyl)-[1,2,4]thiadiazol-5-yl]-ethane-1,2-diamine (example 91).

By analogy with example 76, the following intermediate compounds are also synthesised from propylenediamine and the relevant 3-(substituted benzyl)-5-chloro-1,2,4-thiadiazole derivative from examples 2 to 13, while using the above mentioned experimental conditions:
N-[3-(4-methyl-benzyl)-[1,2,4]thiadiazol-5-yl]-propane-1,3-diamine (example 92),
N-[3-(4-fluoro-benzyl)-[1,2,4]thiadiazol-5-yl]-propane-1,3-diamine (example 93),
N-[3-(3-fluoro-benzyl)-[1,2,4]thiadiazol-5-yl]-propane-1,3-diamine (example 94),
N-[3-(2-fluoro-benzyl)-[1,2,4]thiadiazol-5-yl]-propane-1,3-diamine (example 95),
N-[3-(3-benzyl)-[1,2,4]thiadiazol-5-yl]-propane-1,3-diamine (example 96),
N-[3-(3-methyl-benzyl)-[1,2,4]thiadiazol-5-yl]-propane-1,3-diamine (example 97),
N-[3-(2-methyl-benzyl)-[1,2,4]thiadiazol-5-yl]-propane-1,3-diamine (example 98),
N-[3-(2-methoxy-benzyl)-[1,2,4]thiadiazol-5-yl]-propane-1,3-diamine (example 99),
N-[3-(4-methoxy-benzyl)-[1,2,4]thiadiazol-5-yl]-propane-1,3-diamine (example 100),
N-[3-(3-methyl-4-fluoro-benzyl)-[1,2,4]thiadiazol-5-yl]-propane-1,3-diamine (example 101), and
N-[3-(4-chloro-benzyl)-[1,2,4]thiadiazol-5-yl]-propane-1,3-diamine (example 102).

By analogy with example 77, the following intermediate compounds are also synthesised from ethylenediamine and the relevant 3-(substituted benzyl)-5-chloro-1,2,4-thiadiazole derivative from examples 2 to 13, while using the above mentioned experimental conditions:
N-[3-(4-methyl-benzyl)-[1,2,4]thiadiazol-5-yl]-N-methyl-ethane-1,2-diamine (example 103),
N-[3-(4-fluoro-benzyl)-[1,2,4]thiadiazol-5-yl]-N-methyl-ethane-1,2-diamine (example 104),
N-[3-(3-fluoro-benzyl)-[1,2,4]thiadiazol-5-yl]-N-methyl-ethane-1,2-diamine (example 105),
N-[3-(2-fluoro-benzyl)-[1,2,4]thiadiazol-5-yl]-N-methyl-ethane-1,2-diamine (example 106),
N-[3-(3-benzyl)-[1,2,4]thiadiazol-5-yl]-N-methyl-ethane-1,2-diamine (example 107),
N-[3-(3-methyl-benzyl)-[1,2,4]thiadiazol-5-yl]-N-methyl-ethane-1,2-diamine (example 108),
N-[3-(2-methyl-benzyl)-[1,2,4]thiadiazol-5-yl]-N-methyl-ethane-1,2-diamine (example 109),
N-[3-(2-methoxy-benzyl)-[1,2,4]thiadiazol-5-yl]-N-methyl-ethane-1,2-diamine (example 110),
N-[3-(4-methoxy-benzyl)-[1,2,4]thiadiazol-5-yl]-N-methyl-ethane-1,2-diamine (example 111),
N-[3-(3-methyl-4-fluoro-benzyl)-[1,2,4]thiadiazol-5-yl]-N-methyl-ethane-1,2-diamine (example 112), and
N-[3-(4-chloro-benzyl)-[1,2,4]thiadiazol-5-yl]-N-methyl-ethane-1,2-diamine (example 113).

By analogy with example 78, the following intermediate compounds are also synthesised from ethylenediamine and the relevant 3-(substituted benzyl)-5-chloro-1,2,4-thiadiazole derivative from examples 2 to 13, while using the above mentioned experimental conditions:
N-[3-(4-methyl-benzyl)-[1,2,4]thiadiazol-5-yl]-N'-methyl-ethane-1,2-diamine (example 114),
N-[3-(4-fluoro-benzyl)-[1,2,4]thiadiazol-5-yl]-N'-methyl-ethane-1,2-diamine (example 115),
N-[3-(3-fluoro-benzyl)-[1,2,4]thiadiazol-5-yl]-N'-methyl-ethane-1,2-diamine (example 116),
N-[3-(2-fluoro-benzyl)-[1,2,4]thiadiazol-5-yl]-N'-methyl-ethane-1,2-diamine (example 117),
N-[3-(3-benzyl)-[1,2,4]thiadiazol-5-yl]-N'-methyl-ethane-1,2-diamine (example 118),
N-[3-(3-methyl-benzyl)-[1,2,4]thiadiazol-5-yl]-N'-methyl-ethane-1,2-diamine (example 119),
N-[3-(2-methyl-benzyl)-[1,2,4]thiadiazol-5-yl]-N'-methyl-ethane-1,2-diamine (example 120),
N-[3-(2-methoxy-benzyl)-[1,2,4]thiadiazol-5-yl]-N'-methyl-ethane-1,2-diamine (example 121),
N-[3-(4-methoxy-benzyl)-[1,2,4]thiadiazol-5-yl]-N'-methyl-ethane-1,2-diamine (example 122),
N-[3-(3-methyl-4-fluoro-benzyl)-[1,2,4]thiadiazol-5-yl]-N'-methyl-ethane-1,2-diamine (example 123), and
N-[3-(4-chloro-benzyl)-[1,2,4]thiadiazol-5-yl]-N'-methyl-ethane-1,2-diamine (example 124).

By analogy with example 79, the following intermediate compounds are also synthesised from propylenediamine and the relevant 3-(substituted benzyl)-5-chloro-1,2,4-thiadiazole derivative from examples 2 to 13, while using the above mentioned experimental conditions:

N-[3-(4-methyl-benzyl)-[1,2,4]thiadiazol-5-yl]-propane-1,2-diamine (example 125),
N-[3-(4-fluoro-benzyl)-[1,2,4]thiadiazol-5-yl]-propane-1,2-diamine (example 126),
N-[3-(3-fluoro-benzyl)-[1,2,4]thiadiazol-5-yl]-propane-1,2-diamine (example 127),
N-[3-(2-fluoro-benzyl)-[1,2,4]thiadiazol-5-yl]-propane-1,2-diamine (example 128),
N-[3-(3-benzyl)-[1,2,4]thiadiazol-5-yl]-propane-1,2-diamine (example 129),
N-[3-(3-methyl-benzyl)-[1,2,4]thiadiazol-5-yl]-propane-1,2-diamine (example 130),
N-[3-(2-methyl-benzyl)-[1,2,4]thiadiazol-5-yl]-propane-1,2-diamine (example 131),
N-[3-(2-methoxy-benzyl)-[1,2,4]thiadiazol-5-yl]-propane-1,2-diamine (example 132),
N-[3-(4-methoxy-benzyl)-[1,2,4]thiadiazol-5-yl]-propane-1,2-diamine (example 133),
N-[3-(3-methyl-4-fluoro-benzyl)-[1,2,4]thiadiazol-5-yl]-propane-1,2-diamine (example 134), and
N-[3-(4-chloro-benzyl)-[1,2,4]thiadiazol-5-yl]-propane-1,2-diamine (example 135).

By analogy with example 80, the following intermediate compounds are also synthesised from ethylenediamine and the relevant 3-(substituted benzyl)-5-chloro-1,2,4-thiadiazole derivative from examples 2 to 13, while using the above mentioned experimental conditions:
N-[3-(4-methyl-benzyl)-[1,2,4]thiadiazol-5-yl]-N,N'-dimethyl-ethane-1,2-diamine (example 136),
N-[3-(4-fluoro-benzyl)-[1,2,4]thiadiazol-5-yl]-N,N'-dimethyl-ethane-1,2-diamine (example 137),
N-[3-(3-fluoro-benzyl)-[1,2,4]thiadiazol-5-yl]-N,N'-dimethyl-ethane-1,2-diamine (example 138),
N-[3-(2-fluoro-benzyl)-[1,2,4]thiadiazol-5-yl]-N,N'-dimethyl-ethane-1,2-diamine (example 139),
N-[3-(3-benzyl)-[1,2,4]thiadiazol-5-yl]-N,N'-dimethyl-ethane-1,2-diamine (example 140),
N-[3-(3-methyl-benzyl)-[1,2,4]thiadiazol-5-yl]-N,N'-dimethyl-ethane-1,2-diamine (example 141),
N-[3-(2-methyl-benzyl)-[1,2,4]thiadiazol-5-yl]-N,N'-dimethyl-ethane-1,2-diamine (example 142),
N-[3-(2-methoxy-benzyl)-[1,2,4]thiadiazol-5-yl]-N,N'-dimethyl-ethane-1,2-diamine (example 143),
N-[3-(4-methoxy-benzyl)-[1,2,4]thiadiazol-5-yl]-N,N'-dimethyl-ethane-1,2-diamine (example 144),
N-[3-(3-methyl-4-fluoro-benzyl)-[1,2,4]thiadiazol-5-yl]-N,N'-dimethyl-ethane-1,2-diamine (example 145), and
N-[3-(4-chloro-benzyl)-[1,2,4]thiadiazol-5-yl]-N,N'-dimethyl-ethane-1,2-diamine (example 146).

The following intermediate compounds are also synthesised from N,N'-diethylethylenediamine and the relevant 3-(substituted benzyl)-5-chloro-1,2,4-thiadiazole derivative from examples 2 to 13, while using the above mentioned experimental conditions:
N-[3-(4-methyl-benzyl)-[1,2,4]thiadiazol-5-yl]-N,N'-diethyl-ethane-1,2-diamine (example 147),
N-[3-(4-fluoro-benzyl)-[1,2,4]thiadiazol-5-yl]-N,N'-diethyl-ethane-1,2-diamine (example 148),
N-[3-(3-methoxy-benzyl)-[1,2,4]thiadiazol-5-yl]-N,N'-diethyl-ethane-1,2-diamine (example 149),
N-[3-(3-fluoro-benzyl)-[1,2,4]thiadiazol-5-yl]-N,N'-diethyl-ethane-1,2-diamine (example 150),
N-[3-(2-fluoro-benzyl)-[1,2,4]thiadiazol-5-yl]-N,N'-diethyl-ethane-1,2-diamine (example 151),
N-[3-(3-benzyl)-[1,2,4]thiadiazol-5-yl]-N,N'-diethyl-ethane-1,2-diamine (example 152),
N-[3-(3-methyl-benzyl)-[1,2,4]thiadiazol-5-yl]-N,N'-diethyl-ethane-1,2-diamine (example 153),
N-[3-(2-methyl-benzyl)-[1,2,4]thiadiazol-5-yl]-N,N'-diethyl-ethane-1,2-diamine (example 154),
N-[3-(2-methoxy-benzyl)-[1,2,4]thiadiazol-5-yl]-N,N'-diethyl-ethane-1,2-diamine (example 155),
N-[3-(4-methoxy-benzyl)-[1,2,4]thiadiazol-5-yl]-N,N'-diethyl-ethane-1,2-diamine (example 156),
N-[3-(3-methyl-4-fluoro-benzyl)-[1,2,4]thiadiazol-5-yl]-N,N'-diethyl-ethane-1,2-diamine (example 157), and
N-[3-(4-chloro-benzyl)-[1,2,4]thiadiazol-5-yl]-N,N'-diethyl-ethane-1,2-diamine (example 158).

The following intermediate compounds are also synthesised from N,N'-diisopropylethylenediamine and the relevant 3-(substituted benzyl)-5-chloro-1,2,4-thiadiazole derivative from examples 2 to 13, while using the above mentioned experimental conditions:
N-[3-(4-methyl-benzyl)-[1,2,4]thiadiazol-5-yl]-N,N'-diisopropyl-ethane-1,2-diamine (example 159),
N-[3-(4-fluoro-benzyl)-[1,2,4]thiadiazol-5-yl]-N,N'-diisopropyl-ethane-1,2-diamine (example 160),
N-[3-(3-methoxy-benzyl)-[1,2,4]thiadiazol-5-yl]-N,N'-diisopropyl-ethane-1,2-diamine (example 161),
N-[3-(3-fluoro-benzyl)-[1,2,4]thiadiazol-5-yl]-N,N'-diisopropyl-ethane-1,2-diamine (example 162),
N-[3-(2-fluoro-benzyl)-[1,2,4]thiadiazol-5-yl]-N,N'-diisopropyl-ethane-1,2-diamine (example 163),
N-[3-(3-benzyl)-[1,2,4]thiadiazol-5-yl]-N,N'-diisopropyl-ethane-1,2-diamine (example 164),
N-[3-(3-methyl-benzyl)-[1,2,4]thiadiazol-5-yl]-N,N'-diisopropyl-ethane-1,2-diamine (example 165),
N-[3-(2-methyl-benzyl)-[1,2,4]thiadiazol-5-yl]-N,N'-diisopropyl-ethane-1,2-diamine (example 166),
N-[3-(2-methoxy-benzyl)-[1,2,4]thiadiazol-5-yl]-N,N'-diisopropyl-ethane-1,2-diamine (example 167),
N-[3-(4-methoxy-benzyl)-[1,2,4]thiadiazol-5-yl]-N,N'-diisopropyl-ethane-1,2-diamine (example 168),
N-[3-(3-methyl-4-fluoro-benzyl)-[1,2,4]thiadiazol-5-yl]-N,N'-diisopropyl-ethane-1,2-diamine (example 169), and
N-[3-(4-chloro-benzyl)-[1,2,4]thiadiazol-5-yl]-N,N'-diisopropyl-ethane-1,2-diamine (example 170).

The following intermediate compounds are also synthesised from 1,4-diaminobutane and the relevant 3-(substituted benzyl)-5-chloro-1,2,4-thiadiazole derivative from examples 2 to 13, while using the above mentioned experimental conditions:
N-[3-(4-methyl-benzyl)-[1,2,4]thiadiazol-5-yl]-butane-1,4-diamine (example 171),
N-[3-(4-fluoro-benzyl)-[1,2,4]thiadiazol-5-yl]-butane-1,4-diamine (example 172),
N-[3-(3-fluoro-benzyl)-[1,2,4]thiadiazol-5-yl]-butane-1,4-diamine (example 173),
N-[3-(2-fluoro-benzyl)-[1,2,4]thiadiazol-5-yl]-butane-1,4-diamine (example 174),
N-[3-(3-benzyl)-[1,2,4]thiadiazol-5-yl]-butane-1,4-diamine (example 175),
N-[3-(3-methyl-benzyl)-[1,2,4]thiadiazol-5-yl]-butane-1,4-diamine (example 176),
N-[3-(2-methyl-benzyl)-[1,2,4]thiadiazol-5-yl]-butane-1,4-diamine (example 177),
N-[3-(2-methoxy-benzyl)-[1,2,4]thiadiazol-5-yl]-butane-1,4-diamine (example 178),
N-[3-(4-methoxy-benzyl)-[1,2,4]thiadiazol-5-yl]-butane-1,4-diamine (example 179),
N-[3-(3-methyl-4-fluoro-benzyl)-[1,2,4]thiadiazol-5-yl]-butane-1,4-diamine (example 180), N-[3-(3-methoxy-benzyl)-[1,2,4]thiadiazol-5-yl]-butane-1,4-diamine (example 181), and N-[3-(4-chloro-benzyl)-[1,2,4]thiadiazol-5-yl]-butane-1,4-diamine (example 182).

The following intermediate compounds are also synthesised from 1,5-diaminopentane and the relevant 3-(substituted benzyl)-5-chloro-1,2,4-thiadiazole derivative from examples 2 to 13, while using the above mentioned experimental conditions:

N-[3-(4-methyl-benzyl)-[1,2,4]thiadiazol-5-yl]-pentane-1,5-diamine (example 183), N-[3-(4-fluoro-benzyl)-[1,2,4]thiadiazol-5-yl]-pentane-1,5-diamine (example 184), N-[3-(3-fluoro-benzyl)-[1,2,4]thiadiazol-5-yl]-pentane-1,5-diamine (example 185), N-[3-(2-fluoro-benzyl)-[1,2,4]thiadiazol-5-yl]-pentane-1,5-diamine (example 186), N-[3-(3-benzyl)-[1,2,4]thiadiazol-5-yl]-pentane-1,5-diamine (example 187), N-[3-(3-methyl-benzyl)-[1,2,4]thiadiazol-5-yl]-pentane-1,5-diamine (example 188), N-[3-(2-methyl-benzyl)-[1,2,4]thiadiazol-5-yl]-pentane-1,5-diamine (example 189), N-[3-(2-methoxy-benzyl)-[1,2,4]thiadiazol-5-yl]-pentane-1,5-diamine (example 190), N-[3-(4-methoxy-benzyl)-[1,2,4]thiadiazol-5-yl]-pentane-1,5-diamine (example 191), N-[3-(3-methyl-4-fluoro-benzyl)-[1,2,4]thiadiazol-5-yl]-pentane-1,5-diamine (example 192), N-[3-(3-methoxy-benzyl)-[1,2,4]thiadiazol-5-yl]-pentane-1,5-diamine (example 193), and N-[3-(4-chloro-benzyl)-[1,2,4]thiadiazol-5-yl]-pentane-1,5-diamine (example 194).

The following intermediate compounds are also synthesised from 1,6-diaminohexane and the relevant 3-(substituted benzyl)-5-chloro-1,2,4-thiadiazole derivative from examples 2 to 13, while using the above mentioned experimental conditions:

N-[3-(4-methyl-benzyl)-[1,2,4]thiadiazol-5-yl]-hexane-1,6-diamine (example 195), N-[3-(4-fluoro-benzyl)-[1,2,4]thiadiazol-5-yl]-hexane-1,6-diamine (example 196), N-[3-(3-fluoro-benzyl)-[1,2,4]thiadiazol-5-yl]-hexane-1,6-diamine (example 197), N-[3-(2-fluoro-benzyl)-[1,2,4]thiadiazol-5-yl]-hexane-1,6-diamine (example 198), N-[3-(3-benzyl)-[1,2,4]thiadiazol-5-yl]-hexane-1,6-diamine (example 199), N-[3-(3-methyl-benzyl)-[1,2,4]thiadiazol-5-yl]-hexane-1,6-diamine (example 200), N-[3-(2-methyl-benzyl)-[1,2,4]thiadiazol-5-yl]-hexane-1,6-diamine (example 201), N-[3-(2-methoxy-benzyl)-[1,2,4]thiadiazol-5-yl]-hexane-1,6-diamine (example 202), N-[3-(4-methoxy-benzyl)-[1,2,4]thiadiazol-5-yl]-hexane-1,6-diamine (example 203), N-[3-(3-methyl-4-fluoro-benzyl)-[1,2,4]thiadiazol-5-yl]-hexane-1,6-diamine (example 204), N-[3-(3-methoxy-benzyl)-[1,2,4]thiadiazol-5-yl]-hexane-1,6-diamine (example 205), and N-[3-(4-chloro-benzyl)-[1,2,4]thiadiazol-5-yl]-hexane-1,6-diamine (example 206).

Example 207

N-sulfonylation of 1,2,4-thiadiazole Intermediate Derivatives Represented by the Structural Formulae (IV) and (VI)

1,2,4-thiadiazole compounds represented by the structural formulae (A) to (F) have been obtained according to scheme 2 through reaction of a 1,2,4-thiadiazole intermediate derivative represented by the structural formula (IVA), (IVB) or (VI) with an aryl or heteroaryl sulfonyl halide such as, but not limited to, an arylsulfonyl chloride having the structural formula (VB). The reaction is more schematically shown in scheme 5 below for making 1,2,4-thiadiazole compounds represented by the structural formula (B), i.e. wherein $Ar^1$ is $R_1,R_2,R_3,R_4,R_5$-substituted phenyl, $R^2$ corresponds to $R_6$, X is $SO_2$, and $R^3$ is $R_7,R_8,R_9,R_{10},R_{11}$-substituted phenyl, using the following detailed procedure. 1,2,4-thiadiazole compounds represented by the structural formulae (C) and (F) have also been obtained by analogy to scheme 5 through the reaction of a 1,2,4-thiadiazole intermediate derivative represented by the structural formula (VI) with an aryl or heteroaryl sulfonyl halide such as an arylsulfonyl chloride having the structural formula (VB).

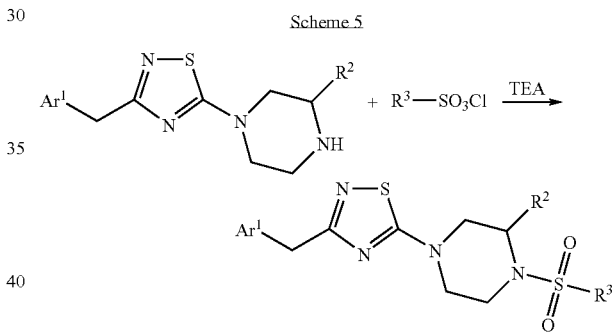

Scheme 5

To the substituted 1,2,4-thiadiazole intermediate derivative represented by the structural formula (IVA) or (IVB) or (VI) (250 μmole) dissolved in DCM (2-3 ml) TEA (500 μmole) was added. The reaction mixture was stirred at room temperature and then the appropriate aryl or heteroaryl sulfonyl chloride derivative (250 μmole) was added. The reaction mixture was further stirred at room temperature until total consumption of the starting products. The course of the reaction was monitored by TLC using dichloroethane (DCE)-EtOH 10:1 as an eluent mixture. The reaction time varied between 2 hours and 5 hours. When the reaction was complete DCM (2-3 ml) was added and the resulting solution was washed with a 5% aqueous citric acid solution (5 ml), water (5 ml), a 5% aqueous $Na_2CO_3$ solution, and water (5 ml), respectively. The organic phase was separated, dried over $MgSO_4$, filtered and, evaporated to dryness. The residue was crystallised by diethyl ether to yield the desired compound.

More specifically, the following compounds (wherein compound numbers refer to table 1 below) have been obtained while using the above-mentioned detailed procedure:

compound 60: 1-[4-methoxyphenylsulfonyl]-4-[3-(4-methylbenzyl)-1,2,4-thiadiazol-5-yl]-2-methylpiperazine: starting from 3-methyl-1-[3-(4-methyl-benzyl)-[1,2,4]

thiadiazol-5-yl]-piperazine (1.25 mmol) and 1 equivalent of 4-methoxy-phenylsulphonyl chloride, after 4 hours reaction time the title compound was obtained in 99% yield.

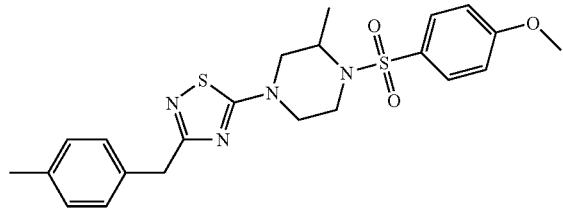

compound 74: 1-[4-methoxyphenylsulfonyl]-4-[3-(4-fluorobenzyl)-1,2,4-thiadiazol-5-yl]piperazine: starting from 400 mg 1-[3-(4-fluoro-benzyl)-[1,2,4]thiadiazol-5-yl]-piperazine (1.237 mmole) and 1 equivalent of 4-methoxy-phenylsulphonyl chloride, 453 mg of the title compound was obtained after 3 hours of reaction (70% yield).

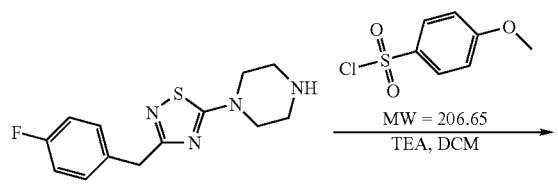

compound 44: 1-[3-methoxyphenylsulfonyl]-4-[3-(4-fluorobenzyl)-1,2,4-thiadiazol-5-yl]piperazine: starting from 80 mg 1-[3-(4-fluoro-benzyl)-[1,2,4]thiadiazol-5-yl]-piperazine (0.287 mmole) and 1 equivalent of 3-methoxyphenylsulfonyl chloride, 102 mg of the title compound was obtained after 4 hours of reaction in 79% yield.

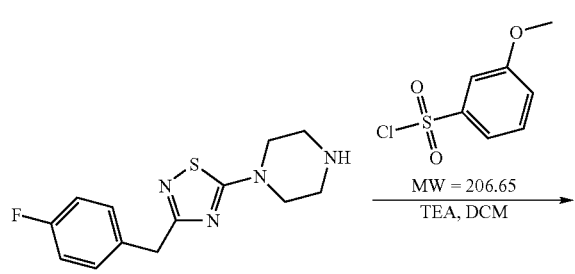

-continued

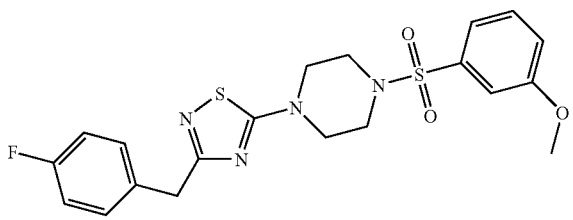

compound 53: 1-[4-methoxyphenylsulfonyl]-4-[3-(3-methoxybenzyl)-1,2,4-thiadiazol-5-yl]piperazine: starting from 150 mg 1-[3-(3-methoxybenzyl)-[1,2,4]thiadiazol-5-yl]-piperazine (0.517 mmol) and 1 equivalent of 4-methoxyphenylsulfonyl chloride, 156 mg of the title compound was obtained after 5 hours of reaction in 66% yield.

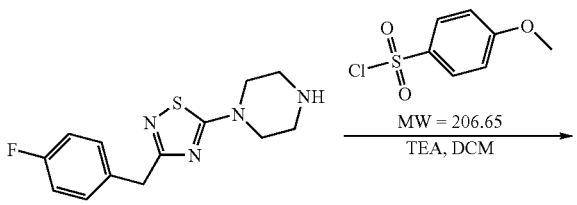

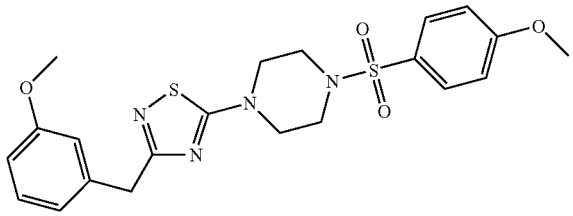

compound 192: 1-[4-methoxyphenylsulfonyl]-4-[3-(4-chloro-benzyl)-1,2,4-thiadiazol-5-yl]piperazine: starting from 1-[3-(4-chlorobenzyl)-[1,2,4]thiadiazol-5-yl]piperazine and 4-methoxyphenylsulfonyl chloride, 75 mg of the title compound was obtained after 2 hours of reaction in 48% yield.

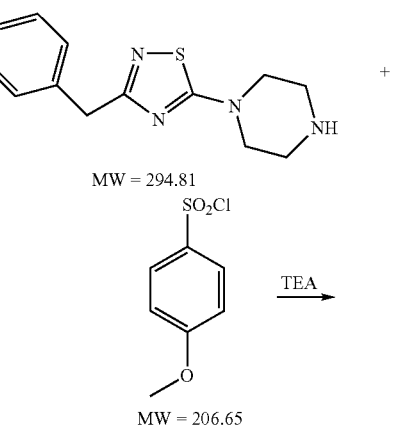

-continued

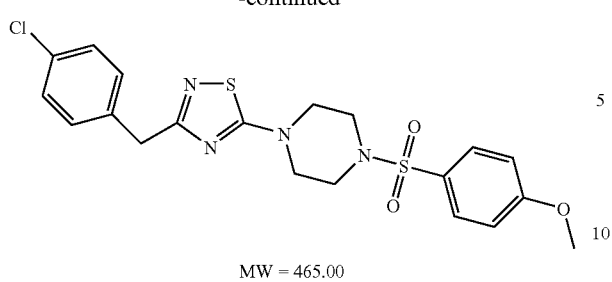

MW = 465.00 compound 193: 1-[4-methoxyphenylsulfonyl]-4-[3-(3-fluoro-benzyl)-1,2,4-thiadiazol-5-yl]piperazine: starting from 1-[3-(3-fluoro-benzyl)-[1,2,4]thiadiazol-5-yl]-piperazine and 4-methoxyphenylsulfonyl chloride, 118 mg of the title compound was obtained after 2 hours of reaction in 49% yield.

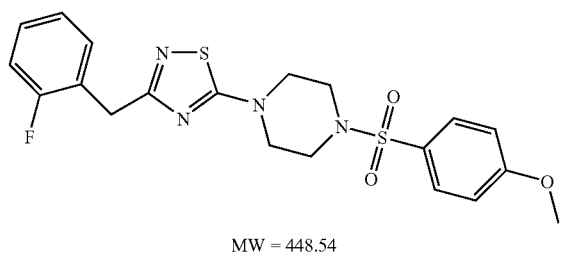

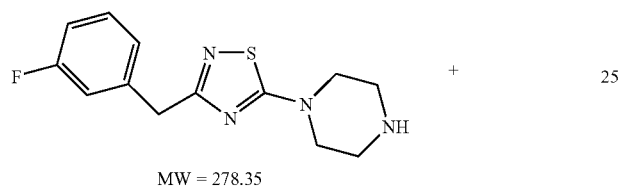

MW = 448.54 compound 194: 1-[4-methoxyphenylsulfonyl]-4-[3-(2-fluoro-benzyl)-1,2,4-thiadiazol-5-yl]piperazine: starting from 1-[3-(2-fluorobenzyl)-[1,2,4]thiadiazol-5-yl]-piperazine and 4-methoxyphenylsulfonyl chloride, 142 mg of the title compound was obtained after 2 hours of reaction in 59% yield.

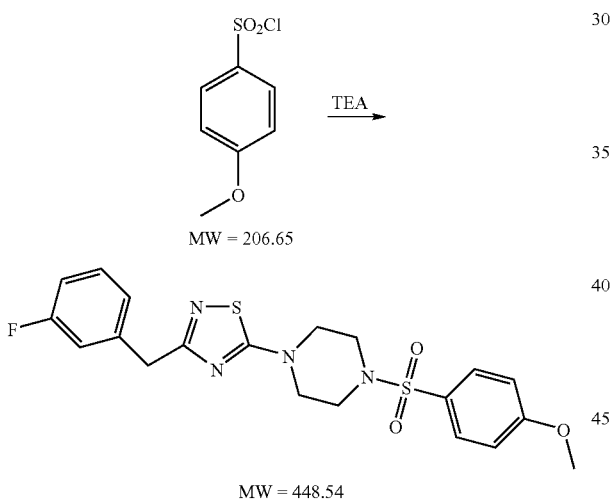

-continued

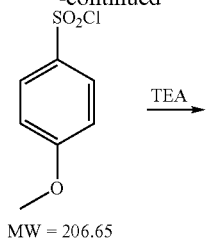

MW = 206.65

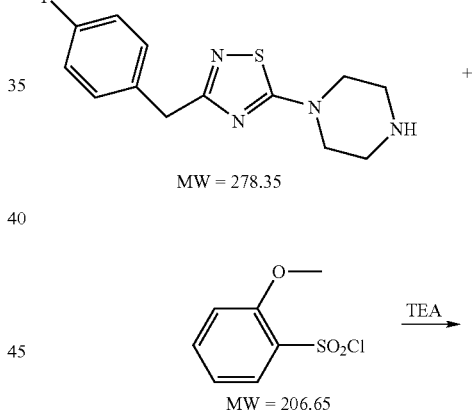

MW = 448.54 compound 195: 1-[4-methoxyphenylsulfonyl]-4-[3-(4-fluoro-benzyl)-1,2,4-thiadiazol-5-yl]piperazine: starting from 1-[3-(4-fluoro-benzyl)-[1,2,4]thiadiazol-5-yl]piperazine and 2-methoxyphenylsulfonyl chloride, 251 mg of the title compound was obtained (78% yield).

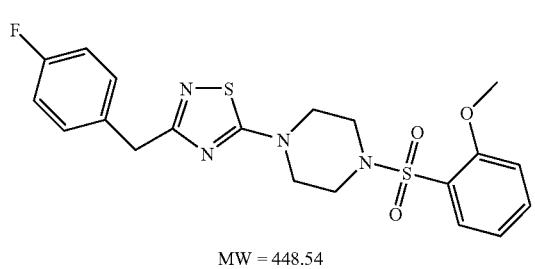

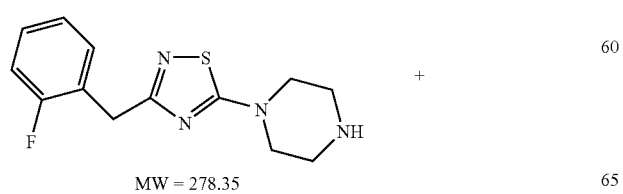

MW = 448.54 compound 196: 1-[4-ethoxyphenylsulfonyl]-4-[3-(4-fluoro-benzyl)-1,2,4-thiadiazol-5-yl]piperazine: starting from 1-[3-(4-fluoro-benzyl)-[1,2,4]thiadiazol-5-yl]-piperazine and 4-ethoxyphenylsulfonyl chloride, 125 mg of the title compound was obtained (50% yield) after 4 hours reaction time.

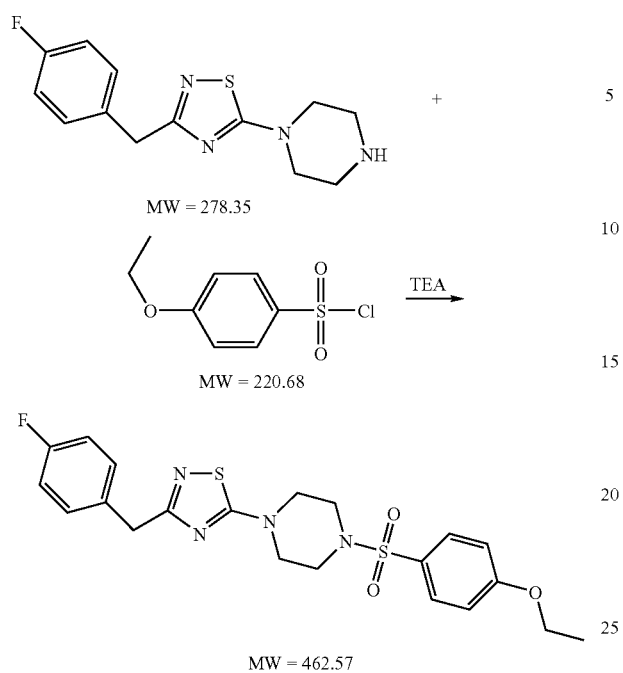

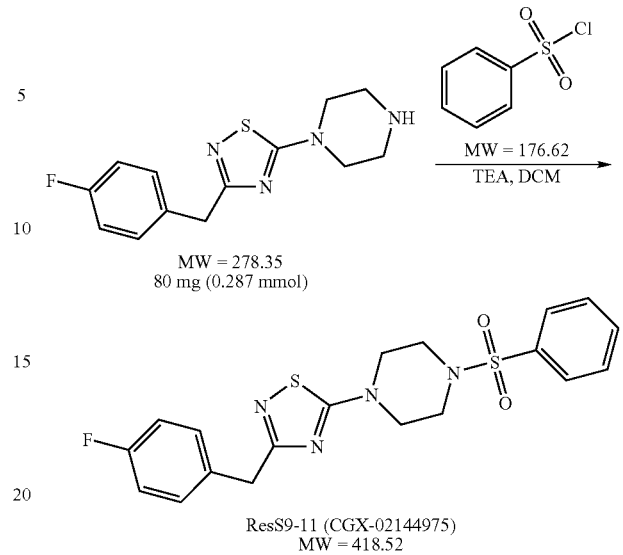

compound 197: 1-[4-ethylphenylsulfonyl]-4-[3-(4-fluoro-benzyl)-1,2,4-thiadiazol-5-yl]piperazine: starting from 1-[3-(4-fluoro-benzyl)-[1,2,4]thiadiazol-5-yl]-piperazine and 4-ethylphenylsulfonyl chloride, 158 mg of the title compound was obtained (66% yield) after 7 hours reaction time.

compound 199: 1-[4-methoxyphenylsulfonyl]-4-[3-benzyl-1,2,4-thiadiazol-5-yl]piperazine: starting from 1-[3-benzyl-[1,2,4]thiadiazol-5-yl]-piperazine and 4-methoxyphenylsulfonyl chloride, 170 mg of the title compound was obtained (69% yield) after 2 hours reaction time.

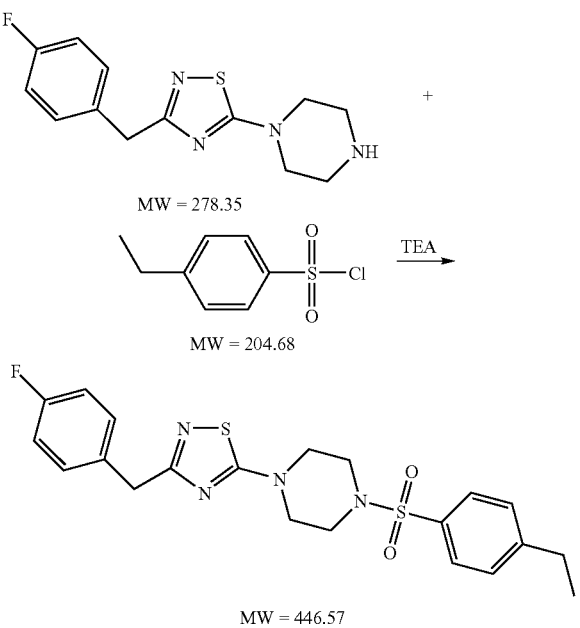

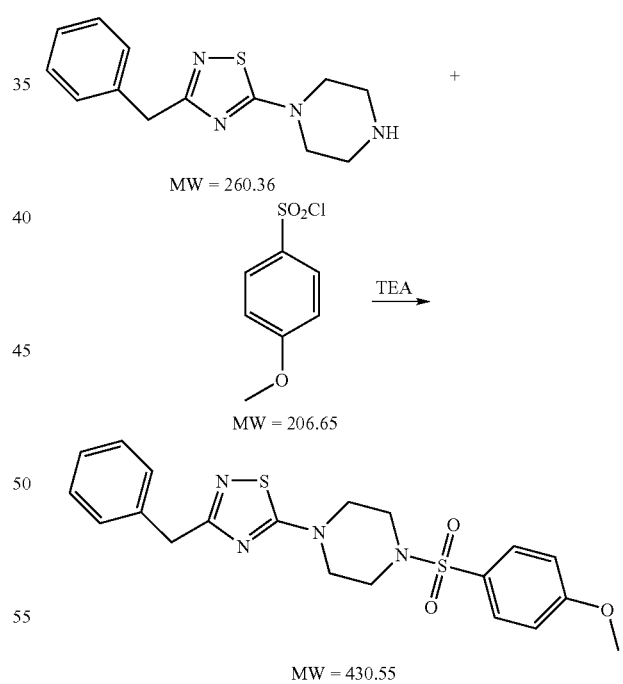

compound 198: 1-phenylsulfonyl-4-[3-(4-fluoro-benzyl)-1,2,4-thiadiazol-5-yl]piperazine: starting from 1-[3-(4-fluoro-benzyl)-[1,2,4]thiadiazol-5-yl]-piperazine and phenylsulfonyl chloride, 85 mg of the title compound was obtained (71% yield) after 5 hours reaction time.

compound 200: 1-(4-propionyloxy)benzenesulfonyl-4-[3-(4-fluoro-benzyl)-1,2,4-thiadiazol-5-yl]piperazine: starting from 1-[3-(4-fluoro-benzyl)-[1,2,4]thiadiazol-5-yl]-piperazine and 4-propionyloxybenzene-sulfonyl chloride, 90 mg of the title compound was obtained (20% yield) after 6 hours reaction time. The crude product was purified by column chromatography using chloroform as eluent.

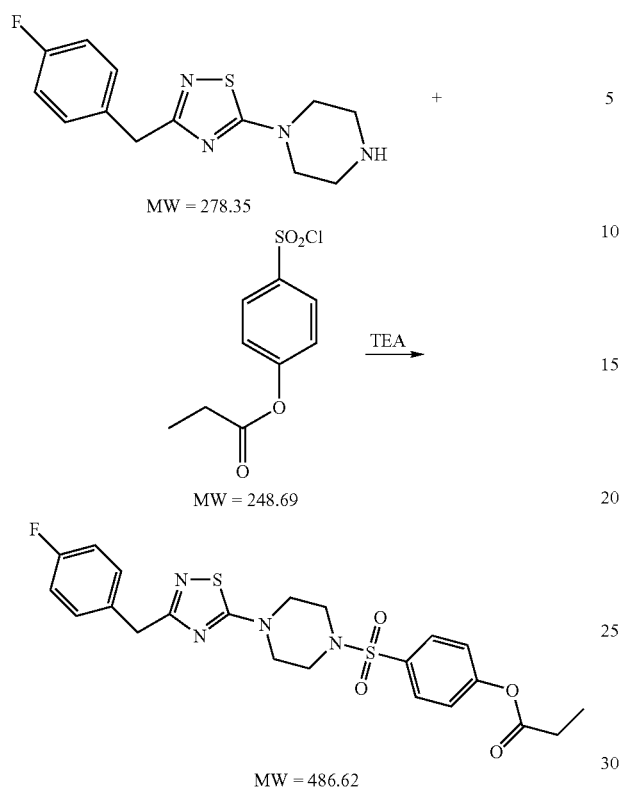

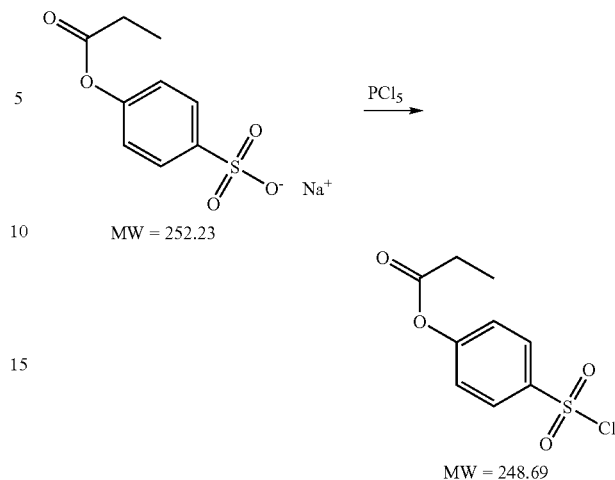

The sulfonic acid sodium salt (928 mg) and phosphorus pentachloride (766 mg; 3.68 mmole) were heated at 120° C. for 4 hours. The mixture was poured onto ice-water and the precipitated desired product (521 mg) was collected by filtration.

compound 201: 1-[4-methoxyphenylsulfonyl]-4-[3-(3-methyl-benzyl-1,2,4-thiadiazol-5-yl]piperazine: starting from 1-[3-(3-methyl-benzyl)-[1,2,4]thiadiazol-5-yl]-piperazine and 4-methoxyphenylsulfonyl chloride, 982 mg of the title compound was obtained (76% yield) after 5 hours reaction time.

For this purpose, 4-propionyloxybenzenesulfonyl chloride itself was made in two steps being schematically shown as follows:

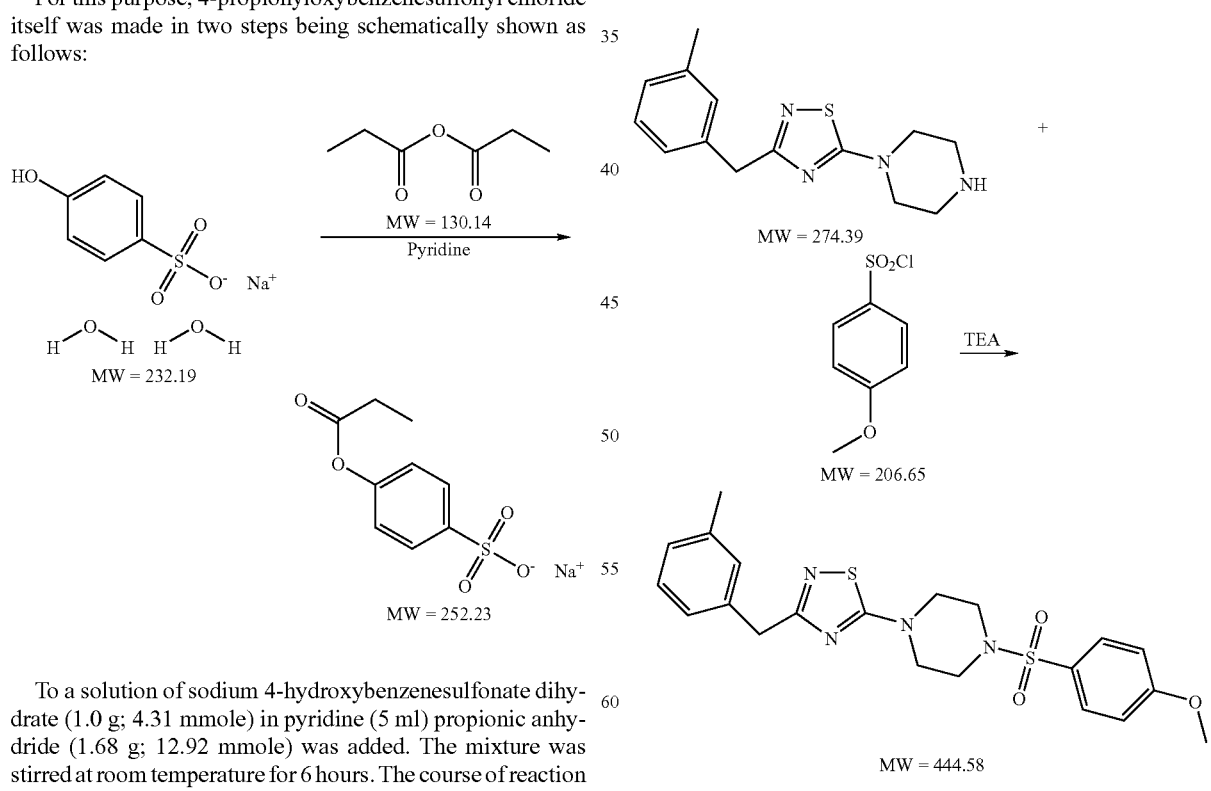

To a solution of sodium 4-hydroxybenzenesulfonate dihydrate (1.0 g; 4.31 mmole) in pyridine (5 ml) propionic anhydride (1.68 g; 12.92 mmole) was added. The mixture was stirred at room temperature for 6 hours. The course of reaction was monitored by TLC using DCE-EtOH 5:1 as an eluent mixture. The precipitated acylated product (928 mg; 3.68 mmole) was collected by filtration and dried in a vacuum desiccator.

compound 202: 1-[4-methoxyphenylsulfonyl]-4-[3-(2-methyl-benzyl-1,2,4-thiadiazol-5-yl]piperazine: starting from 1-[3-(2-methyl-benzyl)-[1,2,4]thiadiazol-5- yl]-piperazine and 4-methoxyphenylsulfonyl chloride, 159 mg of the title compound was obtained (65% yield) after 4 hours reaction time.

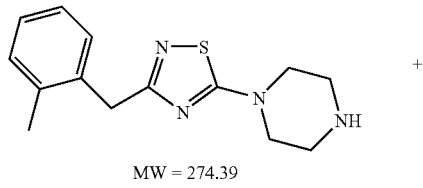

MW = 274.39

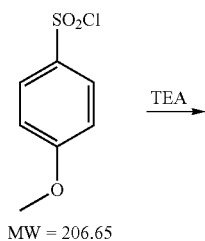

MW = 206.65

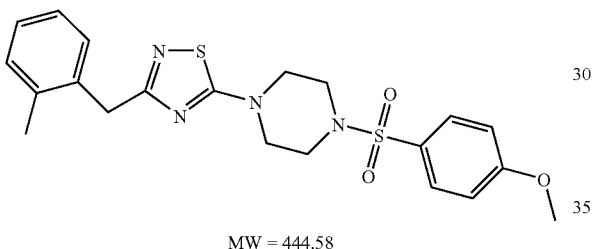

MW = 444.58 compound 203: 1-[4-methoxyphenylsulfonyl]-4-[3-(2-methoxy-benzyl-1,2,4-thiadiazol-5-yl]piperazine: starting from 1-[3-(2-methoxy-benzyl)-[1,2,4]thiadiazol-5-yl]piperazine and 4-methoxyphenylsulfonyl chloride, 61 mg of the title compound was obtained (26% yield) after 2 hours reaction time.

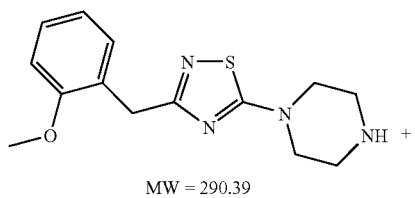

MW = 290.39

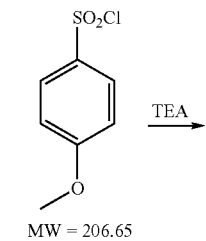

MW = 206.65

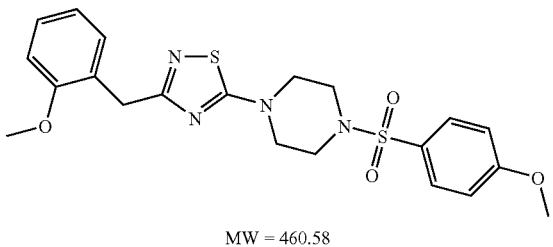

MW = 460.58 compound 204: 1-[4-methoxyphenylsulfonyl]-4-[3-(3-methyl-4-fluoro-benzyl-1,2,4-thiadiazol-5-yl]piperazine: starting from 1-[3-(3-methyl-4-fluoro-benzyl)-[1,2,4]thiadiazol-5-yl]-piperazine and 4-methoxyphenylsulfonyl chloride, 229 mg of the title compound was obtained (96% yield) after 6 hours reaction time.

MW = 292.38

MW = 206.65

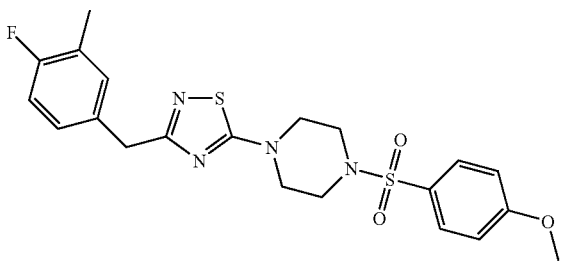

MW = 462.57 compound 205: 1-[4-methoxyphenylsulfonyl]-4-[3-(4-methoxy-benzyl-1,2,4-thiadiazol-5-yl]piperazine: starting from 1-[3-(4-methoxy-benzyl)-[1,2,4]thiadiazol-5-yl]-piperazine and 4-methoxyphenylsulfonyl chloride, 117 mg of the title compound was obtained (49% yield) after 4 hours reaction time.

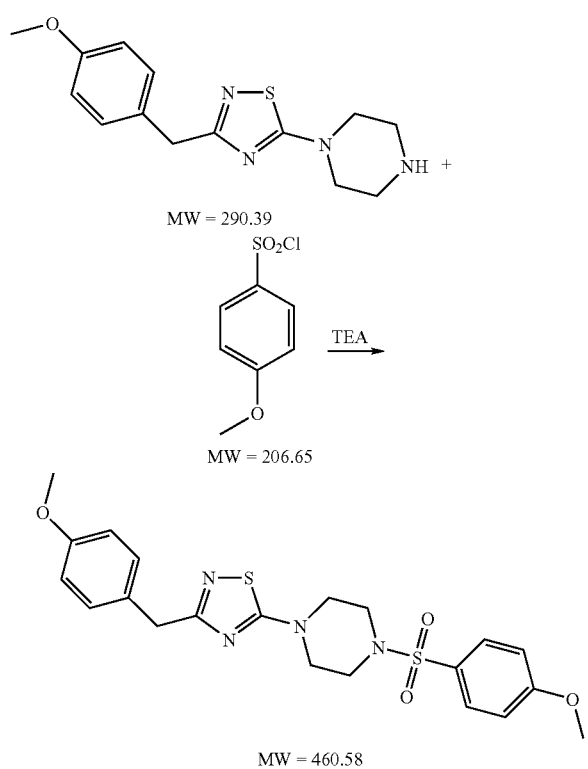

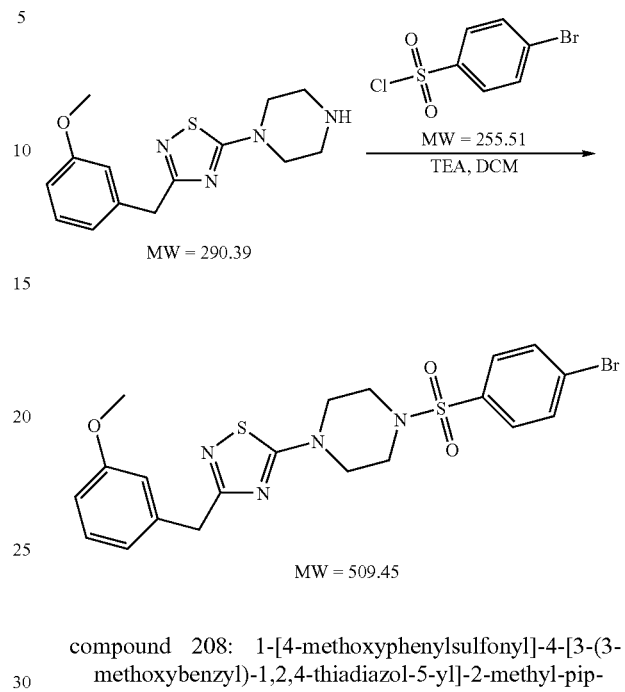

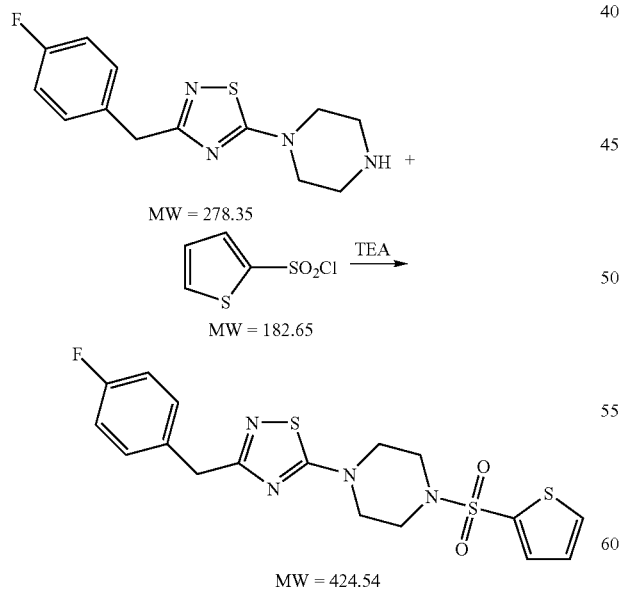

compound 206: 1-[2-thienylsulfonyl]-4-[3-(2-methyl-benzyl-1,2,4-thiadiazol-5-yl]piperazine: starting from 1-[3-(2-methyl-benzyl)-[1,2,4]thiadiazol-5-yl]-piperazine and 2-thienylsulfonyl chloride, 143 mg of the title compound was obtained (63% yield) after 4 hours reaction time.

compound 207: 1-[4-bromophenylsulfonyl]-4-[3-(3-methoxy-benzyl-1,2,4-thiadiazol-5-yl]piperazine: starting from 1-[3-(3-methoxy-benzyl)-[1,2,4]thiadia-zol-5-yl]-piperazine and 4-bromophenylsulfonyl chloride, 146 mg of the title compound was obtained (83% yield) after 4 hours reaction time.

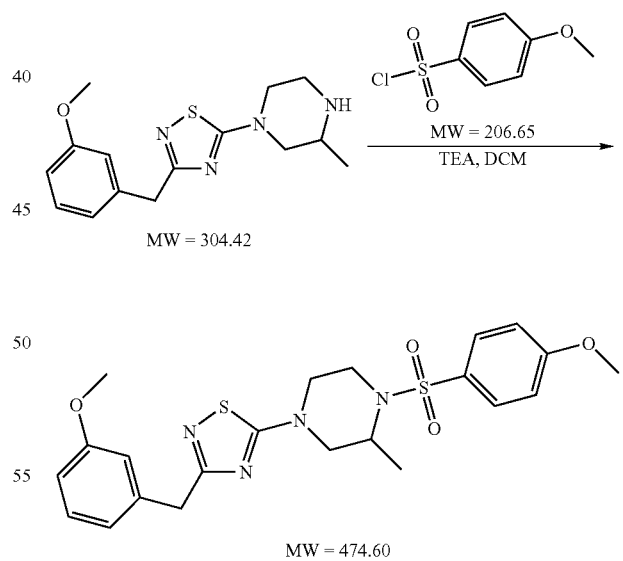

compound 208: 1-[4-methoxyphenylsulfonyl]-4-[3-(3-methoxybenzyl)-1,2,4-thiadiazol-5-yl]-2-methyl-piperazine: starting from 1-[3-(3-methoxybenzyl)-[1,2,4]thiadiazol-5-yl]-2-methyl-piperazine and 4-methoxyphenylsulfonyl chloride, 141 mg of the title compound was obtained after 2 hours of reaction in 90% yield.

compound 209: 1-N-[4-methoxyphenylsulfonyl]-N'-[3-(3-methoxybenzyl)-1,2,4-thiadiazol-5-yl]-ethane-1,2-diamine: starting from the N-[3-(3-methoxy-benzyl)-[1,2,4]thiadiazol-5-yl]-ethane-1,2-diamine of example 75 and 4-methoxyphenylsulfonyl chloride, 135 mg of the title compound was obtained after 5 hours of reaction in 82% yield.

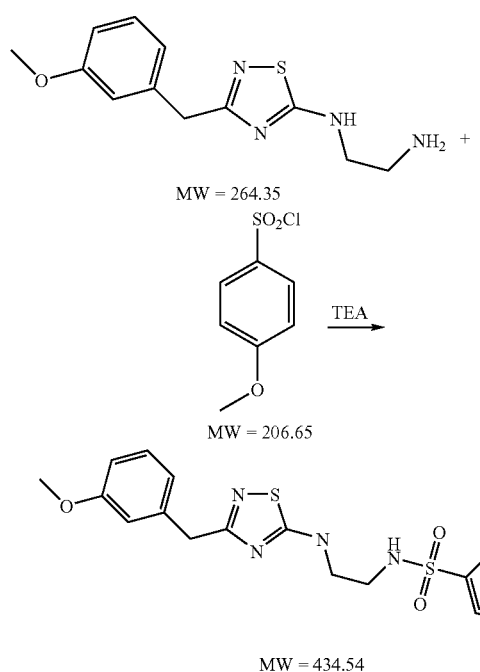

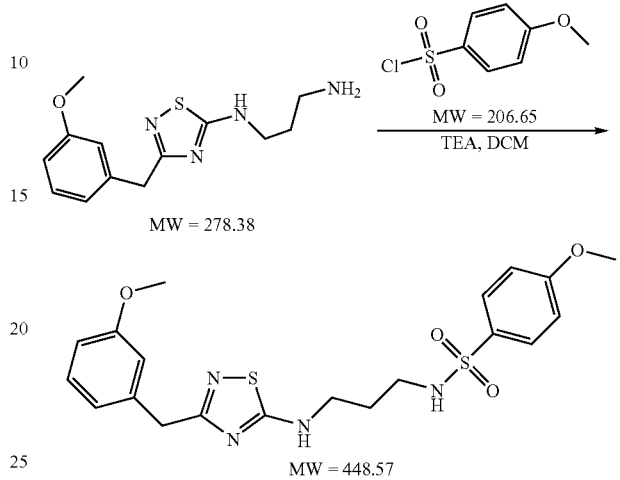

amine: starting from the N-[3-(3-methoxybenzyl)-[1,2,4]thiadiazol-5-yl]-propane-1,3-diamine of example 76 and 4-methoxyphenylsulfonyl chloride, 124 mg of the title compound was obtained after 5 hours of reaction in 77% yield.

compound 210: N-[4-methoxyphenylsulfonyl]-N'-[3-(3-methoxybenzyl)-1,2,4-thiadiazol-5-yl]-propane-1,2-diamine: starting from the N-[3-(3-methoxybenzyl)-[1,2,4]thiadiazol-5-yl]-propane-1,2-diamine of example 79 and 4-methoxyphenylsulfonyl chloride, 149 mg of the title compound was obtained after 2 hours of reaction in 92% yield.

compound 212: 1-[4-methoxyphenylsulfonyl]-4-[3-(3-methoxybenzyl)-1,2,4-thiadiazol-5-yl]diazepane: starting from the 1-[3-(3-methoxybenzyl)-[1,2,4]thiadiazol-5-yl]-diazepane of example 39 and 4-methoxyphenylsulfonyl chloride, 133 mg of the title compound was obtained after 2 hours of reaction in 85% yield.

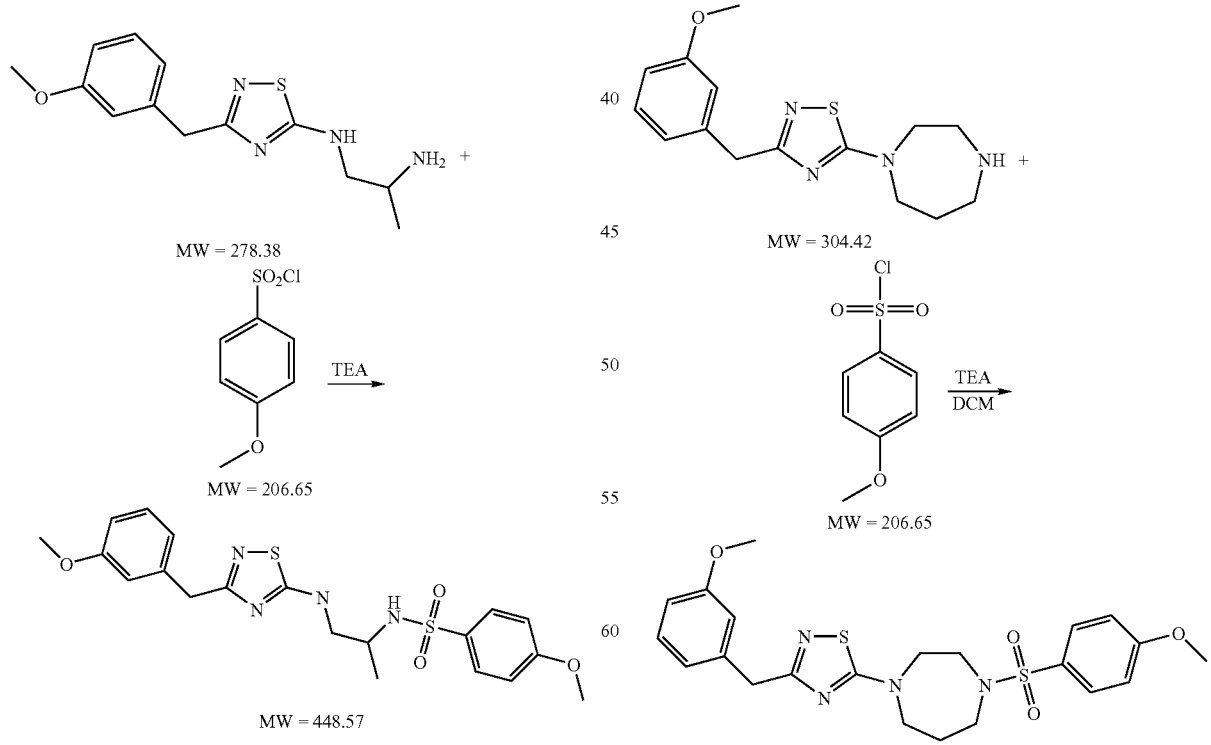

compound 211: N-[4-methoxyphenylsulfonyl]-N'-[3-(3-methoxybenzyl)-1,2,4-thiadiazol-5-yl]-propane-1,3-dicompound 213: N'-[4-methoxyphenylsulfonyl]-N-[3-(3-methoxybenzyl)-1,2,4-thiadiazol-5-yl]-N-methyl-ethane-1,2-diamine: starting from the N-[3-(3-methoxybenzyl)-[1,2,4]thiadiazol-5-yl]-N-methylethane-1,2-diamine of example 77 and 4-methoxyphenylsulfonyl chloride, 133 mg of the title compound was obtained after 2 hours of reaction in 83% yield.

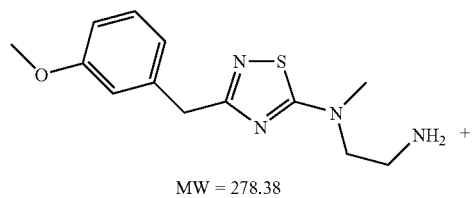

MW = 278.38

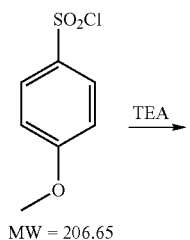

MW = 206.65

TEA

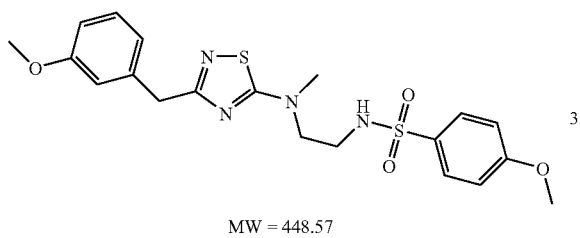

MW = 448.57 compound 214: N'-[4-methoxyphenylsulfonyl]-N-[3-(3-methoxybenzyl)-1,2,4-thiadiazol-5-yl]-N'-methyl-ethane-1,2-diamine: starting from the N-[3-(3-methoxybenzyl)-[1,2,4]thiadiazol-5-yl]-N'-methylethane-1,2-diamine of example 78 and 4-methoxyphenylsulfonyl chloride, 56 mg of the title compound was obtained after 2 hours of reaction in 41% yield.

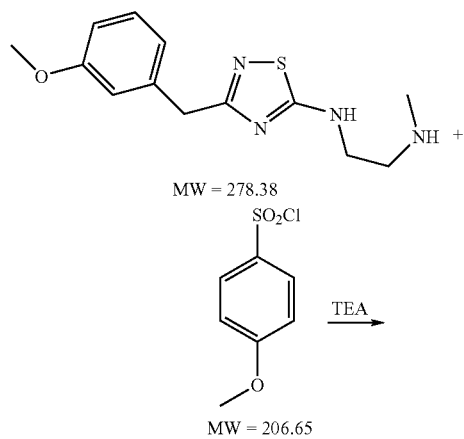

MW = 278.38

MW = 206.65

TEA

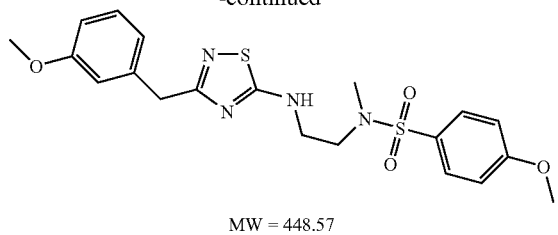

MW = 448.57 compound 215: N'-[4-methoxyphenylsulfonyl]-N-[3-(3-methoxybenzyl)-1,2,4-thiadiazol-5-yl]-N,N'-dimethyl-ethane-1,2-diamine: starting from the N-[3-(3-methoxybenzyl)-[1,2,4]thiadiazol-5-yl]-N,N'-dimethylethane-1,2-diamine of example 80 and 4-methoxyphenylsulfonyl chloride, 133 mg of the title compound was obtained after 2 hours of reaction in 84% yield.

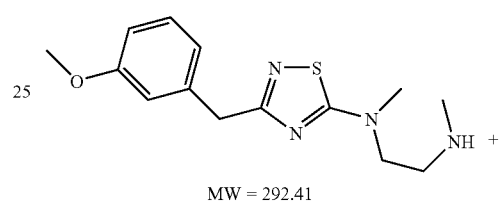

MW = 292.41

MW = 206.65

TEA

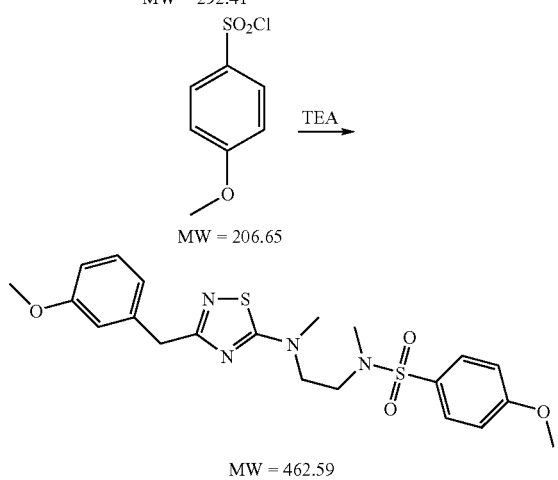

MW = 462.59

The final compounds 30 to 85 named and structurally shown in table 1 were also synthesised using these experimental conditions.

Example 208

N-acylation of 1,2,4-thiadiazole Intermediate Derivatives Represented by the Structural Formulae (IV) and (VI)

1,2,4-thiadiazole compounds represented by the structural formulae (A) to (F) have been obtained according to scheme 2 through reaction of a 1,2,4-thiadiazole intermediate derivative represented by a structural formula (IVA), (IVB) or (VI) with a suitable aryl or heteroaryl carbonyl chloride. A more detailed synthetic procedure is as follows.

To a 1,2,4-thiadiazole intermediate derivative produced according to a previous example (approximately 250 µmole) dissolved in DCM (2-3 ml) triethylamine (500 µmole) was added. The reaction mixture was stirred at room temperature and then the appropriate acyl chloride derivative (1.0 molar equivalent) was added. The reaction mixture was further stirred at room temperature until total consumption of the starting product. The course of the reaction was monitored by TLC using dichloroethane(DCE)-EtOH 10:1 as an eluent mixture. The reaction time varied between 2 hours and 5 hours. When the reaction was complete, DCM (2-3 ml) was added to it and the resulting solution was washed with a 5% aqueous citric acid solution (5 ml), water (5 ml), a 5% aqueous $Na_2CO_3$ solution, and water (5 ml), respectively. The organic phase was separated, dried over $MgSO_4$, filtered and, evaporated to dryness. The residue was crystallised by diethyl ether to yield the desired compound.

compound 1: 4-phenylacetyl-1-[3-(4-fluorobenzyl)-1,2,4-thiadiazol-5-yl]piperazine: starting from 1-[3-(4-fluorobenzyl)-1,2,4-thiadiazol-5-yl]piperazine and 1 equivalent of phenylacetyl chloride, the title compound was obtained.

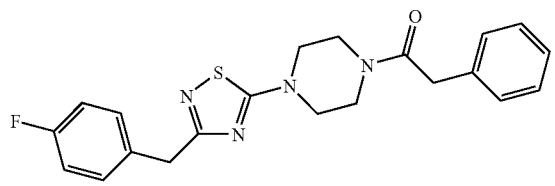

The title compound was characterised by mass spectrometry as follows: MS (m/z): 397.18 ([M+H]$^+$, 100).

compound 216: 4-(4-methoxybenzoyl)-1-[3-(3-methoxybenzyl)-1,2,4-thiadiazol-5-yl]piperazine: starting from 1-[3-(3-methoxybenzyl)-1,2,4-thiadiazol-5-yl]piperazine and 4-methoxybenzoyl chloride (59 mg; 344 μmole), 118 mg of the title compound (yield: 81%) was obtained after 2 hours reaction time.

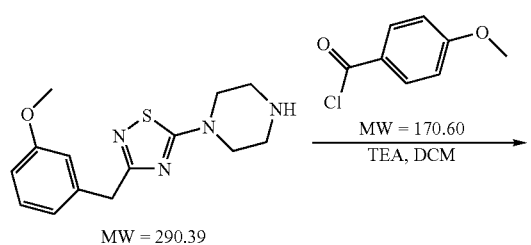

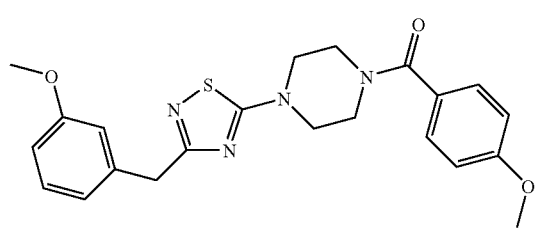

The final compounds 1-8, 86-90, 94-112, 115-184 and 189-191 named and structurally shown in table 1 were also synthesised using these experimental conditions.

Example 209

N-alkylation of 1,2,4-thiadiazole Intermediate Derivatives Represented by the Structural Formulae (IV) and (VI)

1,2,4-thiadiazole compounds represented by the structural formulae (A) to (F) have been obtained according to scheme 2 through reaction of a 1,2,4-thiadiazole intermediate derivative represented by the structural formula (IVA), (IVB) or (VI) with a suitable heteroaryl carboxylic acid halide, phenylalkyl carboxylic acid halide (such as the phenylacetyl chloride represented by the structural formula VC) or phenylalkenyl carboxylic acid halide or phenylalkynyl carboxylic acid halide. A suitable synthetic procedure is detailed as follows. The reaction can be performed starting from acid chlorides such as, but not limited to, phenylacetyl chloride, 2-phenylbutyric acid chloride, 3-phenylbutyric acid chloride, 4-phenylbutyric acid chloride, 2-phenylpropionic acid chloride, hydrocinnamoyl chloride, 5-phenylvaleric acid chloride, cinnamoyl chloride, phenylpropiolic acid chloride, styrylacetic acid chloride and the like.

To the substituted a 1,2,4-thiadiazole intermediate derivative (approximately 250 μmole) dissolved in DCM (2-3 ml), triethylamine (2.0 molar equivalent) was added. The reaction mixture was stirred at room temperature and then the appropriate phenylalkyl or phenylalkenyl or phenylalkynyl carboxylic acid chloride derivative (1.0 molar equivalent) was added. The reaction mixture was further stirred at room temperature until total consumption of the starting intermediate. The course of reaction was monitored by TLC using dichloroethane(DCE)-EtOH 10:1 as an eluent mixture. The reaction time varied between 3 and 5 hours. When the reaction was complete, DCM (2-3 ml) was added to it and the resulting solution was washed with 5% aqueous citric acid solution (5 ml), water (5 ml), 5% aqueous $Na_2CO_3$ solution, and water (5 ml), respectively. The organic phase was separated, dried over $MgSO_4$, filtered and, evaporated to dryness. The residue was crystallized by diethyl ether to yield the desired compound.

The final compounds 91-93 (starting from cinnamoyl chloride) and 113-114 named and structurally shown in table 1 were synthesised using these experimental conditions.

Example 210

Urea-Linkage and Thiourea-Linkage Formation onto 1,2,4-thiadiazole Intermediate Derivatives Represented by the Structural Formulae (IV) and (VI)

To a solution of an aryl isocyanate (represented by the structural formula V-E), heteroaryl isocyanate, aryl isothiocyanate or heteroaryl isothiocyanate (approximately 250 μmole) in tetrahydrofuran with a trace of DMF (2-3 ml) diisopropylethyl amine (2.2 molar equivalent) was added. Subsequently, 1 molar equivalent of the substituted 1,2,4-thiadiazole intermediate derivative represented by a structural formulae (IVA), (IVB) or (VI) was added. The reaction mixture was stirred at room temperature until total consumption of the starting intermediate. The course of reaction was monitored by TLC using dichloroethane (DCE)-EtOH 10:1 as an eluent mixture. Suitable reaction times were between 3 and 5 hours. When reaction was completed, the reaction mixture was evaporated until almost dry. DCM (2-3 ml) was added to it and the resulting mixture was washed with a 5% aqueous citric acid solution (5 ml), water (5 ml), a 5% aqueous $Na_2CO_3$ solution, and water (5 ml), respectively. The organic phase was separated, dried over MgSO$_4$, filtered and, evaporated to dryness. The residue was crystallised by diethyl ether to yield the desired compound. The following final compounds 9 to 29 of the invention were synthesised using these experimental conditions.

Example 211

Synthesis of 1-(4-hydroxybenzenesulfonyl)-4-[3-(4-fluoro-benzyl)-1,2,4-thiadiazol-5-yl]piperazine 1-(4-propionyloxy)benzenesulfonyl-4-[3-(4-fluoro-benzyl)-1,2,4-thiadiazol-5-yl]piperazine from a previous example (compound 200) was further chemically modified according to the following scheme:

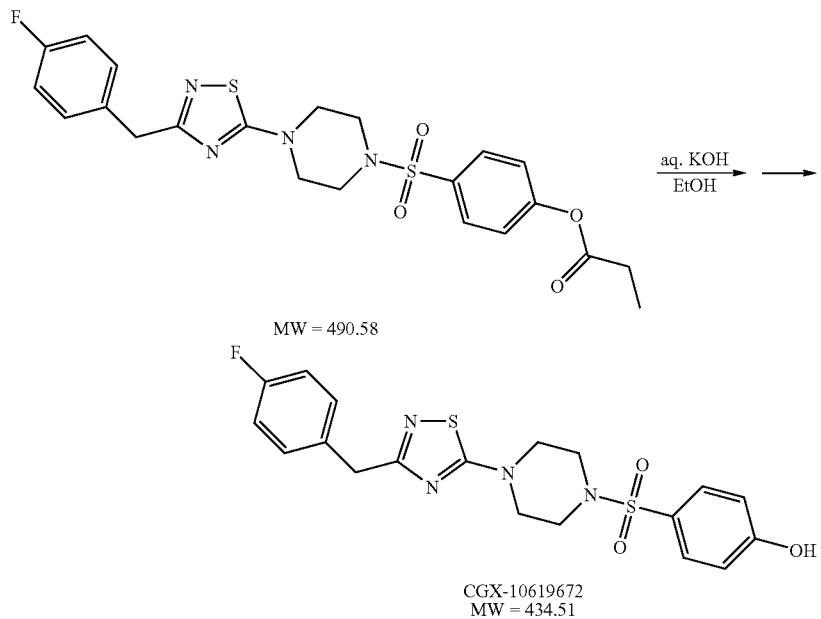

More specifically, to a solution of the starting 1,2,4-thiadiazolyl derivative (80 mg; 163 μmole) in EtOH (1 ml) KOH (18 mg; 326 μmole) and a few drops of water were added. The mixture was stirred at room temperature for 80 minutes and the course of reaction was monitored by TLC using DCE-EtOH 10:1 as an eluent mixture. After the reaction was completed, the reaction mixture was evaporated to dryness. The residue was dissolved in a minimal amount of water and pH was set at 5 by the dropwise addition of 5% aqueous HCl. The precipitate was collected by filtration and dried in a vacuum dessiccator until weight remained constant, thus resulting in 16 mg (yield: 23%) of the pure desired 1-(4-hydroxybenzenesulfonyl)-4-[3-(4-fluoro-benzyl)-1,2,4-thiadiazol-5-yl]piperazine (compound 217).

Example 212

Construction of an α-Synuclein Over-Expressing Cell Line

An α-synuclein expression plasmid was constructed by sub-cloning the NcoI/XhoI fragment from 212T-SYN(WT) (Griffioen et al., *Biochem Biophys Acta* (2006) 1762(3):312-318) containing the cDNA of human wild type α-synuclein correspondingly into a standard mammalian expression vector pcDNA3.1 (Invitrogen) resulting into the plasmid pcDNA3.1-SYNwt. Plasmids pcDNA3.1 and pcDNA3.1-SYNwt were transfected to human neuroblastoma cells (ATCC No. CRL-2267) and independent clonal lines with the plasmids stably integrated into the genome were selected. These resulted in cell lines named M17 (transfected with pcDNA3.1) and M17-SYNwt (transfected with pcDNA3.1-SYNwt). Over-expression of α-synuclein in M17-SYNwt cell lines was confirmed by Western analysis.

Example 213

Use of α-Synuclein Expressing Cells as a Model for Neuronal Degradation

Due to the high levels of α-synuclein M17-SYNwt cells are exquisitely sensitivity to paraquat, a well-known risk factor of synuclein-dependent neuronal degeneration. In degenerated or dead cells lactate dehydrogenase (LDH) is leaked out of the cells into the extracellular environment due to a loss of plasma-membrane integrity. This principle was used to determine cytotoxicity by quantifying the level of leaked LDH into the growth medium.

The detailed method for determining α-synuclein cytotoxicity was as follows: From appropriate precultures of M17 and M17-SYN cells were seeded at 50,000 cells/cm$^2$ in Optimem Reduced Serum without phenol red (available from InVitrogen, Cat. 31985-047) supplemented with 5% fetal calf serum, 1 mM sodium pyruvate, 1× non-essential amino acids, 500 μg/ml G418 0,5× antibiotic/antimycotic. After 3 hours of incubation at 37° C./5% CO$_2$ paraquat was added to the cells (final concentration of 32 mM), together with the test compound and the cells were further incubated for 40 hours. Subsequently, LDH activity was determined using Promega Cytotox 96 Non-Radioactive cytotoxicity assay, (Cat. G1780) according the instructions of the supplier.

FIG. 1 shows that treatment of M17-SYNwt cells, but not of M17 cells with paraquat led to a relatively high level of LDH leaked into the medium demonstrating that α-synuclein mediates cellular degeneration or cell death in response to paraquat.

Example 214

Use of α-Synuclein Expressing Cells in Screening Exemplary Compounds for Synuclein-Mediated Toxicity α-synuclein expressing neuroblastoma cells made it possible to assess the ability of compounds of the invention to counteract α-synuclein cytotoxicity. Active inhibitors of α-synuclein cytotoxicity were found to provoke a decrease of LDH leakage in paraquat-treated M17-SYNwt cells. Since this method monitors leaked LDH from degenerated or dead cells only non-toxic compounds will be identified as active inhibitors of α-synuclein-mediated cytotoxicity. Lack of toxicity is an important characteristic for compounds to be administered as a medicament to patients in need thereof.

A compound was considered to be active in this test when inhibiting α-synuclein cytotoxicity by more than 25% relative to untreated M17-SYNwt cells at a concentration of 20 µg/mL or lower. In these experiments, the control group consisted of M17-SYNwt cells treated with DMSO, the untreated paraquat group consisted of M17-SYNwt cells treated with paraquat and DMSO, and the treated paraquat group consisted of M17-SYNwt cells treated with paraquat and the test compound dissolved in DMSO.

In order to determine $EC_{50}$, exemplary compounds of the present invention were tested at different concentrations ranging from a poorly or non-effective (i.e. a relatively low) concentration to an effective (i.e. relatively higher) concentration. These data were also used for calculation of percent inhibition (referred as "% Inhib." in table 2). Percent inhibition was calculated as the synuclein toxicity inhibition by the compound in treated paraquat cells, relatively to the synuclein cytotoxicity in untreated paraquat cells, thus corresponding to the following equation:

(LDH release of treated paraquat cells at non-effective concentration of test cmpd)−(LDH release of treated paraquat cells at most effective concentration of test cmpd)/(LDH release of untreated paraquat cells)−(LDH release control cells) *100%.

Compounds 19 (N-(2,6-dimethylphenyl)-4-[3-(4-fluorobenzyl)-1,2,4-thiadiazol-5-yl]-2-methylpiperazine-1-carboxamide) and 111 (2-phenyl-N-{2-[4-[3-(4-fluoro-benzyl)-1,2,4-thiadiazol-5-yl]piperazin-1-yl]ethyl}butanamide) were tested using the α-synuclein cytotoxicity assay as described above. FIG. 2 shows that these two compounds (compound 19=squares; compound 111=triangles) were able, in a dose-dependent manner, to reduce LDH activity in the medium demonstrating that the respective compounds alleviate α-synuclein-mediated cytotoxicity.

Dose responses were carried out on all exemplary compounds found to be active (10-point curves performed in duplicate) based on the above activity definition. Although the pharmacological properties of the compounds disclosed in this invention vary with structural changes in various parts of the molecules—including the linker X, the substituting pattern on the aryl rings, and the type of cyclic or non-cyclic diamino moiety between the linker X and the 1,2,4-thiazolyl moiety—as expected, active exemplary compounds more particularly possess $EC_{50}$ in a cell-based assay of synuclein cytotoxicity in the range from about 0.0001 µM to about 6 µM. $EC_{50}$ data obtained for compounds from Table 1 are presented in Table 2.

Example 215

In Vivo Inhibition of Synuclein-Mediated Instigated Loss of Substantia Nigra Neurons In order to model neuronal loss in the substantia nigra region of the brain, mice are treated with paraquat at a dose not higher than 8 mg/kg/day for a continuous period of 15-100 days. These mice are also chronically co-treated during that period with:
- either exemplary compound 60 (1-[4-methoxyphenylsulfonyl]-4-[3-(4-methylbenzyl)-1,2,4-thiadiazol-5-yl]-2-methylpiperazine), or
- exemplary compound 74 (1-[4-methoxyphenylsulfonyl]-4-[3-(4-fluorobenzyl)-1,2,4-thiadiazol-5-yl]piperazine), or
- exemplary compound 53 (1-[4-methoxyphenylsulfonyl]-4-[3-(3-methoxy-benzyl)-1,2,4-thiadiazol-5-yl]piperazine), each being administered at a dose not higher than 20 mg/kg body weight/day), or by vehicle only (no active compound). Mice treatment by means of vehicle or a compound of the invention is started preferably 1 or 2 days before administration of paraquat.

At the end of the treatment period, mice are sacrificed and the corresponding brains are used for immunohistochemical analysis. The substantia nigra brain region has a relatively high percentage of cells with high levels of tyrosine hydroxylase. Using antibodies raised against tyrosin hydroxylase (anti-tyrosin hydroxylase), tyrosine hydroxylase containing neurons in the brains are detected. The area of tyrosin hydroxylase staining in the substantia nigra regions are then quantified. Subsequently, the quantified tyrosin hydroxylase positive areas of mice treated with a compound of this invention versus mice treated with vehicle are compared. This analysis revealed that the substantia nigra area in mice treated with compound is significantly larger than in vehicle treated mice, indicating that the corresponding compound is able to inhibit paraquat-triggered degeneration of substantia nigra cells in vivo.

Example 216

In Vivo Inhibition of 6-hydroxydopamine (6-OHDA) Instigated Loss of Substantia Nigra Neurons Unilateral substantia nigra lesions by 6-OHDA are obtained by stereotactic striatal injections in brains of living rats as described by Vercammen et al. in *Molecular Therapy* (2006) 14(5):716-723. These rats are also chronically co-treated with the same exemplary compounds and at the same dose as mentioned in example 215, or by vehicle only (no active compound).

Daily treatment of compound or vehicle is started preferably 1 or 2 days before administration of 6-OHDA and lasted between 7 to 30 days after the 6-OHDA injection.

At the end of the treatment period, rats are sacrificed and the corresponding brains were used for immunohistochemical analysis. The substantia nigra brain region has a relatively high percentage of cells with high levels of tyrosine hydroxylase. Using antibodies raised against tyrosin hydroxylase (anti-tyrosine hydroxylase) tyrosine hydroxylase containing neurons in the brains were detected. The nigral lesion volumes and/or the tyrosine hydroxylase positive cell numbers were quantified as described in Vercammen et al. (cited supra).

This analysis reveals that the nigral lesion volumes are significantly reduced in rats treated with a compound according to this invention, as compared to vehicle treated rats, thus indicating that the compound is able to inhibit 6-OHDA triggered degeneration of substantia nigra cells in vivo.

This analysis also reveals that tyrosine hydroxylase positive cell numbers are higer in rats treated with a compound according to this invention as compared to vehicle treated rats, thus providing confirmation that the compound is able to inhibit 6-OHDA triggered degeneration of substantia nigra cells in vivo.

| No. | Compound name | Compound structure |
|---|---|---|
| 1 | 4-phenylacetyl-1-[3-(4-fluorobenzyl)-1,2,4-thiadiazol-5-yl]piperazine | 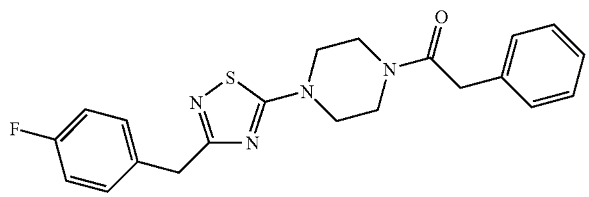 |
| 2 | 4-(4-fluorophenylacetyl),-1-[3-(4-fluorobenzyl)-1,2,4-thiadiazol-5-yl]piperazine | 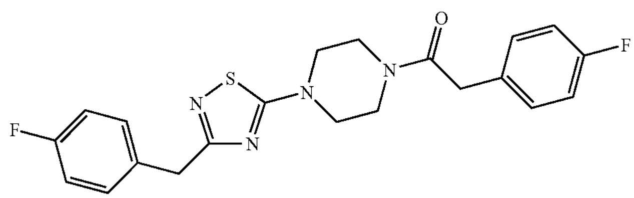 |
| 3 | 1-(4-fluorophenylacetyl)-4-[3-(4-methylbenzyl)-1,2,4-thiadiazol-5-yl]-2-methylpiperazine | 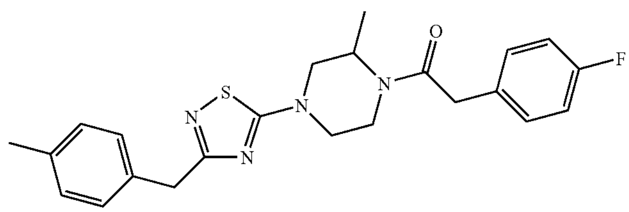 |
| 4 | 1-(4-methoxyphenylacetyl)-4-[3-(4-fluorobenzyl)-1,2,4-thiadiazol-5-yl]-2-methylpiperazine | 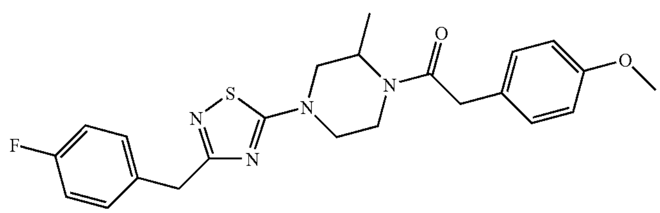 |
| 5 | 1-phenylacetyl-4-[3-(4-fluorobenzyl)-1,2,4-thiadiazol-5-yl]-2-methylpiperazine | 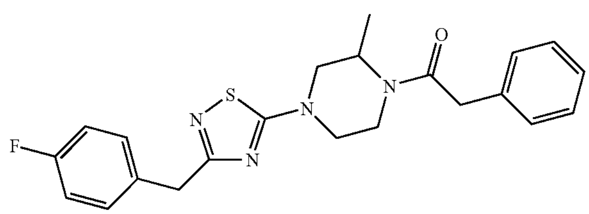 |
| 6 | 1-(4-fluorophenylacetyl-4-[3-(4-fluorobenzyl)-1,2,4-thiadiazol-5-yl]-2-methylpiperazine | 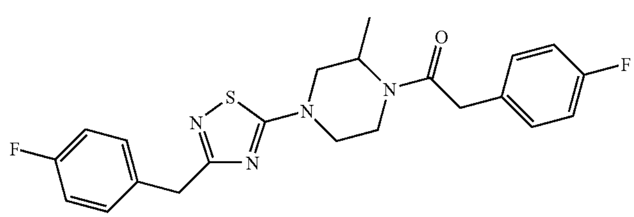 |

| No. | Compound name | Compound structure |
|---|---|---|
| 7 | 1-[chloro(phenyl)acetyl]-4-[3-(4-fluorobenzyl)-1,2,4-thiadiazol-5-yl]-2-methylpiperazine | 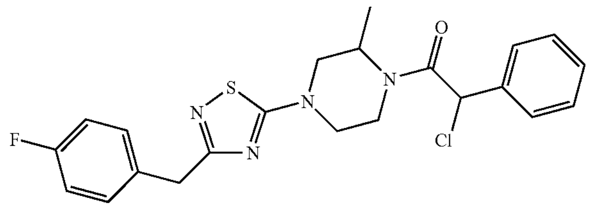 |
| 8 | 1-(2-phenylbutanoyl)-4-[3-(4-fluorobenzyl)-1,2,4-thiadiazol-5-yl]-2-methylpiperazine | 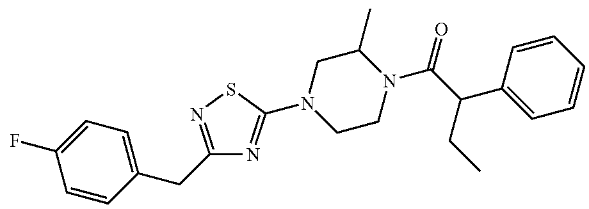 |
| 9 | N-(3-fluorophenyl)-4-[3-(4-fluorobenzyl)-1,2,4-thiadiazol-5-yl]piperazine-1-carboxamide | 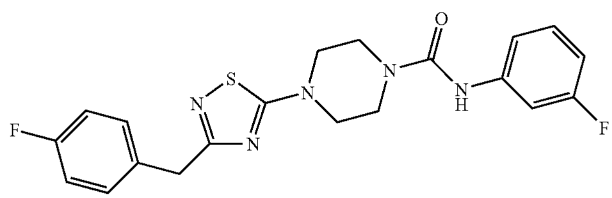 |
| 10 | N-(2-methylphenyl)-4-[3-(4-fluorobenzyl)-1,2,4-thiadiazol-5-yl]-2-methylpiperazine-1-carboxamide | 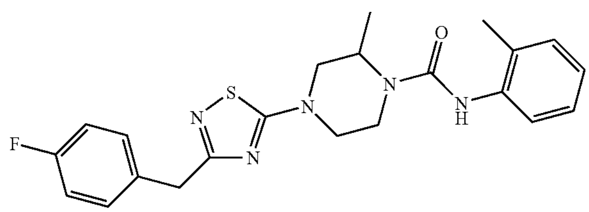 |
| 11 | N-(4-ethylphenyl)-4-[3-(4-fluorobenzyl)-1,2,4-thiadiazol-5-yl]-2-methylpiperazine-1-carboxamide | 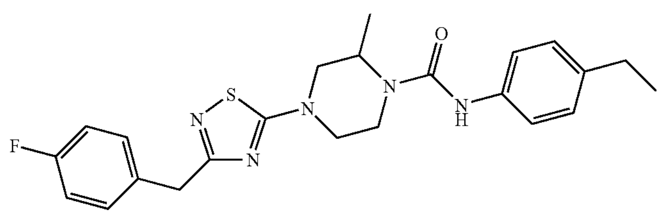 |
| 12 | N-(2-ethylphenyl)-4-[3-(4-fluorobenzyl)-1,2,4-thiadiazol-5-yl]-2-methylpiperazine-1-carboxamide | 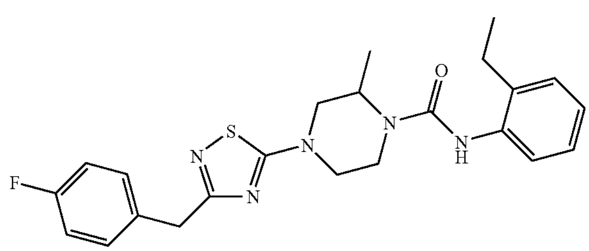 |
| 13 | N-phenyl-4-[3-(4-fluorobenzyl)-1,2,4-thiadiazol-5-yl]piperazine-1-carboxamide | 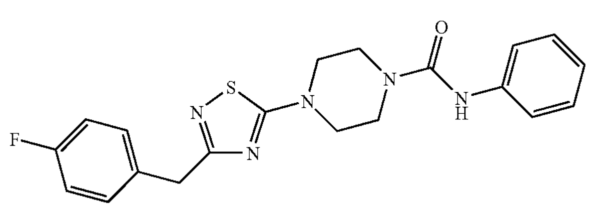 |

-continued

| No. | Compound name | Compound structure |
|---|---|---|
| 14 | N-(4-ethoxyphenyl)-4-[3-(4-fluorobenzyl)-1,2,4-thiadiazol-5-yl]-2-methylpiperazine-1-carboxamide | 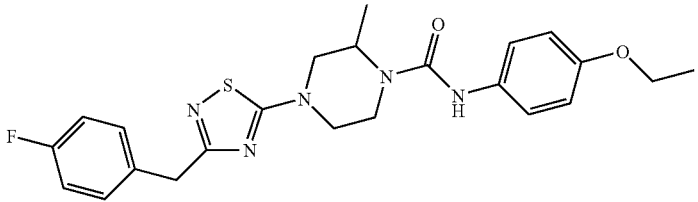 |
| 15 | N-(2-methylphenyl)-4-[3-(4-fluorobenzyl)-1,2,4-thiadiazol-5-yl]piperazine-1-carboxamide | 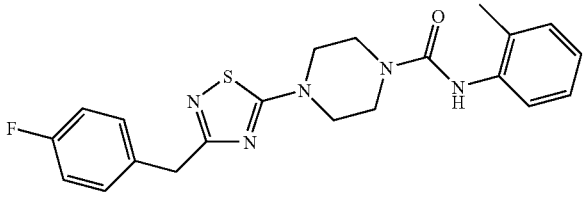 |
| 16 | N-(2-fluorophenyl)-4-[3-(4-fluorobenzyl)-1,2,4-thiadiazol-5-yl]piperazine-1-carboxamide | 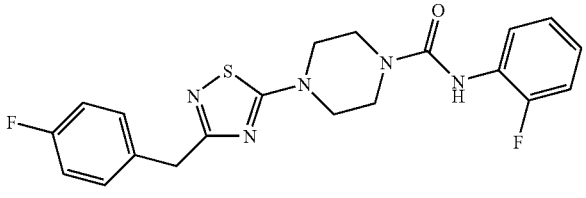 |
| 17 | N-(2-trifluoromethylphenyl)-4-[3-(4-fluorobenzyl)-1,2,4-thiadiazol-5-yl]piperazine-1-carboxamide | 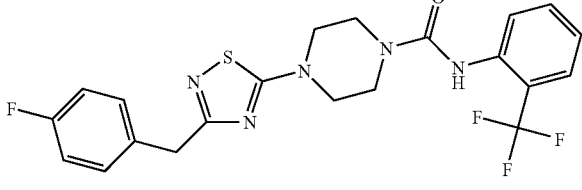 |
| 18 | N-(2-trifluoromethylphenyl)-4-[3-(4-fluorobenzyl)-1,2,4-thiadiazol-5-yl]-2-methylpiperazine-1-carboxamide | 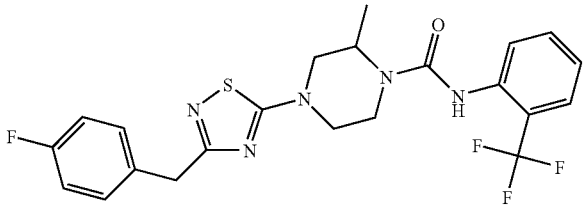 |
| 19 | N-(2,6-dimethylphenyl)-4-[3-(4-fluorobenzyl)-1,2,4-thiadiazol-5-yl]-2-methylpiperazine-1-carboxamide | 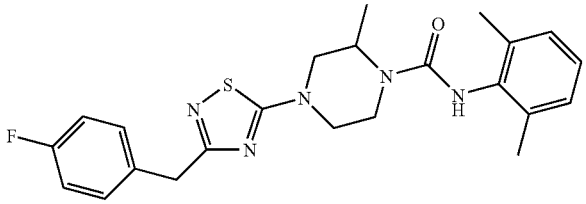 |
| 20 | N-(2,4-dimethylphenyl)-4-[3-(4-fluorobenzyl)-1,2,4-thiadiazol-5-yl]-2-methylpiperazine-1-carboxamide | 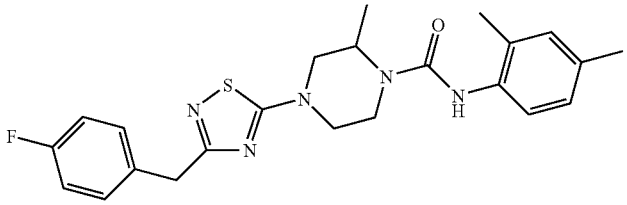 |

| No. | Compound name | Compound structure |
|---|---|---|
| 21 | N-(2,6-dichlorophenyl)-4-[3-(4-fluorobenzyl)-1,2,4-thiadiazol-5-yl]-2-methylpiperazine-1-carboxamide | 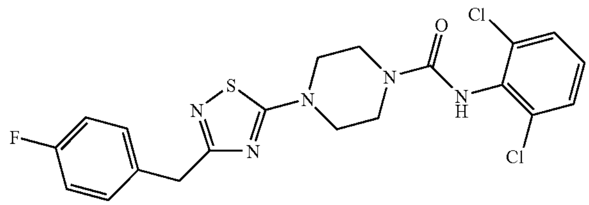 |
| 22 | N-(3-cyanophenyl)-4-[3-(4-fluorobenzyl)-1,2,4-thiadiazol-5-yl]-2-methylpiperazine-1-carboxamide | 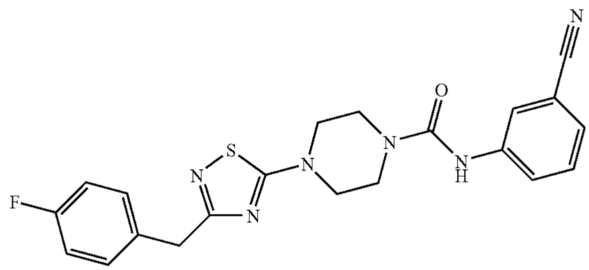 |
| 23 | N-(2,4-difluorophenyl)-4-[3-(4-fluorobenzyl)-1,2,4-thiadiazol-5-yl]-2-methylpiperazine-1-carboxamide | 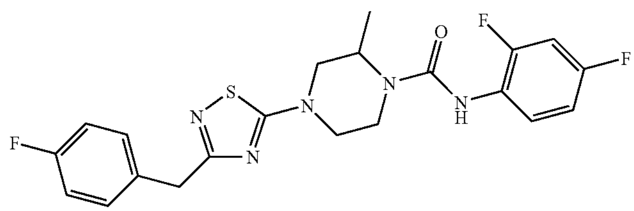 |
| 24 | N-(2,6-dimethylphenyl)-4-[3-(4-fluorobenzyl)-1,2,4-thiadiazol-5-yl]piperazine-1-carboxamide | 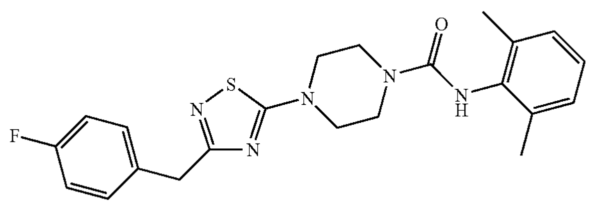 |
| 25 | N-1-naphtyl-4-[3-(4-fluorobenzyl)-1,2,4-thiadiazol-5-yl]-2-methylpiperazine-1-carboxamide | 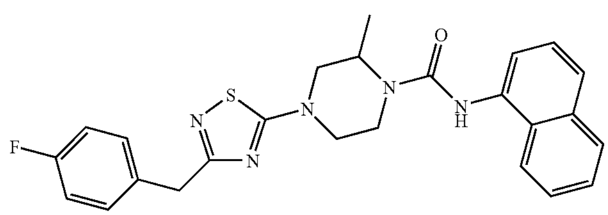 |
| 26 | N-(3,4-difluorophenyl)-4-[3-(4-fluorobenzyl)-1,2,4-thiadiazol-5-yl]-2-methylpiperazine-1-carboxamide | 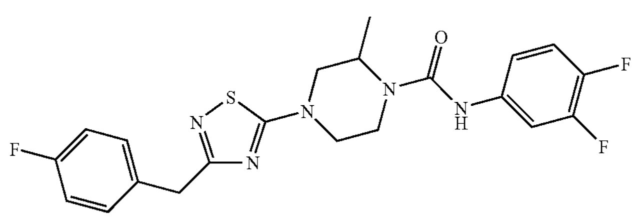 |
| 27 | N-(2,4-dimethoxyphenyl)-4-[3-(4-fluorobenzyl)-1,2,4-thiadiazol-5-yl]piperazine-1-carboxamide | 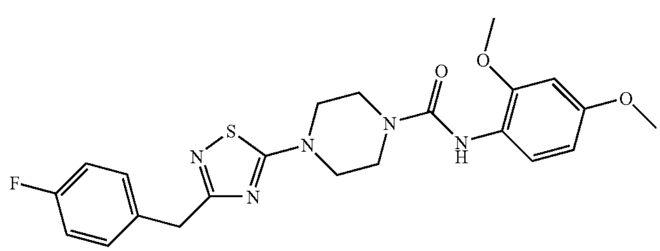 |

| No. | Compound name |
|---|---|
| 28 | N-(3,4-difluorophenyl)-4-[3-(4-fluorobenzyl)-1,2,4-thiadiazol-5-yl]piperazine-1-carboxamide |
| 29 | N-(3,5-dimethoxyphenyl)-4-[3-(4-fluorobenzyl)-1,2,4-thiadiazol-5-yl]-2-methylpiperazine-1-carboxamide |
| 30 | 1-[4-tert-butylphenylsulfonyl]-4-[3-(4-fluorobenzyl)-1,2,4-thiadiazol-5-yl]piperazine |
| 31 | 1-[4-methoxyphenylsulfonyl]-4-[3-(4-chlorobenzyl)-1,2,4-thiadiazol-5-yl]piperazine |
| 32 | 1-[4-methoxyphenylsulfonyl]-4-[3-(4-fluorobenzyl)-1,2,4-thiadiazol-5-yl]piperazine |
| 33 | 1-[4-fluorophenylsulfonyl]-4-[3-(4-chlorobenzyl)-1,2,4-thiadiazol-5-yl]piperazine |
| 34 | 1-[4-chlorophenylsulfonyl]-4-[3-(4-methylbenzyl)-1,2,4-thiadiazol-5-yl]-2-methylpiperazine |

| No. | Compound name |
|---|---|
| 35 | 1-[1-naphtylsulfonyl]-4-[3-(4-methylbenzyl)-1,2,4-thiadiazol-5-yl]piperazine |
| 36 | 1-[2,5-dichlorophenylsulfonyl]-4-[3-(4-methylbenzyl)-1,2,4-thiadiazol-5-yl]-2-methylpiperazine |
| 37 | 1-[2,4,6-trimethylphenylsulfonyl]-4-[3-(4-methylbenzyl)-1,2,4-thiadiazol-5-yl]piperazine |
| 38 | 1-[2-naphtylsulfonyl]-4-[3-(4-methylbenzyl)-1,2,4-thiadiazol-5-yl]piperazine |
| 39 | 1-[2,5-dichlorophenylsulfonyl]-4-[3-(4-chlorobenzyl)-1,2,4-thiadiazol-5-yl]piperazine |
| 40 | 1-[4-bromophenylsulfonyl]-4-[3-(4-methylbenzyl)-1,2,4-thiadiazol-5-yl]-3-methylpiperazine |

| No. | Compound name | Compound structure |
|---|---|---|
| 41 | 1-[1-naphtylsulfonyl]-4-[3-(4-methylbenzyl)-1,2,4-thiadiazol-5-yl]-3-methylpiperazine | 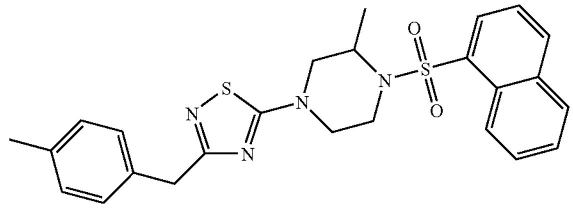 |
| 42 | 1-[4-tert-butylphenylsulfonyl]-4-[3-(4-methylbenzyl)-1,2,4-thiadiazol-5-yl]-2-methylpiperazine | 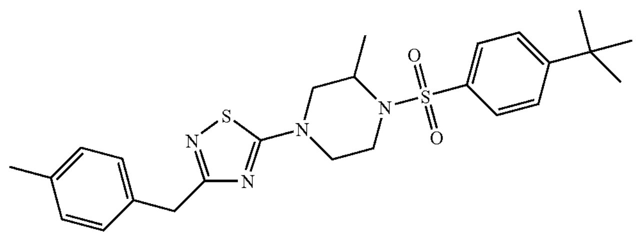 |
| 43 | 1-[1-naphtylsulfonyl]-4-[3-(4-chlorobenzyl)-1,2,4-thiadiazol-5-yl]-2-methylpiperazine | 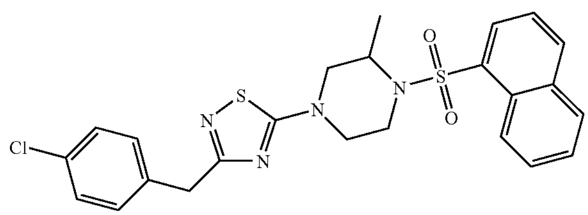 |
| 44 | 1-[3-methoxyphenylsulfonyl]-4-[3-(4-fluorobenzyl)-1,2,4-thiadiazol-5-yl]piperazine | 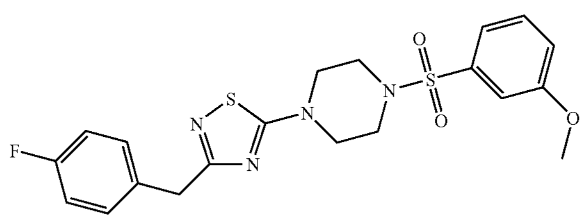 |
| 45 | 1-[2,4,6-trimethylphenylsulfonyl]-4-[3-(4-methylbenzyl)-1,2,4-thiadiazol-5-yl]-2-methylpiperazine | 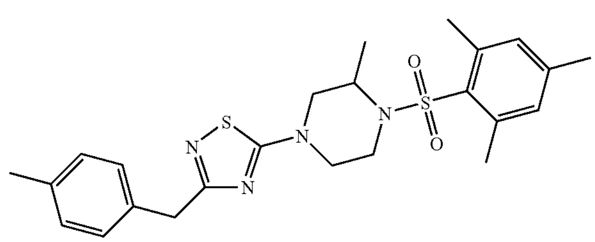 |
| 46 | 1-[3-trifluorophenylsulfonyl]-4-[3-(4-fluorobenzyl)-1,2,4-thiadiazol-5-yl]-2-methylpiperazine | 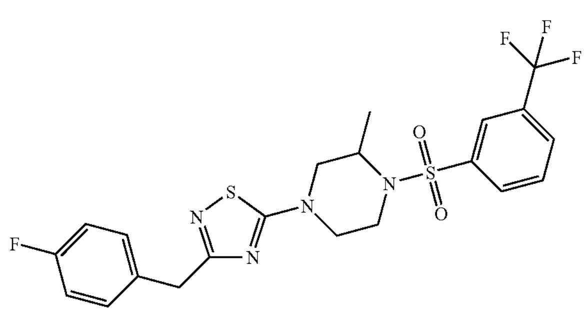 |

| No. | Compound name | Compound structure |
|---|---|---|
| 47 | 1-phenylsulfonyl-4-[3-(4-fluorobenzyl)-1,2,4-thiadiazol-5-yl]-2-methylpiperazine | 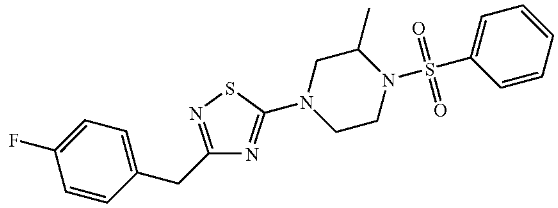 |
| 48 | 1-[4-acetamidophenylsulfonyl]-4-[3-(4-methylbenzyl)-1,2,4-thiadiazol-5-yl]-2-methylpiperazine | 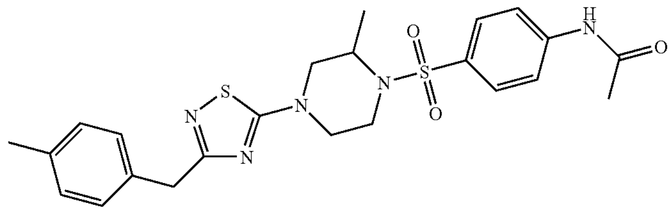 |
| 49 | 1-[4-acetamidophenylsulfonyl]-4-[3-(4-methylbenzyl)-1,2,4-thiadiazol-5-yl]piperazine | 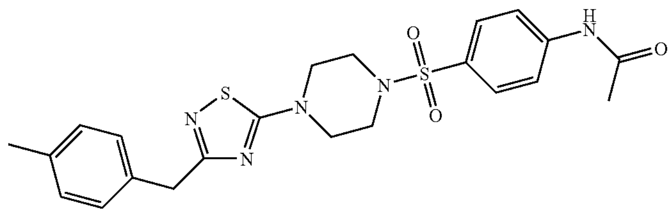 |
| 50 | 1-[4-methyl phenylsulfonyl]-4-[3-(4-methylbenzyl)-1,2,4-thiadiazol-5-yl]-2-methylpiperazine | 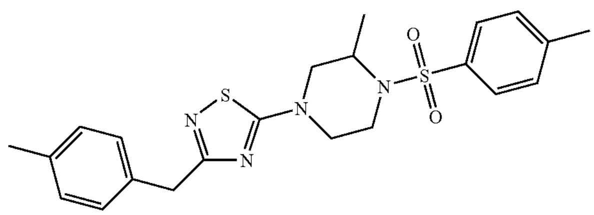 |
| 51 | 1-[4-methoxyphenylsulfonyl]-4-[3-(4-chlorobenzyl)-1,2,4-thiadiazol-5-yl]-2-methylpiperazine | 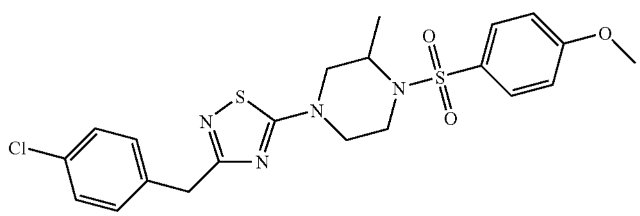 |
| 52 | 1-[2-naphtylsulfonyl]-4-[3-(4-chlorobenzyl)-1,2,4-thiadiazol-5-yl]piperazine | 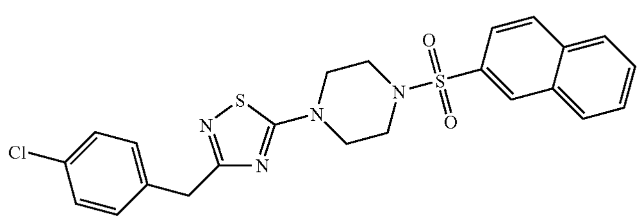 |
| 53 | 1-[4-methoxyphenylsulfonyl]-4-[3-(3-methoxybenzyl)-1,2,4-thiadiazol-5-yl]piperazine | 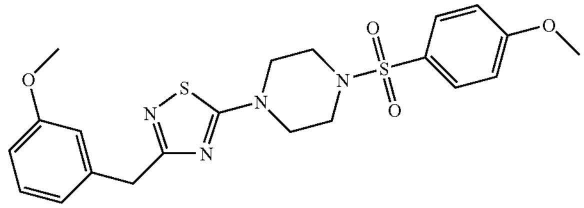 |

-continued

| No. | Compound name | Compound structure |
|-----|---------------|--------------------|
| 54 | 1-[4-tert-butylphenylsulfonyl]-4-[3-(4-fluorobenzyl)-1,2,4-thiadiazol-5-yl]-2-methylpiperazine | 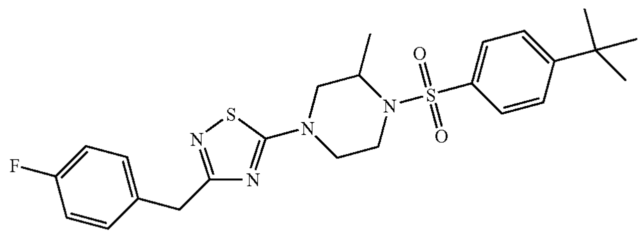 |
| 55 | 1-[4-acetamidophenylsulfonyl]-4-[3-(4-fluorobenzyl)-1,2,4-thiadiazol-5-yl]-2-methylpiperazine | 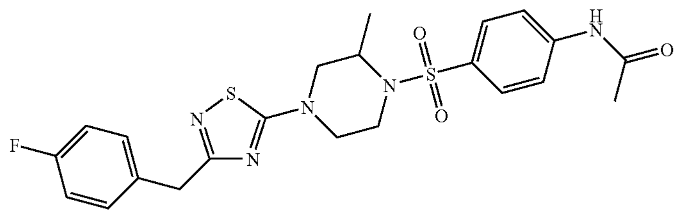 |
| 56 | 1-[3-trifluoromethylphenylsulfonyl]-4-[3-(4-methylbenzyl)-1,2,4-thiadiazol-5-yl]-2-methylpiperazine | 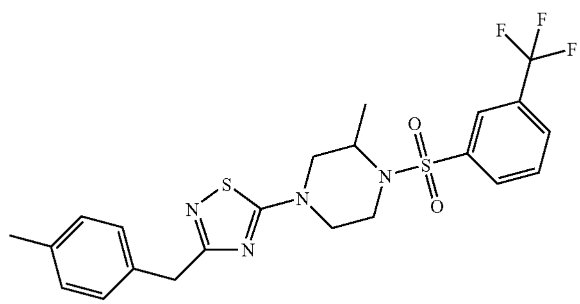 |
| 57 | 1-[4-fluorophenylsulfonyl]-4-[3-(4-methylbenzyl)-1,2,4-thiadiazol-5-yl]piperazine | 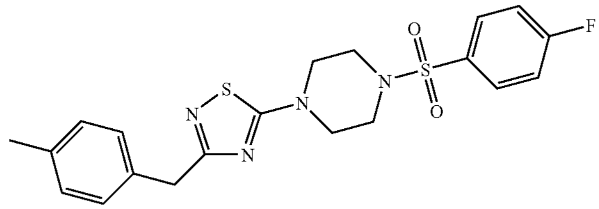 |
| 58 | 1-[4-fluorophenylsulfonyl]-4-[3-(4-methylbenzyl)-1,2,4-thiadiazol-5-yl]-2-methylpiperazine | 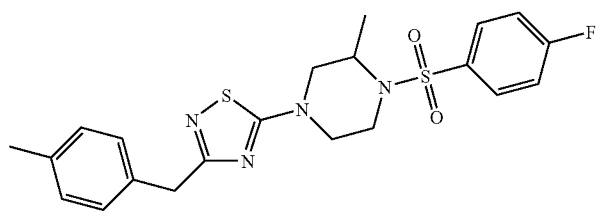 |
| 59 | 1-[4-fluorophenylsulfonyl]-4-[3-(4-fluorobenzyl)-1,2,4-thiadiazol-5-yl]-2-methylpiperazine | 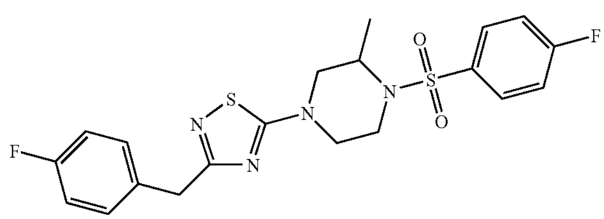 |

| No. | Compound name | Compound structure |
|---|---|---|
| 60 | 1-[4-methoxyphenylsulfonyl]-4-[3-(4-methylbenzyl)-1,2,4-thiadiazol-5-yl]-2-methylpiperazine | 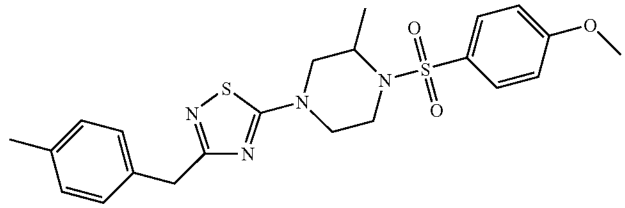 |
| 61 | 1-[4-ter-butylphenylsulfonyl]-4-[3-(4-fluorobenzyl)-1,2,4-thiadiazol-5-yl]piperazine | 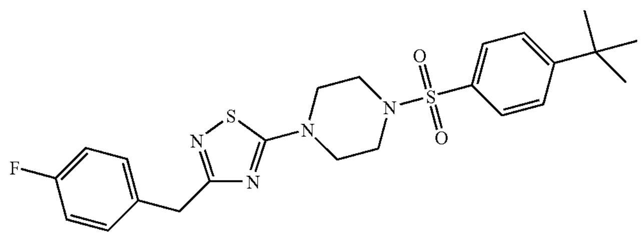 |
| 62 | 1-[3-trifluoromethylphenylsulfonyl]-4-[3-(4-methylbenzyl)-1,2,4-thiadiazol-5-yl]piperazine | 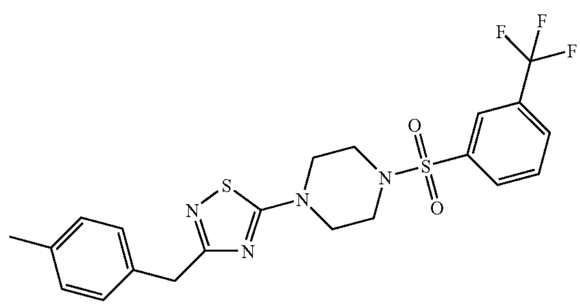 |
| 63 | 1-[4-methylphenylsulfonyl]-4-[3-(4-chlorobenzyl)-1,2,4-thiadiazol-5-yl]piperazine | 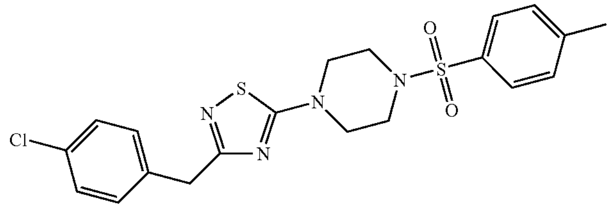 |
| 64 | 1-[4-bromophenylsulfonyl]-4-[3-(4-methylbenzyl)-1,2,4-thiadiazol-5-yl]piperazine | 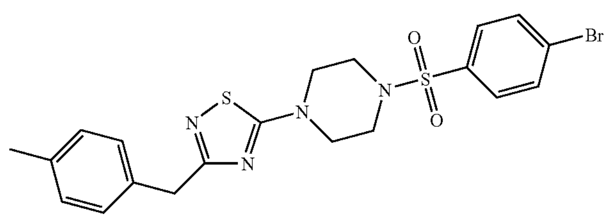 |
| 65 | 1-[2-naphtylsulfonyl]-4-[3-(4-methylbenzyl)-1,2,4-thiadiazol-5-yl]piperazine | 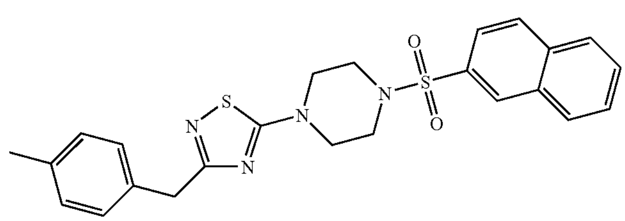 |

| No. | Compound name | Compound structure |
|---|---|---|
| 66 | 1-[4-chlorophenylsulfonyl]-4-[3-(4-methylbenzyl)-1,2,4-thiadiazol-5-yl]piperazine | 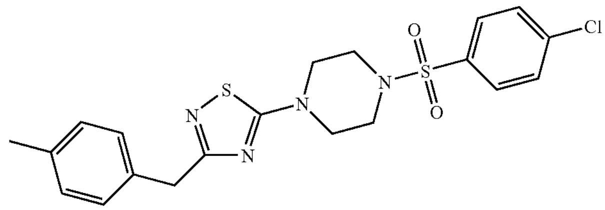 |
| 67 | 1-[4-tert-butylphenylsulfonyl]-4-[3-(4-methylbenzyl)-1,2,4-thiadiazol-5-yl]piperazine | 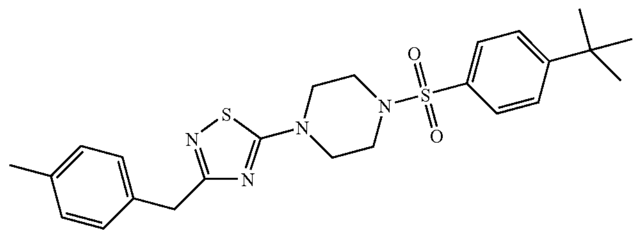 |
| 68 | 1-[4-methoxyphenylsulfonyl]-4-[3-(4-methylbenzyl)-1,2,4-thiadiazol-5-yl]piperazine | 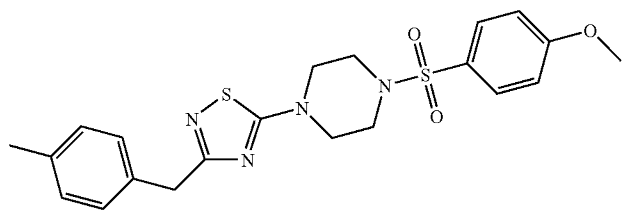 |
| 69 | 1-[4-tert-butylphenylsulfonyl]-4-[3-(4-chlorobenzyl)-1,2,4-thiadiazol-5-yl]piperazine | 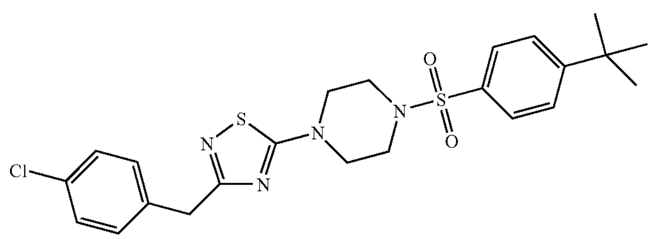 |
| 70 | 1-[quinoline-8-sulfonyl]-4-[3-(4-methylbenzyl)-1,2,4-thiadiazol-5-yl]piperazine | 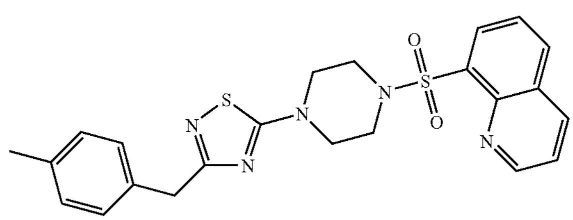 |
| 71 | 1-[4-nitrophenylsulfonyl]-4-[3-(4-methylbenzyl)-1,2,4-thiadiazol-5-yl]-2-methylpiperazine | 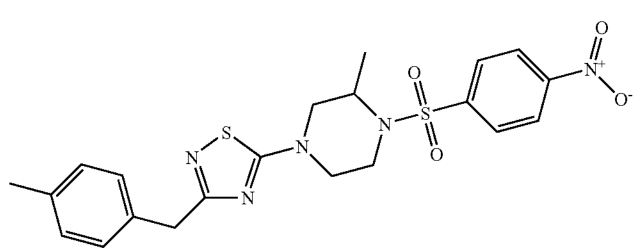 |

-continued

| No. | Compound name | Compound structure |
|---|---|---|
| 72 | 1-[3-nitro-4-chlorophenylsulfonyl]-4-[3-(4-methylbenzyl)-1,2,4-thiadiazol-5-yl]-2-methylpiperazine | 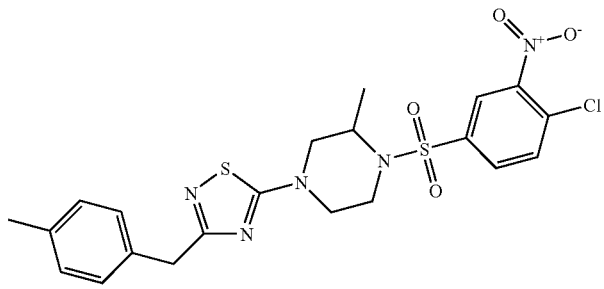 |
| 73 | 1-[4-nitrophenylsulfonyl]-4-[3-(4-fluorobenzyl)-1,2,4-thiadiazol-5-yl]-2-methylpiperazine | 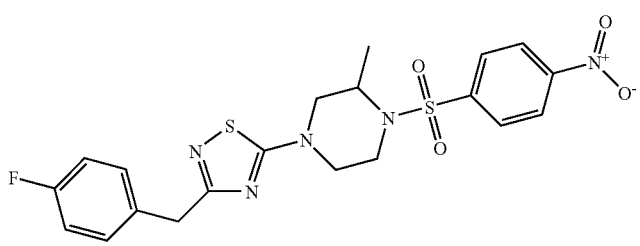 |
| 74 | 1-[4-methoxyphenylsulfonyl]-4-[3-(4-fluorobenzyl)-1,2,4-thiadiazol-5-yl]piperazine | 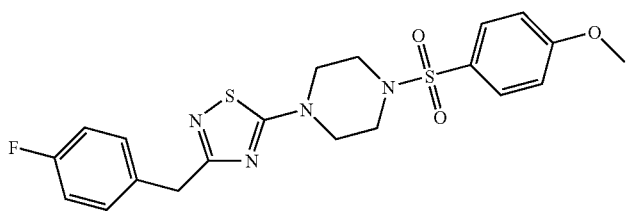 |
| 75 | 1-[3-nitro-4-chlorophenylsulfonyl]-4-[3-(4-methylbenzyl)-1,2,4-thiadiazol-5-yl]piperazine | 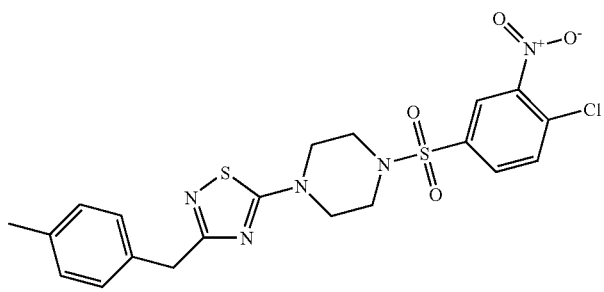 |
| 76 | 1-(benzylsulfonyl)-4-[3-(4-chlorobenzyl)-1,2,4-thiadiazol-5-yl]piperazine | 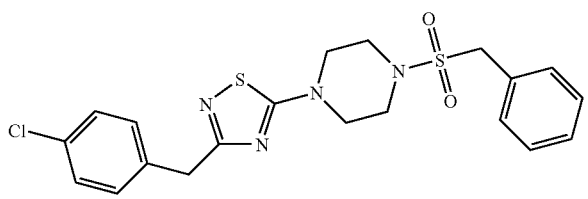 |
| 77 | 1-(benzylsulfonyl)-4-[3-(4-methylbenzyl)-1,2,4-thiadiazol-5-yl]piperazine | 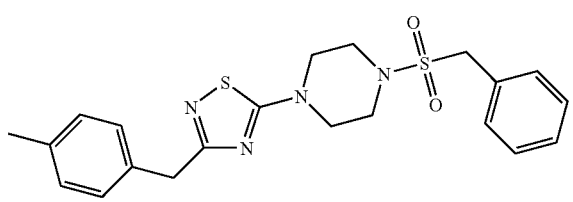 |

-continued

| No. | Compound name | Compound structure |
|---|---|---|
| 78 | 1-(phenylprop-2-ensulfonyl)-4-[3-(4-fluorobenzyl)-1,2,4-thiadiazol-5-yl]piperazine | 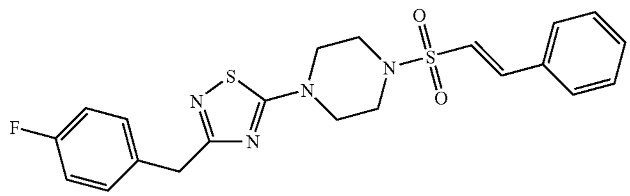 |
| 79 | 1-(phenylprop-2-ensulfonyl)-4-[3-(4-methylbenzyl)-1,2,4-thiadiazol-5-yl]-2-methylpiperazine | 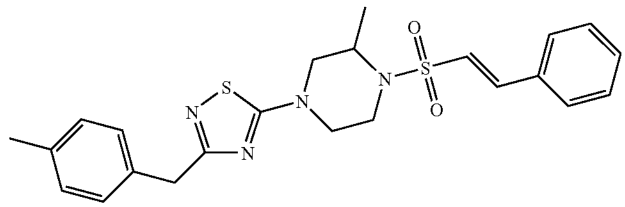 |
| 80 | 1-(phenylprop-2-ensulfonyl)-4-[3-(4-methylbenzyl)-1,2,4-thiadiazol-5-yl]piperazine | 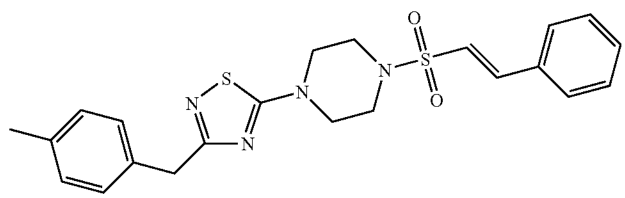 |
| 81 | 1-(butylsulfonyl)-4-[3-(4-chlorobenzyl)-1,2,4-thiadiazol-5-yl]piperazine | 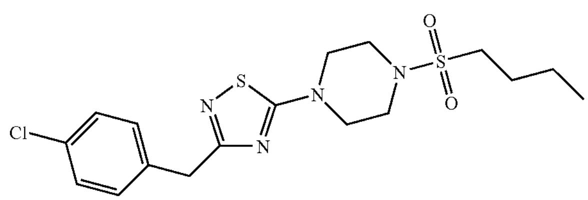 |
| 82 | 1-(octylsulfonyl)-4-[3-(4-methylbenzyl)-1,2,4-thiadiazol-5-yl]piperazine | 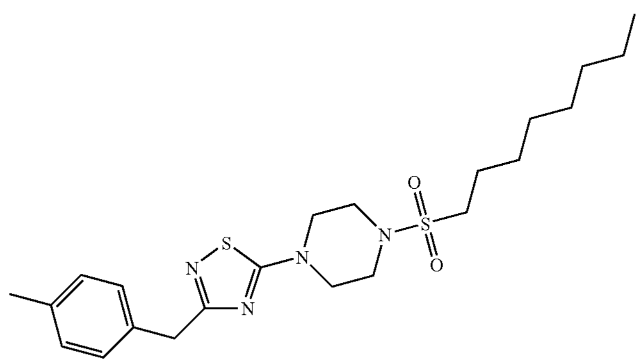 |
| 83 | 1-(butylsulfonyl)-4-[3-(4-methylbenzyl)-1,2,4-thiadiazol-5-yl]piperazine | 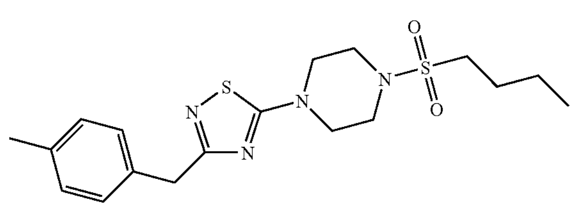 |
| 84 | 1-(ethylsulfonyl)-4-[3-(4-chlorobenzyl)-1,2,4-thiadiazol-5-yl]piperazine | 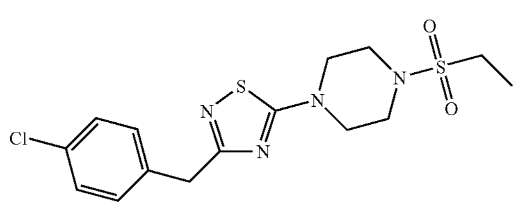 |

| No. | Compound name | Compound structure |
|---|---|---|
| 85 | 1-(isopropylsulfonyl)-4-[3-(4-methylbenzyl)-1,2,4-thiadiazol-5-yl]piperazine | 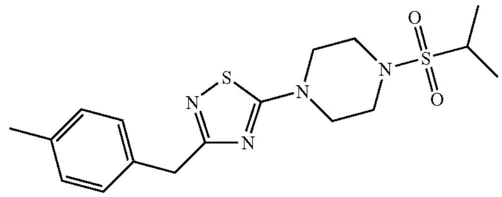 |
| 86 | 1-[(2E)-3-phenylprop-2-enoyl]-4-[3-(4-chlorobenzyl)-1,2,4-thiadiazol-5-yl]2-methylpiperazine | 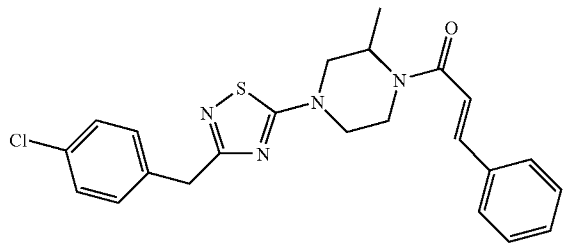 |
| 87 | 1-[(2E)-3-phenylprop-2-enoyl]-4-[3-(4-fluorobenzyl)-1,2,4-thiadiazol-5-yl]-2-methylpiperazine | 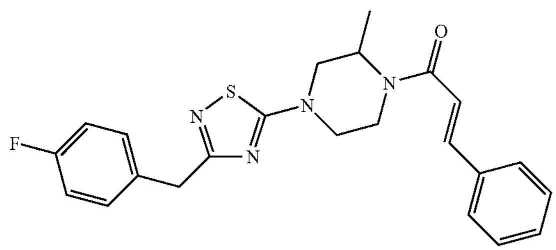 |
| 88 | [(2E)-3-phenylprop-2-enoyl]-4-[3-(4-chlorobenzyl)-1,2,4-thiadiazol-5-yl]piperazine | 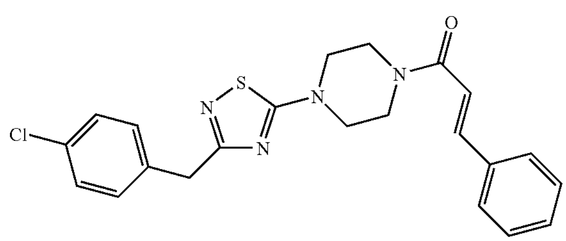 |
| 89 | 1-(3-phenylpropanoyl)-4-[3-(4-fluorobenzyl)-1,2,4-thiadiazol-5-yl]-2-methylpiperazine | 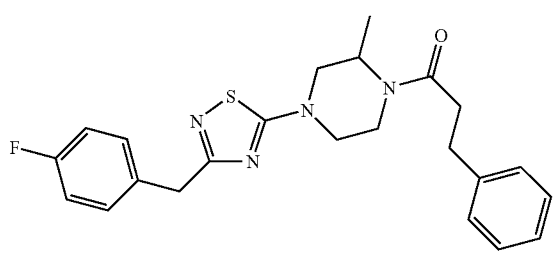 |
| 90 | 1-(3-phenylpropanoyl)-4-[3-(4-fluorobenzyl)-1,2,4-thiadiazol-5-yl]piperazine | 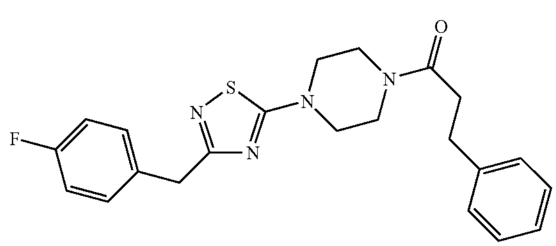 |

-continued

| No. | Compound name | Compound structure |
|---|---|---|
| 91 | 1-[3-phenylprop-2-enyl]-4-[3-(4-methylbenzyl)-1,2,4-thiadiazol-5-yl]piperazine | 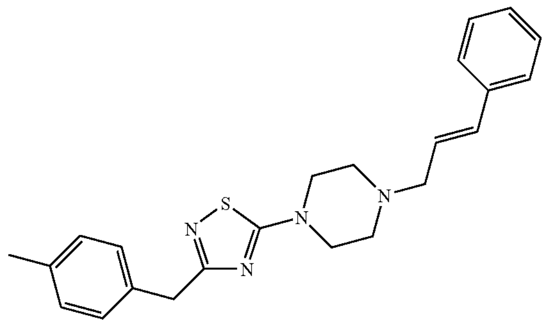 |
| 92 | 1-[3-phenylprop-2-enyl]-4-[3-(4-chlorobenzyl)-1,2,4-thiadiazol-5-yl]piperazine | 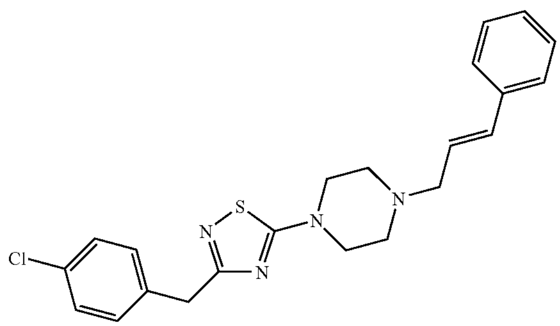 |
| 93 | 1-[3-phenylprop-2-enyl]-4-[3-(4-fluorobenzyl)-1,2,4-thiadiazol-5-yl]piperazine | 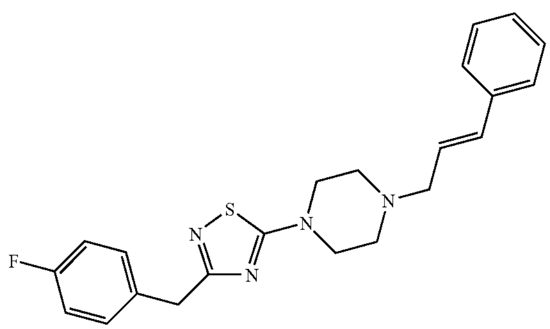 |
| 94 | 4-pentyl-N-{2-[4-[3-(4-fluorobenzyl)-1,2,4-thiadiazol-5-yl]piperazin-1-yl]ethyl}benzamide | 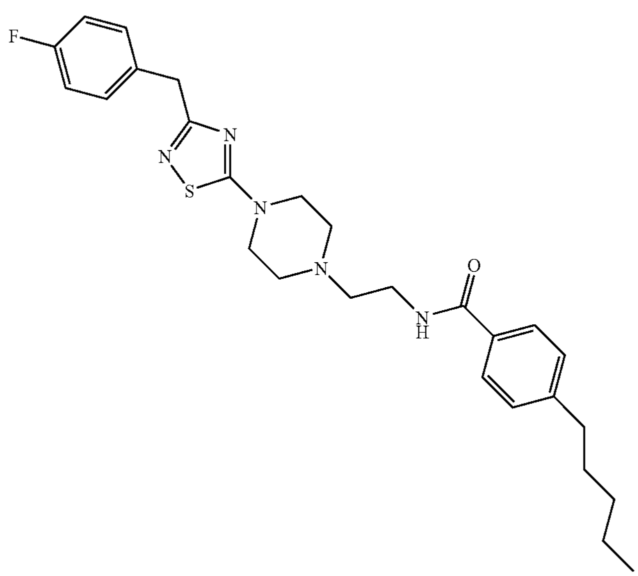 |

-continued

| No. | Compound name | Compound structure |
|---|---|---|
| 95 | 4-butyl-N-{2-[4-[3-(4-fluorobenzyl)-1,2,4-thiadiazol-5-yl]piperazin-1-yl]ethyl}benzamide | 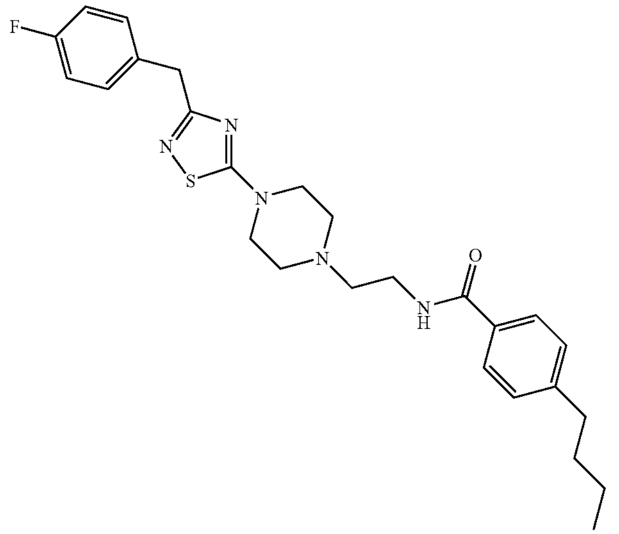 |
| 96 | 4-hexyl-N-{2-[4-[3-(4-fluorobenzyl)-1,2,4-thiadiazol-5-yl]piperazin-1-yl]ethyl}benzamide | 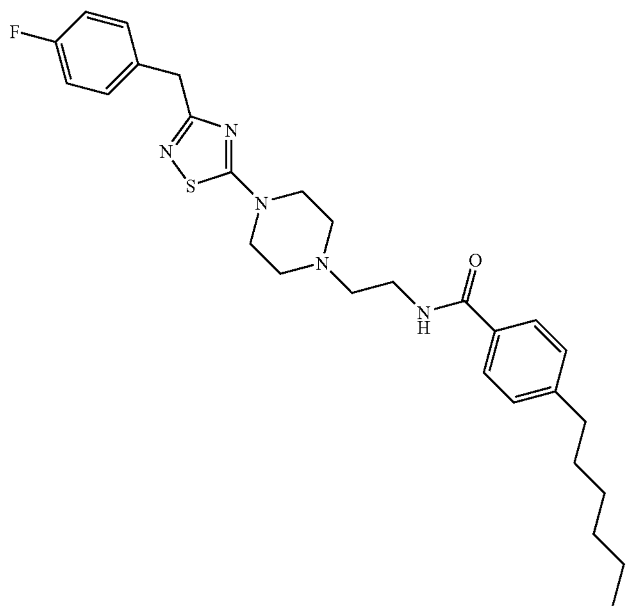 |
| 97 | 4-chloro-N-{2-[4-[3-(4-fluorobenzyl)-1,2,4-thiadiazol-5-yl]piperazin-1-yl]ethyl}benzamide | 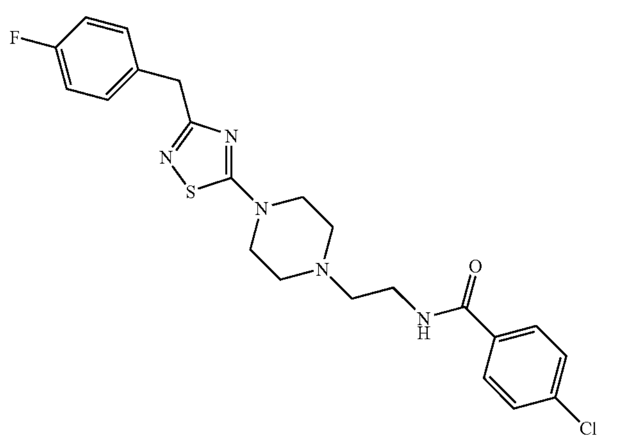 |

| No. | Compound name | Compound structure |
|---|---|---|
| 98 | 3,5-dichloro-N-{2-[4-[3-(4-fluorobenzyl)-1,2,4-thiadiazol-5-yl]piperazin-1-yl]ethyl}benzamide | 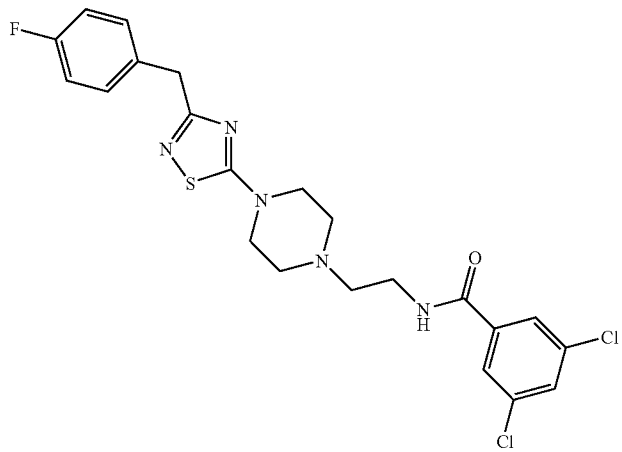 |
| 99 | 2-methyl-N-{2-[4-[3-(4-fluorobenzyl)-1,2,4-thiadiazol-5-yl]piperazin-1-yl]ethyl}benzamide | 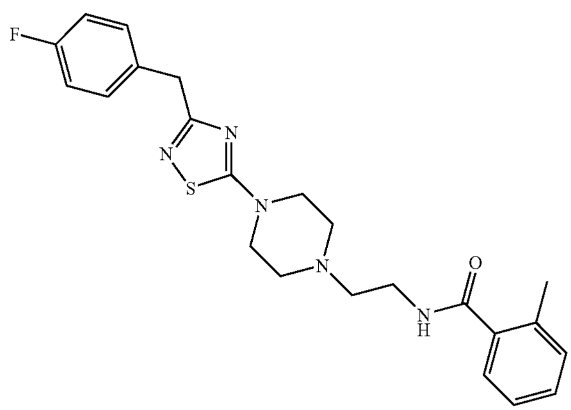 |
| 100 | 3-fluoro-N-{2-[4-[3-(4-chlorobenzyl)-1,2,4-thiadiazol-5-yl]piperazin-1-yl]ethyl}benzamide | 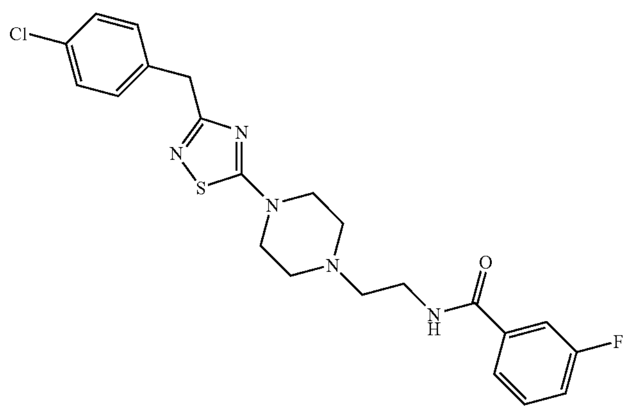 |

-continued

| No. | Compound name | Compound structure |
|---|---|---|
| 101 | 4-methyl-N-{2-[4-[3-(4-fluorobenzyl)-1,2,4-thiadiazol-5-yl]piperazin-1-yl]ethyl}benzamide | 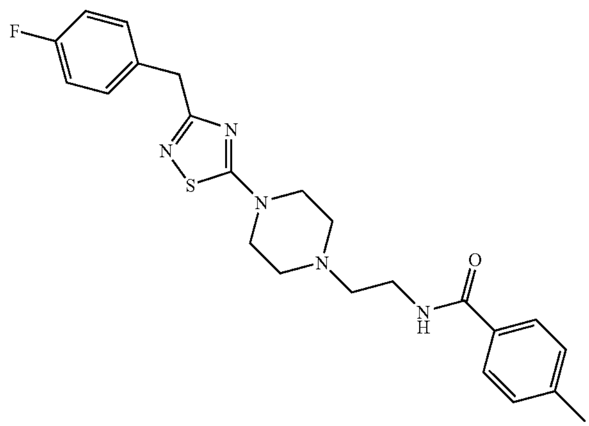 |
| 102 | 4-fluoro-N-{2-[4-[3-(4-fluorobenzyl)-1,2,4-thiadiazol-5-yl]piperazin-1-yl]ethyl}benzamide | 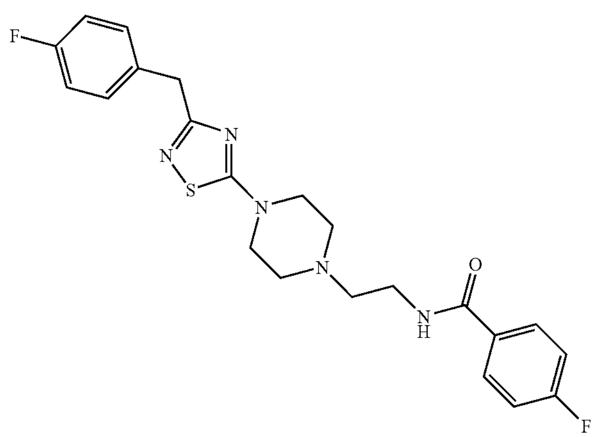 |
| 103 | 4-ethyl-N-{2-[4-[3-(4-fluorobenzyl)-1,2,4-thiadiazol-5-yl]piperazin-1-yl]ethyl}benzamide | 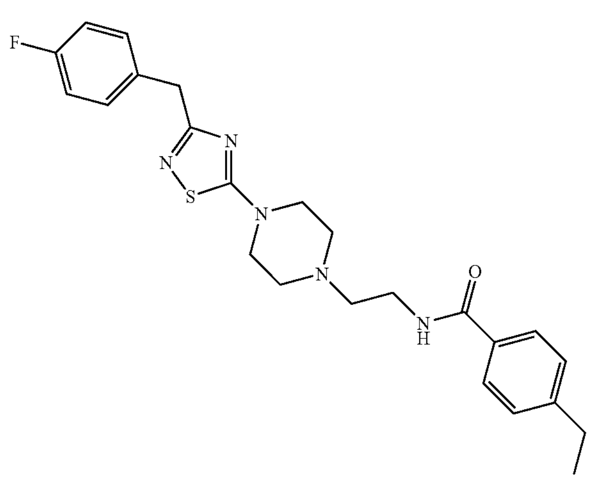 |

| No. | Compound name | Compound structure |
|---|---|---|
| 104 | N-{2-[4-[3-(4-fluorobenzyl)-1,2,4-thiadiazol-5-yl]piperazin-1-yl]ethyl}benzamide | 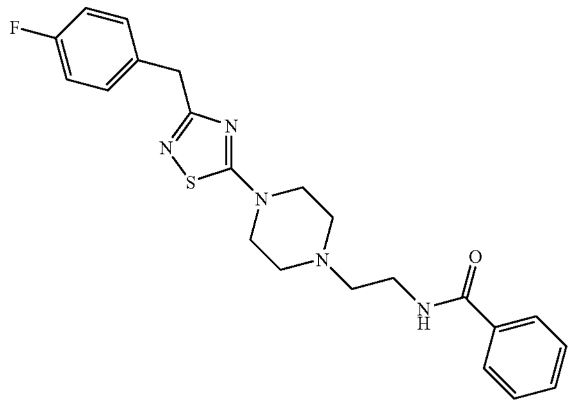 |
| 105 | 3-fluoro-N-{2-[4-[3-(4-fluorobenzyl)-1,2,4-thiadiazol-5-yl]piperazin-1-yl]ethyl}benzamide | 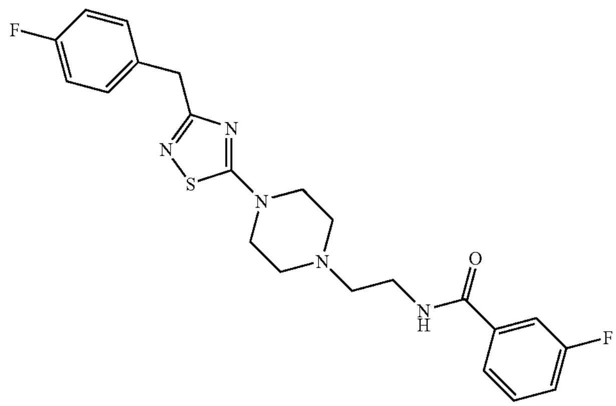 |
| 106 | 3-fluoro-N-{2-[4-[3-benzyl-1,2,4-thiadiazol-5-yl]piperazin-1-yl]ethyl}benzamide | 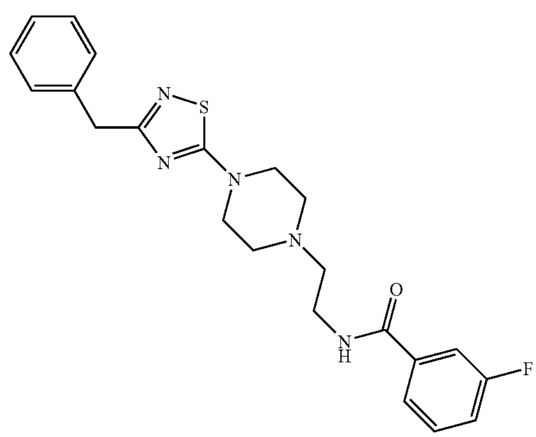 |
| 107 | 2-(4-fluorophenyl)-N-{2-[4-[3-(4-fluorobenzyl)-1,2,4-thiadiazol-5-yl]piperazin-1-yl]ethyl}acetamide | 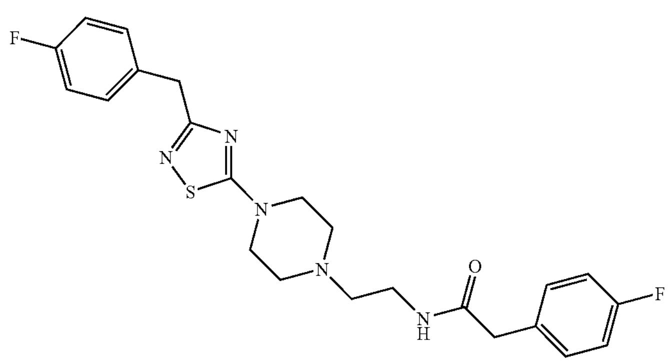 |

| No. Compound name | Compound structure |
|---|---|
| 108 2-phenyl-N-{2-[4-[3-(4-fluorobenzyl)-1,2,4-thiadiazol-5-yl]piperazin-1-yl]ethyl}acetamide | |
| 109 2-(4-fluorophenyl)-N-{2-[4-[3-(4-methylbenzyl)-1,2,4-thiadiazol-5-yl]piperazin-1-yl]ethyl}acetamide | |
| 110 N-benzyl-N'-{2-[4-[3-(4-fluorobenzyl)-1,2,4-thiadiazol-5-yl]piperazin-1-yl]ethyl}urea | |

| No. | Compound name | Compound structure |
|---|---|---|
| 111 | 2-phenyl-N-{2-[4-[3-(4-fluorobenzyl)-1,2,4-thiadiazol-5-yl]piperazin-1-yl]ethyl}butanamide | 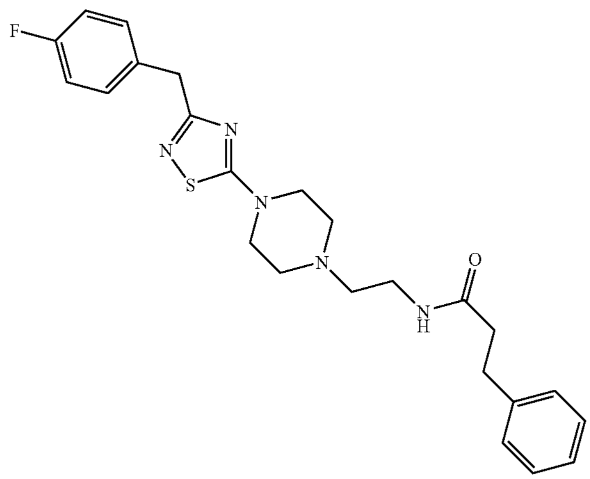 |
| 112 | 3-phenyl-N-{2-[4-[3-(4-fluorobenzyl)-1,2,4-thiadiazol-5-yl]piperazin-1-yl]ethyl}propanamide | 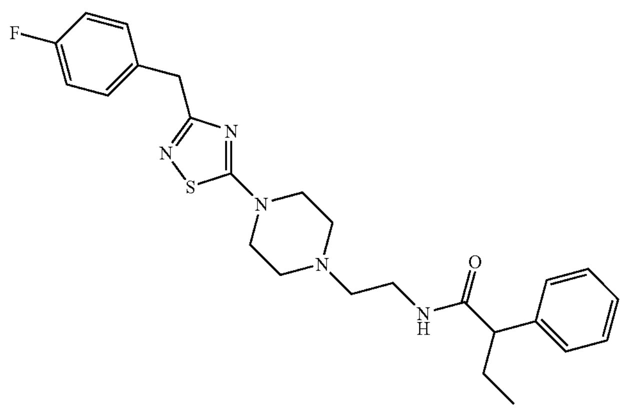 |
| 113 | 1-benzyl-4-[3-(4-fluorobenzyl)-1,2,4-thiadiazol-5-yl]piperazine | 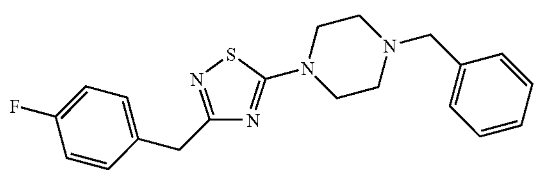 |
| 114 | 1-(1,3-benzodioxol-5-ylmethyl)-4-[3-(4-fluorobenzyl)-1,2,4-thiadiazol-5-yl]piperazine | 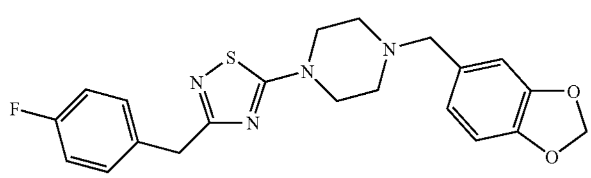 |
| 115 | 1-(2-fluorobenzoyl)-4-[3-(3-methoxybenzyl)-1,2,4-thiadiazol-5-yl]-2-methylpiperazine | 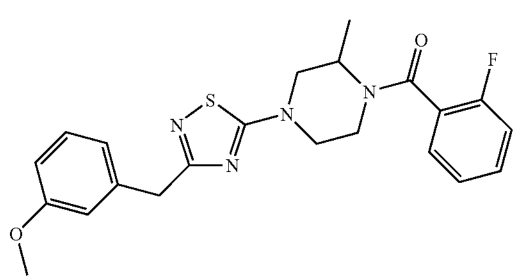 |

| No. | Compound name | Compound structure |
|---|---|---|
| 116 | 1-(4-ethylbenzoyl)-4-[3-(4-fluorobenzyl)-1,2,4-thiadiazol-5-yl]-2-methylpiperazine | 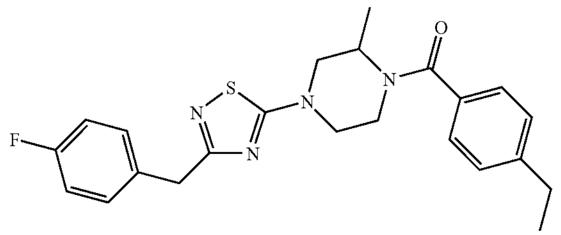 |
| 117 | 1-(4-butylbenzoyl)-4-[3-(4-methylbenzyl)-1,2,4-thiadiazol-5-yl]-2-methylpiperazine | 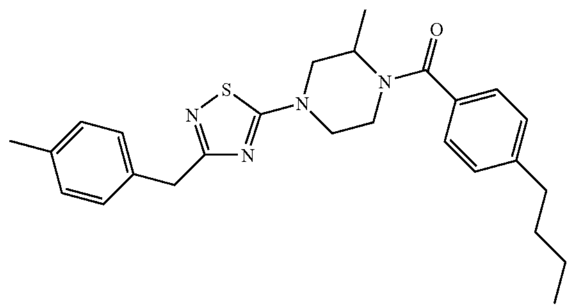 |
| 118 | 1-(4-methoxybenzoyl)-4-[3-(4-fluorobenzyl)-1,2,4-thiadiazol-5-yl]-2-methylpiperazine | 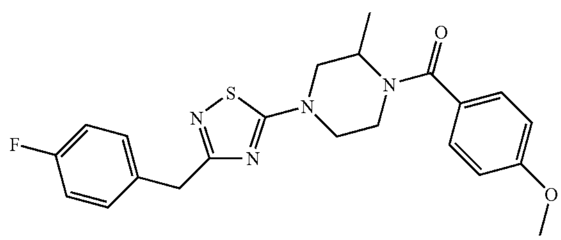 |
| 119 | 1-(1,3-benzodioxol-5-ylcarbonyl)-4-[3-(3-methoxybenzyl)-1,2,4-thiadiazol-5-yl]-2-methylpiperazine | 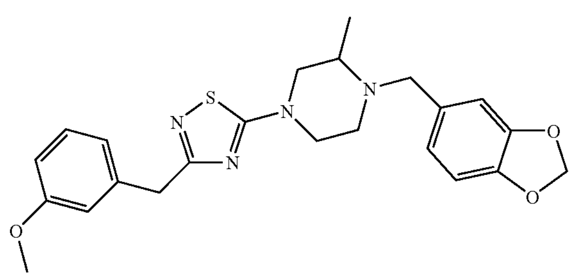 |
| 120 | 1-(4-butyl benzoyl)-4-[3-(4-fluorobenzyl)-1,2,4-thiadiazol-5-yl]-2-methylpiperazine | 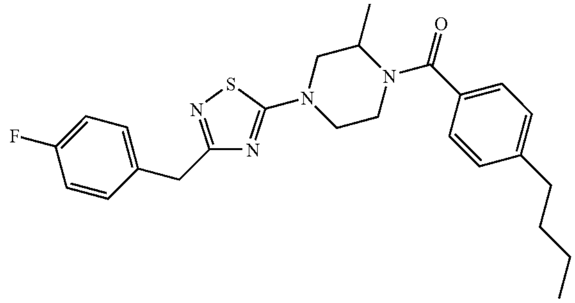 |

-continued

| No. Compound name | Compound structure |
|---|---|
| 121 1-(4-hexylbenzoyl)-4-[3-(4-fluorobenzyl)-1,2,4-thiadiazol-5-yl]piperazine | |
| 122 1-(3-chlorobenzoyl)-4-[3-(4-fluorobenzyl)-1,2,4-thiadiazol-5-yl]-2-methylpiperazine | |
| 123 1-(4-fluorobenzoyl)-4-[3-(3-methoxybenzyl)-1,2,4-thiadiazol-5-yl]-2-methylpiperazine | |
| 124 1-(4-methylbenzoyl)-4-[3-(3-methoxybenzyl)-1,2,4-thiadiazol-5-yl]-2-methylpiperazine | |
| 125 1-(3-fluorobenzoyl)-4-[3-(4-chlorobenzyl)-1,2,4-thiadiazol-5-yl]-2-methylpiperazine | |
| 126 1-benzoyl-4-[3-(4-fluorobenzyl)-1,2,4-thiadiazol-5-yl]-2-methylpiperazine | |

| No. | Compound name | Compound structure |
|---|---|---|
| 127 | 1-(4-fluorobenzoyl)-4-[3-(4-fluorobenzyl)-1,2,4-thiadiazol-5-yl]-2-methylpiperazine | 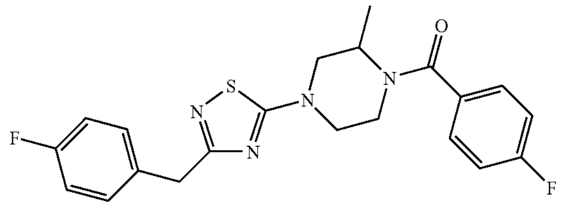 |
| 128 | 1-(4-tert-butylbenzoyl)-4-[3-(4-fluorobenzyl)-1,2,4-thiadiazol-5-yl]-2-methylpiperazine | 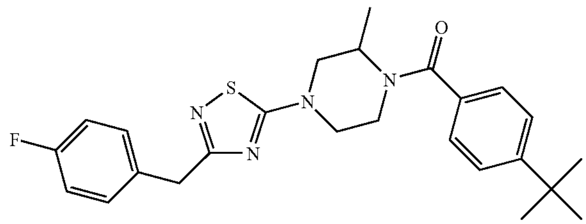 |
| 129 | 1-(1,1'-biphenyl-4-ylcarbonyl)-4-[3-(4-fluorobenzyl)-1,2,4-thiadiazol-5-yl]-2-methylpiperazine | 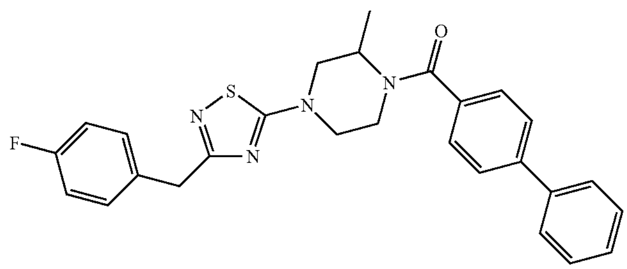 |
| 130 | 1-(4-methoxybenzoyl)-4-[3-(4-methylbenzyl)-1,2,4-thiadiazol-5-yl]-2-methylpiperazine | 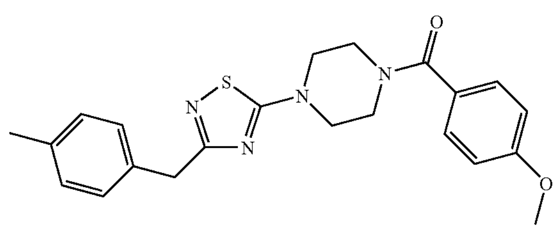 |
| 131 | 1-(4-ethylbenzoyl)-4-[3-(4-methylbenzyl)-1,2,4-thiadiazol-5-yl]piperazine | 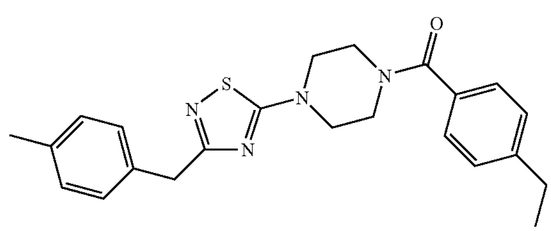 |
| 132 | 1-(2-naphthoyl)-4-[3-(4-fluorobenzyl)-1,2,4-thiadiazol-5-yl]-2-methylpiperazine | 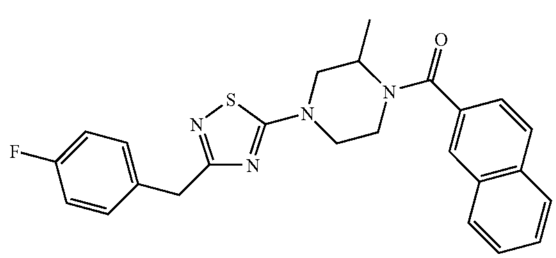 |

| No. | Compound name | Compound structure |
|---|---|---|
| 133 | 1-(2-methoxybenzoyl)-4-[3-(4-fluorobenzyl)-1,2,4-thiadiazol-5-yl]-2-methylpiperazine | 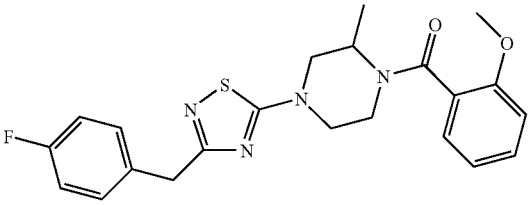 |
| 134 | 1-(4-pentylbenzoyl)-4-[3-(4-methylbenzyl)-1,2,4-thiadiazol-5-yl]-2-methylpiperazine | 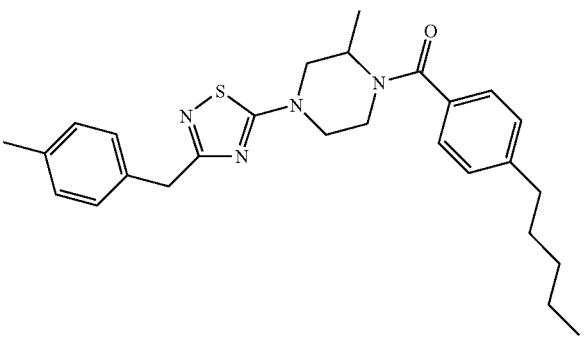 |
| 135 | 1-(4-bromobenzoyl)-4-[3-(4-fluorobenzyl)-1,2,4-thiadiazol-5-yl]-2-methylpiperazine | 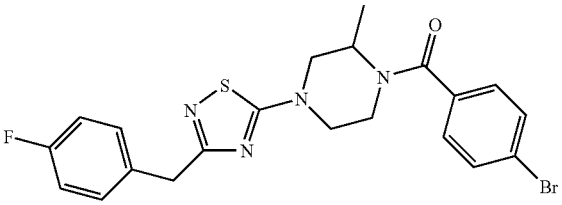 |
| 136 | 1-(2,4-dimethoxybenzoyl)-4-[3-(4-fluorobenzyl)-1,2,4-thiadiazol-5-yl]-2-methylpiperazine | 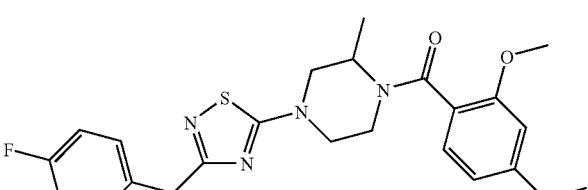 |
| 137 | 1-(3,5-dichlorobenzoyl)-4-[3-(4-fluorobenzyl)-1,2,4-thiadiazol-5-yl]piperazine | 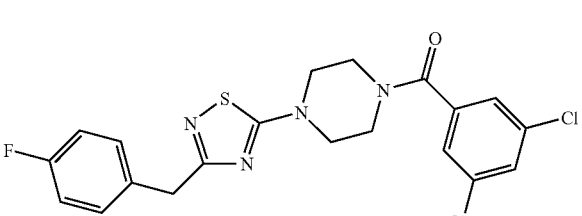 |
| 138 | 1-(3-chlorobenzoyl)-4-[3-(4-fluorobenzyl)-1,2,4-thiadiazol-5-yl]piperazine | 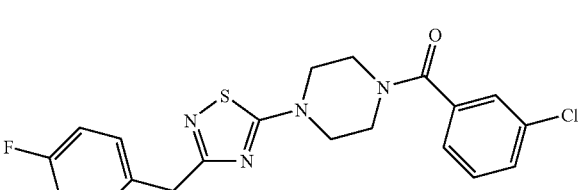 |

-continued

| No. | Compound name | Compound structure |
|---|---|---|
| 139 | 1-(4-methylbenzoyl)-4-[3-(4-fluorobenzyl)-1,2,4-thiadiazol-5-yl]-2-methylpiperazine | 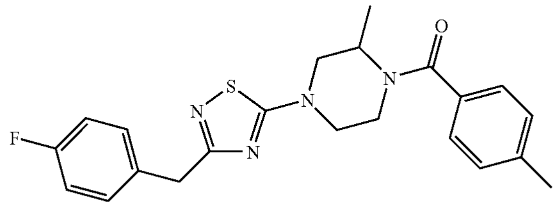 |
| 140 | 1-(2-methylbenzoyl)-4-[3-(4-fluorobenzyl)-1,2,4-thiadiazol-5-yl]-2-methylpiperazine | 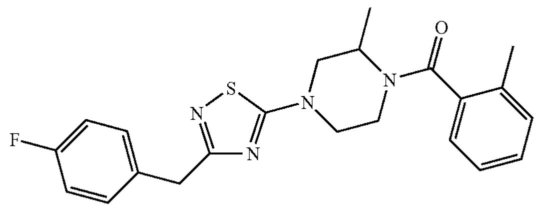 |
| 141 | 1-(4-methylbenzoyl)-4-[3-(4-fluorobenzyl)-1,2,4-thiadiazol-5-yl]piperazine | 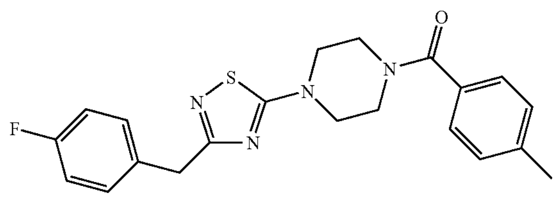 |
| 142 | 1-(3-bromobenzoyl)-4-[3-(4-fluorobenzyl)-1,2,4-thiadiazol-5-yl]-2-methylpiperazine | 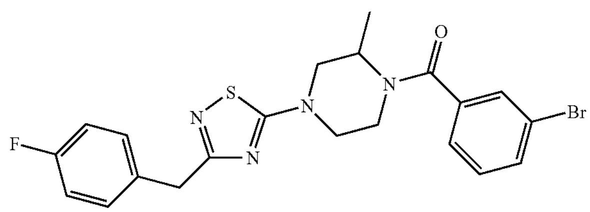 |
| 143 | 1-(4-ethylbenzoyl)-4-[3-(3-methoxybenzyl)-1,2,4-thiadiazol-5-yl]-2-methylpiperazine | 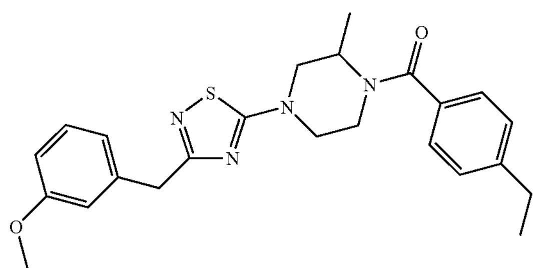 |
| 144 | 1-(3-methylbenzoyl)-4-[3-(4-methylbenzyl)-1,2,4-thiadiazol-5-yl]-2-methylpiperazine | 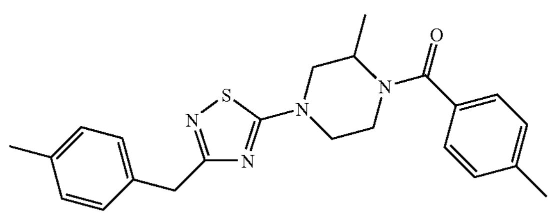 |
| 145 | 1-(3-trifluoromethylbenzoyl)-4-[3-(4-fluorobenzyl)-1,2,4-thiadiazol-5-yl]-2-methylpiperazine | 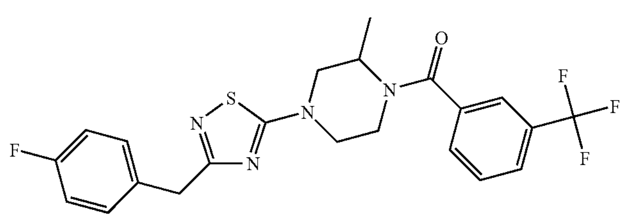 |

-continued

| No. | Compound name | Compound structure |
|---|---|---|
| 146 | 1-(4-tert-butylbenzoyl)-4-[3-(3-methoxybenzyl)-1,2,4-thiadiazol-5-yl]-2-methylpiperazine | 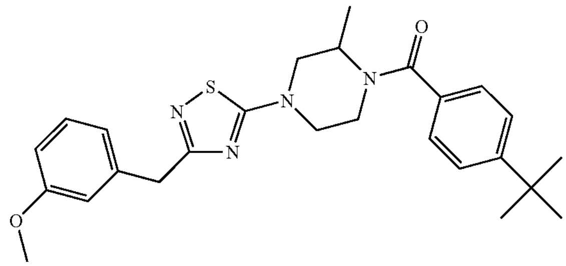 |
| 147 | 1-(4-ethylbenzoyl)-4-[3-(4-methylbenzyl)-1,2,4-thiadiazol-5-yl]-2-methylpiperazine | 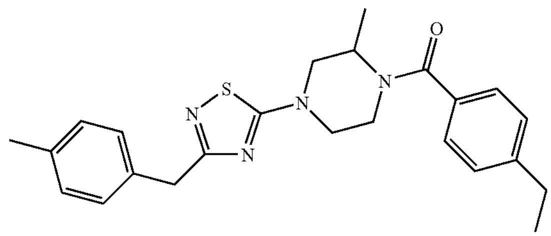 |
| 148 | 1-(2-bromobenzoyl)-4-[3-(4-fluorobenzyl)-1,2,4-thiadiazol-5-yl]-2-methylpiperazine | 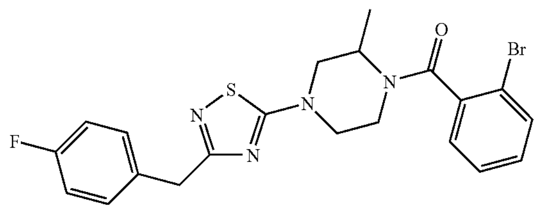 |
| 149 | 1-(2-fluorobenzoyl)-4-[3-(4-methylbenzyl)-1,2,4-thiadiazol-5-yl]-2-methylpiperazine | 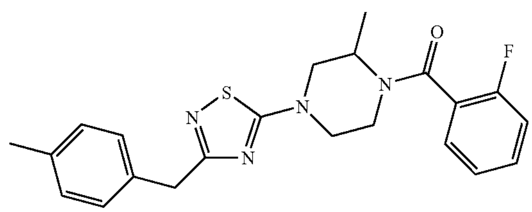 |
| 150 | 1-(3-fluorobenzoyl)-4-[3-benzyl-1,2,4-thiadiazol-5-yl]-2-methylpiperazine | 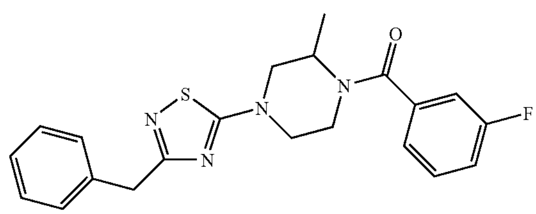 |
| 151 | 1-(4-fluorobenzoyl)-4-[3-(4-methylbenzyl)-1,2,4-thiadiazol-5-yl]-2-methylpiperazine | 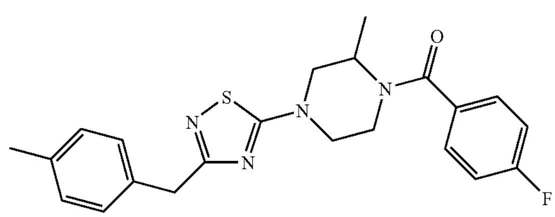 |
| 152 | 1-(2-methylbenzoyl)-4-[3-(4-fluorobenzyl)-1,2,4-thiadiazol-5-yl]piperazine | 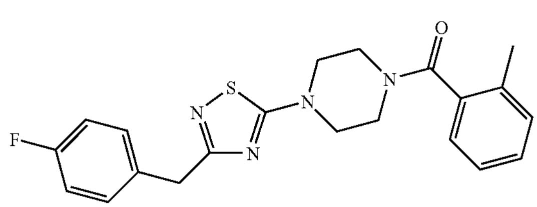 |

| No. | Compound name | Compound structure |
|---|---|---|
| 153 | 1-(4-fluorobenzoyl)-4-[3-(4-chlorobenzyl)-1,2,4-thiadiazol-5-yl]piperazine | 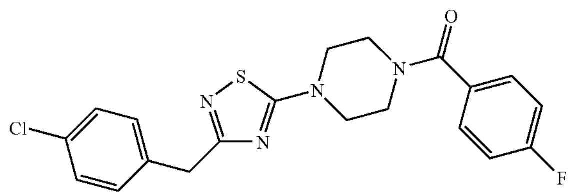 |
| 154 | 1-(4-fluorobenzoyl)-4-[3-benzyl-1,2,4-thiadiazol-5-yl]-2-methylpiperazine | 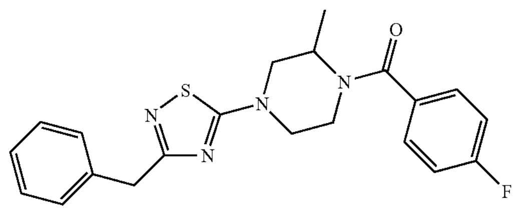 |
| 155 | 1-(4-chlorobenzoyl)-4-[3-(4-methylbenzyl)-1,2,4-thiadiazol-5-yl]piperazine | 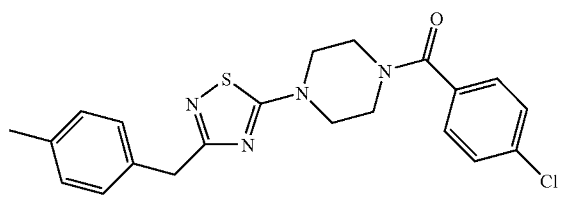 |
| 156 | 1-(3-fluorobenzoyl)-4-[3-(4-methylbenzyl)-1,2,4-thiadiazol-5-yl]-2-methylpiperazine | 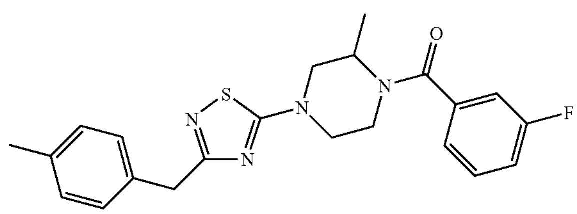 |
| 157 | 1-(3-fluorobenzoyl)-4-[3-(4-chlorobenzyl)-1,2,4-thiadiazol-5-yl]piperazine | 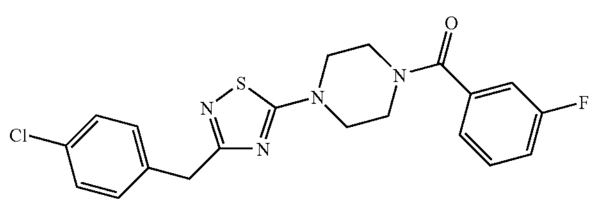 |
| 158 | 1-benzoyl-4-[3-(4-methylbenzyl)-1,2,4-thiadiazol-5-yl]piperazine | 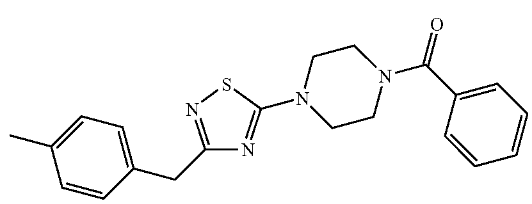 |
| 159 | 1-(2-fluorobenzoyl)-4-[3-(4-chlorobenzyl)-1,2,4-thiadiazol-5-yl]piperazine | 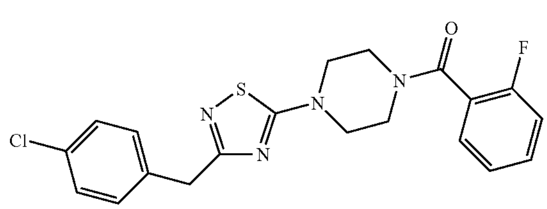 |

-continued

| No. Compound name | Compound structure |
|---|---|
| 160 1-(4-fluorobenzoyl)-4-[3-(4-methylbenzyl)-1,2,4-thiadiazol-5-yl]piperazine | |
| 161 1-(1,3-benzodioxol-5-ylcarbonyl)-4-[3-(4-methylbenzyl)-1,2,4-thiadiazol-5-yl]-2-methyl + B176piperazine | |
| 162 1-(3-flurorbenzoyl)-4-[3-(4-methylbenzyl)-1,2,4-thiadiazol-5-yl]piperazine | |
| 163 1-(4-fluorobenzoyl)-4-[3-benzyl-1,2,4-thiadiazol-5-yl]piperazine | |
| 164 1-(4-bromobenzoyl)-4-[3-(4-methylbenzyl)-1,2,4-thiadiazol-5-yl]piperazine | |
| 165 1-(4-ethylbenzoyl)-4-[3-(4-chlorobenzyl)-1,2,4-thiadiazol-5-yl]piperazine | |
| 166 1-(2-chlorobenzoyl)-4-[3-(4-fluorobenzyl)-1,2,4-thiadiazol-5-yl]-2-methylpiperazine | |

| No. | Compound name | Compound structure |
|---|---|---|
| 167 | 1-(2-fluorobenzoyl)-4-[3-(4-chlorobenzyl)-1,2,4-thiadiazol-5-yl]-2-methylpiperazine | 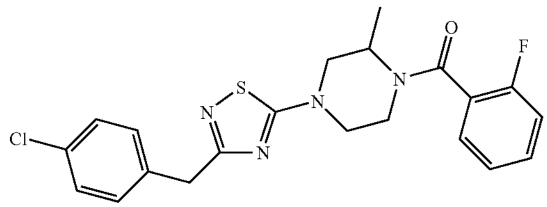 |
| 168 | 1-(4-trifluoromethylbenzoyl)-4-[3-(3-methoxybenzyl)-1,2,4-thiadiazol-5-yl]-2-methylpiperazine | 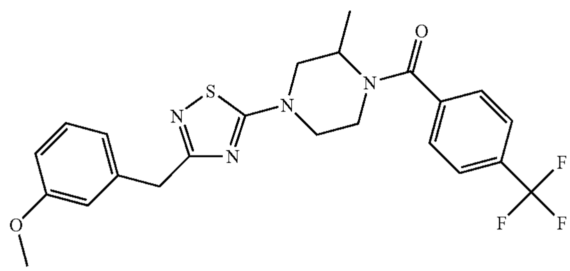 |
| 169 | 1-benzoyl-4-[3-(4-methylbenzyl)-1,2,4-thiadiazol-5-yl]-2-methylpiperazine | 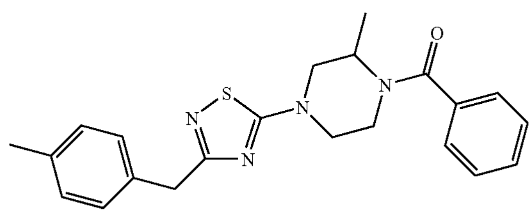 |
| 170 | 1-(4-bromobenzoyl)-4-[3-(3-methoxybenzyl)-1,2,4-thiadiazol-5-yl]-2-methylpiperazine | 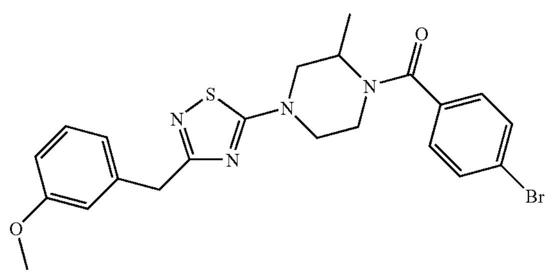 |
| 171 | 1-(4-trifluoromethylbenzoyl)-4-[3-(4-methylbenzyl-1,2,4-thiadiazol-5-yl]piperazine | 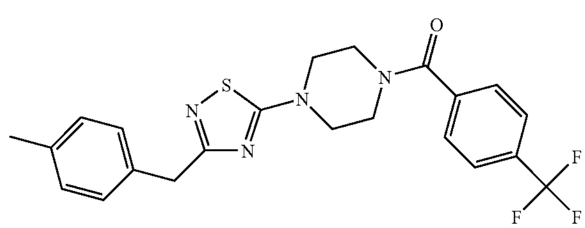 |
| 172 | 1-(3-nitro-4-methylbenzoyl)-4-[3-(4-fluorobenzyl)-1,2,4-thiadiazol-5-yl]-2-methylpiperazine | 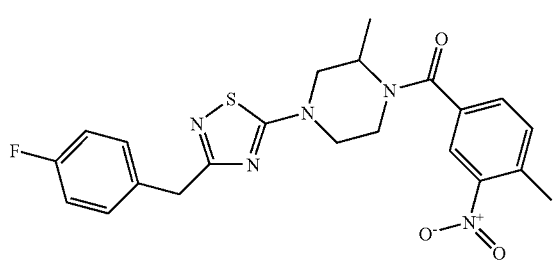 |

| No. | Compound name | Compound structure |
|---|---|---|
| 173 | 1-benzoyl-4-[3-(3-methoxybenzyl)-1,2,4-thiadiazol-5-yl]-2-methylpiperazine | 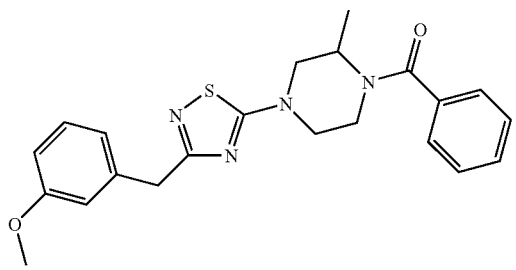 |
| 174 | 1-(4-chlorobenzoyl)-4-[3-(3-methoxybenzyl)-1,2,4-thiadiazol-5-yl]-2-methylpiperazine | 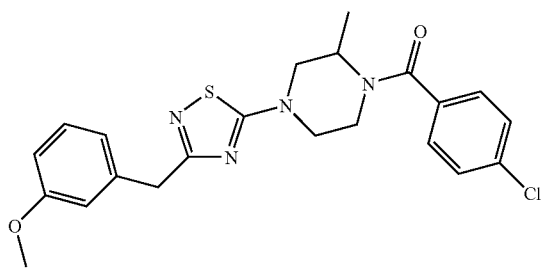 |
| 175 | 1-(2-fluorobenzoyl)-4-[3-(4-methylbenzyl)-1,2,4-thiadiazol-5-yl]piperazine | 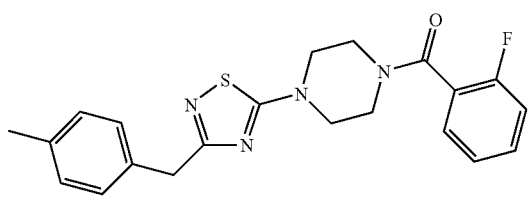 |
| 176 | 1-(4-hexylbenzoyl)-4-[3-(4-methylbenzyl)-1,2,4-thiadiazol-5-yl]piperazine | 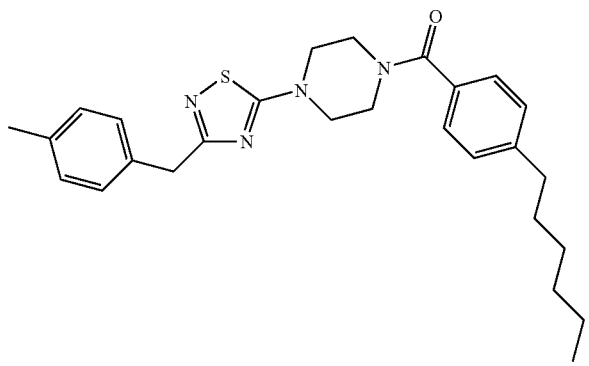 |
| 177 | 1-(2-chloro-4-nitrobenzoyl)-4-[3-(4-fluorobenzyl)-1,2,4-thiadiazol-5-yl]-2-methylpiperazine | 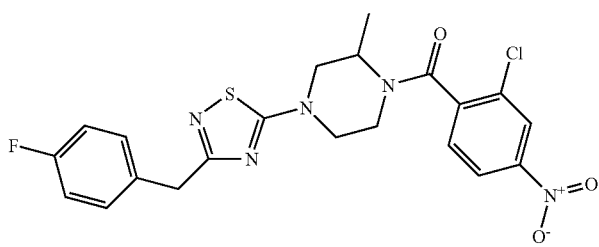 |
| 178 | 1-(1,3-benzodioxol-5-ylcarbonyl)-4-[3-(4-fluorobenzyl)-1,2,4-thiadiazol-5-yl]-2-methylpiperazine | 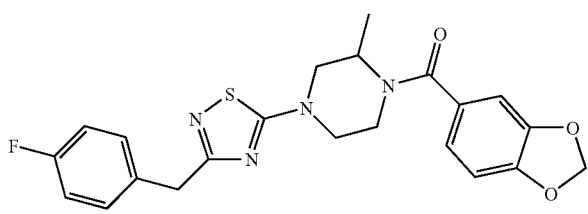 |

| No. | Compound name |
|---|---|
| 179 | 1-(3-fluorobenzoyl)-4-[3-(4-fluorobenzyl)-1,2,4-thiadiazol-5-yl]-2-methylpiperazine |
| 180 | 1-(4-tert-butylbenzoyl)-4-[3-(4-fluorobenzyl)-1,2,4-thiadiazol-5-yl]piperazine |
| 181 | 1-benzoyl-4-[3-(4-fluorobenzyl)-1,2,4-thiadiazol-5-yl]piperazine |
| 182 | 1-(4-butylbenzoyl)-4-[3-(4-methylbenzyl)-1,2,4-thiadiazol-5-yl]piperazine |
| 183 | 1-(4-tert-butylbenzoyl)-4-[3-(4-methylbenzyl)-1,2,4-thiadiazol-5-yl]piperazine |
| 184 | 1-(4-nitrobenzoyl)-4-[3-(4-fluorobenzyl)-1,2,4-thiadiazol-5-yl]-2-methylpiperazine |

| No. | Compound name | Compound structure |
|---|---|---|
| 185 | 1-(2-methylphenyl)-4-[3-(4-fluorobenzyl)-1,2,4-thiadiazol-5-yl]piperazine | 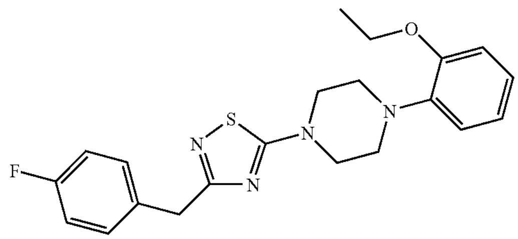 |
| 186 | 1-(2-ethoxyphenyl)-4-[3-(4-fluorobenzyl)-1,2,4-thiadiazol-5-yl]piperazine | 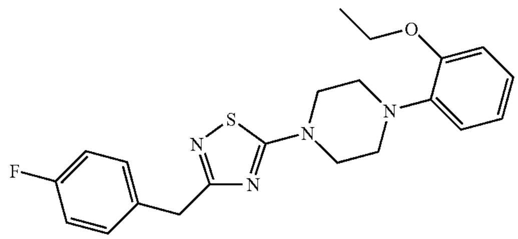 |
| 187 | 1-(2-fluorophenyl)-4-[3-(4-fluorobenzyl)-1,2,4-thiadiazol-5-yl]piperazine | 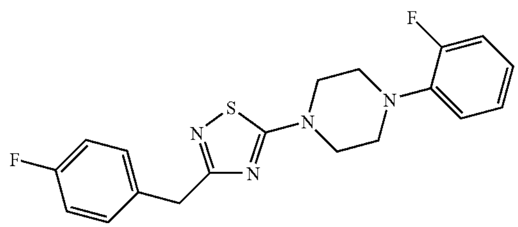 |
| 188 | 1-(3-trifluoromethylphenyl)-4-[3-(4-fluorobenzyl)-1,2,4-thiadiazol-5-yl]piperazine | 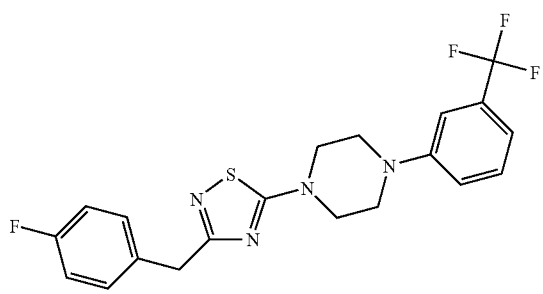 |
| 189 | 1-(4-chlorobenzoyl)-4-[3-(4-fluorobenzyl)-1,2,4-thiadiazol-5-yl]-1,4-diazepane | 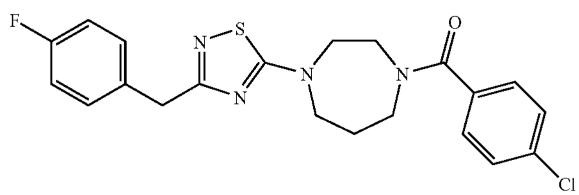 |
| 190 | 1-(4-methylbenzoyl)-4-[3-(4-fluorobenzyl)-1,2,4-thiadiazol-5-yl]-1,4-diazepane | 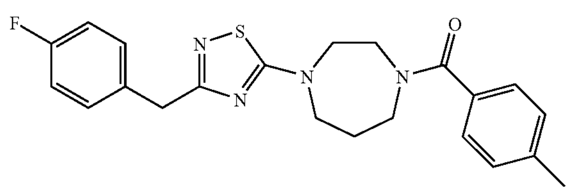 |
| 191 | 1-(1,3-benzodioxol-5-ylcarbonyl)-4-[3-(4-fluorobenzyl)-1,2,4-thiadiazol-5-yl]-1,4-diazepane | 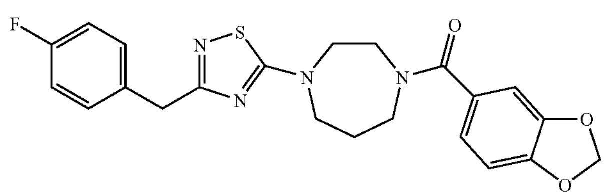 |

| No. | Compound name | Compound structure |
|---|---|---|
| 193 | 1-[4-methoxyphenylsulfonyl]-4-[3-(3-fluoro-benzyl)-1,2,4-thiadiazol-5-yl]piperazine | 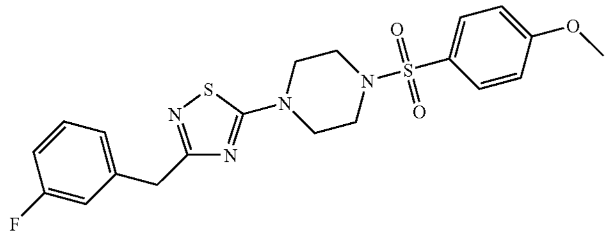 |
| 194 | 1-[4-methoxyphenylsulfonyl]-4-[3-(2-fluoro-benzyl)-1,2,4-thiadiazol-5-yl]piperazine | 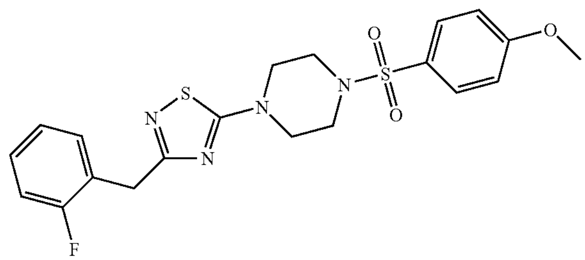 |
| 195 | 1-(2-methoxyphenylsulfonyl)-4-[3-(4-fluoro-benzyl)-1,2,4-thiadiazol-5-yl]piperazine | 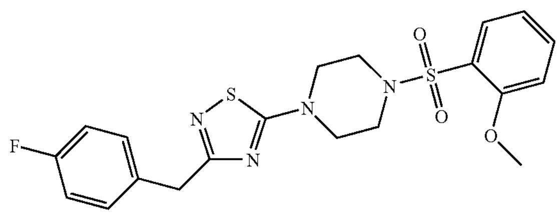 |
| 196 | 1-[4-ethoxyphenylsulfonyl]-4-[3-(4-fluoro-benzyl)-1,2,4-thiadiazol-5-yl]piperazine | 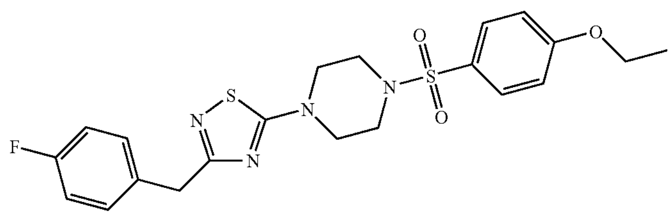 |
| 197 | 1-[4-ethylphenylsulfonyl]-4-[3-(4-fluoro-benzyl)-1,2,4-thiadiazol-5-yl]piperazine | 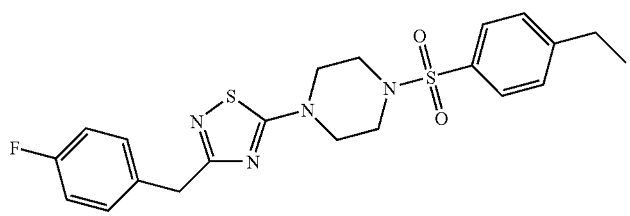 |
| 198 | 1-phenylsulfonyl-4-[3-(4-fluoro-benzyl)-1,2,4-thiadiazol-5-yl]piperazine | 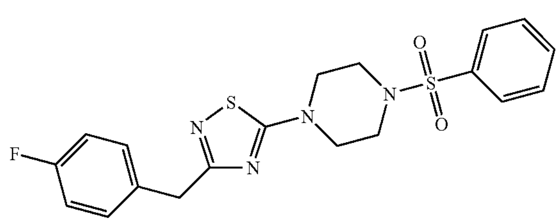 |
| 199 | 1-(4-methoxyphenylsulfonyl)-4-[3-benzyl-1,2,4-thiadiazol-5-yl]piperazine | 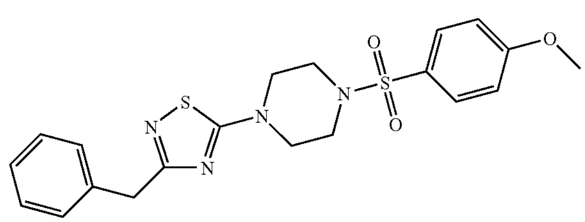 |

| No. | Compound name | Compound structure |
|---|---|---|
| 200 | 1-(4-propionyloxy)benzene-sulfonyl-4-[3-(4-fluoro-benzyl)-1,2,4-thiadiazol-5-yl]piperazine | 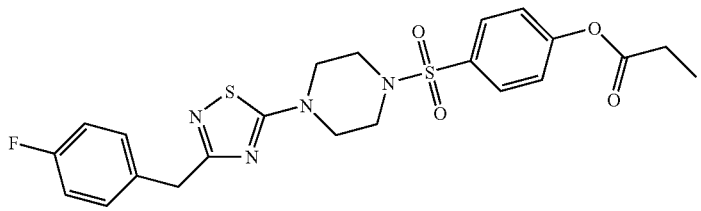 |
| 201 | 1-[4-methoxyphenylsulfonyl]-4-[3-(3-methyl-benzyl-1,2,4-thiadiazol-5-yl]piperazine | 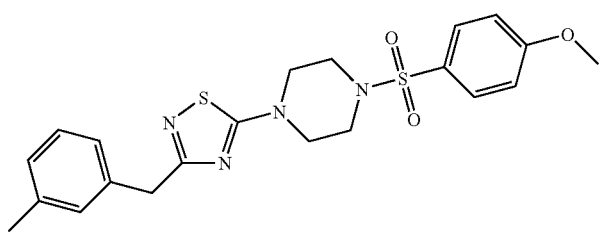 |
| 202 | 1-[4-methoxyphenylsulfonyl]-4-[3-(2-methyl-benzyl-1,2,4-thiadiazol-5-yl]piperazine | 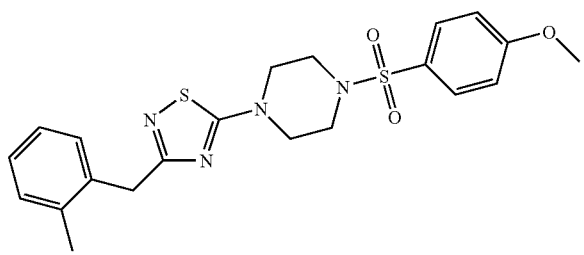 |
| 203 | 1-[4-methoxyphenylsulfonyl]-4-[3-(2-methoxy-benzyl-1,2,4-thiadiazol-5-yl]piperazine | 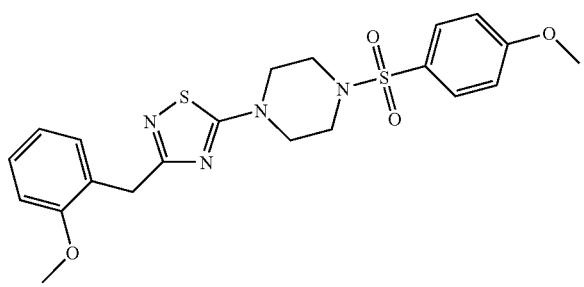 |
| 204 | 1-[4-methoxyphenylsulfonyl]-4-[3-(3-methyl-4-fluoro-benzyl-1,2,4-thiadiazol-5-yl]piperazine | 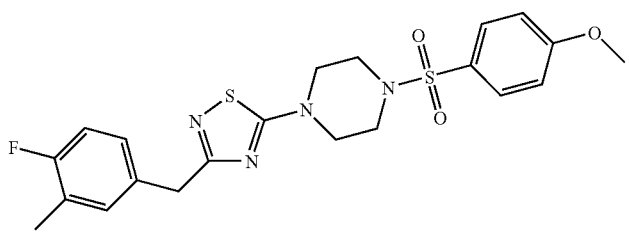 |
| 205 | 1-[4-methoxyphenylsulfonyl]-4-[3-(4-methoxy-benzyl-1,2,4-thiadiazol-5-yl]piperazine | 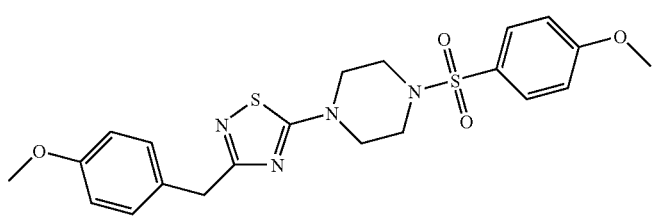 |

| No. | Compound name | Compound structure |
|---|---|---|
| 206 | 1-[2-thienylsulfonyl]-4-[3-(2-methyl-benzyl-1,2,4-thiadiazol-5-yl]piperazine | 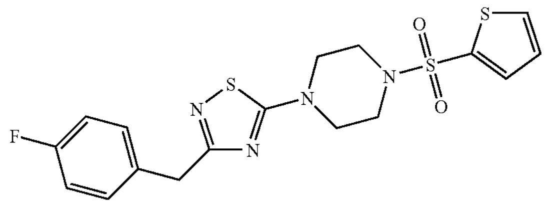 |
| 207 | 1-[4-bromophenylsulfonyl]-4-[3-(3-methoxy-benzyl-1,2,4-thiadiazol-5-yl]piperazine | 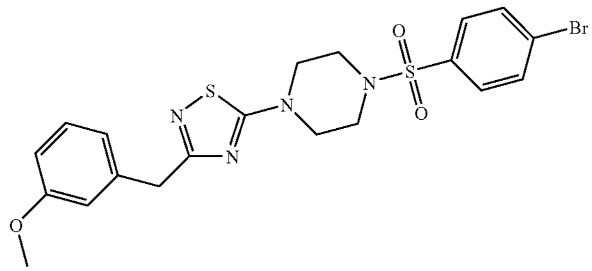 |
| 208 | 1-[4-methoxyphenylsulfonyl]-4-[3-(3-methoxybenzyl)-1,2,4-thia-diazol-5-yl]-2-methyl-piperazine | 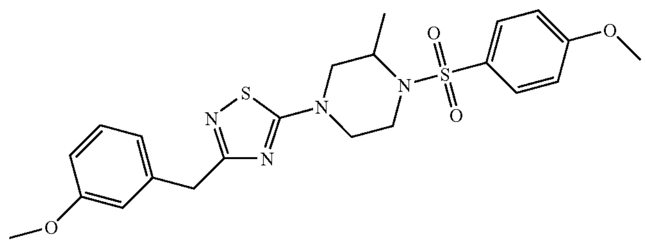 |
| 209 | N-[4-methoxyphenylsulfonyl]-N'-[3-(3-methoxybenzyl)-1,2,4-thia-diazol-5-yl]-ethane-1,2-diamine | 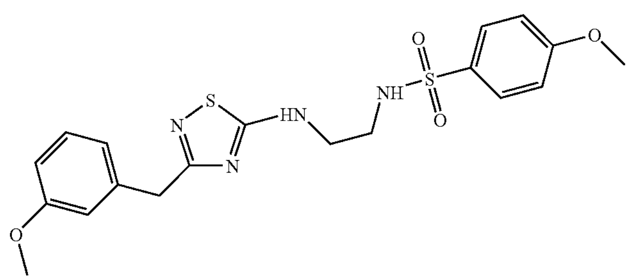 |
| 210 | N-(4-methoxyphenylsulfonyl]-N'-[3-(3-methoxybenzyl)-1,2,4-thia-diazol-5-yl]-propane-1,2-diamine | 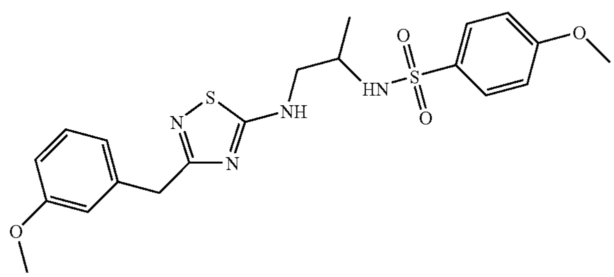 |
| 211 | N-[4-methoxyphenylsulfonyl]-N'-[3-(3-methoxybenzyl)-1,2,4-thia-diazol-5-yl]-propane-1,3-diamine | 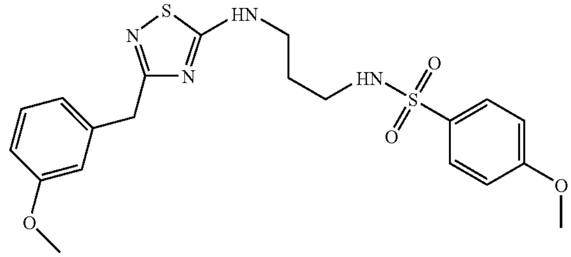 |

-continued

| No. | Compound name | Compound structure |
|---|---|---|
| 212 | 1-[4-methoxyphenylsulfonyl]-4-[3-(3-methoxybenzyl)-1,2,4-thiadiazol-5-yl]diazepane | 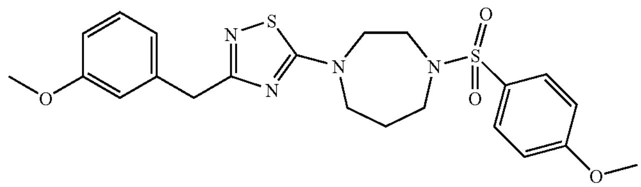 |
| 213 | N'-[4-methoxyphenylsulfonyl]-N-[3-(3-methoxybenzyl)-1,2,4-thiadiazol-5-yl]-N-methylethane-1,2-diamine | 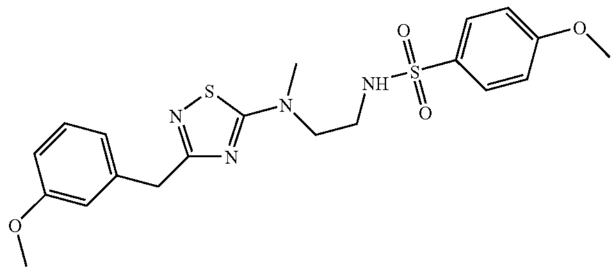 |
| 214 | N'-[4-methoxyphenylsulfonyl]-N-[3-(3-methoxybenzyl)-1,2,4-thiadiazol-5-yl]-N'-methylethane-1,2-diamine | 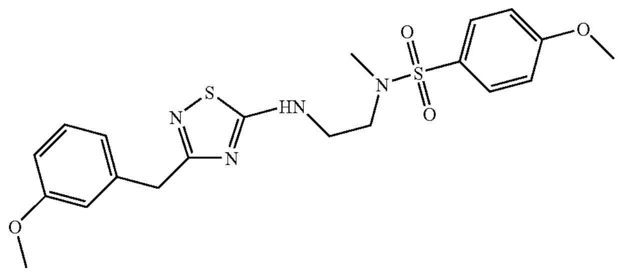 |
| 215 | N'-[4-methoxyphenylsulfonyl]-N-[3-(3-methoxybenzyl)-1,2,4-thiadiazol-5-yl]-N,N'-dimethylethane-1,2-diamine | 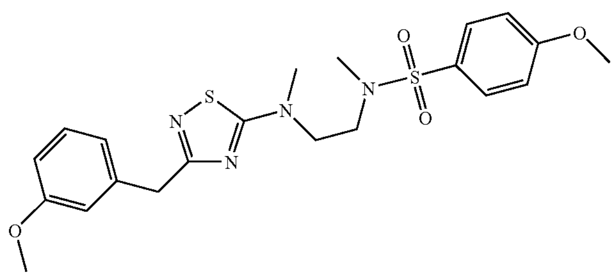 |
| 217 | 1-(4-hydroxybenzenesulfonyl)-4-[3-(4-fluoro-benzyl)-1,2,4-thiadiazol-5-yl]piperazine | 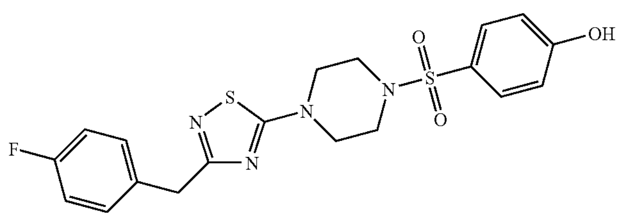 |

(end of Table 1)

TABLE 2 biological activity of exemplary compounds

| No. | Name | % Inhib. | EC50 (μM) |
|---|---|---|---|
| 60 | 1-[4-methoxyphenylsulfonyl]-4-[3-(4-methylbenzyl)-1,2,4-thiadiazol-5-yl]-2-methylpiperazine | 93 | 0.000033 |
| 74 | 1-[4-methoxyphenylsulfonyl]-4-[3-(4-fluorobenzyl)-1,2,4-thiadiazol-5-yl]piperazine | 44 | 0.000105 |
| 49 | 1-[4-acetamidophenylsulfonyl]-4-[3-(4-methylbenzyl)-1,2,4-thiadiazol-5-yl]piperazine | 77 | 0.000106 |

TABLE 2-continued biological activity of exemplary compounds

| No. | Name | % Inhib. | EC50 (µM) |
|---|---|---|---|
| 31 | 1-[4-methoxyphenylsulfonyl]-4-[3-(4-chlorobenzyl)-1,2,4-thiadiazol-5-yl]piperazine | 59 | 0.000169 |
| 68 | 1-[4-methoxyphenylsulfonyl]-4-[3-(4-methylbenzyl)-1,2,4-thiadiazol-5-yl]piperazine | 53 | 0.000255 |
| 51 | 1-[4-methoxyphenylsulfonyl]-4-[3-(4-chlorobenzyl)-1,2,4-thiadiazol-5-yl]-2-methylpiperazine | 94 | 0.001346 |
| 33 | 1-[4-fluorophenylsulfonyl]-4-[3-(4-chlorobenzyl)-1,2,4-thiadiazol-5-yl]piperazine | 53 | 0.002818 |
| 48 | 1-[4-acetamidophenylsulfonyl]-4-[3-(4-methylbenzyl)-1,2,4-thiadiazol-5-yl]-2-methylpiperazine | 91 | 0.008439 |
| 57 | 1-[4-fluorophenylsulfonyl]-4-[3-(4-methylbenzyl)-1,2,4-thiadiazol-5-yl]piperazine | 88 | 0.010360 |
| 115 | 1-(2-fluorobenzoyl)-4-[3-(3-methoxybenzyl)-1,2,4-thiadiazol-5-yl]-2-methylpiperazine | 75 | 0.036080 |
| 65 | 1-[2-naphtylsulfonyl]-4-[3-(4-methylbenzyl)-1,2,4-thiadiazol-5-yl]piperazine | 78 | 0.039270 |
| 35 | 1-[1-naphtylsulfonyl]-4-[3-(4-methylbenzyl)-1,2,4-thiadiazol-5-yl]piperazine | 47 | 0.047235 |
| 116 | 1-(4-ethylbenzoyl)-4-[3-(4-fluorobenzyl)-1,2,4-thiadiazol-5-yl]-2-methylpiperazine | 71 | 0.052160 |
| 80 | 1-(phenylprop-2-ensulfonyl)-4-[3-(4-methylbenzyl)-1,2,4-thiadiazol-5-yl]piperazine | 70 | 0.056880 |
| 58 | 1-[4-fluorophenylsulfonyl]-4-[3-(4-methylbenzyl)-1,2,4-thiadiazol-5-yl]-2-methylpiperazine | 58 | 0.061030 |
| 34 | 1-[4-chlorophenylsulfonyl]-4-[3-(4-methylbenzyl)-1,2,4-thiadiazol-5-yl]-2-methylpiperazine | 66 | 0.065695 |
| 37 | 1-[2,4,6-trimethylphenylsulfonyl]-4-[3-(4-methylbenzyl)-1,2,4-thiadiazol-5-yl]piperazine | 48 | 0.073110 |
| 55 | 1-[4-acetamidophenylsulfonyl]-4-[3-(4-fluorobenzyl)-1,2,4-thiadiazol-5-yl]-2-methylpiperazine | 114 | 0.078150 |
| 63 | 1-[4-methylphenylsulfonyl]-4-[3-(4-chlorobenzyl)-1,2,4-thiadiazol-5-yl]piperazine | 83 | 0.080740 |
| 117 | 1-(4-butylbenzoyl)-4-[3-(4-methylbenzyl)-1,2,4-thiadiazol-5-yl]-2-methylpiperazine | 82 | 0.084110 |
| 118 | 1-(4-methoxybenzoyl)-4-[3-(4-fluorobenzyl)-1,2,4-thiadiazol-5-yl]-2-methylpiperazine | 64 | 0.091145 |
| 119 | 1-(1,3-benzodioxol-5-ylcarbonyl)-4-[3-(3-methoxybenzyl)-1,2,4-thiadiazol-5-yl]-2-methylpiperazine | 72 | 0.095050 |
| 120 | 1-(4-butylbenzoyl)-4-[3-(4-fluorobenzyl)-1,2,4-thiadiazol-5-yl]-2-methylpiperazine | 120 | 0.098730 |
| 40 | 1-[4-bromophenylsulfonyl]-4-[3-(4-methylbenzyl)-1,2,4-thiadiazol-5-yl]-3-methylpiperazine | 77 | 0.099855 |
| 36 | 1-[2,5-dichlorophenylsulfonyl]-4-[3-(4-methylbenzyl)-1,2,4-thiadiazol-5-yl]-2-methylpiperazine | 52 | 0.10 |
| 52 | 1-[2-naphtylsulfonyl]-4-[3-(4-chlorobenzyl)-1,2,4-thiadiazol-5-yl]piperazine | 104 | 0.10 |
| 121 | 1-(4-hexylbenzoyl)-4-[3-(4-fluorobenzyl)-1,2,4-thiadiazol-5-yl]piperazine | 64 | 0.12 |
| 78 | 1-(phenylprop-2-ensulfonyl)-4-[3-(4-fluorobenzyl)-1,2,4-thiadiazol-5-yl]piperazine | 75 | 0.13 |
| 38 | 1-[2-naphtylsulfonyl]-4-[3-(4-methylbenzyl)-1,2,4-thiadiazol-5-yl]-2-methylpiperazine | 78 | 0.13 |
| 122 | 1-(3-chlorobenzoyl)-4-[3-(4-fluorobenzyl)-1,2,4-thiadiazol-5-yl]-2-methylpiperazine | 92 | 0.14 |
| 123 | 1-(4-fluorobenzoyl)-4-[3-(3-methoxybenzyl)-1,2,4-thiadiazol-5-yl]-2-methylpiperazine | 95 | 0.14 |
| 124 | 1-(4-methylbenzoyl)-4-[3-(3-methoxybenzyl)-1,2,4-thiadiazol-5-yl]-2-methylpiperazine | 57 | 0.14 |
| 1 | 4-phenylacetyl-1-[3-(4-fluorobenzyl)-1,2,4-thiadiazol-5-yl]piperazine | 75 | 0.15 |
| 39 | 1-[2,5-dichlorophenylsulfonyl]-4-[3-(4-chlorobenzyl)-1,2,4-thiadiazol-5-yl]piperazine | 25 | 0.16 |
| 125 | 1-(3-fluorobenzoyl)-4-[3-(4-chlorobenzyl)-1,2,4-thiadiazol-5-yl]-2-methylpiperazine | 68 | 0.16 |
| 189 | 1-(4-chlorobenzoyl)-4-[3-(4-fluorobenzyl)-1,2,4-thiadiazol-5-yl]-1,4-diazepane | 85 | 0.17 |
| 79 | 1-(phenylprop-2-ensulfonyl)-4-[3-(4-methylbenzyl)-1,2,4-thiadiazol-5-yl]-2-methylpiperazine | 53 | 0.17 |
| 19 | N-(2,6-dimethylphenyl)-4-[3-(4-fluorobenzyl)-1,2,4-thiadiazol-5-yl]-2-methylpiperazine-1-carboxamide | 95 | 0.20 |
| 126 | 1-benzoyl-4-[3-(4-fluorobenzyl)-1,2,4-thiadiazol-5-yl]-2-methylpiperazine | 63 | 0.21 |
| 127 | 1-(4-fluorobenzoyl)-4-[3-(4-fluorobenzyl)-1,2,4-thiadiazol-5-yl]-2-methylpiperazine | 108 | 0.23 |

TABLE 2-continued biological activity of exemplary compounds

| No. | Name | % Inhib. | EC50 (µM) |
|---|---|---|---|
| 128 | 1-(4-tert-butylbenzoyl)-4-[3-(4-fluorobenzyl)-1,2,4-thiadiazol-5-yl]-2-methylpiperazine | 95 | 0.24 |
| 129 | 1-(1,1'-biphenyl-4-ylcarbonyl)-4-[3-(4-fluorobenzyl)-1,2,4-thiadiazol-5-yl]-2-methylpiperazine | 61 | 0.24 |
| 2 | 4-(4-fluorophenylacetyl), 1-[3-(4-fluorobenzyl)-1,2,4-thiadiazol-5-yl]piperazine | 54 | 0.25 |
| 130 | 1-(4-methoxybenzoyl)-4-[3-(4-methylbenzyl)-1,2,4-thiadiazol-5-yl]-2-methylpiperazine | 118 | 0.25 |
| 131 | 1-(4-ethylbenzoyl)-4-[3-(4-methylbenzyl)-1,2,4-thiadiazol-5-yl]piperazine | 91 | 0.25 |
| 107 | 2-(4-fluorophenyl)-N-{2-[4-[3-(4-fluorobenzyl)-1,2,4-thiadiazol-5-yl]piperazin-1-yl]ethyl}acetamide | 80 | 0.26 |
| 132 | 1-(2-naphthoyl)-4-[3-(4-fluorobenzyl)-1,2,4-thiadiazol-5-yl]-2-methylpiperazine | 74 | 0.26 |
| 133 | 1-(2-methoxybenzoyl)-4-[3-(4-fluorobenzyl)-1,2,4-thiadiazol-5-yl]-2-methylpiperazine | 118 | 0.29 |
| 134 | 1-(4-pentylbenzoyl)-4-[3-(4-methylbenzyl)-1,2,4-thiadiazol-5-yl]-2-methylpiperazine | 75 | 0.30 |
| 135 | 1-(4-bromobenzoyl)-4-[3-(4-fluorobenzyl)-1,2,4-thiadiazol-5-yl]-2-methylpiperazine | 73 | 0.31 |
| 136 | 1-(2,4-dimethoxybenzoyl)-4-[3-(4-fluorobenzyl)-1,2,4-thiadiazol-5-yl]-2-methylpiperazine | 83 | 0.34 |
| 137 | 1-(3,5-dichlorobenzoyl)-4-[3-(4-fluorobenzyl)-1,2,4-thiadiazol-5-yl]piperazine | 68 | 0.35 |
| 94 | 4-pentyl-N-{2-[4-[3-(4-fluorobenzyl)-1,2,4-thiadiazol-5-yl]piperazin-1-yl]ethyl}benzamide | 90 | 0.35 |
| 81 | 1-(butylsulfonyl)-4-[3-(4-chlorobenzyl)-1,2,4-thiadiazol-5-yl]piperazine | 80 | 0.35 |
| 138 | 1-(3-chlorobenzoyl)-4-[3-(4-fluorobenzyl)-1,2,4-thiadiazol-5-yl]piperazine | 81 | 0.36 |
| 185 | 1-(2-methylphenyl)-4-[3-(4-fluorobenzyl)-1,2,4-thiadiazol-5-yl]piperazine | 114 | 0.38 |
| 95 | 4-butyl-N-{2-[4-[3-(4-fluorobenzyl)-1,2,4-thiadiazol-5-yl]piperazin-1-yl]ethyl}benzamide | 78 | 0.38 |
| 139 | 1-(4-methylbenzoyl)-4-[3-(4-fluorobenzyl)-1,2,4-thiadiazol-5-yl]-2-methylpiperazine | 87 | 0.40 |
| 140 | 1-(2-methylbenzoyl)-4-[3-(4-fluorobenzyl)-1,2,4-thiadiazol-5-yl]-2-methylpiperazine | 56 | 0.45 |
| 141 | 1-(4-methylbenzoyl)-4-[3-(4-fluorobenzyl)-1,2,4-thiadiazol-5-yl]piperazine | 75 | 0.49 |
| 142 | 1-(3-bromobenzoyl)-4-[3-(4-fluorobenzyl)-1,2,4-thiadiazol-5-yl]-2-methylpiperazine | 72 | 0.50 |
| 9 | N-(3-fluorophenyl)-4-[3-(4-fluorobenzyl)-1,2,4-thiadiazol-5-yl]piperazine-1-carboxamide | 53 | 0.52 |
| 41 | 1-[1-naphthylsulfonyl]-4-[3-(4-methylbenzyl)-1,2,4-thiadiazol-5-yl]-3-methylpiperazine | 54 | 0.53 |
| 112 | 3-phenyl-N-{2-[4-[3-(4-fluorobenzyl)-1,2,4-thiadiazol-5-yl]piperazin-1-yl]ethyl}propanamide | 91 | 0.55 |
| 143 | 1-(4-ethylbenzoyl)-4-[3-(3-methoxybenzyl)-1,2,4-thiadiazol-5-yl]-2-methylpiperazine | 89 | 0.56 |
| 144 | 1-(3-methylbenzoyl)-4-[3-(4-methylbenzyl)-1,2,4-thiadiazol-5-yl]-2-methylpiperazine | 64 | 0.56 |
| 89 | 1-(3-phenylpropanoyl)-4-[3-(4-fluorobenzyl)-1,2,4-thiadiazol-5-yl]-2-methylpiperazine | 86 | 0.60 |
| 10 | N-(2-methylphenyl)-4-[3-(4-fluorobenzyl)-1,2,4-thiadiazol-5-yl]-2-methylpiperazine-1-carboxamide | 72 | 0.60 |
| 145 | 1-(3-trifluoromethylbenzoyl)-4-[3-(4-fluorobenzyl)-1,2,4-thiadiazol-5-yl]-2-methylpiperazine | 60 | 0.62 |
| 11 | N-(4-ethylphenyl)-4-[3-(4-fluorobenzyl)-1,2,4-thiadiazol-5-yl]-2-methylpiperazine-1-carboxamide | 73 | 0.69 |
| 91 | 1-[3-phenylprop-2-enyl]-4-[3-(4-methylbenzyl)-1,2,4-thiadiazol-5-yl]piperazine | 90 | 0.71 |
| 146 | 1-(4-tert-butylbenzoyl)-4-[3-(3-methoxybenzyl)-1,2,4-thiadiazol-5-yl]-2-methylpiperazine | 94 | 0.72 |
| 92 | 1-[3-phenylprop-2-enyl]-4-[3-(4-chlorobenzyl)-1,2,4-thiadiazol-5-yl]piperazine | 69 | 0.75 |
| 20 | N-(2,4-dimethylphenyl)-4-[3-(4-fluorobenzyl)-1,2,4-thiadiazol-5-yl]-2-methylpiperazine-1-carboxamide | 106 | 0.76 |
| 21 | N-(2,6-dichlorophenyl)-4-[3-(4-fluorobenzyl)-1,2,4-thiadiazol-5-yl]-2-methylpiperazine-1-carboxamide | 70 | 0.79 |

TABLE 2-continued biological activity of exemplary compounds

| No. | Name | % Inhib. | EC50 (µM) |
|---|---|---|---|
| 96 | 4-hexyl-N-{2-[4-[3-(4-fluorobenzyl)-1,2,4-thiadiazol-5-yl]piperazin-1-yl]ethyl}benzamide | 72 | 0.80 |
| 4 | 1-(4-methoxyphenylacetyl)-4-[3-(4-fluorobenzyl)-1,2,4-thiadiazol-5-yl]-2-methylpiperazine | 56 | 0.82 |
| 147 | 1-(4-ethylbenzoyl)-4-[3-(4-methylbenzyl)-1,2,4-thiadiazol-5-yl]-2-methylpiperazine | 88 | 0.84 |
| 148 | 1-(2-bromobenzoyl)-4-[3-(4-fluorobenzyl)-1,2,4-thiadiazol-5-yl]-2-methylpiperazine | 56 | 0.86 |
| 42 | 1-[4-tert-butylphenylsulfonyl]-4-[3-(4-methylbenzyl)-1,2,4-thiadiazol-5-yl]-2-methylpiperazine | 33 | 0.87 |
| 22 | N-(3-cyanophenyl)-4-[3-(4-fluorobenzyl)-1,2,4-thiadiazol-5-yl]-2-methylpiperazine-1-carboxamide | 59 | 0.88 |
| 43 | 1-[1-naphtylsulfonyl]-4-[3-(4-chlorobenzyl)-1,2,4-thiadiazol-5-yl]-2-methylpiperazine | 35 | 0.89 |
| 12 | N-(2-ethylphenyl)-4-[3-(4-fluorobenzyl)-1,2,4-thiadiazol-5-yl]-2-methylpiperazine-1-carboxamide | 92 | 0.89 |
| 23 | N-(2,4-difluorophenyl)-4-[3-(4-fluorobenzyl)-1,2,4-thiadiazol-5-yl]-2-methylpiperazine-1-carboxamide | 66 | 0.94 |
| 149 | 1-(2-fluorobenzoyl)-4-[3-(4-methylbenzyl)-1,2,4-thiadiazol-5-yl]-2-methylpiperazine | 105 | 0.98 |
| 86 | 1-[(2E)-3-phenylprop-2-enoyl]-4-[3-(4-chlorobenzyl)-1,2,4-thiadiazol-5-yl]-2-methylpiperazine | 81 | 1.13 |
| 150 | 1-(3-fluorobenzoyl)-4-[3-benzyl-1,2,4-thiadiazol-5-yl]-2-methylpiperazine | 99 | 1.14 |
| 151 | 1-(4-fluorobenzoyl)-4-[3-(4-methylbenzyl)-1,2,4-thiadiazol-5-yl]-2-methylpiperazine | 73 | 1.14 |
| 152 | 1-(2-methylbenzoyl)-4-[3-(4-fluorobenzyl)-1,2,4-thiadiazol-5-yl]piperazine | 66 | 1.15 |
| 45 | 1-[2,4,6-trimethylphenylsulfonyl]-4-[3-(4-methylbenzyl)-1,2,4-thiadiazol-5-yl]-2-methylpiperazine | 56 | 1.20 |
| 24 | N-(2,6-dimethylphenyl)-4-[3-(4-fluorobenzyl)-1,2,4-thiadiazol-5-yl]piperazine-1-carboxamide | 124 | 1.20 |
| 13 | N-phenyl-4-[3-(4-fluorobenzyl)-1,2,4-thiadiazol-5-yl]piperazine-1-carboxamide | 71 | 1.23 |
| 97 | 4-chloro-N-{2-[4-[3-(4-fluorobenzyl)-1,2,4-thiadiazol-5-yl]piperazin-1-yl]ethyl}benzamide | 68 | 1.29 |
| 46 | 1-[3-trifluorophenylsulfonyl]-4-[3-(4-fluorobenzyl)-1,2,4-thiadiazol-5-yl]-2-methylpiperazine | 64 | 1.34 |
| 90 | 1-(3-phenylpropanoyl)-4-[3-(4-fluorobenzyl)-1,2,4-thiadiazol-5-yl]piperazine | 73 | 1.41 |
| 98 | 3,5-dichloro-N-{2-[4-[3-(4-fluorobenzyl)-1,2,4-thiadiazol-5-yl]piperazin-1-yl]ethyl}benzamide | 102 | 1.42 |
| 153 | 1-(4-fluorobenzoyl)-4-[3-(4-chlorobenzyl)-1,2,4-thiadiazol-5-yl]piperazine | 53 | 1.44 |
| 8 | 1-(2-phenylbutanoyl)-4-[3-(4-fluorobenzyl)-1,2,4-thiadiazol-5-yl]-2-methylpiperazine | 71 | 1.49 |
| 113 | 1-benzyl-4-[3-(4-fluorobenzyl)-1,2,4-thiadiazol-5-yl]piperazine | 65 | 1.54 |
| 99 | 2-methyl-N-{2-[4-[3-(4-fluorobenzyl)-1,2,4-thiadiazol-5-yl]piperazin-1-yl]ethyl}benzamide | 97 | 1.58 |
| 154 | 1-(4-fluorobenzoyl)-4-[3-benzyl-1,2,4-thiadiazol-5-yl]-2-methylpiperazine | 75 | 1.58 |
| 82 | 1-(octylsulfonyl)-4-[3-(4-methylbenzyl)-1,2,4-thiadiazol-5-yl]piperazine | 50 | 1.58 |
| 155 | 1-(4-chlorobenzoyl)-4-[3-(4-methylbenzyl)-1,2,4-thiadiazol-5-yl]piperazine | 76 | 1.64 |
| 156 | 1-(3-fluorobenzoyl)-4-[3-(4-methylbenzyl)-1,2,4-thiadiazol-5-yl]-2-methylpiperazine | 86 | 1.67 |
| 25 | N-naphtyl-4-[3-(4-fluorobenzyl)-1,2,4-thiadiazol-5-yl]-2-methylpiperazine-1-carboxamide | 97 | 1.69 |
| 157 | 1-(3-fluorobenzoyl)-4-[3-(4-chlorobenzyl)-1,2,4-thiadiazol-5-yl]piperazine | 70 | 1.70 |
| 14 | N-(4-ethoxyphenyl)-4-[3-(4-fluorobenzyl)-1,2,4-thiadiazol-5-yl]-2-methylpiperazine-1-carboxamide | 70 | 1.73 |
| 111 | 2-phenyl-N-{2-[4-[3-(4-fluorobenzyl)-1,2,4-thiadiazol-5-yl]piperazin-1-yl]ethyl}butanamide | 79 | 1.79 |
| 100 | 3-fluoro-N-{2-[4-[3-(4-chlorobenzyl)-1,2,4-thiadiazol-5-yl]piperazin-1-yl]ethyl}benzamide | 75 | 1.79 |
| 101 | 4-methyl-N-{2-[4-[3-(4-fluorobenzyl)-1,2,4-thiadiazol-5-yl]piperazin-1-yl]ethyl}benzamide | 68 | 1.94 |
| 102 | 4-fluoro-N-{2-[4-[3-(4-fluorobenzyl)-1,2,4-thiadiazol-5-yl]piperazin-1-yl]ethyl}benzamide | 80 | 1.99 |

TABLE 2-continued biological activity of exemplary compounds

| No. | Name | % Inhib. | EC50 (μM) |
|---|---|---|---|
| 93 | 1-[3-phenylprop-2-enyl]-4-[3-(4-fluorobenzyl)-1,2,4-thiadiazol-5-yl]piperazine | 91 | 1.99 |
| 186 | 1-(2-ethoxyphenyl)-4-[3-(4-fluorobenzyl)-1,2,4-thiadiazol-5-yl]piperazine | 94 | 2.05 |
| 108 | 2-phenyl-N-{2-[4-[3-(4-fluorobenzyl)-1,2,4-thiadiazol-5-yl]piperazin-1-yl]ethyl}acetamide | 63 | 2.06 |
| 158 | 1-benzoyl-4-[3-(4-methylbenzyl)-1,2,4-thiadiazol-5-yl]piperazine | 57 | 2.10 |
| 3 | 1-(4-fluorophenylacetyl)-4-[3-(4-methylbenzyl)-1,2,4-thiadiazol-5-yl]-2-methylpiperazine | 76 | 2.20 |
| 103 | 4-ethyl-N-{2-[4-[3-(4-fluorobenzyl)-1,2,4-thiadiazol-5-yl]piperazin-1-yl]ethyl}benzamide | 139 | 2.32 |
| 87 | 1-[(2E)-3-phenylprop-2-enoyl]-4-[3-(4-fluorobenzyl)-1,2,4-thiadiazol-5-yl]-2-methylpiperazine | 94 | 2.49 |
| 83 | 1-(butylsulfonyl)-4-[3-(4-methylbenzyl)-1,2,4-thiadiazol-5-yl]piperazine | 36 | 2.64 |
| 190 | 1-(4-methylbenzoyl)-4-[3-(4-fluorobenzyl)-1,2,4-thiadiazol-5-yl]-1,4-diazepane | 87 | 2.77 |
| 187 | 1-(2-fluorophenyl)-4-[3-(4-fluorobenzyl)-1,2,4-thiadiazol-5-yl]piperazine | 83 | 2.81 |
| 159 | 1-(2-fluorobenzoyl)-4-[3-(4-chlorobenzyl)-1,2,4-thiadiazol-5-yl]piperazine | 48 | 2.85 |
| 160 | 1-(4-fluorobenzoyl)-4-[3-(4-methylbenzyl)-1,2,4-thiadiazol-5-yl]piperazine | 88 | 2.87 |
| 161 | 1-(1,3-benzodioxol-5-ylcarbonyl)-4-[3-(4-methylbenzyl)-1,2,4-thiadiazol-5-yl]-2-methyl + B176piperazine | 101 | 3.36 |
| 162 | 1-(3-flurorbenzoyl)-4-[3-(4-methylbenzyl)-1,2,4-thiadiazol-5-yl]piperazine | 101 | 3.40 |
| 84 | 1-(ethylsulfonyl)-4-[3-(4-chlorobenzyl)-1,2,4-thiadiazol-5-yl]piperazine | 53 | 3.48 |
| 109 | 2-(4-fluorophenyl)-N-{2-[4-[3-(4-methylbenzyl)-1,2,4-thiadiazol-5-yl]piperazin-1-yl]ethyl}acetamide | 93 | 3.52 |
| 163 | 1-(4-fluorobenzoyl)-4-[3-benzyl-1,2,4-thiadiazol-5-yl]piperazine | 67 | 3.61 |
| 85 | 1-(isopropylsulfonyl)-4-[3-(4-methylbenzyl)-1,2,4-thiadiazol-5-yl]piperazine | 69 | 3.65 |
| 104 | N-{2-[4-[3-(4-fluorobenzyl)-1,2,4-thiadiazol-5-yl]piperazin-1-yl]ethyl}benzamide | 65 | 3.82 |
| 164 | 1-(4-bromobenzoyl)-4-[3-(4-methylbenzyl)-1,2,4-thiadiazol-5-yl]piperazine | 60 | 3.86 |
| 15 | N-(2-methylphenyl)-4-[3-(4-fluorobenzyl)-1,2,4-thiadiazol-5-yl]piperazine-1-carboxamide | 65 | 5.01 |
| 16 | N-(2-fluorophenyl)-4-[3-(4-fluorobenzyl)-1,2,4-thiadiazol-5-yl]piperazine-1-carboxamide | 72 | 5.68 |
| 30 | 1-[4-tert-butylphenylsulfonyl]-4-[3-(4-fluorobenzyl)-1,2,4-thiadiazol-5-yl]piperazine | 51 | |
| 77 | 1-(benzylsulfonyl)-4-[3-(4-methylbenzyl)-1,2,4-thiadiazol-5-yl]piperazine | 81 | |
| 5 | 1-phenylacetyl-4-[3-(4-fluorobenzyl)-1,2,4-thiadiazol-5-yl]-2-methylpiperazine | 83 | |
| 6 | 1-(4-fluorophenylacetyl)-4-[3-(4-fluorobenzyl)-1,2,4-thiadiazol-5-yl]-2-methylpiperazine | 75 | |
| 7 | 1-[chloro(phenyl)acetyl]-4-[3-(4-fluorobenzyl)-1,2,4-thiadiazol-5-yl]-2-methylpiperazine | 69 | |
| 17 | N-(2-trifluoromethylphenyl)-4-[3-(4-fluorobenzyl)-1,2,4-thiadiazol-5-yl]piperazine-1-carboxamide | 46 | |
| 18 | N-(2-trifluoromethylphenyl)-4-[3-(4-fluorobenzyl)-1,2,4-thiadiazol-5-yl]-2-methylpiperazine-1-carboxamide | 41 | |
| 26 | N-(3,4-difluorophenyl)-4-[3-(4-fluorobenzyl)-1,2,4-thiadiazol-5-yl]-2-methylpiperazine-1-carboxamide | 70 | |
| 27 | N-(2,4-dimethoxyphenyl)-4-[3-(4-fluorobenzyl)-1,2,4-thiadiazol-5-yl]piperazine-1-carboxamide | 67 | |
| 28 | N-(3,4-difluorophenyl)-4-[3-(4-fluorobenzyl)-1,2,4-thiadiazol-5-yl]piperazine-1-carboxamide | 64 | |
| 29 | N-(3,5-dimethoxyphenyl)-4-[3-(4-fluorobenzyl)-1,2,4-thiadiazol-5-yl]-2-methylpiperazine-1-carboxamide | 51 | |
| 47 | 1-phenylsulfonyl-4-[3-(4-fluorobenzyl)-1,2,4-thiadiazol-5-yl]-2-methylpiperazine | 129 | |
| 50 | 1-[4-methylphenylsulfonyl]-4-[3-(4-methylbenzyl)-1,2,4-thiadiazol-5-yl]-2-methylpiperazine | 105 | |

TABLE 2-continued biological activity of exemplary compounds

| No. | Name | % Inhib. | EC50 (µM) |
|---|---|---|---|
| 54 | 1-[4-tert-butylphenylsulfonyl]-4-[3-(4-fluorobenzyl)-1,2,4-thiadiazol-5-yl]-2-methylpiperazine | 60 | |
| 56 | 1-[3-trifluoromethylphenylsulfonyl]-4-[3-(4-methylbenzyl)-1,2,4-thiadiazol-5-yl]-2-methylpiperazine | 87 | |
| 59 | 1-[4-fluorophenylsulfonyl]-4-[3-(4-fluorobenzyl)-1,2,4-thiadiazol-5-yl]-2-methylpiperazine | 42 | |
| 61 | 1-[4-ter-butylphenylsulfonyl]-4-[3-(4-fluorobenzyl)-1,2,4-thiadiazol-5-yl]piperazine | 47 | |
| 62 | 1-[3-trifluoromethylphenylsulfonyl]-4-[3-(4-methylbenzyl)-1,2,4-thiadiazol-5-yl]piperazine | 45 | |
| 64 | 1-[4-bromophenylsulfonyl]-4-[3-(4-methylbenzyl)-1,2,4-thiadiazol-5-yl]piperazine | 58 | |
| 66 | 1-[4-chlorophenylsulfonyl]-4-[3-(4-methylbenzyl)-1,2,4-thiadiazol-5-yl]piperazine | 81 | |
| 67 | 1-[4-tert-butylphenylsulfonyl]-4-[3-(4-methylbenzyl)-1,2,4-thiadiazol-5-yl]piperazine | 41 | |
| 69 | 1-[4-tert-butylphenylsulfonyl]-4-[3-(4-chlorobenzyl)-1,2,4-thiadiazol-5-yl]piperazine | 31 | |
| 70 | 1-[quinoline-8-sulfonyl]-4-[3-(4-methylbenzyl)-1,2,4-thiadiazol-5-yl]piperazine | 44 | |
| 71 | 1-[4-nitrophenylsulfonyl]-4-[3-(4-methylbenzyl)-1,2,4-thiadiazol-5-yl]-2-methylpiperazine | 33 | |
| 73 | 1-[4-nitrophenylsulfonyl]-4-[3-(4-fluorobenzyl)-1,2,4-thiadiazol-5-yl]-2-methylpiperazine | 33 | |
| 76 | 1-(benzylsulfonyl)-4-[3-(4-chlorobenzyl)-1,2,4-thiadiazol-5-yl]piperazine | 40 | |
| 88 | 1-[(2E)-3-phenylprop-2-enoyl]-4-[3-(4-chlorobenzyl)-1,2,4-thiadiazol-5-yl]piperazine | 72 | |
| 105 | 3-fluoro-N-{2-[4-[3-(4-fluorobenzyl)-1,2,4-thiadiazol-5-yl]piperazin-1-yl]ethyl}benzamide | 115 | |
| 106 | 3-fluoro-N-{2-[4-[3-benzyl-1,2,4-thiadiazol-5-yl]piperazin-1-yl]ethyl}benzamide | 49 | |
| 110 | N-benzyl-N'-{2-[4-[3-(4-fluorobenzyl)-1,2,4-thiadiazol-5-yl]piperazin-1-yl]ethyl}urea | 77 | |
| 114 | 1-(1,3-benzodioxol-5-ylmethyl)-4-[3-(4-fluorobenzyl)-1,2,4-thiadiazol-5-yl]piperazine | 86 | |
| 165 | 1-(4-ethylbenzoyl)-4-[3-(4-chlorobenzyl)-1,2,4-thiadiazol-5-yl]piperazine | 133 | |
| 166 | 1-(2-chlorobenzoyl)-4-[3-(4-fluorobenzyl)-1,2,4-thiadiazol-5-yl]-2-methylpiperazine | 123 | |
| 167 | 1-(2-fluorobenzoyl)-4-[3-(4-chlorobenzyl)-1,2,4-thiadiazol-5-yl]-2-methylpiperazine | 117 | |
| 168 | 1-(4-trifluoromethylbenzoyl)-4-[3-(3-methoxybenzyl)-1,2,4-thiadiazol-5-yl]-2-methylpiperazine | 91 | |
| 169 | 1-benzoyl-4-[3-(4-methylbenzyl)-1,2,4-thiadiazol-5-yl]-2-methylpiperazine | 91 | |
| 170 | 1-(4-bromobenzoyl)-4-[3-(3-methoxybenzyl)-1,2,4-thiadiazol-5-yl]-2-methylpiperazine | 89 | |
| 171 | 1-(4-trifluoromethylbenzoyl)-4-[3-(4-methylbenzyl)-1,2,4-thiadiazol-5-yl]piperazine | 86 | |
| 172 | 1-(3-nitro-4-methylbenzoyl)-4-[3-(4-fluorobenzyl)-1,2,4-thiadiazol-5-yl]-2-methylpiperazine | 86 | |
| 173 | 1-benzoyl-4-[3-(3-methoxybenzyl)-1,2,4-thiadiazol-5-yl]-2-methylpiperazine | 85 | |
| 174 | 1-(4-chlorobenzoyl)-4-[3-(3-methoxybenzyl)-1,2,4-thiadiazol-5-yl]-2-methylpiperazine | 83 | |
| 175 | 1-(2-fluorobenzoyl)-4-[3-(4-methylbenzyl)-1,2,4-thiadiazol-5-yl]piperazine | 78 | |
| 176 | 1-(4-hexylbenzoyl)-4-[3-(4-methylbenzyl)-1,2,4-thiadiazol-5-yl]piperazine | 77 | |
| 177 | 1-(2-chloro-4-nitrobenzoyl)-4-[3-(4-fluorobenzyl)-1,2,4-thiadiazol-5-yl]-2-methylpiperazine | 77 | |
| 178 | 1-(1,3-benzodioxol-5-ylcarbonyl)-4-[3-(4-fluorobenzyl)-1,2,4-thiadiazol-5-yl]-2-methylpiperazine | 68 | |
| 179 | 1-(3-fluorobenzoyl)-4-[3-(4-fluorobenzyl)-1,2,4-thiadiazol-5-yl]-2-methylpiperazine | 68 | |
| 180 | 1-(4-tert-butylbenzoyl)-4-[3-(4-fluorobenzyl)-1,2,4-thiadiazol-5-yl]piperazine | 62 | |
| 181 | 1-benzoyl-4-[3-(4-fluorobenzyl)-1,2,4-thiadiazol-5-yl]piperazine | 60 | |
| 182 | 1-(4-butylbenzoyl)-4-[3-(4-methylbenzyl)-1,2,4-thiadiazol-5-yl]piperazine | 57 | |
| 183 | 1-(4-tert-butylbenzoyl)-4-[3-(4-methylbenzyl)-1,2,4-thiadiazol-5-yl]piperazine | 52 | |

TABLE 2-continued

| No. | Name | % Inhib. | EC50 (μM) |
|---|---|---|---|
| 184 | 1-(4-nitrobenzoyl)-4-[3-(4-fluorobenzyl)-1,2,4-thiadiazol-5-yl]-2-methylpiperazine | 52 | |
| 188 | 1-(3-trifluoromethylphenyl)-4-[3-(4-fluorobenzyl)-1,2,4-thiadiazol-5-yl]piperazine | 96 | |
| 191 | 1-(1,3-benzodioxol-5-ylcarbonyl)-4-[3-(4-fluorobenzyl)-1,2,4-thiadiazol-5-yl]-1,4-diazepane | 63 | |
| 193 | 1-[4-methoxyphenylsulfonyl]-4-[3-(3-fluoro-benzyl)-1,2,4-thiadiazol-5-yl]piperazine | 68 | 0.0107 |
| 194 | 1-[4-methoxyphenylsulfonyl]-4-[3-(2-fluoro-benzyl)-1,2,4-thiadiazol-5-yl]piperazine | 102 | 0.0027 |
| 195 | 1-[2-methoxyphenylsulfonyl]-4-[3-(4-fluoro-benzyl)-1,2,4-thiadiazol-5-yl]piperazine | 99 | 0.0567 |
| 196 | 1-[4-ethoxyphenylsulfonyl]-4-[3-(4-fluoro-benzyl)-1,2,4-thiadiazol-5-yl]piperazine | 42 | 0.0176 |
| 197 | 1-[4-ethylphenylsulfonyl]-4-[3-(4-fluoro-benzyl)-1,2,4-thiadiazol-5-yl]piperazine | 84 | 0.535 |
| 198 | 1-phenylsulfonyl-4-[3-(4-fluoro-benzyl)-1,2,4-thiadiazol-5-yl]piperazine | 25 | 0.349 |
| 199 | 1-[4-methoxyphenylsulfonyl]-4-[3-benzyl-1,2,4-thiadiazol-5-yl]piperazine | 38 | 0.0038 |
| 200 | 1-(4-propionyloxy)benzene-sulfonyl-4-[3-(4-fluoro-benzyl)-1,2,4-thiadiazol-5-yl]piperazine | 80 | 0.103 |
| 201 | 1-[4-methoxyphenylsulfonyl]-4-[3-(3-methyl-benzyl-1,2,4-thiadiazol-5-yl]piperazine | 97 | 0.0047 |
| 202 | 1-[4-methoxyphenylsulfonyl]-4-[3-(2-methyl-benzyl-1,2,4-thiadiazol-5-yl]piperazine | 63 | 0.0168 |
| 203 | 1-[4-methoxyphenylsulfonyl]-4-[3-(2-methoxy-benzyl-1,2,4-thiadiazol-5-yl]piperazine | 61 | 0.0134 |
| 204 | 1-[4-methoxyphenylsulfonyl]-4-[3-(3-methyl-4-fluoro-benzyl-1,2,4-thiadiazol-5-yl]piperazine | 90 | 0.0022 |
| 205 | 1-[4-methoxyphenylsulfonyl]-4-[3-(4-methoxy-benzyl-1,2,4-thiadiazol-5-yl]piperazine | 53 | 0.0024 |
| 206 | 1-[2-thienylsulfonyl]-4-[3-(2-methyl-benzyl-1,2,4-thiadiazol-5-yl]piperazine | 106 | 0.468 |
| 207 | 1-[4-bromophenylsulfonyl]-4-[3-(3-methoxy-benzyl-1,2,4-thiadiazol-5-yl]piperazine | 83 | 0.055 |
| 208 | 1-[4-methoxyphenylsulfonyl]-4-[3-(3-methoxybenzyl)-1,2,4-thia-diazol-5-yl]-2-methyl-piperazine | 92 | 0.0073 |
| 209 | N-[4-methoxyphenylsulfonyl]-N'-[3-(3-methoxybenzyl)-1,2,4-thia-diazol-5-yl]-ethane-1,2-diamine | 100 | 0.317 |
| 210 | N-[4-methoxyphenylsulfonyl]-N'-[3-(3-methoxybenzyl)-1,2,4-thia-diazol-5-yl]-propane-1,2-diamine | 107 | 0.289 |
| 211 | N-[4-methoxyphenylsulfonyl]-N'-[3-(3-methoxybenzyl)-1,2,4-thia-diazol-5-yl]-propane-1,3-diamine | 100 | 0.367 |
| 212 | 1-[4-methoxyphenylsulfonyl]-4-[3-(3-methoxybenzyl)-1,2,4-thiadiazol-5-yl]diazepane | 99 | 0.109 |
| 213 | N'-[4-methoxyphenylsulfonyl]-N-[3-(3-methoxybenzyl)-1,2,4-thia-diazol-5-yl]-N-methylethane-1,2-diamine | 94 | 0.361 |
| 214 | N'-[4-methoxyphenylsulfonyl]-N-[3-(3-methoxybenzyl)-1,2,4-thia-diazol-5-yl]-N'-methylethane-1,2-diamine | 95 | 0.498 |
| 215 | N'-[4-methoxyphenylsulfonyl]-N-[3-(3-methoxybenzyl)-1,2,4-thia-diazol-5-yl]-N,N'-dimethylethane-1,2-diamine | 105 | 0.301 |
| 217 | 1-(4-hydroxybenzenesulfonyl)-4-[3-(4-fluoro-benzyl)-1,2,4-thiadiazol-5-yl]piperazine | 77 | 0.077 |
| 44 | 1-[3-methoxyphenylsulfonyl]-4-[3-(4-fluorobenzyl)-1,2,4-thiadiazol-5-yl]piperazine | 99 | 0.128 |
| 53 | 1-[4-methoxyphenylsulfonyl]-4-[3-(3-methoxybenzyl)-1,2,4-thiadiazol-5-yl]piperazine | 83 | 0.0014 |

(end of Table 2)

Examples 217 to 294

N-arylsulfonylation of 1,2,4-thiadiazole Intermediates Represented by the Structural Formula (VI) into 1,2,4-thiadiazole Compounds Represented by the Structural Formula (C)

By analogy with example 207 (especially compound 209), the following compounds are also synthesised from 4-methoxyphenylsulfonyl chloride and the relevant intermediates from examples 81 to 91:

N-[4-methoxyphenylsulfonyl]-N'-[3-(4-methylbenzyl)-1,2,4-thiadiazol-5-yl]-ethane-1,2-diamine,
N-[4-methoxyphenylsulfonyl]-N'-[3-(4-fluorobenzyl)-1,2,4-thiadiazol-5-yl]-ethane-1,2-diamine,
N-[4-methoxyphenylsulfonyl]-N'-[3-(3-fluorobenzyl)-1,2,4-thiadiazol-5-yl]-ethane-1,2-diamine,
N-[4-methoxyphenylsulfonyl]-N'-[3-(2-fluorobenzyl)-1,2,4-thiadiazol-5-yl]-ethane-1,2-diamine,
N-[4-methoxyphenylsulfonyl]-N'-[3-(3-benzyl)-1,2,4-thiadiazol-5-yl]-ethane-1,2-diamine,
N-[4-methoxyphenylsulfonyl]-N'-[3-(3-methylbenzyl)-1,2,4-thiadiazol-5-yl]-ethane-1,2-diamine,
N-[4-methoxyphenylsulfonyl]-N'-[3-(2-methylbenzyl)-1,2,4-thiadiazol-5-yl]-ethane-1,2-diamine,
N-[4-methoxyphenylsulfonyl]-N'-[3-(2-methoxybenzyl)-1,2,4-thiadiazol-5-yl]-ethane-1,2-diamine,
N-[4-methoxyphenylsulfonyl]-N'-[3-(4-methoxybenzyl)-1,2,4-thiadiazol-5-yl]-ethane-1,2-diamine,
N-[4-methoxyphenylsulfonyl]-N'-[3-(3-methyl-4-fluorobenzyl)-1,2,4-thiadiazol-5-yl]-ethane-1,2-diamine, and
N-[4-methoxyphenylsulfonyl]-N'-[3-(4-chlorobenzyl)-1,2,4-thiadiazol-5-yl]-ethane-1,2-diamine.

By analogy with example 207 (especially compound 211), the following compounds are also synthesised from 4-methoxyphenylsulfonyl chloride and the relevant intermediates from examples 92 to 102:

N-[4-methoxyphenylsulfonyl]-N'-[3-(4-methylbenzyl)-1,2,4-thiadiazol-5-yl]-propane-1,3-diamine,
N-[4-methoxyphenylsulfonyl]-N'-[3-(4-fluorobenzyl)-1,2,4-thiadiazol-5-yl]-propane-1,3-diamine,
N-[4-methoxyphenylsulfonyl]-N'-[3-(3-fluorobenzyl)-1,2,4-thiadiazol-5-yl]-propane-1,3-diamine,
N-[4-methoxyphenylsulfonyl]-N'-[3-(2-fluorobenzyl)-1,2,4-thiadiazol-5-yl]-propane-1,3-diamine,
N-[4-methoxyphenylsulfonyl]-N'-[3-(3-benzyl)-1,2,4-thiadiazol-5-yl]-propane-1,3-diamine,
N-[4-methoxyphenylsulfonyl]-N'-[3-(3-methylbenzyl)-1,2,4-thiadiazol-5-yl]-propane-1,3-diamine,
N-[4-methoxyphenylsulfonyl]-N-'-[3-(2-methylbenzyl)-1,2,4-thiadiazol-5-yl]-propane-1,3-diamine,
N-[4-methoxyphenylsulfonyl]-N'-[3-(2-methoxybenzyl)-1,2,4-thiadiazol-5-yl]-propane-1,3-diamine,
N-[4-methoxyphenylsulfonyl]-N'-[3-(4-methoxybenzyl)-1,2,4-thiadiazol-5-yl]-propane-1,3-diamine,
N-[4-methoxyphenylsulfonyl]-N'-[3-(3-methyl-4-fluorobenzyl)-1,2,4-thiadiazol-5-yl]-propane-1,3-diamine, and
N-[4-methoxyphenylsulfonyl]-N'-[3-(4-chlorobenzyl)-1,2,4-thiadiazol-5-yl]-propane-1,3-diamine.

By analogy with example 207 (especially compound 210), the following compounds are also synthesised from 4-methoxyphenylsulfonyl chloride and the relevant intermediates from examples 125 to 135:

N-[4-methoxyphenylsulfonyl]-N'-[3-(4-methylbenzyl)-1,2,4-thiadiazol-5-yl]-propane-1,2-diamine,
N-[4-methoxyphenylsulfonyl]-N'-[3-(4-fluorobenzyl)-1,2,4-thiadiazol-5-yl]-propane-1,2-diamine,
N-[4-methoxyphenylsulfonyl]-N'-[3-(3-fluorobenzyl)-1,2,4-thiadiazol-5-yl]-propane-1,2-diamine,
N-[4-methoxyphenylsulfonyl]-N'-[3-(2-fluorobenzyl)-1,2,4-thiadiazol-5-yl]-propane-1,2-diamine,
N-[4-methoxyphenylsulfonyl]-N'-[3-(3-benzyl)-1,2,4-thiadiazol-5-yl]-propane-1,2-diamine,
N-[4-methoxyphenylsulfonyl]-N'-[3-(3-methylbenzyl)-1,2,4-thiadiazol-5-yl]-propane-1,2-diamine,
N-[4-methoxyphenylsulfonyl]-N'-[3-(2-methylbenzyl)-1,2,4-thiadiazol-5-yl]-propane-1,2-diamine,
N-[4-methoxyphenylsulfonyl]-N'-[3-(2-methoxybenzyl)-1,2,4-thiadiazol-5-yl]-propane-1,2-diamine,
N-[4-methoxyphenylsulfonyl]-N'-[3-(4-methoxybenzyl)-1,2,4-thiadiazol-5-yl]-propane-1,2-diamine,
N-[4-methoxyphenylsulfonyl]-N'-[3-(3-methyl-4-fluorobenzyl)-1,2,4-thiadiazol-5-yl]-propane-1,2-diamine, and
N-[4-methoxyphenylsulfonyl]-N'[3-(4-chlorobenzyl)-1,2,4-thiadiazol-5-yl]-propane-1,2-diamine.

By analogy with example 207 (especially compound 213), the following compounds are also synthesised from 4-methoxyphenylsulfonyl chloride and the relevant intermediates from examples 103 to 113:

N-[4-methoxyphenylsulfonyl]-N'-[3-(4-methylbenzyl)-1,2,4-thiadiazol-5-yl]-N-methyl-ethane-1,2-diamine,
N-[4-methoxyphenylsulfonyl]-N'-[3-(4-fluorobenzyl)-1,2,4-thiadiazol-5-yl]-N-methyl-ethane-1,2-diamine,
N-[4-methoxyphenylsulfonyl]-N'-[3-(3-fluorobenzyl)-1,2,4-thiadiazol-5-yl]-N-methyl-ethane-1,2-diamine,
N-[4-methoxyphenylsulfonyl]-N'-[3-(2-fluorobenzyl)-1,2,4-thiadiazol-5-yl]-N-methyl-ethane-1,2-diamine,
N-[4-methoxyphenylsulfonyl]-N'-[3-(3-benzyl)-1,2,4-thiadiazol-5-yl]-N-methyl-ethane-1,2-diamine,
N-[4-methoxyphenylsulfonyl]-N'-[3-(3-methylbenzyl)-1,2,4-thiadiazol-5-yl]-N-methyl-ethane-1,2-diamine,
N-[4-methoxyphenylsulfonyl]-N'-[3-(2-methylbenzyl)-1,2,4-thiadiazol-5-yl]-N-methyl-ethane-1,2-diamine,
N-[4-methoxyphenylsulfonyl]-N'-[3-(2-methoxybenzyl)-1,2,4-thiadiazol-5-yl]-N-methyl-ethane-1,2-diamine,
N-[4-methoxyphenylsulfonyl]-N'-[3-(4-methoxybenzyl)-1,2,4-thiadiazol-5-yl]-N-methyl-ethane-1,2-diamine,
N-[4-methoxyphenylsulfonyl]-N'-[3-(3-methyl-4-fluorobenzyl)-1,2,4-thiadiazol-5-yl]-N-methyl-ethane-1,2-diamine, and
N-[4-methoxyphenylsulfonyl]-N'-[3-(4-chlorobenzyl)-1,2,4-thiadiazol-5-yl]-N-methyl-ethane-1,2-diamine.

By analogy with example 207 (especially compound 214), the following compounds are also synthesised from 4-methoxyphenylsulfonyl chloride and the relevant intermediates from examples 114 to 124:

N-[4-methoxyphenylsulfonyl]-N'-[3-(4-methylbenzyl)-1,2,4-thiadiazol-5-yl]-N'-methyl-ethane-1,2-diamine,
N-[4-methoxyphenylsulfonyl]-N'-[3-(4-fluorobenzyl)-1,2,4-thiadiazol-5-yl]-N'-methyl-ethane-1,2-diamine,
N-[4-methoxyphenylsulfonyl]-N'-[3-(3-fluorobenzyl)-1,2,4-thiadiazol-5-yl]-N'-methyl-ethane-1,2-diamine,
N-[4-methoxyphenylsulfonyl]-N'-[3-(2-fluorobenzyl)-1,2,4-thiadiazol-5-yl]-N'-methyl-ethane-1,2-diamine,
N-[4-methoxyphenylsulfonyl]-N'-[3-(3-benzyl)-1,2,4-thiadiazol-5-yl]-N'-methyl-ethane-1,2-diamine,
N-[4-methoxyphenylsulfonyl]-N'-[3-(3-methylbenzyl)-1,2,4-thiadiazol-5-yl]-N'-methyl-ethane-1,2-diamine,
N-[4-methoxyphenylsulfonyl]-N'-[3-(2-methylbenzyl)-1,2,4-thiadiazol-5-yl]-N'-methyl-ethane-1,2-diamine, N-[4-methoxyphenylsulfonyl]-N'-[3-(2-methoxybenzyl)-1,2,4-thiadiazol-5-yl]-N'-methyl-ethane-1,2-diamine,
N-[4-methoxyphenylsulfonyl]-N'-[3-(4-methoxybenzyl)-1,2,4-thiadiazol-5-yl]-N'-methyl-ethane-1,2-diamine,
N-[4-methoxyphenylsulfonyl]-N'-[3-(3-methyl-4-fluorobenzyl)-1,2,4-thiadiazol-5-yl]-N'-methyl-ethane-1,2-diamine, and
N-[4-methoxyphenylsulfonyl]-N'-[3-(4-chlorobenzyl)-1,2,4-thiadiazol-5-yl]-N'-methyl-ethane-1,2-diamine.

By analogy with example 207 (especially compound 215), the following compounds are also synthesised from 4-methoxyphenylsulfonyl chloride and the relevant intermediates from examples 136 to 146:
N-[4-methoxyphenylsulfonyl]-N'-[3-(4-methylbenzyl)-1,2,4-thiadiazol-5-yl]-N,N'-dimethyl-ethane-1,2-diamine,
N-[4-methoxyphenylsulfonyl]-N'-[3-(4-fluorobenzyl)-1,2,4-thiadiazol-5-yl]-N,N'-dimethyl-ethane-1,2-diamine,
N-[4-methoxyphenylsulfonyl]-N'-[3-(3-fluorobenzyl)-1,2,4-thiadiazol-5-yl]-N,N'-dimethyl-ethane-1,2-diamine,
N-[4-methoxyphenylsulfonyl]-N'-[3-(2-fluorobenzyl)-1,2,4-thiadiazol-5-yl]-N,N'-dimethyl-ethane-1,2-diamine,
N-[4-methoxyphenylsulfonyl]-N'-[3-(3-benzyl)-1,2,4-thiadiazol-5-yl]-N,N'-dimethyl-ethane-1,2-diamine,
N-[4-methoxyphenylsulfonyl]-N'-[3-(3-methylbenzyl)-1,2,4-thiadiazol-5-yl]-N,N'-dimethyl-ethane-1,2-diamine,
N-[4-methoxyphenylsulfonyl]-N'-[3-(2-methylbenzyl)-1,2,4-thiadiazol-5-yl]-N,N'-dimethyl-ethane-1,2-diamine,
N-[4-methoxyphenylsulfonyl]-N'-[3-(2-methoxybenzyl)-1,2,4-thiadiazol-5-yl]-N,N'-dimethyl-ethane-1,2-diamine,
N-[4-methoxyphenylsulfonyl]-N'-[3-(4-methoxybenzyl)-1,2,4-thiadiazol-5-yl]-N,N'-dimethyl-ethane-1,2-diamine,
N-[4-methoxyphenylsulfonyl]-N'-[3-(3-methyl-4-fluorobenzyl)-1,2,4-thiadiazol-5-yl]-N,N'-dimethyl-ethane-1,2-diamine, and
N-[4-methoxyphenylsulfonyl]-N'-[3-(4-chlorobenzyl)-1,2,4-thiadiazol-5-yl]-N,N'-dimethyl-ethane-1,2-diamine.

By analogy with example 207, the following compounds are also synthesised from 4-methoxyphenylsulfonyl chloride and the relevant intermediates from examples 147 to 158:
N-[4-methoxyphenylsulfonyl]-N'-[3-(4-methylbenzyl)-1,2,4-thiadiazol-5-yl]-N,N'-diethyl-ethane-1,2-diamine,
N-[4-methoxyphenylsulfonyl]-N'-[3-(4-fluorobenzyl)-1,2,4-thiadiazol-5-yl]-N,N'-diethyl-ethane-1,2-diamine,
N-[4-methoxyphenylsulfonyl]-N'-[3-(3-fluorobenzyl)-1,2,4-thiadiazol-5-yl]-N,N'-diethyl-ethane-1,2-diamine,
N-[4-methoxyphenylsulfonyl]-N'-[3-(2-fluorobenzyl)-1,2,4-thiadiazol-5-yl]-N,N'-diethyl-ethane-1,2-diamine,
N-[4-methoxyphenylsulfonyl]-N'-[3-(3-benzyl)-1,2,4-thiadiazol-5-yl]-N,N'-diethyl-ethane-1,2-diamine,
N-[4-methoxyphenylsulfonyl]-N'-[3-(3-methylbenzyl)-1,2,4-thiadiazol-5-yl]-N,N'-diethyl-ethane-1,2-diamine,
N-[4-methoxyphenylsulfonyl]-N'-[3-(2-methylbenzyl)-1,2,4-thiadiazol-5-yl]-N,N'-diethyl-ethane-1,2-diamine,
N-[4-methoxyphenylsulfonyl]-N'-[3-(2-methoxybenzyl)-1,2,4-thiadiazol-5-yl]-N,N'-diethyl-ethane-1,2-diamine,
N-[4-methoxyphenylsulfonyl]-N'-[3-(4-methoxybenzyl)-1,2,4-thiadiazol-5-yl]-N,N'-diethyl-ethane-1,2-diamine,
N-[4-methoxyphenylsulfonyl]-N'-[3-(3-methyl-4-fluorobenzyl)-1,2,4-thiadiazol-5-yl]-N,N'-diethyl-ethane-1,2-diamine, and
N-[4-methoxyphenylsulfonyl]-N'-[3-(4-chlorobenzyl)-1,2,4-thiadiazol-5-yl]-N,N'-diethyl-ethane-1,2-diamine.

It should be understood that in the foregoing examples 217 to 294, 4-methoxyphenylsulfonyl chloride was only used to illustrate the feasibility of arylsulfonylation of 1,2,4-thiadiazole intermediates represented by the structural formula (VI). Similar compounds can also be synthesised from any arylsulfonyl chloride represented by the structural formula (VB) according to the list provided herein-before in the detailed description of the invention.

Examples 295 to 378

N-heteroarylsulfonylation of 1,2,4-thiadiazole Intermediates Represented by the Structural Formula (VI) into 1,2,4-thiadiazole Compounds Represented by the Structural Formula (F)

By analogy with example 207 (especially compound 206), the following compounds are also synthesised from 2-thienylsulfonyl chloride and the relevant intermediates from examples 75 to 158:
N-[2-thienylsulfonyl]-N'-[3-(3-methoxybenzyl)-1,2,4-thiadiazol-5-yl]-ethane-1,2-diamine,
N-[2-thienylsulfonyl]-N'-[3-(3-methoxybenzyl)-1,2,4-thiadiazol-5-yl]-propane-1,2-diamine,
N-[2-thienylsulfonyl]-N'-[3-(3-methoxybenzyl)-1,2,4-thiadiazol-5-yl]-propane-1,3-diamine,
N'-[2-thienylsulfonyl]-N-[3-(3-methoxybenzyl)-1,2,4-thiadiazol-5-yl]-N-methylethane-1,2-diamine,
N'-[2-thienylsulfonyl]-N-[3-(3-methoxybenzyl)-1,2,4-thiadiazol-5-yl]-N'-methylethane-1,2-diamine,
N'-[2-thienylsulfonyl]-N-[3-(3-methoxybenzyl)-1,2,4-thiadiazol-5-yl]-N,N'-dimethylethane-1,2-diamine,
N-[2-thienylsulfonyl]-N'-[3-(4-methylbenzyl)-1,2,4-thiadiazol-5-yl]-ethane-1,2-diamine,
N-[2-thienylsulfonyl]-N'-[3-(4-fluorobenzyl)-1,2,4-thiadiazol-5-yl]-ethane-1,2-diamine,
N-[2-thienylsulfonyl]-N'-[3-(3-fluorobenzyl)-1,2,4-thiadiazol-5-yl]-ethane-1,2-diamine,
N-[2-thienylsulfonyl]-N'-[3-(2-fluorobenzyl)-1,2,4-thiadiazol-5-yl]-ethane-1,2-diamine,
N-[2-thienylsulfonyl]-N'-[3-(3-benzyl)-1,2,4-thiadiazol-5-yl]-ethane-1,2-diamine,
N-[2-thienylsulfonyl]-N'-[3-(3-methylbenzyl)-1,2,4-thiadiazol-5-yl]-ethane-1,2-diamine,
N-[2-thienylsulfonyl]-N'-[3-(2-methylbenzyl)-1,2,4-thiadiazol-5-yl]-ethane-1,2-diamine,
N-[2-thienylsulfonyl]-N'-[3-(2-methoxybenzyl)-1,2,4-thiadiazol-5-yl]-ethane-1,2-diamine,
N-[2-thienylsulfonyl]-N'-[3-(4-methoxybenzyl)-1,2,4-thiadiazol-5-yl]ethane-1,2-diamine,
N-[2-thienylsulfonyl]-N'-[3-(3-methyl-4-fluorobenzyl)-1,2,4-thiadiazol-5-yl]-ethane-1,2-diamine,
N-[2-thienylsulfonyl]-N'-[3-(4-chlorobenzyl)-1,2,4-thiadiazol-5-yl]ethane-1,2-diamine,
N-[2-thienylsulfonyl]-N'-[3-(4-methylbenzyl)-1,2,4-thiadiazol-5-yl]propane-1,3-diamine,
N-[2-thienylsulfonyl]-N'-[3-(4-fluorobenzyl)-1,2,4-thiadiazol-5-yl]-propane-1,3-diamine,
N-[2-thienylsulfonyl]-N'-[3-(3-fluorobenzyl)-1,2,4-thiadiazol-5-yl]-propane-1,3-diamine,
N-[2-thienylsulfonyl]-N'-[3-(2-fluorobenzyl)-1,2,4-thiadiazol-5-yl]-propane-1,3-diamine,
N-[2-thienylsulfonyl]-N'-[3-(3-benzyl)-1,2,4-thiadiazol-5-yl]-propane-1,3-diamine,
N-[2-thienylsulfonyl]-N'-[3-(3-methylbenzyl)-1,2,4-thiadiazol-5-yl]-propane-1,3-diamine,
N-[2-thienylsulfonyl]-N'-[3-(2-methylbenzyl)-1,2,4-thiadiazol-5-yl]-propane-1,3-diamine,
N-[2-thienylsulfonyl]-N'-[3-(2-methoxybenzyl)-1,2,4-thiadiazol-5-yl]-propane-1,3-diamine,
N-[2-thienylsulfonyl]-N'-[3-(4-methoxybenzyl)-1,2,4-thiadiazol-5-yl]-propane-1,3-diamine, N-[2-thienylsulfonyl]-N'-[3-(3-methyl-4-fluorobenzyl)-1,2,4-thiadiazol-5-yl]-propane-1,3-diamine,
N-[2-thienylsulfonyl]-N'-[3-(4-chlorobenzyl)-1,2,4-thiadiazol-5-yl]-propane-1,3-diamine,
N-[2-thienylsulfonyl]-N'-[3-(4-methylbenzyl)-1,2,4-thiadiazol-5-yl]-propane-1,2-diamine,
N-[2-thienylsulfonyl]-N'-[3-(4-fluorobenzyl)-1,2,4-thiadiazol-5-yl]-propane-1,2-diamine,
N-[2-thienylsulfonyl]-N'-[3-(3-fluorobenzyl)-1,2,4-thiadiazol-5-yl]-propane-1,2-diamine,
N-[2-thienylsulfonyl]-N'-[3-(2-fluorobenzyl)-1,2,4-thiadiazol-5-yl]-propane-1,2-diamine,
N-[2-thienylsulfonyl]-N'-[3-(3-benzyl)-1,2,4-thiadiazol-5-yl]-propane-1,2-diamine,
N-[2-thienylsulfonyl]-N'-[3-(3-methylbenzyl)-1,2,4-thiadiazol-5-yl]-propane-1,2-diamine,
N-[2-thienylsulfonyl]-N'-[3-(2-methylbenzyl)-1,2,4-thiadiazol-5-yl]-propane-1,2-diamine,
N-[2-thienylsulfonyl]-N'-[3-(2-methoxybenzyl)-1,2,4-thiadiazol-5-yl]-propane-1,2-diamine,
N-[2-thienylsulfonyl]-N'-[3-(4-methoxybenzyl)-1,2,4-thiadiazol-5-yl]-propane-1,2-diamine,
N-[2-thienylsulfonyl]-N'-[3-(3-methyl-4-fluorobenzyl)-1,2,4-thiadiazol-5-yl]-propane-1,2-diamine,
N-[2-thienylsulfonyl]-N'-[3-(4-chlorobenzyl)-1,2,4-thiadiazol-5-yl]-propane-1,2-diamine,
N-[2-thienylsulfonyl]-N'-[3-(4-methylbenzyl)-1,2,4-thiadiazol-5-yl]-N-methyl-ethane-1,2-diamine,
N-[2-thienylsulfonyl]-N'-[3-(4-fluorobenzyl)-1,2,4-thiadiazol-5-yl]-N-methyl-ethane-1,2-diamine,
N-[2-thienylsulfonyl]-N'-[3-(3-fluorobenzyl)-1,2,4-thiadiazol-5-yl]-N-methyl-ethane-1,2-diamine,
N-[2-thienylsulfonyl]-N'-[3-(2-fluorobenzyl)-1,2,4-thiadiazol-5-yl]-N-methyl-ethane-1,2-diamine,
N-[2-thienylsulfonyl]-N'-[3-(3-benzyl)-1,2,4-thiadiazol-5-yl]-N-methyl-ethane-1,2-diamine,
N-[2-thienylsulfonyl]-N'-[3-(3-methylbenzyl)-1,2,4-thiadiazol-5-yl]-N-methyl-ethane-1,2-diamine,
N-[2-thienylsulfonyl]-N'-[3-(2-methylbenzyl)-1,2,4-thiadiazol-5-yl]-N-methyl-ethane-1,2-diamine,
N-[2-thienylsulfonyl]-N'-[3-(2-methoxybenzyl)-1,2,4-thiadiazol-5-yl]-N-methyl-ethane-1,2-diamine,
N-[2-thienylsulfonyl]-N'-[3-(4-methoxybenzyl)-1,2,4-thiadiazol-5-yl]-N-methyl-ethane-1,2-diamine,
N-[2-thienylsulfonyl]-N'-[3-(3-methyl-4-fluorobenzyl)-1,2,4-thiadiazol-5-yl]-N-methyl-ethane-1,2-diamine,
N-[2-thienylsulfonyl]-N'-[3-(4-chlorobenzyl)-1,2,4-thiadiazol-5-yl]-N-methyl-ethane-1,2-diamine,
N-[2-thienylsulfonyl]-N'-[3-(4-methylbenzyl)-1,2,4-thiadiazol-5-yl]-N,N'-dimethyl-ethane-1,2-diamine,
N-[2-thienylsulfonyl]-N'-[3-(4-fluorobenzyl)-1,2,4-thiadiazol-5-yl]-N,N'-dimethyl-ethane-1,2-diamine,
N-[2-thienylsulfonyl]-N'-[3-(3-fluorobenzyl)-1,2,4-thiadiazol-5-yl]-N,N'-dimethyl-ethane-1,2-diamine,
N-[2-thienylsulfonyl]-N'-[3-(2-fluorobenzyl)-1,2,4-thiadiazol-5-yl]-N,N'-dimethyl-ethane-1,2-diamine,
N-[2-thienylsulfonyl]-N'-[3-(3-benzyl)-1,2,4-thiadiazol-5-yl]-N,N'-dimethyl-ethane-1,2-diamine,
N-[2-thienylsulfonyl]-N'-[3-(3-methylbenzyl)-1,2,4-thiadiazol-5-yl]-N,N'-dimethyl-ethane-1,2-diamine,
N-[2-thienylsulfonyl]-N'-[3-(2-methylbenzyl)-1,2,4-thiadiazol-5-yl]-N,N'-dimethyl-ethane-1,2-diamine,
N-[2-thienylsulfonyl]-N'-[3-(2-methoxybenzyl)-1,2,4-thiadiazol-5-yl]-N,N'-dimethyl-ethane-1,2-diamine,
N-[2-thienylsulfonyl]-N'-[3-(4-methoxybenzyl)-1,2,4-thiadiazol-5-yl]-N,N'-dimethyl-ethane-1,2-diamine,
N-[2-thienylsulfonyl]-N'-[3-(3-methyl-4-fluorobenzyl)-1,2,4-thia-diazol-5-yl]-N,N'-dimethyl-ethane-1,2-diamine,
N-[2-thienylsulfonyl]-N'-[3-(4-chlorobenzyl)-1,2,4-thiadiazol-5-yl]-N,N'-dimethyl-ethane-1,2-diamine,
N-[2-thienylsulfonyl]-N'-[3-(4-methylbenzyl)-1,2,4-thiadiazol-5-yl]-N,N'-diethyl-ethane-1,2-diamine,
N-[2-thienylsulfonyl]-N'-[3-(4-fluorobenzyl)-1,2,4-thiadiazol-5-yl]-N,N'-diethyl-ethane-1,2-diamine,
N-[2-thienylsulfonyl]-N'-[3-(3-fluorobenzyl)-1,2,4-thiadiazol-5-yl]-N,N'-diethyl-ethane-1,2-diamine,
N-[2-thienylsulfonyl]-N'-[3-(2-fluorobenzyl)-1,2,4-thiadiazol-5-yl]-N,N'-diethyl-ethane-1,2-diamine,
N-[2-thienylsulfonyl]-N'-[3-(3-benzyl)-1,2,4-thiadiazol-5-yl]-N,N'-diethyl-ethane-1,2-diamine,
N-[2-thienylsulfonyl]-N'-[3-(3-methylbenzyl)-1,2,4-thiadiazol-5-yl]-N,N'-diethyl-ethane-1,2-diamine,
N-[2-thienylsulfonyl]-N'-[3-(2-methylbenzyl)-1,2,4-thiadiazol-5-yl]-N,N'-diethyl-ethane-1,2-diamine,
N-[2-thienylsulfonyl]-N'-[3-(2-methoxybenzyl)-1,2,4-thiadiazol-5-yl]-N,N'-diethyl-ethane-1,2-diamine,
N-[2-thienylsulfonyl]-N'-[3-(4-methoxybenzyl)-1,2,4-thiadiazol-5-yl]-N,N'-diethyl-ethane-1,2-diamine,
N-[2-thienylsulfonyl]-N'-[3-(3-methyl-4-fluorobenzyl)-1,2,4-thia-diazol-5-yl]-N,N'-diethyl-ethane-1,2-diamine, and
N-[2-thienylsulfonyl]-N'-[3-(4-chlorobenzyl)-1,2,4-thiadiazol-5-yl]-N,N'-diethyl-ethane-1,2-diamine.

It should be understood that in the foregoing examples 295 to 378, 2-thienylsulfonyl chloride was only used to illustrate the feasibility of heteroarylsulfonylation of 1,2,4-thiadiazole intermediates represented by the structural formula (VI). Similar compounds can also be synthesised from any other heteroarylsulfonyl chloride.

Examples 379 to 438

Nucleophilic Replacement with diaminoalkanes onto 5-chloro-3-(substituted benzyl)-1,2,4-thiadiazole Derivatives The following intermediate compounds are synthesised from 2,3-diamino butane and the relevant 3-(substituted benzyl)-5-chloro-1,2,4-thiadiazole derivative from examples 2 to 13, while using the experimental conditions of examples 75 to 80:

$N^2$-[3-(4-methyl-benzyl)-[1,2,4]thiadiazol-5-yl]-2,3-diamino butane (example 379),
$N^2$-[3-(4-fluoro-benzyl)-[1,2,4]thiadiazol-5-yl]-2,3-diamino butane (example 380),
$N^2$-[3-(3-methoxy-benzyl)-[1,2,4]thiadiazol-5-yl]-2,3-diamino butane (example 381),
$N^2$-[3-(3-fluoro-benzyl)-[1,2,4]thiadiazol-5-yl]-2,3-diamino butane (example 382),
$N^2$-[3-(2-fluoro-benzyl)-[1,2,4]thiadiazol-5-yl]-2,3-diamino butane (example 383),
$N^2$-[3-(3-benzyl)-[1,2,4]thiadiazol-5-yl]-2,3-diamino butane (example 384),
$N^2$-[3-(3-methyl-benzyl)-[1,2,4]thiadiazol-5-yl]-2,3-diamino butane (example 385),
$N^2$-[3-(2-methyl-benzyl)-[1,2,4]thiadiazol-5-yl]-2,3-diamino butane (example 386),
$N^2$-[3-(2-methoxy-benzyl)-[1,2,4]thiadiazol-5-yl]-2,3-diamino butane (example 387),
$N^2$-[3-(4-methoxy-benzyl)-[1,2,4]thiadiazol-5-yl]-2,3-diamino butane (example 388),
$N^2$-[3-(3-methyl-4-fluoro-benzyl)-[1,2,4]thiadiazol-5-yl]-2,3-diamino butane (example 389), and N²-[3-(4-chloro-benzyl)-[1,2,4]thiadiazol-5-yl]-2,3-diamino butane (example 390).

The following intermediate compounds are synthesised from 1,3-diamino butane and the relevant 3-(substituted benzyl)-5-chloro-1,2,4-thiadiazole derivative from examples 2 to 13, while using the experimental conditions of examples 75 to 80:

N-[3-(4-methyl-benzyl)-[1,2,4]thiadiazol-5-yl]-1,3-diamino butane (example 391),
N-[3-(4-fluoro-benzyl)-[1,2,4]thiadiazol-5-yl]-1,3-diamino butane (example 392),
N-[3-(3-methoxy-benzyl)-[1,2,4]thiadiazol-5-yl]-1,3-diamino butane (example 393),
N-[3-(3-fluoro-benzyl)-[1,2,4]thiadiazol-5-yl]-1,3-diamino butane (example 394),
N-[3-(2-fluoro-benzyl)-[1,2,4]thiadiazol-5-yl]-1,3-diamino butane (example 395),
N-[3-(3-benzyl)-[1,2,4]thiadiazol-5-yl]-1,3-diamino butane (example 396),
N-[3-(3-methyl-benzyl)-[1,2,4]thiadiazol-5-yl]-1,3-diamino butane (example 397),
N-[3-(2-methyl-benzyl)-[1,2,4]thiadiazol-5-yl]-1,3-diamino butane (example 398),
N-[3-(2-methoxy-benzyl)-[1,2,4]thiadiazol-5-yl]-1,3-diamino butane (example 399),
N-[3-(4-methoxy-benzyl)-[1,2,4]thiadiazol-5-yl]-1,3-diamino butane (example 400),
N-[3-(3-methyl-4-fluoro-benzyl)-[1,2,4]thiadiazol-5-yl]-1,3-diamino butane (example 401), and
N-[3-(4-chloro-benzyl)-[1,2,4]thiadiazol-5-yl]-1,3-diamino butane (example 402).

The following intermediate compounds are synthesised from 1,2-diamino butane and the relevant 3-(substituted benzyl)-5-chloro-1,2,4-thiadiazole derivative from examples 2 to 13, while using the experimental conditions of examples 75 to 80:

N-[3-(4-methyl-benzyl)-[1,2,4]thiadiazol-5-yl]-1,2-diamino butane (example 403),
N-[3-(4-fluoro-benzyl)-[1,2,4]thiadiazol-5-yl]-1,2-diamino butane (example 404),
N-[3-(3-methoxy-benzyl)-[1,2,4]thiadiazol-5-yl]-1,2-diamino butane (example 405),
N-[3-(3-fluoro-benzyl)-[1,2,4]thiadiazol-5-yl]-1,2-diamino butane (example 406),
N-[3-(2-fluoro-benzyl)-[1,2,4]thiadiazol-5-yl]-1,2-diamino butane (example 407),
N-[3-(3-benzyl)-[1,2,4]thiadiazol-5-yl]-1,2-diamino butane (example 408),
N-[3-(3-methyl-benzyl)-[1,2,4]thiadiazol-5-yl]-1,2-diamino butane (example 409),
N-[3-(2-methyl-benzyl)-[1,2,4]thiadiazol-5-yl]-1,2-diamino butane (example 410),
N-[3-(2-methoxy-benzyl)-[1,2,4]thiadiazol-5-yl]-1,2-diamino butane (example 411),
N-[3-(4-methoxy-benzyl)-[1,2,4]thiadiazol-5-yl]-1,2-diamino butane (example 412),
N-[3-(3-methyl-4-fluoro-benzyl)-[1,2,4]thiadiazol-5-yl]-1,2-diamino butane (example 413), and
N-[3-(4-chloro-benzyl)-[1,2,4]thiadiazol-5-yl]-1,2-diamino butane (example 414).

The following intermediate compounds are synthesised from 1,2-diamino pentane and the relevant 3-(substituted benzyl)-5-chloro-1,2,4-thiadiazole derivative from examples 2 to 13, while using the experimental conditions of examples 75 to 80:

N-[3-(4-methyl-benzyl)-[1,2,4]thiadiazol-5-yl]-1,2-diamino pentane (example 415),
N-[3-(4-fluoro-benzyl)-[1,2,4]thiadiazol-5-yl]-1,2-diamino pentane (example 416),
N-[3-(3-methoxy-benzyl)-[1,2,4]thiadiazol-5-yl]-1,2-diamino pentane (example 417),
N-[3-(3-fluoro-benzyl)-[1,2,4]thiadiazol-5-yl]-1,2-diamino pentane (example 418),
N-[3-(2-fluoro-benzyl)-[1,2,4]thiadiazol-5-yl]-1,2-diamino pentane (example 419),
N-[3-(3-benzyl)-[1,2,4]thiadiazol-5-yl]-1,2-diamino pentane (example 420),
N-[3-(3-methyl-benzyl)-[1,2,4]thiadiazol-5-yl]-1,2-diamino pentane (example 421),
N-[3-(2-methyl-benzyl)-[1,2,4]thiadiazol-5-yl]-1,2-diamino pentane (example 422),
N-[3-(2-methoxy-benzyl)-[1,2,4]thiadiazol-5-yl]-1,2-diamino pentane (example 423),
N-[3-(4-methoxy-benzyl)-[1,2,4]thiadiazol-5-yl]-1,2-diamino pentane (example 424),
N-[3-(3-methyl-4-fluoro-benzyl)-[1,2,4]thiadiazol-5-yl]-1,2-diamino pentane (example 425), and
N-[3-(4-chloro-benzyl)-[1,2,4]thiadiazol-5-yl]-1,2-diamino pentane (example 426).

The following intermediate compounds are synthesised from 1,3-diamino pentane and the relevant 3-(substituted benzyl)-5-chloro-1,2,4-thiadiazole derivative from examples 2 to 13, while using the experimental conditions of examples 75 to 80:

N-[3-(4-methyl-benzyl)-[1,2,4]thiadiazol-5-yl]-1,3-diamino pentane (example 427),
N-[3-(4-fluoro-benzyl)-[1,2,4]thiadiazol-5-yl]-1,3-diamino pentane (example 428),
N-[3-(3-methoxy-benzyl)-[1,2,4]thiadiazol-5-yl]-1,3-diamino pentane (example 429),
N-[3-(3-fluoro-benzyl)-[1,2,4]thiadiazol-5-yl]-1,3-diamino pentane (example 430),
N-[3-(2-fluoro-benzyl)-[1,2,4]thiadiazol-5-yl]-1,3-diamino pentane (example 431),
N-[3-(3-benzyl)-[1,2,4]thiadiazol-5-yl]-1,3-diamino pentane (example 432),
N-[3-(3-methyl-benzyl)-[1,2,4]thiadiazol-5-yl]-1,3-diamino pentane (example 433),
N-[3-(2-methyl-benzyl)-[1,2,4]thiadiazol-5-yl]-1,3-diamino pentane (example 434),
N-[3-(2-methoxy-benzyl)-[1,2,4]thiadiazol-5-yl]-1,3-diamino pentane (example 435),
N-[3-(4-methoxy-benzyl)-[1,2,4]thiadiazol-5-yl]-1,3-diamino pentane (example 436),
N-[3-(3-methyl-4-fluoro-benzyl)-[1,2,4]thiadiazol-5-yl]-1,3-diamino pentane (example 437), and
N-[3-(4-chloro-benzyl)-[1,2,4]thiadiazol-5-yl]-1,3-diamino pentane (example 438).

Examples 439 to 498

N-sulfonylation of 1,2,4-thiadiazole Intermediate Compounds 379 to 438

By analogy with example 207, the following compounds are synthesised from 4-methoxyphenyl-sulfonyl chloride and the relevant intermediate compounds 379 to 438:

N³-(4-methoxy-phenyl sulfonyl)-N²-[3-(4-methyl-benzyl)-[1,2,4]thiadiazol-5-yl]-2,3-diamino butane (example 439),
N³-(4-methoxy-phenyl sulfonyl)-N²-[3-(4-fluoro-benzyl)-[1,2,4]thiadiazol-5-yl]-2,3-diamino butane (example 440),
N³-(4-methoxy-phenyl sulfonyl)-N²-[3-(3-methoxy-benzyl)-[1,2,4]thiadiazol-5-yl]-2,3-diamino butane (example 441), $N^3$-(4-methoxy-phenyl sulfonyl)-$N^2$-[3-(3-fluoro-benzyl)-[1,2,4]thiadiazol-5-yl]-2,3-diamino butane (example 442),
$N^3$-(4-methoxy-phenyl sulfonyl)-$N^2$-[3-(2-fluoro-benzyl)-[1,2,4]thiadiazol-5-yl]-2,3-diamino butane (example 443),
$N^3$-(4-methoxy-phenyl sulfonyl)-$N^2$-[3-(3-benzyl)-[1,2,4]thiadiazol-5-yl]-2,3-diamino butane (example 444),
$N^3$-(4-methoxy-phenyl sulfonyl)-$N^2$-[3-(3-methyl-benzyl)-[1,2,4]thiadiazol-5-yl]-2,3-diamino butane (example 445),
$N^3$-(4-methoxy-phenyl sulfonyl)-$N^2$-[3-(2-methyl-benzyl)-[1,2,4]thiadiazol-5-yl]-2,3-diamino butane (example 446),
$N^3$-(4-methoxy-phenyl sulfonyl)-$N^2$-[3-(2-methoxy-benzyl)-[1,2,4]thiadiazol-5-yl]-2,3-diamino butane (example 447),
$N^3$-(4-methoxy-phenyl sulfonyl)-$N^2$-[3-(4-methoxy-benzyl)-[1,2,4]thiadiazol-5-yl]-2,3-diamino butane (example 448),
$N^3$-(4-methoxy-phenyl sulfonyl)-$N^2$-[3-(3-methyl-4-fluoro-benzyl)-[1,2,4]thiadiazol-5-yl]-2,3-diamino butane (example 449), and
$N^3$-(4-methoxy-phenyl sulfonyl)-$N^2$-[3-(4-chloro-benzyl)-[1,2,4]thiadiazol-5-yl]-2,3-diamino butane (example 450).
$N^3$-(4-methoxy-phenyl sulfonyl)-$N^1$-[3-(4-methyl-benzyl)-[1,2,4]thiadiazol-5-yl]-1,3-diamino butane (example 451),
$N^3$-(4-methoxy-phenyl sulfonyl)-$N^1$-[3-(4-fluoro-benzyl)-[1,2,4]thiadiazol-5-yl]-1,3-diamino butane (example 452),
$N^3$-(4-methoxy-phenyl sulfonyl)-$N^1$-[3-(3-methoxy-benzyl)-[1,2,4]thiadiazol-5-yl]-1,3-diamino butane (example 453),
$N^3$-(4-methoxy-phenyl sulfonyl)-$N^1$-[3-(3-fluoro-benzyl)-[1,2,4]thiadiazol-5-yl]-1,3-diamino butane (example 454),
$N^3$-(4-methoxy-phenyl sulfonyl)-$N^1$-[3-(2-fluoro-benzyl)-[1,2,4]thiadiazol-5-yl]-1,3-diamino butane (example 455),
$N^3$-(4-methoxy-phenyl sulfonyl)-$N^1$-[3-(3-benzyl)-[1,2,4]thiadiazol-5-yl]-1,3-diamino butane (example 456),
$N^3$-(4-methoxy-phenyl sulfonyl)-$N^1$-[3-(3-methyl-benzyl)-[1,2,4]thiadiazol-5-yl]-1,3-diamino butane (example 457),
$N^3$-(4-methoxy-phenyl sulfonyl)-$N^1$-[3-(2-methyl-benzyl)-[1,2,4]thiadiazol-5-yl]-1,3-diamino butane (example 458),
$N^3$-(4-methoxy-phenyl sulfonyl)-$N^1$-[3-(2-methoxy-benzyl)-[1,2,4]thiadiazol-5-yl]-1,3-diamino butane (example 459),
$N^3$-(4-methoxy-phenyl sulfonyl)-$N^1$-[3-(4-methoxy-benzyl)-[1,2,4]thiadiazol-5-yl]-1,3-diamino butane (example 460),
$N^3$-(4-methoxy-phenyl sulfonyl)-$N^1$-[3-(3-methyl-4-fluoro-benzyl)-[1,2,4]thiadiazol-5-yl]-1,3-diamino butane (example 461),
$N^3$-(4-methoxy-phenyl sulfonyl)-$N^1$-[3-(4-chloro-benzyl)-[1,2,4]thiadiazol-5-yl]-1,3-diamino butane (example 462),
$N^2$-(4-methoxy-phenyl sulfonyl)-$N^1$-[3-(4-methyl-benzyl)-[1,2,4]thiadiazol-5-yl]-1,2-diamino butane (example 463),
$N^2$-(4-methoxy-phenyl sulfonyl)-N-[3-(4-fluoro-benzyl)-[1,2,4]thiadiazol-5-yl]-1,2-diamino butane (example 464),
$N^2$-(4-methoxy-phenyl sulfonyl)-$N^1$-[3-(3-methoxy-benzyl)-[1,2,4]thiadiazol-5-yl]-1,2-diamino butane (example 465),
$N^2$-(4-methoxy-phenyl sulfonyl)-$N^1$-[3-(3-fluoro-benzyl)-[1,2,4]thiadiazol-5-yl]-1,2-diamino butane (example 466),
$N^2$-(4-methoxy-phenyl sulfonyl)-$N^1$-[3-(2-fluoro-benzyl)-[1,2,4]thiadiazol-5-yl]-1,2-diamino butane (example 467),
$N^2$-(4-methoxy-phenyl sulfonyl)-$N^1$-[3-(3-benzyl)-[1,2,4]thiadiazol-5-yl]-1,2-diamino butane (example 468),
$N^2$-(4-methoxy-phenyl sulfonyl)-$N^1$-[3-(3-methyl-benzyl)-[1,2,4]thiadiazol-5-yl]-1,2-diamino butane (example 469),
$N^2$-(4-methoxy-phenyl sulfonyl)-$N^1$-[3-(2-methyl-benzyl)-[1,2,4]thiadiazol-5-yl]-1,2-diamino butane (example 470),
$N^2$-(4-methoxy-phenyl sulfonyl)-$N^1$-[3-(2-methoxy-benzyl)-[1,2,4]thiadiazol-5-yl]-1,2-diamino butane (example 471),
$N^2$-(4-methoxy-phenyl sulfonyl)-$N^1$-[3-(4-methoxy-benzyl)-[1,2,4]thiadiazol-5-yl]-1,2-diamino butane (example 472),
$N^2$-(4-methoxy-phenyl sulfonyl)-$N^1$-[3-(3-methyl-4-fluoro-benzyl)-[1,2,4]thiadiazol-5-yl]-1,2-diamino butane (example 473),
$N^2$-(4-methoxy-phenyl sulfonyl)-$N^1$-[3-(4-chloro-benzyl)-[1,2,4]thiadiazol-5-yl]-1,2-diamino butane (example 474),
$N^2$-(4-methoxy-phenyl sulfonyl)-$N^1$-[3-(4-methyl-benzyl)-[1,2,4]thiadiazol-5-yl]-1,2-diamino pentane (example 475),
$N^2$-(4-methoxy-phenyl sulfonyl)-$N^1$-[3-(4-fluoro-benzyl)-[1,2,4]thiadiazol-5-yl]-1,2-diamino pentane (example 476),
$N^2$-(4-methoxy-phenyl sulfonyl)-$N^1$-[3-(3-methoxy-benzyl)-[1,2,4]thiadiazol-5-yl]-1,2-diamino pentane (example 477),
$N^2$-(4-methoxy-phenyl sulfonyl)-$N^1$-[3-(3-fluoro-benzyl)-[1,2,4]thiadiazol-5-yl]-1,2-diamino pentane (example 478),
$N^2$-(4-methoxy-phenyl sulfonyl)-$N^1$-[3-(2-fluoro-benzyl)-[1,2,4]thiadiazol-5-yl]-1,2-diamino pentane (example 479),
$N^2$-(4-methoxy-phenyl sulfonyl)-$N^1$-[3-(3-benzyl)-[1,2,4]thiadiazol-5-yl]-1,2-diamino pentane (example 480),
$N^2$-(4-methoxy-phenyl sulfonyl)-$N^1$-[3-(3-methyl-benzyl)-[1,2,4]thiadiazol-5-yl]-1,2-diamino pentane (example 481),
$N^2$-(4-methoxy-phenyl sulfonyl)-$N^1$-[3-(2-methyl-benzyl)-[1,2,4]thiadiazol-5-yl]-1,2-diamino pentane (example 482),
$N^2$-(4-methoxy-phenyl sulfonyl)-$N^1$-[3-(2-methoxy-benzyl)-[1,2,4]thiadiazol-5-yl]-1,2-diamino pentane (example 483),
$N^2$-(4-methoxy-phenyl sulfonyl)-$N^1$-[3-(4-methoxy-benzyl)-[1,2,4]thiadiazol-5-yl]-1,2-diamino pentane (example 484),
$N^2$-(4-methoxy-phenyl sulfonyl)-$N^1$-[3-(3-methyl-4-fluoro-benzyl)-[1,2,4]thiadiazol-5-yl]-1,2-diamino pentane (example 485),
$N^2$-(4-methoxy-phenyl sulfonyl)-$N^1$-[3-(4-chloro-benzyl)-[1,2,4]thiadiazol-5-yl]-1,2-diamino pentane (example 486),
$N^3$-(4-methoxy-phenyl sulfonyl)-$N^1$-[3-(4-methyl-benzyl)-[1,2,4]thiadiazol-5-yl]-1,3-diamino pentane (example 487),
$N^3$-(4-methoxy-phenyl sulfonyl)-$N^1$-[3-(4-fluoro-benzyl)-[1,2,4]thiadiazol-5-yl]-1,3-diamino pentane (example 488),
$N^3$-(4-methoxy-phenyl sulfonyl)-$N^1$-[3-(3-methoxy-benzyl)-[1,2,4]thiadiazol-5-yl]-1,3-diamino pentane (example 489),
$N^3$-(4-methoxy-phenyl sulfonyl)-$N^1$-[3-(3-fluoro-benzyl)-[1,2,4]thiadiazol-5-yl]-1,3-diamino pentane (example 490),
$N^3$-(4-methoxy-phenyl sulfonyl)-$N^1$-[3-(2-fluoro-benzyl)-[1,2,4]thiadiazol-5-yl]-1,3-diamino pentane (example 491),
$N^3$-(4-methoxy-phenyl sulfonyl)-$N^1$-[3-(3-benzyl)-[1,2,4]thiadiazol-5-yl]-1,3-diamino pentane (example 492),
$N^3$-(4-methoxy-phenyl sulfonyl)-$N^1$-[3-(3-methyl-benzyl)-[1,2,4]thiadiazol-5-yl]-1,3-diamino pentane (example 493), $N^3$-(4-methoxy-phenyl sulfonyl)-$N^1$-[3-(2-methyl-benzyl)-[1,2,4]thiadiazol-5-yl]-1,3-diamino pentane (example 494), $N^3$-(4-methoxy-phenyl sulfonyl)-$N^1$-[3-(2-methoxy-benzyl)-[1,2,4]thiadiazol-5-yl]-1,3-diamino pentane (example 495), $N^3$-(4-methoxy-phenyl sulfonyl)-$N^1$-[3-(4-methoxy-benzyl)-[1,2,4]thiadiazol-5-yl]-1,3-diamino pentane (example 496), $N^3$-(4-methoxy-phenyl sulfonyl)-$N^1$-[3-(3-methyl-4-fluoro-benzyl)-[1,2,4]thiadiazol-5-yl]-1,3-diamino pentane (example 497), and $N^3$-(4-methoxy-phenyl sulfonyl)-$N^1$-[3-(4-chloro-benzyl)-[1,2,4]thiadiazol-5-yl]-1,3-diamino pentane (example 498).

It should be understood that in the foregoing examples 439 to 498, 4-methoxyphenylsulfonyl chloride was only used to illustrate the feasibility of arylsulfonylation of 1,2,4-thiadiazole intermediates that are diaminoalkane derivatised. Similar compounds can also be synthesised from any arylsulfonyl chloride or heteroarylsulfonyl chloride according to the lists provided herein-before in the detailed description of the invention.

Examples 499 to 558

N-acylation of 1,2,4-thiadiazole Intermediate Compounds 379 to 438

By analogy with example 208, the following compounds are synthesised from 4-methoxybenzoyl chloride and the relevant intermediate compounds 379 to 438:

$N^3$-(4-methoxy-benzoyl)-$N^2$-[3-(4-methyl-benzyl)-[1,2,4]thiadiazol-5-yl]-2,3-diamino butane (example 499), $N^3$-(4-methoxy-benzoyl)-$N^2$-[3-(4-fluoro-benzyl)-[1,2,4]thiadiazol-5-yl]-2,3-diamino butane (example 500), $N^3$-(4-methoxy-benzoyl)-$N^2$-[3-(3-methoxy-benzyl)-[1,2,4]thiadiazol-5-yl]-2,3-diamino butane (example 501), $N^3$-(4-methoxy-benzoyl)-$N^2$-[3-(3-fluoro-benzyl)-[1,2,4]thiadiazol-5-yl]-2,3-diamino butane (example 502), $N^3$-(4-methoxy-benzoyl)-$N^2$-[3-(2-fluoro-benzyl)-[1,2,4]thiadiazol-5-yl]-2,3-diamino butane (example 503), $N^3$-(4-methoxy-benzoyl)-$N^2$-[3-(3-benzyl)-[1,2,4]thiadiazol-5-yl]-2,3-diamino butane (example 504), $N^3$-(4-methoxy-benzoyl)-$N^2$-[3-(3-methyl-benzyl)-[1,2,4]thiadiazol-5-yl]-2,3-diamino butane (example 505), $N^3$-(4-methoxy-benzoyl)-$N^2$-[3-(2-methyl-benzyl)-[1,2,4]thiadiazol-5-yl]-2,3-diamino butane (example 506), $N^3$-(4-methoxy-benzoyl)-$N^2$-[3-(2-methoxy-benzyl)-[1,2,4]thiadiazol-5-yl]-2,3-diamino butane (example 507), $N^3$-(4-methoxy-benzoyl)-$N^2$-[3-(4-methoxy-benzyl)-[1,2,4]thiadiazol-5-yl]-2,3-diamino butane (example 508), $N^3$-(4-methoxy-benzoyl)-$N^2$-[3-(3-methyl-4-fluoro-benzyl)-[1,2,4]thiadiazol-5-yl]-2,3-diamino butane (example 509), $N^3$-(4-methoxy-benzoyl)-$N^2$-[3-(4-chloro-benzyl)-[1,2,4]thiadiazol-5-yl]-2,3-diamino butane (example 510), $N^3$-(4-methoxy-benzoyl)-$N^1$-[3-(4-methyl-benzyl)-[1,2,4]thiadiazol-5-yl]-1,3-diamino butane (example 511), $N^3$-(4-methoxy-benzoyl)-$N^1$-[3-(4-fluoro-benzyl)-[1,2,4]thiadiazol-5-yl]-1,3-diamino butane (example 512), $N^3$-(4-methoxy-benzoyl)-$N^1$-[3-(3-methoxy-benzyl)-[1,2,4]thiadiazol-5-yl]-1,3-diamino butane (example 513), $N^3$-(4-methoxy-benzoyl)-$N^1$-[3-(3-fluoro-benzyl)-[1,2,4]thiadiazol-5-yl]-1,3-diamino butane (example 514), $N^3$-(4-methoxy-benzoyl)-$N^1$-[3-(2-fluoro-benzyl)-[1,2,4]thiadiazol-5-yl]-1,3-diamino butane (example 515), $N^3$-(4-methoxy-benzoyl)-$N^1$-[3-(3-benzyl)-[1,2,4]thiadiazol-5-yl]-1,3-diamino butane (example 516), $N^3$-(4-methoxy-benzoyl)-$N^1$-[3-(3-methyl-benzyl)-[1,2,4]thiadiazol-5-yl]-1,3-diamino butane (example 517), $N^3$-(4-methoxy-benzoyl)-$N^1$-[3-(2-methyl-benzyl)-[1,2,4]thiadiazol-5-yl]-1,3-diamino butane (example 518), $N^3$-(4-methoxy-benzoyl)-$N^1$-[3-(2-methoxy-benzyl)-[1,2,4]thiadiazol-5-yl]-1,3-diamino butane (example 519), $N^3$-(4-methoxy-benzoyl)-$N^1$-[3-(4-methoxy-benzyl)-[1,2,4]thiadiazol-5-yl]-1,3-diamino butane (example 520), $N^3$-(4-methoxy-benzoyl)-$N^1$-[3-(3-methyl-4-fluoro-benzyl)-[1,2,4]thiadiazol-5-yl]-1,3-diamino butane (example 521), $N^3$-(4-methoxy-benzoyl)-$N^1$-[3-(4-chloro-benzyl)-[1,2,4]thiadiazol-5-yl]-1,3-diamino butane (example 522), $N^2$-(4-methoxy-benzoyl)-$N^1$-[3-(4-methyl-benzyl)-[1,2,4]thiadiazol-5-yl]-1,2-diamino butane (example 523), $N^2$-(4-methoxy-benzoyl)-$N^1$-[3-(4-fluoro-benzyl)-[1,2,4]thiadiazol-5-yl]-1,2-diamino butane (example 524), $N^2$-(4-methoxy-benzoyl)-$N^1$-[3-(3-methoxy-benzyl)-[1,2,4]thiadiazol-5-yl]-1,2-diamino butane (example 525), $N^2$-(4-methoxy-benzoyl)-$N^1$-[3-(3-fluoro-benzyl)-[1,2,4]thiadiazol-5-yl]-1,2-diamino butane (example 526), $N^2$-(4-methoxy-benzoyl)-$N^1$-[3-(2-fluoro-benzyl)-[1,2,4]thiadiazol-5-yl]-1,2-diamino butane (example 527), $N^2$-(4-methoxy-benzoyl)-$N^1$-[3-(3-benzyl)-[1,2,4]thiadiazol-5-yl]-1,2-diamino butane (example 528), $N^2$-(4-methoxy-benzoyl)-$N^1$-[3-(3-methyl-benzyl)-[1,2,4]thiadiazol-5-yl]-1,2-diamino butane (example 529), $N^2$-(4-methoxy-benzoyl)-$N^1$-[3-(2-methyl-benzyl)-[1,2,4]thiadiazol-5-yl]-1,2-diamino butane (example 530), $N^2$-(4-methoxy-benzoyl)-$N^1$-[3-(2-methoxy-benzyl)-[1,2,4]thiadiazol-5-yl]-1,2-diamino butane (example 531), $N^2$-(4-methoxy-benzoyl)-$N^1$-[3-(4-methoxy-benzyl)-[1,2,4]thiadiazol-5-yl]-1,2-diamino butane (example 532), $N^2$-(4-methoxy-benzoyl)-$N^1$-[3-(3-methyl-4-fluoro-benzyl)-[1,2,4]thiadiazol-5-yl]-1,2-diamino butane (example 533), $N^2$-(4-methoxy-benzoyl)-$N^1$-[3-(4-chloro-benzyl)-[1,2,4]thiadiazol-5-yl]-1,2-diamino butane (example 534), $N^2$-(4-methoxy-benzoyl)-$N^1$-[3-(4-methyl-benzyl)-[1,2,4]thiadiazol-5-yl]-1,2-diamino pentane (example 535), $N^2$-(4-methoxy-benzoyl)-$N^1$-[3-(4-fluoro-benzyl)-[1,2,4]thiadiazol-5-yl]-1,2-diamino pentane (example 536), $N^2$-(4-methoxy-benzoyl)-$N^1$-[3-(3-methoxy-benzyl)-[1,2,4]thiadiazol-5-yl]-1,2-diamino pentane (example 537), $N^2$-(4-methoxy-benzoyl)-$N^1$-[3-(3-fluoro-benzyl)-[1,2,4]thiadiazol-5-yl]-1,2-diamino pentane (example 538), $N^2$-(4-methoxy-benzoyl)-$N^1$-[3-(2-fluoro-benzyl)-[1,2,4]thiadiazol-5-yl]-1,2-diamino pentane (example 539), $N^2$-(4-methoxy-benzoyl)-$N^1$-[3-(3-benzyl)-[1,2,4]thiadiazol-5-yl]-1,2-diamino pentane (example 540), $N^2$-(4-methoxy-benzoyl)-$N^1$-[3-(3-methyl-benzyl)-[1,2,4]thiadiazol-5-yl]-1,2-diamino pentane (example 541), $N^2$-(4-methoxy-benzoyl)-$N^1$-[3-(2-methyl-benzyl)-[1,2,4]thiadiazol-5-yl]-1,2-diamino pentane (example 542), $N^2$-(4-methoxy-benzoyl)-$N^1$-[3-(2-methoxy-benzyl)-[1,2,4]thiadiazol-5-yl]-1,2-diamino pentane (example 543), $N^2$-(4-methoxy-benzoyl)-$N^1$-[3-(4-methoxy-benzyl)-[1,2,4]thiadiazol-5-yl]-1,2-diamino pentane (example 544), $N^2$-(4-methoxy-benzoyl)-$N^1$-[3-(3-methyl-4-fluoro-benzyl)-[1,2,4]thiadiazol-5-yl]-1,2-diamino pentane (example 545), $N^2$-(4-methoxy-benzoyl)-$N^1$-[3-(4-chloro-benzyl)-[1,2,4]thiadiazol-5-yl]-1,2-diamino pentane (example 546), $N^3$-(4-methoxy-benzoyl)-$N^1$-[3-(4-methyl-benzyl)-[1,2,4]thiadiazol-5-yl]-1,3-diamino pentane (example 547), $N^3$-(4-methoxy-benzoyl)-$N^1$-[3-(4-fluoro-benzyl)-[1,2,4]thiadiazol-5-yl]-1,3-diamino pentane (example 548),
$N^3$-(4-methoxy-benzoyl)-$N^1$-[3-(3-methoxy-benzyl)-[1,2,4]thiadiazol-5-yl]-1,3-diamino pentane (example 549),
$N^3$-(4-methoxy-benzoyl)-$N^1$-[3-(3-fluoro-benzyl)-[1,2,4]thiadiazol-5-yl]-1,3-diamino pentane (example 550),
$N^3$-(4-methoxy-benzoyl)-$N^1$-[3-(2-fluoro-benzyl)-[1,2,4]thiadiazol-5-yl]-1,3-diamino pentane (example 551),
$N^3$-(4-methoxy-benzoyl)-$N^1$-[3-(3-benzyl)-[1,2,4]thiadiazol-5-yl]-1,3-diamino pentane (example 552),
$N^3$-(4-methoxy-benzoyl)-$N^1$-[3-(3-methyl-benzyl)-[1,2,4]thiadiazol-5-yl]-1,3-diamino pentane (example 553),
$N^3$-(4-methoxy-benzoyl)-$N^1$-[3-(2-methyl-benzyl)-[1,2,4]thiadiazol-5-yl]-1,3-diamino pentane (example 554),
$N^3$-(4-methoxy-benzoyl)-$N^1$-[3-(2-methoxy-benzyl)-[1,2,4]thiadiazol-5-yl]-1,3-diamino pentane (example 555),
$N^3$-(4-methoxy-benzoyl)-$N^1$-[3-(4-methoxy-benzyl)-[1,2,4]thiadiazol-5-yl]-1,3-diamino pentane (example 556),
$N^3$-(4-methoxy-benzoyl)-$N^1$-[3-(3-methyl-4-fluoro-benzyl)-[1,2,4]thiadiazol-5-yl]-1,3-diamino pentane (example 557), and
$N^3$-(4-methoxy-benzoyl)-$N^1$-[3-(4-chloro-benzyl)-[1,2,4]thiadiazol-5-yl]-1,3-diamino pentane (example 558).

It should be understood that in the foregoing examples 499 to 558, 4-methoxybenzoyl chloride was only used to illustrate the feasibility of acylation of 1,2,4-thiadiazole intermediates represented by the structural formula (VI). Similar compounds can also be synthesised from any acyl chloride according to the list provided herein-before in the detailed description of the invention.

The invention claimed is:
1. A 1,2,4-thiadiazole derivative according to the structural formula (C):

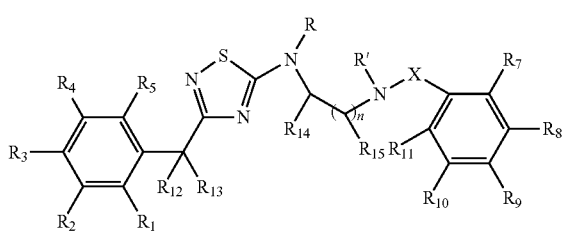

(C)

wherein
$R_1$, $R_2$, $R_3$, $R_4$ and $R_5$ are each independently selected from the group consisting of hydrogen, $C_{1-4}$ alkyl, $C_{1-4}$ alkoxy, aryl, aryloxy, aryl-$C_{1-4}$ alkyloxy, heteroaryloxy, benzenesulfonate, amino, hydroxy, nitro, trifluoromethyl, trifluoromethoxy and halogen, or any two adjacent substituents selected from the group consisting of $R_1$, $R_2$, $R_3$, $R_4$ and $R_5$ form, together with the phenyl ring carbon atoms to which they are attached, a saturated or unsaturated ring fused to said phenyl ring and having from 5 to 7 ring members, said saturated or unsaturated ring optionally comprising one or two oxygen atoms and being optionally substituted with one or more halogen atoms;
$R_7$, $R_8$, $R_9$, $R_{10}$ and $R_{11}$ are each independently selected from the group consisting of hydrogen, $C_{1-10}$ alkyl, $C_{1-6}$ alkoxy, aryl, hydroxy, acetyl, nitro, trifluoromethyl, trifluoromethoxy, mono-$C_{1-6}$alkylamino, di-$C_{1-6}$alkylamino, $C_{1-6}$alkylcarbonyloxy, $C_{1-6}$ alkylthio, cyano, heterocyclic, benzyloxy, dialkylaminosulfonyl and halogen; or any two adjacent substituents selected from the group consisting of $R_7$, $R_8$, $R_9$, $R_{10}$ and $R_{11}$ form, together with the phenyl ring carbon atoms to which they are attached, a saturated or unsaturated ring fused to said phenyl ring and having from 5 to 7 ring members, said saturated or unsaturated ring optionally comprising one or two heteroatoms independently selected from the group consisting of oxygen, sulfur and nitrogen; and each of said $C_{1-6}$ alkyl, $C_{1-6}$ alkoxy, aryl or fused ring is optionally substituted with one or more halogen atoms;
$R_{12}$ and $R_{13}$ are each independently selected from the group consisting of hydrogen, $C_{1-6}$ alkyl, aryl-$C_{1-4}$ alkyl, aryl and N-containing heterocyclic rings, or $R_{12}$ and $R_{13}$ together form a $C_{3-6}$ cycloalkyl or heterocyclic group;
X is a linking moiety selected from the group consisting of a single bond; —C(=O)—; —S(=O)$_2$—; divalent saturated, ethylenically unsaturated or acetylenically unsaturated non-cyclic hydrocarbon groups comprising from 1 to 6 atoms in the main chain, each of said atoms in the main chain being independently selected from the group consisting of carbon, nitrogen and sulfur, and each of said carbon atoms in the main chain being optionally substituted with one or more substituents independently selected from the group consisting of oxo, thioxo, $C_{1-4}$ alkyl and halogen, provided that the number of heteroatoms in the main chain of said divalent saturated or unsaturated non-cyclic hydrocarbon group is 0, 1 or 2; and divalent saturated or unsaturated heterocyclic groups comprising from 2 to 6 carbon atoms and from 1 to 3 heteroatoms independently selected from the group consisting of oxygen, sulfur and nitrogen in the said heterocyclic group; or X together with one of $R_7$ and $R_{11}$ forms a saturated or unsaturated ring having from 5 to 7 ring members and being fused to the phenyl ring bearing said one of $R_7$ and $R_{11}$, said saturated or unsaturated ring optionally comprising one or two heteroatoms independently selected from the group consisting of oxygen, sulfur and nitrogen, and said saturated or unsaturated ring optionally comprising one or more substituents independently selected from the group consisting of $C_{1-4}$ alkyl and trifluoromethyl;
n is an integer from 0 to 11;
R and R' are each independently selected from hydrogen and $C_{1-4}$ alkyl; and
$R_{14}$ and $R_{15}$ are each independently selected from hydrogen and $C_{1-4}$alkyl or according to the structural formula (F):

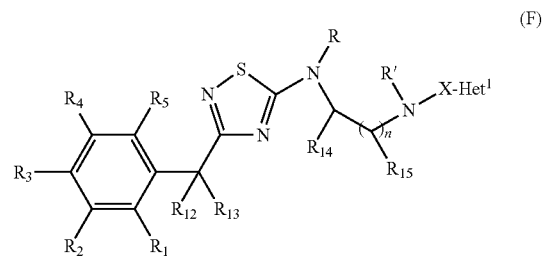

(F)

wherein X, $R_1$, $R_2$, $R_3$, $R_4$, $R_5$, $R_6$, $R_{12}$, $R_{13}$, R, R', $R_{14}$, $R_{15}$ and n are as defined with respect to formula (C), and further wherein Het$^1$ is a heteroaryl group optionally substituted with one or more substituents independently selected from the group consisting of halogen, trifluoromethyl, nitro, cyano and $C_{1-10}$alkyl, or a stereoisomer, or a pharmaceutically acceptable salt thereof.

2. The 1,2,4-thiadiazole derivative according to claim 1, wherein Het[1] is selected from the group consisting of furyl, thienyl, pyrrolyl, oxazolyl, thiazolyl, imidazolyl, cyanoimidazolyl, dicyanoimidazolyl, isoxazolyl, isothiazolyl, 1,2,3-triazolyl, 1,2,4-triazolyl, pyranyl, pyridyl, ethylpyridinyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, benzothiophenyl, indazolyl, benzimidazolyl, benzthiazolyl, benzisothiazolyl, benzisoxazolyl, purinyl, quinazolinyl, quinolizinyl, quinolinyl, isoquinolinyl, ethylquinolinyl, quinoxalinyl, naphthyridinyl, pteridinyl carbazolyl, azepinyl, diazepinyl, acridinyl, pyrrolinyl, pyrazolinyl, indolinyl, pyrrolidinyl, piperidinyl, piperazinyl, azepinyl, diazepinyl, morpholinyl, thiomorpholinyl, oxazolidinyl, oxazolinyl, oxazepinyl, aziridinyl and tetrahydrofuranyl.

3. The 1,2,4-thiadiazole derivative according to claim 1, wherein the linking moiety X is $SO_2$.

4. The 1,2,4-thiadiazole derivative according to claim 1, wherein X is a divalent saturated group comprising a carbon atom and a nitrogen atom in the main chain, said carbon atom being substituted with oxo or thioxo.

5. The 1,2,4-thiadiazole derivative according to claim 1, wherein at least two of $R_1$, $R_2$, $R_3$, $R_4$ and $R_5$ are hydrogen.

6. The 1,2,4-thiadiazole derivative according to claim 1, wherein at least one of $R_1$, $R_2$, $R_3$, $R_4$ and $R_5$ is methoxy.

7. The 1,2,4-thiadiazole derivative according to claim 1, wherein n is 1 or 2.

8. The 1,2,4-thiadiazole derivative according to claim 1, wherein R and R' are both hydrogen.

9. The 1,2,4-thiadiazole derivative according to claim 1, wherein at least one of R and R' is methyl.

10. The 1,2,4-thiadiazole derivative according to claim 1, wherein two adjacent substituents selected from the group consisting of $R_7$, $R_8$, $R_9$, $R_{10}$ and $R_{11}$ form, together with the phenyl ring carbon atoms to which they are attached, a homocyclic or heterocyclic group fused to said phenyl ring.

11. A pharmaceutical composition comprising a therapeutic effective amount of a 1,2,4-thiadiazole derivative according to claim 1.

12. The pharmaceutical composition according to claim 11, further comprising a therapeutic amount of one or more drugs selected from the group consisting of neuro-protective agents and α-synuclein deposition inhibitors.

13. A method of treating neurological disorders characterized by cytotoxic α-synucleopathy, comprising the administration of a therapeutic effective amount of a 1,2,4-thiadiazole derivative according to claim 1, to a patient in need thereof.

14. The method of treatment according to claim 13, wherein said neurological disorders are selected from the group consisting of Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy and Alzheimer's disease.

15. The 1,2,4-thiadiazole derivative according to claim 1, being selected from the group consisting of:
N-[4-methoxyphenylsulfonyl]-N'-[3-(3-methoxybenzyl)-1,2,4-thiadiazol-5-yl]-ethane-1,2-diamine,
N-[4-methoxyphenylsulfonyl]-N'-[3-(3-methoxybenzyl)-1,2,4-thiadiazol-5-yl]-propane-1,2-diamine,
N-[4-methoxyphenylsulfonyl]-N'-[3-(3-methoxybenzyl)-1,2,4-thiadiazol-5-yl]-propane-1,3-diamine,
N'-[4-methoxyphenylsulfonyl]-N-[3-(3-methoxybenzyl)-1,2,4-thiadiazol-5-yl]-N-methylethane-1,2-diamine,
N'-[4-methoxyphenylsulfonyl]-N-[3-(3-methoxybenzyl)-1,2,4-thiadiazol-5-yl]-N'-methylethane-1,2-diamine,
N'-[4-methoxyphenylsulfonyl]-N-[3-(3-methoxybenzyl)-1,2,4-thiadiazol-5-yl]-N,N'-dimethylethane-1,2-diamine,
N-[4-methoxyphenylsulfonyl]-N'-[3-(4-methylbenzyl)-1,2,4-thiadiazol-5-yl]-ethane-1,2-diamine,
N-[4-methoxyphenylsulfonyl]-N'-[3-(4-fluorobenzyl)-1,2,4-thiadiazol-5-yl]-ethane-1,2-diamine,
N-[4-methoxyphenylsulfonyl]-N'-[3-(3-fluorobenzyl)-1,2,4-thiadiazol-5-yl]-ethane-1,2-diamine,
N-[4-methoxyphenylsulfonyl]-N'-[3-(2-fluorobenzyl)-1,2,4-thiadiazol-5-yl]-ethane-1,2-diamine,
N-[4-methoxyphenylsulfonyl]-N'-[3-(3-benzyl)-1,2,4-thiadiazol-5-yl]-ethane-1,2-diamine,
N-[4-methoxyphenylsulfonyl]-N'-[3-(3-methylbenzyl)-1,2,4-thiadiazol-5-yl]-ethane-1,2-diamine,
N-[4-methoxyphenylsulfonyl]-N'-[3-(2-methylbenzyl)-1,2,4-thiadiazol-5-yl]-ethane-1,2-diamine,
N-[4-methoxyphenylsulfonyl]-N'-[3-(2-methoxybenzyl)-1,2,4-thiadiazol-5-yl]-ethane-1,2-diamine,
N-[4-methoxyphenylsulfonyl]-N'-[3-(4-methoxybenzyl)-1,2,4-thiadiazol-5-yl]-ethane-1,2-diamine,
N-[4-methoxyphenylsulfonyl]-N'-[3-(3-methyl-4-fluorobenzyl)-1,2,4-thiadiazol-5-yl]-ethane-1,2-diamine,
N-[4-methoxyphenylsulfonyl]-N'-[3-(4-chlorobenzyl)-1,2,4-thiadiazol-5-yl]-ethane-1,2-diamine,
N-[4-methoxyphenylsulfonyl]-N'-[3-(4-methylbenzyl)-1,2,4-thiadiazol-5-yl]-propane-1,3-diamine,
N-[4-methoxyphenylsulfonyl]-N'-[3-(4-fluorobenzyl)-1,2,4-thiadiazol-5-yl]-propane-1,3-diamine,
N-[4-methoxyphenylsulfonyl]-N'-[3-(3-fluorobenzyl)-1,2,4-thiadiazol-5-yl]-propane-1,3-diamine,
N-[4-methoxyphenylsulfonyl]-N'-[3-(2-fluorobenzyl)-1,2,4-thiadiazol-5-yl]-propane-1,3-diamine,
N-[4-methoxyphenylsulfonyl]-N'-[3-(3-benzyl)-1,2,4-thiadiazol-5-yl]-propane-1,3-diamine,
N-[4-methoxyphenylsulfonyl]-N'-[3-(3-methylbenzyl)-1,2,4-thiadiazol-5-yl]-propane-1,3-diamine,
N-[4-methoxyphenylsulfonyl]-N'-[3-(2-methylbenzyl)-1,2,4-thiadiazol-5-yl]-propane-1,3-diamine,
N-[4-methoxyphenylsulfonyl]-N'-[3-(2-methoxybenzyl)-1,2,4-thiadiazol-5-yl]-propane-1,3-diamine,
N-[4-methoxyphenylsulfonyl]-N'-[3-(4-methoxybenzyl)-1,2,4-thiadiazol-5-yl]-propane-1,3-diamine,
N-[4-methoxyphenylsulfonyl]-N'-[3-(3-methyl-4-fluorobenzyl)-1,2,4-thiadiazol-5-yl]-propane-1,3-diamine,
N-[4-methoxyphenylsulfonyl]-N'-[3-(4-chlorobenzyl)-1,2,4-thiadiazol-5-yl]-propane-1,3-diamine,
N-[4-methoxyphenylsulfonyl]-N'-[3-(4-methylbenzyl)-1,2,4-thiadiazol-5-yl]-propane-1,2-diamine,
N-[4-methoxyphenylsulfonyl]-N'-[3-(4-fluorobenzyl)-1,2,4-thiadiazol-5-yl]-propane-1,2-diamine,
N-[4-methoxyphenylsulfonyl]-N'-[3-(3-fluorobenzyl)-1,2,4-thiadiazol-5-yl]-propane-1,2-diamine,
N-[4-methoxyphenylsulfonyl]-N'-[3-(2-fluorobenzyl)-1,2,4-thiadiazol-5-yl]-propane-1,2-diamine,
N-[4-methoxyphenylsulfonyl]-N'-[3-(3-benzyl)-1,2,4-thiadiazol-5-yl]-propane-1,2-diamine,
N-[4-methoxyphenylsulfonyl]-N'-[3-(3-methylbenzyl)-1,2,4-thiadiazol-5-yl]-propane-1,2-diamine,
N-[4-methoxyphenylsulfonyl]-N'-[3-(2-methylbenzyl)-1,2,4-thiadiazol-5-yl]-propane-1,2-diamine,
N-[4-methoxyphenylsulfonyl]-N'-[3-(2-methoxybenzyl)-1,2,4-thiadiazol-5-yl]-propane-1,2-diamine, N-[4-methoxyphenylsulfonyl]-N'-[3-(4-methoxybenzyl)-1,2,4-thiadiazol-5-yl]-propane-1,2-diamine,
N-[4-methoxyphenylsulfonyl]-N'-[3-(3-methyl-4-fluorobenzyl)-1,2,4-thiadiazol-5-yl]-propane-1,2-diamine,
N-[4-methoxyphenylsulfonyl]-N'-[3-(4-chlorobenzyl)-1,2,4-thiadiazol-5-yl]-propane-1,2-diamine,
N-[4-methoxyphenylsulfonyl]-N'-[3-(4-methylbenzyl)-1,2,4-thiadiazol-5-yl]-N-methyl-ethane-1,2-diamine,
N-[4-methoxyphenylsulfonyl]-N'-[3-(4-fluorobenzyl)-1,2,4-thiadiazol-5-yl]-N-methyl-ethane-1,2-diamine,
N-[4-methoxyphenylsulfonyl]-N'-[3-(3-fluorobenzyl)-1,2,4-thiadiazol-5-yl]-N-methyl-ethane-1,2-diamine,
N-[4-methoxyphenylsulfonyl]-N'-[3-(2-fluorobenzyl)-1,2,4-thiadiazol-5-yl]-N-methyl-ethane-1,2-diamine,
N-[4-methoxyphenylsulfonyl]-N'-[3-(3-benzyl)-1,2,4-thiadiazol-5-yl]-N-methyl-ethane-1,2-diamine,
N-[4-methoxyphenylsulfonyl]-N'-[3-(3-methylbenzyl)-1,2,4-thiadiazol-5-yl]-N-methyl-ethane-1,2-diamine,
N-[4-methoxyphenylsulfonyl]-N'-[3-(2-methylbenzyl)-1,2,4-thiadiazol-5-yl]-N-methyl-ethane-1,2-diamine,
N-[4-methoxyphenylsulfonyl]-N'-[3-(2-methoxybenzyl)-1,2,4-thiadiazol-5-yl]-N-methyl-ethane-1,2-diamine,
N-[4-methoxyphenylsulfonyl]-N'-[3-(4-methoxybenzyl)-1,2,4-thiadiazol-5-yl]-N-methyl-ethane-1,2-diamine,
N-[4-methoxyphenylsulfonyl]-N'-[3-(3-methyl-4-fluorobenzyl)-1,2,4-thia-diazol-5-yl]-N-methyl-ethane-1,2-diamine,
N-[4-methoxyphenylsulfonyl]-N'-[3-(4-chlorobenzyl)-1,2,4-thiadiazol-5-yl]-N-methyl-ethane-1,2-diamine,
N-[4-methoxyphenylsulfonyl]-N'-[3-(4-methylbenzyl)-1,2,4-thiadiazol-5-yl]-N,N'-dimethyl-ethane-1,2-diamine,
N-[4-methoxyphenylsulfonyl]-N'-[3-(4-fluorobenzyl)-1,2,4-thiadiazol-5-yl]-N,N'-dimethyl-ethane-1,2-diamine,
N-[4-methoxyphenylsulfonyl]-N'-[3-(3-fluorobenzyl)-1,2,4-thiadiazol-5-yl]-N,N'-dimethyl-ethane-1,2-diamine,
N-[4-methoxyphenylsulfonyl]-N'-[3-(2-fluorobenzyl)-1,2,4-thiadiazol-5-yl]-N,N'-dimethyl-ethane-1,2-diamine,
N-[4-methoxyphenylsulfonyl]-N'-[3-(3-benzyl)-1,2,4-thiadiazol-5-yl]-N,N'-dimethyl-ethane-1,2-diamine,
N-[4-methoxyphenylsulfonyl]-N'-[3-(3-methylbenzyl)-1,2,4-thiadiazol-5-yl]-N,N'-dimethyl-ethane-1,2-diamine,
N-[4-methoxyphenylsulfonyl]-N'-[3-(2-methylbenzyl)-1,2,4-thiadiazol-5-yl]-N,N'-dimethyl-ethane-1,2-diamine,
N-[4-methoxyphenylsulfonyl]-N'-[3-(2-methoxybenzyl)-1,2,4-thiadiazol-5-yl]-N,N'-dimethyl-ethane-1,2-diamine,
N-[4-methoxyphenylsulfonyl]-N'-[3-(4-methoxybenzyl)-1,2,4-thiadiazol-5-yl]-N,N'-dimethyl-ethane-1,2-diamine,
N-[4-methoxyphenylsulfonyl]-N'-[3-(3-methyl-4-fluorobenzyl)-1,2,4-thia-diazol-5-yl]-N,N'-dimethyl-ethane-1,2-diamine,
N-[4-methoxyphenylsulfonyl]-N'-[3-(4-chlorobenzyl)-1,2,4-thiadiazol-5-yl]-N,N'-dimethyl-ethane-1,2-diamine,
N-[4-methoxyphenylsulfonyl]-N'-[3-(4-methylbenzyl)-1,2,4-thiadiazol-5-yl]-N,N'-diethyl-ethane-1,2-diamine,
N-[4-methoxyphenylsulfonyl]-N'-[3-(4-fluorobenzyl)-1,2,4-thiadiazol-5-yl]-N,N'-diethyl-ethane-1,2-diamine,
N-[4-methoxyphenylsulfonyl]-N'-[3-(3-fluorobenzyl)-1,2,4-thiadiazol-5-yl]-N,N'-diethyl-ethane-1,2-diamine,
N-[4-methoxyphenylsulfonyl]-N'-[3-(2-fluorobenzyl)-1,2,4-thiadiazol-5-yl]-N,N'-diethyl-ethane-1,2-diamine,
N-[4-methoxyphenylsulfonyl]-N'-[3-(3-benzyl)-1,2,4-thiadiazol-5-yl]-N,N'-diethyl-ethane-1,2-diamine,
N-[4-methoxyphenylsulfonyl]-N'-[3-(3-methylbenzyl)-1,2,4-thiadiazol-5-yl]-N,N'-diethyl-ethane-1,2-diamine,
N-[4-methoxyphenylsulfonyl]-N'-[3-(2-methylbenzyl)-1,2,4-thiadiazol-5-yl]-N,N'-diethyl-ethane-1,2-diamine,
N-[4-methoxyphenylsulfonyl]-N'-[3-(2-methoxybenzyl)-1,2,4-thiadiazol-5-yl]-N,N'-diethyl-ethane-1,2-diamine,
N-[4-methoxyphenylsulfonyl]-N'-[3-(4-methoxybenzyl)-1,2,4-thiadiazol-5-yl]-N,N'-diethyl-ethane-1,2-diamine,
N-[4-methoxyphenylsulfonyl]-N'-[3-(3-methyl-4-fluorobenzyl)-1,2,4-thia-diazol-5-yl]-N,N'-diethyl-ethane-1,2-diamine,
N-[4-methoxyphenylsulfonyl]-N'-[3-(4-chlorobenzyl)-1,2,4-thiadiazol-5-yl]-N,N'-diethyl-ethane-1,2-diamine,
N-[2-thienylsulfonyl]-N'-[3-(3-methoxybenzyl)-1,2,4-thiadiazol-5-yl]-ethane-1,2-diamine,
N-[2-thienylsulfonyl]-N'-[3-(3-methoxybenzyl)-1,2,4-thiadiazol-5-yl]-propane-1,2-diamine,
N-[2-thienylsulfonyl]-N'-[3-(3-methoxybenzyl)-1,2,4-thiadiazol-5-yl]-propane-1,3-diamine,
N'-[2-thienylsulfonyl]-N-[3-(3-methoxybenzyl)-1,2,4-thiadiazol-5-yl]-N-methylethane-1,2-diamine,
N'-[2-thienylsulfonyl]-N-[3-(3-methoxybenzyl)-1,2,4-thiadiazol-5-yl]-N'-methylethane-1,2-diamine,
N'-[2-thienylsulfonyl]-N-[3-(3-methoxybenzyl)-1,2,4-thiadiazol-5-yl]-N,N'-dimethylethane-1,2-diamine,
N-[2-thienylsulfonyl]-N'-[3-(4-methylbenzyl)-1,2,4-thia-diazol-5-yl]-ethane-1,2-diamine,
N-[2-thienylsulfonyl]-N'-[3-(4-fluorobenzyl)-1,2,4-thia-diazol-5-yl]-ethane-1,2-diamine,
N-[2-thienylsulfonyl]-N'-[3-(3-fluorobenzyl)-1,2,4-thia-diazol-5-yl]-ethane-1,2-diamine,
N-[2-thienylsulfonyl]-N'-[3-(2-fluorobenzyl)-1,2,4-thia-diazol-5-yl]-ethane-1,2-diamine,
N-[2-thienylsulfonyl]-N'-[3-(3-benzyl)-1,2,4-thiadiazol-5-yl]-ethane-1,2-diamine,
N-[2-thienylsulfonyl]-N'-[3-(3-methylbenzyl)-1,2,4-thia-diazol-5-yl]-ethane-1,2-diamine,
N-[2-thienylsulfonyl]-N'-[3-(2-methylbenzyl)-1,2,4-thia-diazol-5-yl]-ethane-1,2-diamine,
N-[2-thienylsulfonyl]-N'-[3-(2-methoxybenzyl)-1,2,4-thiadiazol-5-yl]-ethane-1,2-diamine,
N-[2-thienylsulfonyl]-N'-[3-(4-methoxybenzyl)-1,2,4-thiadiazol-5-yl]-ethane-1,2-diamine,
N-[2-thienylsulfonyl]-N'-[3-(3-methyl-4-fluorobenzyl)-1,2,4-thiadiazol-5-yl]-ethane-1,2-diamine,
N-[2-thienylsulfonyl]-N'-[3-(4-chlorobenzyl)-1,2,4-thia-diazol-5-yl]-ethane-1,2-diamine,
N-[2-thienylsulfonyl]-N'-[3-(4-methylbenzyl)-1,2,4-thia-diazol-5-yl]-propane-1,3-diamine,
N-[2-thienylsulfonyl]-N'-[3-(4-fluorobenzyl)-1,2,4-thia-diazol-5-yl]-propane-1,3-diamine,
N-[2-thienylsulfonyl]-N'-[3-(3-fluorobenzyl)-1,2,4-thia-diazol-5-yl]-propane-1,3-diamine,
N-[2-thienylsulfonyl]-N'-[3-(2-fluorobenzyl)-1,2,4-thia-diazol-5-yl]-propane-1,3-diamine,
N-[2-thienylsulfonyl]-N'-[3-(3-benzyl)-1,2,4-thiadiazol-5-yl]-propane-1,3-diamine,
N-[2-thienylsulfonyl]-N'-[3-(3-methylbenzyl)-1,2,4-thia-diazol-5-yl]-propane-1,3-diamine,
N-[2-thienylsulfonyl]-N'-[3-(2-methylbenzyl)-1,2,4-thia-diazol-5-yl]-propane-1,3-diamine, N-[2-thienylsulfonyl]-N'-[3-(2-methoxybenzyl)-1,2,4-thiadiazol-5-yl]-propane-1,3-diamine,
N-[2-thienylsulfonyl]-N'-[3-(4-methoxybenzyl)-1,2,4-thiadiazol-5-yl]-propane-1,3-diamine,
N-[2-thienylsulfonyl]-N'-[3-(3-methyl-4-fluorobenzyl)-1,2,4-thiadiazol-5-yl]-propane-1,3-diamine,
N-[2-thienylsulfonyl]-N'-[3-(4-chlorobenzyl)-1,2,4-thiadiazol-5-yl]-propane-1,3-diamine,
N-[2-thienylsulfonyl]-N'-[3-(4-methylbenzyl)-1,2,4-thiadiazol-5-yl]-propane-1,2-diamine,
N-[2-thienylsulfonyl]-N'-[3-(4-fluorobenzyl)-1,2,4-thiadiazol-5-yl]-propane-1,2-diamine,
N-[2-thienylsulfonyl]-N'-[3-(3-fluorobenzyl)-1,2,4-thiadiazol-5-yl]-propane-1,2-diamine,
N-[2-thienylsulfonyl]-N'-[3-(2-fluorobenzyl)-1,2,4-thiadiazol-5-yl]-propane-1,2-diamine,
N-[2-thienylsulfonyl]-N'-[3-(3-benzyl)-1,2,4-thiadiazol-5-yl]-propane-1,2-diamine,
N-[2-thienylsulfonyl]-N'-[3-(3-methylbenzyl)-1,2,4-thiadiazol-5-yl]-propane-1,2-diamine,
N-[2-thienylsulfonyl]-N'-[3-(2-methylbenzyl)-1,2,4-thiadiazol-5-yl]-propane-1,2-diamine,
N-[2-thienylsulfonyl]-N'-[3-(2-methoxybenzyl)-1,2,4-thiadiazol-5-yl]-propane-1,2-diamine,
N-[2-thienylsulfonyl]-N'-[3-(4-methoxybenzyl)-1,2,4-thiadiazol-5-yl]-propane-1,2-diamine,
N-[2-thienylsulfonyl]-N'-[3-(3-methyl-4-fluorobenzyl)-1,2,4-thiadiazol-5-yl]-propane-1,2-diamine,
N-[2-thienylsulfonyl]-N'-[3-(4-chlorobenzyl)-1,2,4-thiadiazol-5-yl]-propane-1,2-diamine,
N-[2-thienylsulfonyl]-N'-[3-(4-methylbenzyl)-1,2,4-thiadiazol-5-yl]-N-methyl-ethane-1,2-diamine,
N-[2-thienylsulfonyl]-N'-[3-(4-fluorobenzyl)-1,2,4-thiadiazol-5-yl]-N-methyl-ethane-1,2-diamine,
N-[2-thienylsulfonyl]-N'-[3-(3-fluorobenzyl)-1,2,4-thiadiazol-5-yl]-N-methyl-ethane-1,2-diamine,
N-[2-thienylsulfonyl]-N'-[3-(2-fluorobenzyl)-1,2,4-thiadiazol-5-yl]-N-methyl-ethane-1,2-diamine,
N-[2-thienylsulfonyl]-N'-[3-(3-benzyl)-1,2,4-thiadiazol-5-yl]-N-methyl-ethane-1,2-diamine,
N-[2-thienylsulfonyl]-N'-[3-(3-methylbenzyl)-1,2,4-thiadiazol-5-yl]-N-methyl-ethane-1,2-diamine,
N-[2-thienylsulfonyl]-N'-[3-(2-methylbenzyl)-1,2,4-thiadiazol-5-yl]-N-methyl-ethane-1,2-diamine,
N-[2-thienylsulfonyl]-N'-[3-(2-methoxybenzyl)-1,2,4-thiadiazol-5-yl]-N-methyl-ethane-1,2-diamine,
N-[2-thienylsulfonyl]-N'-[3-(4-methoxybenzyl)-1,2,4-thiadiazol-5-yl]-N-methyl-ethane-1,2-diamine,
N-[2-thienylsulfonyl]-N'-[3-(3-methyl-4-fluorobenzyl)-1,2,4-thia-diazol-5-yl]-N-methyl-ethane-1,2-diamine,
N-[2-thienylsulfonyl]-N'-[3-(4-chlorobenzyl)-1,2,4-thiadiazol-5-yl]-N-methyl-ethane-1,2-diamine,
N-[2-thienylsulfonyl]-N'-[3-(4-methylbenzyl)-1,2,4-thiadiazol-5-yl]-N,N'-dimethyl-ethane-1,2-diamine,
N-[2-thienylsulfonyl]-N'-[3-(4-fluorobenzyl)-1,2,4-thiadiazol-5-yl]-N,N'-dimethyl-ethane-1,2-diamine,
N-[2-thienylsulfonyl]-N'-[3-(3-fluorobenzyl)-1,2,4-thiadiazol-5-yl]-N,N'-dimethyl-ethane-1,2-diamine,
N-[2-thienylsulfonyl]-N'-[3-(2-fluorobenzyl)-1,2,4-thiadiazol-5-yl]-N,N'-dimethyl-ethane-1,2-diamine,
N-[2-thienylsulfonyl]-N'-[3-(3-benzyl)-1,2,4-thiadiazol-5-yl]-N,N'-dimethyl-ethane-1,2-diamine,
N-[2-thienylsulfonyl]-N'-[3-(3-methylbenzyl)-1,2,4-thiadiazol-5-yl]-N,N'-dimethyl-ethane-1,2-diamine,
N-[2-thienylsulfonyl]-N'-[3-(2-methylbenzyl)-1,2,4-thiadiazol-5-yl]-N,N'-dimethyl-ethane-1,2-diamine,
N-[2-thienylsulfonyl]-N'-[3-(2-methoxybenzyl)-1,2,4-thiadiazol-5-yl]-N,N'-dimethyl-ethane-1,2-diamine,
N-[2-thienylsulfonyl]-N'-[3-(4-methoxybenzyl)-1,2,4-thiadiazol-5-yl]-N,N'-dimethyl-ethane-1,2-diamine,
N-[2-thienylsulfonyl]-N'-[3-(3-methyl-4-fluorobenzyl)-1,2,4-thia-diazol-5-yl]-N,N'-dimethyl-ethane-1,2-diamine,
N-[2-thienylsulfonyl]-N'-[3-(4-chlorobenzyl)-1,2,4-thiadiazol-5-yl]-N,N'-dimethyl-ethane-1,2-diamine,
N-[2-thienylsulfonyl]-N'-[3-(4-methylbenzyl)-1,2,4-thiadiazol-5-yl]-N,N'-diethyl-ethane-1,2-diamine,
N-[2-thienylsulfonyl]-N'-[3-(4-fluorobenzyl)-1,2,4-thiadiazol-5-yl]-N,N'-diethyl-ethane-1,2-diamine,
N-[2-thienylsulfonyl]-N'-[3-(3-fluorobenzyl)-1,2,4-thiadiazol-5-yl]-N,N'-diethyl-ethane-1,2-diamine,
N-[2-thienylsulfonyl]-N'-[3-(2-fluorobenzyl)-1,2,4-thiadiazol-5-yl]-N,N'-diethyl-ethane-1,2-diamine,
N-[2-thienylsulfonyl]-N'-[3-(3-benzyl)-1,2,4-thiadiazol-5-yl]-N,N'-diethyl-ethane-1,2-diamine,
N-[2-thienylsulfonyl]-N'-[3-(3-methylbenzyl)-1,2,4-thiadiazol-5-yl]-N,N'-diethyl-ethane-1,2-diamine,
N-[2-thienylsulfonyl]-N'-[3-(2-methylbenzyl)-1,2,4-thiadiazol-5-yl]-N,N'-diethyl-ethane-1,2-diamine,
N-[2-thienylsulfonyl]-N'-[3-(2-methoxybenzyl)-1,2,4-thiadiazol-5-yl]-N,N'-diethyl-ethane-1,2-diamine,
N-[2-thienylsulfonyl]-N'-[3-(4-methoxybenzyl)-1,2,4-thiadiazol-5-yl]-N,N'-diethyl-ethane-1,2-diamine,
N-[2-thienylsulfonyl]-N'-[3-(3-methyl-4-fluorobenzyl)-1,2,4-thia-diazol-5-yl]-N,N'-diethyl-ethane-1,2-diamine, and
N-[2-thienylsulfonyl]-N'-[3-(4-chlorobenzyl)-1,2,4-thiadiazol-5-yl]-N,N'-diethyl-ethane-1,2-diamine.

16. The pharmaceutical composition of claim 11, further comprising at least one pharmaceutically acceptable carrier.

17. The method of claim 13, wherein said therapeutic effective amount of a 1,2,4-thiadiazole derivative is administered to a patient in combination with one or more pharmaceutically acceptable carriers.

18. The method of claim 13, wherein said therapeutic effective amount of a 1,2,4-thiadiazole derivative is administered to a patient in combination with a therapeutic amount of one or more drugs selected from the group consisting of neuro-protective agents and α-synuclein deposition inhibitors.

* * * * *